US007745688B2

(12) United States Patent
Saido et al.

(10) Patent No.: US 7,745,688 B2
(45) Date of Patent: Jun. 29, 2010

(54) MODEL MOUSE OF ALZHEIMER'S DISEASE EXPRESSING FAD APP 716 AND USE THEREOF

(75) Inventors: Takaomi Saido, Wako (JP); Nobuhisa Iwata, Wako (JP); Takashi Saito, Wako (JP); Takahiro Suemoto, Wako (JP); Jiro Takano, Wako (JP)

(73) Assignee: Riken, Wako-shi (JP)

( * ) Notice: Subject to any disclaimer, the term of this patent is extended or adjusted under 35 U.S.C. 154(b) by 0 days.

(21) Appl. No.: 11/765,730

(22) Filed: Jun. 20, 2007

(65) Prior Publication Data

US 2007/0294779 A1 Dec. 20, 2007

(30) Foreign Application Priority Data

Jun. 20, 2006 (JP) ............................ 2006-170776

(51) Int. Cl.
*A01K 67/033* (2006.01)
*G01N 33/00* (2006.01)

(52) U.S. Cl. .............................. 800/12; 800/3; 800/18; 800/25

(58) Field of Classification Search ....................... None
See application file for complete search history.

(56) References Cited

FOREIGN PATENT DOCUMENTS

WO WO 95/20666 A2 8/1995

OTHER PUBLICATIONS

Echeverria et al. Rat Transgenic Models with a Phenotype of Intracellular Aβ Accumulation in Hippocampus and Cortex. J. Alzheimer's Disease. 2004, vol. 6, pp. 209-219.*

Dudal et al. Inflammation Occurs Early During Aβ Deposition Process in TgCRND8 Mice. Neurobiol. Aging. 2004, vol. 25, pp. 861-871.*

Flood et al. FAD Mutant PS-1 Gene-Targeted Mice: Increased Aβ42 and AB Deposition Without APP Overproduction. Neurobiol. Aging. 2002, vol. 23, pp. 335-348.*

Reuame et al. Enhanced Amyloidogenic Procesing of the β-Amyloid Precursor Protein in Gene Targeted Mice Bearing the Swedish Familial Alzheimer's Disease Mutation and a "Humanized" Aβ Sequence. J. Biological Chem. 1996, vol. 271, pp. 23380-23388.*

Ohno et al. Temporal Memory Deficits in Alzheimer's Mouse Models: Rescue by Genetic Deletion of BACE1. European J. Neurosci. 2006, vol. 23, pp. 251-260.*

Wobus et al. Embryonic Stem Cells: Prospects for Developmental Biology and Cell Therapy. Physiol. Rev., 2005, vol. 85, pp. 635-678.*

Borchelt et al., *Neuron*, 17: 1005-1013 (Nov. 1996).

Borchelt et al., *Neuron*, 19: 939-945 (Oct. 1997).

Eckman et al., *Human Molecular Genetics*, 6(12): 2087-2089 (1997).

JAX Mice Data Sheet, retrieved from the Internet on Oct. 2, 2007, URL: http://jaxmice.jax.org/strain/003378.html.

Small et al., *Journal of Neurochemistry*, 73(2): 443-449 (1999).

Duff et al., *Nature*, 383: 710-713 (Oct. 24, 1996).

Games et al, *Nature*, 373: 523-527 (Feb. 9, 1995).

Hsiao et al., *Science*, 274: 99-102 (Oct. 4, 1996).

Lichtenthaler et al., *Proc. Natl. Acad. Sci. USA*, 96: 3053-3058 (Mar. 1999).

Mullan et al., *Nature Genetics*, 1: 345-347 (Aug. 1992).

Staufenbiel et al., *Nature*, 395: 755-756 (Oct. 22, 1998).

Thinakaran et al., *Neuron*, 17: 181-190 (Jul. 1996).

* cited by examiner

*Primary Examiner*—Deborah Crouch
(74) *Attorney, Agent, or Firm*—Leydig, Voit & Mayer, Ltd.

(57) ABSTRACT

The present invention provides a non-human model mammal of Alzheimer's disease (AD) containing chimeric amyloid precursor protein (APP) gene capable of producing human amyloid β peptide (Aβ) or a living part thereof, characterized in that Aβ42/Aβ40 ratio at 8-weeks-old is about 7-fold or more (about 140-fold or more in homozygote) higher compared to that of a corresponding wild-type mammal. Moreover, the present invention provides the mammal or a living part thereof, further characterized in that the level of APP expression is not significantly different compared to the corresponding wild-type mammal, and a screening method for a prophylactic and/or therapeutic drug for AD, a biomarker in biological fluids and molecular imaging of amyloid deposition or other pathological changes in the brain for an early diagnosis of AD using the mammal or a living part thereof.

19 Claims, 3 Drawing Sheets

MODEL MOUSE OF ALZHEIMER'S DISEASE EXPRESSING FAD APP 716 AND USE THEREOF

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 287,817 bytes ASCII (Text) file named "701664CorrectedSequenceListing.txt," created Aug. 20, 2007.

TECHNICAL FIELD

The present invention relates to a novel model animal of Alzheimer's disease and a use thereof. More specifically, the present invention relates to a non-human model mammal of Alzheimer's disease wherein amyloid β peptide (Aβ) sequence in amyloid precursor protein gene is substituted with a human one and gene mutations which promote production of Aβ are introduced, as well as a screening method for a prophylactic and/or therapeutic drug for Alzheimer's disease using the model animal, and a preclinical diagnostic method of the disease.

BACKGROUND OF THE INVENTION

In recent years, the increase of patients with elderly dementia is becoming a great social problem of the aging population. The main cause of elderly dementia is Alzheimer's disease (hereinafter sometimes to be abbreviated as "AD"). Based on genetic abnormality in familial Alzheimer's disease (FAD), the mechanisms of the formation of senile plaque and neurofibrillary tangle and the like have been increasingly revealed.

The major constituent of senile plaque is a highly aggregatable peptide called Aβ consisting of about 40 amino acid residues, which is produced by cleavage of a part of amyloid precursor protein (APP) consisting of 770 amino acids. Since both the responsible gene and susceptibility gene identified in FAD promote production and accumulation of Aβ, the accumulation of Aβ is believed to cause the onset of AD, and intensive studies have been performed to confirm this belief. Aβ has some molecular species having different lengths due to cleavage site (γ-secretase cleavage site) differences at its C terminal. Among these molecular species, Aβ40 consisting of 40 amino acid residues and Aβ42 consisting of 42 amino acid residues are important. Aβ42 is more likely to aggregate, and the pathogenicity thereof is higher than Aβ40.

In FAD with the Swedish mutation, it is known that there are two mutations at 2 amino acid residues just before the Aβ region in APP gene (Nat. Genet., 1(5): 345-7 (1992)), and that the total amount of Aβ in the brain is remarkably higher than that in normal individuals. Moreover, in vitro research involving mutations artificially introduced to each amino acid residue just after the γ-secretase cleavage site indicated that a substitution of the $716^{th}$ isoleucine (Ile) with phenylalanine (Phe) in APP (I716F) increased the Aβ42/Aβ40 ratio by about 30-fold (Proc. Natl. Acad. Sci. USA, 96: 3053-8 (1999)). However, the results of any research involving FAD with such mutations have not been reported.

To reveal the pathology of the disease and to develop a therapeutic drug for the disease, it is necessary to develop a model animal of the disease. Tg2576 mouse, which is currently used worldwide as a model mouse of AD, is an APP transgenic (Tg) mouse brain over-expressing human APP gene with the Swedish mutation, and can reproduce the development of senile plaque and AD pathology, such as learning and memory disorders (Science, 274: 99-102 (1996)). However, subsequent investigations have revealed that the death of neuronal cells and loss of synapses are not observed in the hippocampus of this mouse, and that the reproduction of neurofibrillary tangle and neurodegeneration is insufficient. APP Tg mouse other than Tg2576 mouse (see, e.g. Nature, 373: 523-7 (1995), and Nature, 395: 755-6 (1998)) and a model mouse of AD wherein another gene was modified (see, e.g., Nature, 383: 710-3 (1996), and Neuron, 17: 181-90 (1996)) only reproduce a part of the pathology in the brain of an AD patient, and fail to reproduce all of the series of pathologies occurring in human.

BRIEF SUMMARY OF THE INVENTION

An object of the present invention is to produce a model mouse of AD which can reproduce a series of pathologies in human AD brain, such as an accumulation of Aβ, neurofibrillary tangle, and neurodegeneration, which is useful in developing prophylactic and/or therapeutic drugs and providing methods for early preclinical diagnosis of AD.

To achieve the above-mentioned object, the present inventors first examined the problems of conventional APP Tg mouse and assumed the following items.

(1) Nonphysiologically high expression of APP may influence axonal transport.

(2) Since a soluble fragment (sAPP) having a neuroprotective action and a protease inhibitory action, and an intracellular fragment (AICD) involved in control of transcription are overproduced by cleavage of overexpressed APP, influences thereof (particularly, the neuroprotective action of a sAPP has a suppressive effect on the neurodegeneration) are not excluded. As a result, the AD pathology may not be reproduced appropriately in a strict sense.

(3) Since promoters of prion protein, PDGF, Thy-1, and the like are used, Aβ is also produced nonphysiologically from neuronal cells other than those intrinsically expressing APP and producing Aβ.

Moreover, problems common to Tg mice (in a narrow sense) include an influence of random insertion of transgenes into chromosomes, different gene expression levels between generations, and the like.

Based on the above assumptions, the present inventors have produced a knock-in (KI) mouse by substituting a region comprising an Aβ portion of a mouse endogenous APP gene with a human region in order not to overexpress APP and by further introducing some mutations into the APP gene in order to increase the production of the highly pathogenic Aβ42. As a result of the investigation of the Aβ42/Aβ40 ratio of the obtained KI mouse, it has been discovered that the ratio is already increased by about 7-fold or more in a heterozygote and by about 140-fold or more in a homozygote, even at the 8-week-old stage, as compared to wild-type. Such a remarkable increase in the Aβ42/Aβ40 ratio has not been observed in any known model mice of AD.

The present inventors continued their investigations based on these findings and completed the present invention.

The present invention provides the following.

[1] A non-human mammal or living part thereof comprising a chimeric APP gene encoding a human type Aβ, wherein (a) the mammal or living part thereof has an Aβ42/Aβ40 ratio at 8-weeks-old that is about 7-fold or more higher than that of a corresponding wild-type animal and/or (b) the mammal or living part thereof is a homozygote for the chimeric APP gene and has an Aβ42/Aβ40 ration at 8-week-old that is about 140-fold or more higher than that of a corresponding wild-type animal.

[2] The mammal or living part thereof of above [1], wherein the mammal or living part thereof has an Aβ42/Aβ40 ratio at 8-weeks-old that is about 7-fold or more higher than that of a corresponding wild-type mammal.

[3] The mammal or living part thereof of above [2], which is a heterozygote for the chimeric APP gene.

[4] The mammal or living part thereof of above [2], which is a homozygote for the chimeric APP gene.

[5] The non-human mammal or living part thereof of above [1], wherein the mammal or living part thereof is a homozygote for the chimeric APP gene and has an Aβ42/Aβ40 ratio at 8-weeks-old that is about 140-fold or more higher than that of a corresponding wild-type mammal.

[6] The mammal or a living part thereof of any one of above [1] to [5], wherein an APP expression level is not significantly different from that of the corresponding wild-type mammal.

[7] The mammal or a living part thereof of above [6], which is a knock-in mammal, wherein an Aβ coding sequence of the endogenous APP gene is substituted with a human Aβ coding sequence.

[8] The mammal or a living part thereof of any one of above [1] to [7], wherein the chimeric APP gene comprises at least one mutation that promotes production of Aβ42.

[9] The mammal or a living part thereof of above [8], wherein the mutation is a mutation of an APP gene identified in FAD.

[10] The mammal or a living part thereof of above [8] or [9], wherein the mutation is a Swedish mutation.

[11] The mammal or a living part thereof of above [9] or [10], wherein the chimeric APP gene differs from a human APP gene by a mutation which is a substitution of the $716^{th}$ Ile in the human APP gene by another amino acid.

[12] The mammal or a living part thereof of any one of above [1] to [9], wherein the non-human mammal is a mouse, a rat, or a marmoset.

[13] The mammal or a living part thereof of above [12], wherein the non-human mammal is a mouse.

[14] A mammal or a living part thereof produced by breeding the mammal of any of above [1] to [13] and a non-human model mammal with a neurodegenerative disease comprising a modification in a gene other than the APP gene.

[15] A method of screening for a substance suppressing a brain accumulation of Aβ, which comprises:

applying a test substance to the mammal or a living part thereof of any one of above [1] to [14], and determining the accumulation of Aβ.

[16] A method of screening for a substance suppressing a brain neurofibrillary tangle, which comprises:

applying a test substance to the mammal or a living part thereof of any one of above [1] to [14], and detecting the neurofibrillary tangle.

[17] A method of screening for a substance that improves learning and memory function or synaptic function of a mammal, which comprises:

applying a test substance to the mammal or a living part thereof of any one of above [1] to [14], and determining whether the test substance improves learning and memory function or synaptic function of the mammal.

[18] A method of screening for a substance suppressing a brain lesion, which comprises:

applying a test substance to the mammal or a living part thereof of any one of above [1] to [14], and detecting the lesion.

[19] The method of above [18], wherein the brain lesion is a neurodegeneration or an inflammation reaction.

[20] The method of any one of above [15] to [19], which is used for screening for a prophylactic and/or therapeutic drug for AD.

[21] The method of any one of above [15] to [19], which is used for evaluating the efficacy of a prophylactic and/or therapeutic drug for AD.

[22] A method of screening for a substance having an affinity for Aβ, which comprises:

applying a test substance to the mammal or a living part thereof of any one of above [1] to [14], and determining the presence of the test substance at a site of accumulation of Aβ.

[23] A method of screening for a biomarker of an AD pathology, which comprises:

measuring cyclopaedically a gene transcription product, a gene translation product or a metabolite in a sample obtained from the mammal or a living part thereof of any one of above [1] to [14] before and after expression of the AD pathology, and identifying a substance that changes before and after the expression.

DETAILED DESCRIPTION OF THE INVENTION

Figure 1:
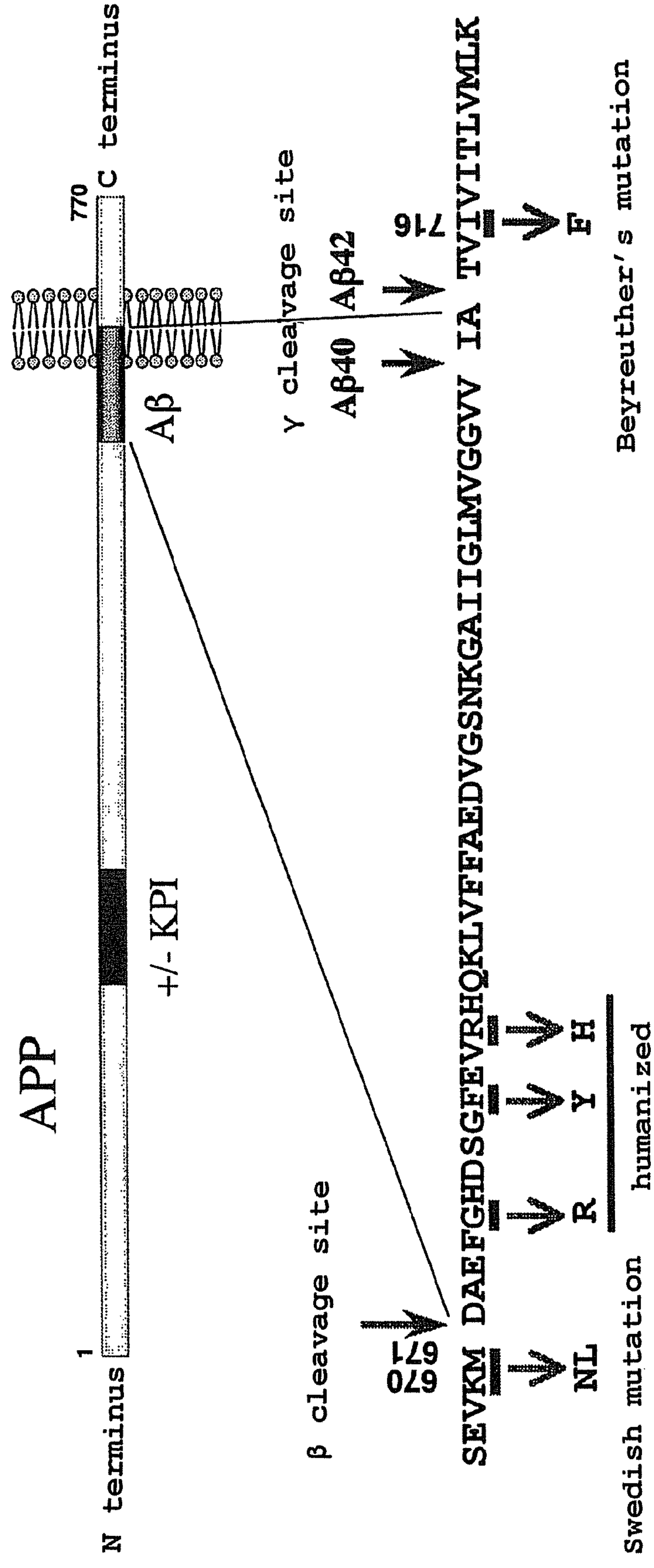
FIG. 1 shows amino acid sequences of Aβ and surrounding region in mouse APP, as well as amino acid substitutions introduced in the KI mouse of the present invention. The amino acids are expressed in 1-letter code.

As the model animal of AD of the present invention highly produces Aβ, particularly Aβ42, without overexpressing APP, an influence on axon transport by APP and an influence on neuroprotective action by a sAPP fragment can be excluded, a faster accumulation of Aβ42 can be realized, and AD pathologies such as neurofibrillary tangle, neurodegeneration and the like which were not sufficiently reproduced in conventional AD models, can be reproduced.

A non-human mammal comprising a chimeric APP gene capable of producing human Aβ (hereinafter sometimes referred as "Tg animal of the present invention") stably carries DNA which encodes a chimeric APP capable of producing human Aβ, in a state enabling the expression of the DNA. "Stably carry" means that the DNA is permanently present in a cell of the animal in a state enabling the expression of the DNA, and the DNA may be incorporated in a host chromosome or may be stably present as an extrachromosomal DNA. Preferably the DNA is incorporated in the host chromosome.

The Tg animal of the present invention is produced by introducing DNA which encodes a chimeric APP encoding human Aβ into, for example, fertilized egg, unfertilized egg, spermatozoon and a precursor cell thereof (primordial germ cell, oogonium, oocyte, fertilized egg, spermatogonium, spermatocyte, sperm cell and the like) of a non-human mammal, preferably at an initial stage in the embryonic development of the fertilized egg (more preferably, before 8-cell stage), by gene transfer methods such as calcium phosphate co-precipitation method, electroporation method, lipofection method, agglutination method, microinjection method, gene gun (particle gun) method, and DEAE-dextran method. It is possible that into a somatic cell, tissue, organ and the like of the non-human mammal is introduced the DNA by the gene transfer methods, and utilized in cell culture, tissue culture and the like. Moreover, the cells can be fused to the above-mentioned embryo (or reproductive) cell by known cell fusion methods to produce the Tg animal. Alternatively, as in case of the production of a knock-out animal, the Tg animal can also be obtained by introducing a DNA comprising human Aβ coding sequence into an embryonic stem cell (ES cell) of a non-human mammal by the above-mentioned gene transfer methods, selecting a clone in which the DNA is stably incorporated, and then producing a chimeric mouse by injection of the ES cell into a blastocyst or aggregation of ES cell cluster and 8-cell embryo, and selecting one having the introduced DNA in germ line.

However, because the model animal of the present invention is preferably characterized in that the level of APP expression is not significantly different as compared to the corresponding wild-type animal, it is desirable that the model animal is a knock-in (KI) animal wherein an Aβ coding sequence of the endogenous APP gene is substituted by a human Aβ coding sequence. Therefore, preferably, the Tg animal of the present invention is produced by introducing the objective DNA into an ES cell by a suitable targeting vector, and substituting an Aβ coding sequence of an endogenous APP gene with a human Aβ coding sequence by homologous recombination.

Although the model animal of AD of the present invention will be explained in detail, with respect to the KI animal for instance in the following discussion, an animal produced by procedures other than the KI technique is encompassed in the model animal of AD of the present invention as long as (i) the animal comprises a chimeric APP gene capable of producing human Aβ, and (ii) Aβ42/Aβ40 ratio at 8-weeks-old is about 7-fold or more higher compared to a corresponding wild-type animal, and preferably further (iii) an amount of APP expression is not significantly different compared to the corresponding wild-type animal.

A living part of the thus-produced Tg animal (preferably, KI animal) (e.g., (1) cells, tissue, organ and the like which stably carry a chimeric APP coding DNA, and (2) cells obtained by culturing cells or tissue therefrom and optionally subcultured, and the like) can be used as "a living part of a non-human mammal carrying a gene which encodes a chimeric APP capable of producing human Aβ, in a state enabling the expression of the DNA" for the same purpose as "a non-human mammal carrying a gene which encodes a chimeric APP capable of producing human Aβ, in a state enabling the expression of the DNA" of the present invention.

A living part of the Tg animal (preferably, KI animal) of the present invention is preferably exemplified by brain, a piece of tissue of a portion of the brain (e.g., olfactory bulb, amygdaloid nucleus, basal ganglia, hippocampus, thalamus, hypothalamus, cerebral cortex, medulla oblongata, cerebellum etc.), cells and the like.

The "non-human mammal" (recipient animal) which can be targeted in the present invention is not limited to a specific one as long as it is a mammal other than human for which a transgenic system (in case of a KI animal, a knock-out system) has been established, and can include, for example, a mouse, rat, cattle, monkey, pig, sheep, goat, rabbit, dog, cat, guinea pig, hamster, marmoset and the like. For the production of a model animal of AD, rodents are preferred because the ontogenesis and biological cycle of the rodents are relatively short, and the propagation is easy. Among them, the mouse (e.g., C57BL/6 strain, BALB/c strain, C3H strain, FVB strain, DBA2 strain and the like as pure strains; $B6C3F_1$ strain, $BDF_1$ strain, $B6D2F_1$ strain, ICR strain and the like as crossed strains) and rat (e.g., Wistar, SD and the like) are preferable.

Other than mammals, birds such as chicken and the like can be used for the same purpose as the "non-human mammal" targeted in the present invention.

A chimeric APP gene comprised in a model animal of AD of the present invention can produce a human Aβ. For example, if the non-human mammal is mouse, a mouse endogenous Aβ differs from human Aβ in that the $5^{th}$ ($676^{th}$ in case of APP) amino acid is not Arg but Gly, the $10^{th}$ ($681^{st}$ in case of APP) amino acid is not Tyr but Phe, and the $13^{th}$ ($684^{th}$ in case of APP) amino acid is not His but Arg. Accordingly, in a chimeric APP gene in the model animal of AD of the present invention, codons which encode the $676^{th}$, $681^{st}$ and $684^{th}$ amino acids of the mouse endogenous APP gene are substituted as to encode amino acid residues of a corresponding human Aβ (FIG. 1).

The model animal of AD of the present invention is characterized in that Aβ42/Aβ40 ratio at 8-weeks-old is about 7-fold or more (e.g., about 10-fold or more, about 15-fold or more, about 20-fold or more, or about 25-fold or more) higher compared to a corresponding wild-type animal. To achieve such a remarkable increase of Aβ42 production, a chimeric APP gene in the model animal of AD of the present invention is more preferably genetically engineered to promote the cleavage of the above-mentioned human Aβ, particularly Aβ42. Therefore, the present invention also provides a model animal of AD characterized in that 1 or more (e.g., 2, 3, 4, 5, 6, 7, 8, 9, 10, or more) mutations capable of promoting production of Aβ42 are introduced into the chimeric APP gene.

Specifically, the mutations which can be introduced into the chimeric APP gene and can promote production of Aβ42 include, for example, a mutation of the APP gene identified in FAD. Such mutations include, but not limited to the Swedish mutation (wherein the $670^{th}$ Lys and $671^{st}$ Met of APP are substituted by Asn and Leu, respectively (FIG. 1); sometimes to be abbreviated as "K670N" and "M671L"), the Hardy mutation (wherein the $717^{th}$ Val of APP is substituted by Ile, Phe or Gly), or a mutation wherein the $692^{nd}$ Ala and the $693^{rd}$ Glu of APP are substituted by Gly, respectively, and the like. Alternatively, mutations which can promote production of Aβ42 other than those identified in FAD include, for example, mutations at amino acid residues surrounding the β- and γ-secretase cleavage site, which influence the cleavage of Aβ. The specific examples include, but are not limited to, a mutation wherein any of the 714$^{th}$ Thr, the 716$^{th}$ Ile, the 717$^{th}$ Val (this mutation is also identified in FAD as the Hardy mutation), the 720$^{th}$ Leu, and the 722$^{nd}$ Met of human APP is substituted by another amino acid, for example, Phe, etc., reported to increase the Aβ42/Aβ40 ratio in vitro in the above-mentioned [Proc. Natl. Acad. Sci. USA, 96: 3053-8 (1999)], and the like. Preferably, the Swedish mutation is the mutation identified in FAD. A mutation wherein the 716$^{th}$ amino acid of human APP is substituted by another amino acid (for example, Phe (FIG. 1); sometimes to be abbreviated as "I716F") is another preferred mutation.

As above described, the model animal of AD of the present invention preferably does not overproduce APP in order to avoid the influence on axon transport by APP and the influence on neuroprotective action by a sAPP fragment. More preferably, the level of APP expression is not significantly different than that of the corresponding wild-type animal. Accordingly, in a preferred embodiment, a model animal of AD of the present invention is a knock-in (KI) animal, wherein at least the Aβ coding region of the endogenous APP gene of the recipient animal is substituted by a human one by gene targeting with homologous recombination.

The KI animal can be produced in the same manner as a knock-out (KO) animal. A nucleotide sequence which encodes an Aβ portion of the APP gene is present in the 16$^{th}$ to 17$^{th}$ exons [see, base sequence SEQ ID NO: 1 (the sequence is a nucleotide sequence shown by base number 84837873-85057149 of the nucleotide sequence of the mouse 16 chromosome (registered in NCBI database as GenBank accession No. NC_000082, Version NC_000082.4 GI: 94471502) (complementary strand)) and FIG. 2]. Therefore, for example, a targeting vector comprising a DNA obtained by excising these regions of the APP gene derived from a recipient animal by a suitable restriction enzyme and inserting a corresponding region of human APP gene instead of the regions can be introduced into an embryonic stem cell (ES cell) derived from the recipient animal according to a conventional method, and an ES cell clone wherein a human Aβ coding DNA is integrated into the endogenous APP gene locus of the animal by homologous recombination can be selected. The corresponding region of the human APP gene can be excised by treating human APP gene with a suitable restriction enzyme as well, or, a DNA comprising a nucleotide sequence encoding the human Aβ portion can be synthesized by site-directed mutagenesis with the human APP gene used as template. In the preferred embodiment of the present invention, because the chimeric APP gene comprises gene mutations which promote the cleavage of Aβ (particularly, Aβ42), more preferably, a human APP gene fragment including these mutation sites is synthesized by site-directed mutagenesis.

Figure 2:
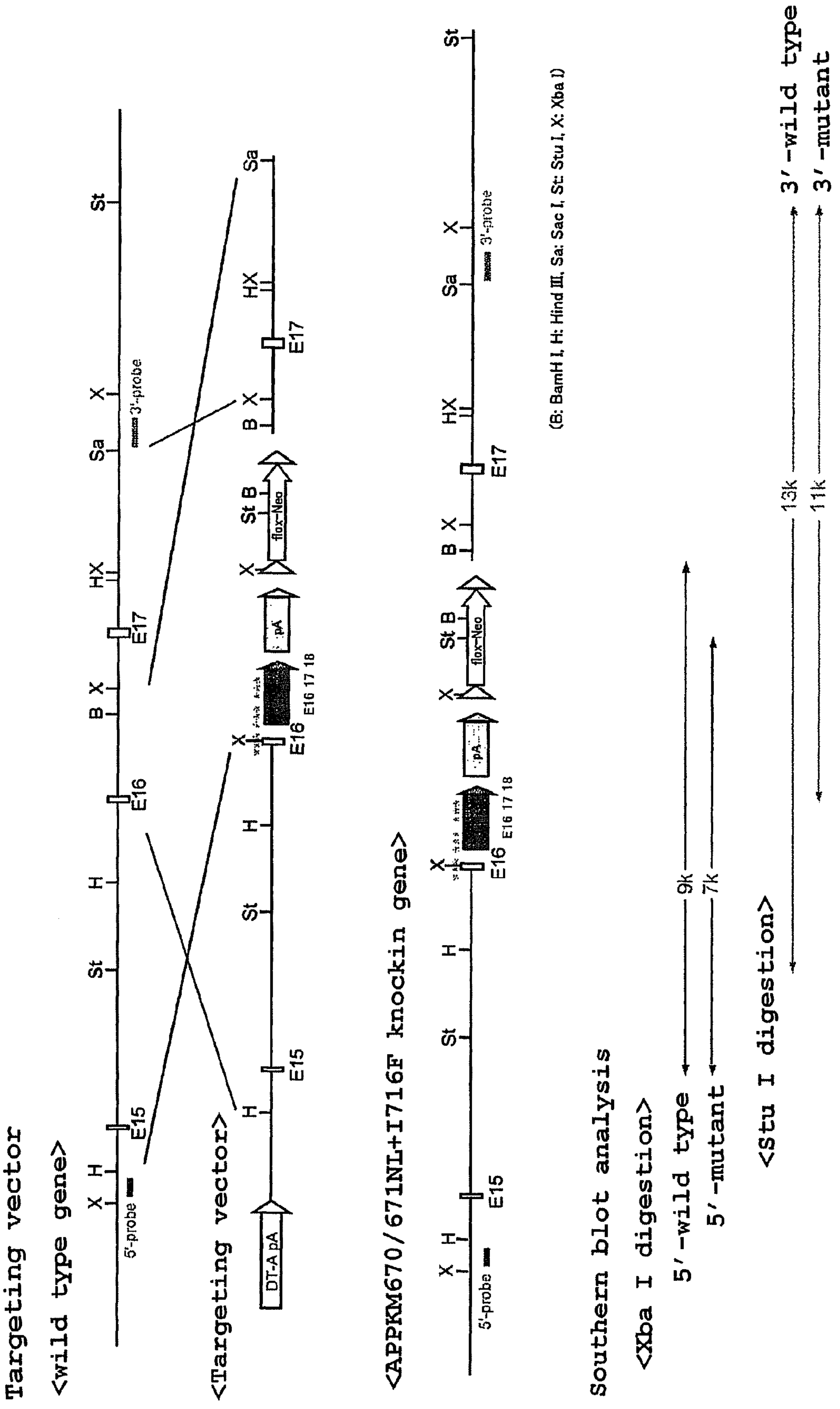
FIG. 2 is a schematic diagram showing a target sequence region of mouse APP gene (the upper panel) and a targeting vector used in the present invention (the lower panel).

Although the Aβ coding region spans the 16$^{th}$ and 17$^{th}$ exons as above-mentioned, a coding region of APP consists of 18 exons. Therefore, in a preferred embodiment, it is possible that a sequence is synthesized by substituting the Aβ portion with the human Aβ sequence, linking the 16$^{th}$ and 17$^{th}$ exons comprising mutations promoting the cleavage of Aβ (particularly, Aβ42), and further linking the 18$^{th}$ exon, and a polyadenylation (poly A) signal (also called a terminator) sequence is placed downstream of the sequence, thereby allowing the termination of the transcription of the chimeric APP mRNA (FIG. 2). For example, terminator sequences derived from virus genes or derived from genes of various mammals or birds can be used to achieve an effective expression of the chimeric APP gene. Preferably, the SV40 terminator from simian virus and the like are used.

The targeting vector comprises regions homologous to an endogenous APP gene of a targeted recipient animal at the 5' side and 3' side of the human APP gene fragment to allow homologous recombination (the HindIII-XbaI fragment of 6.6 kb (the XbaI recognition site occurs in the 16$^{th}$ exon by introduction of the Swedish mutation) and the BamHI-SacI fragment of 4.6 kb in FIG. 2 correspond to the 5' and 3' side arms, respectively).

In addition, the targeting vector is preferably one wherein a selection marker gene such as a drug resistance gene, and a reporter gene (a marker gene for positive selection) is inserted to confirm the integration of DNA. For example, the drug resistance gene includes, but is not limited to, neomycin phosphotransferase II (nptII) gene, hygromycin phosphotransferase (hpt) gene and the like, and the reporter gene includes, but is not limited to, β-galactosidase (lacZ) gene, chloramphenicol acetyltransferase (cat) gene and the like. The marker gene for positive selection is preferably in a form of an expression cassette comprising any promoter capable of functioning in cells of the recipient animal. The marker gene for positive selection is inserted between the 5' and 3' side arms homologous to target sequence in the targeting vector.

Since the marker gene for positive selection may interfere with the expression of the chimeric APP gene, the marker gene for positive selection is preferably excised by using a targeting vector wherein a loxP sequence or frt sequence is placed at the both ends of the marker gene for positive selection thereof, and treating the targeting vector with Cre or Flp recombinase or an expression vector of the recombinase (e.g., adenovirus vector and the like) at a suitable time point after selection of a homologous recombinant. Alternatively, instead of using the Cre-loxP system or Flp-frt system, the marker gene for positive selection can be excised by placing sequences homologous to the target gene at the both ends of the marker gene for positive selection in a tandem repeat, and utilizing intragene recombination between the sequences.

Furthermore, generally, genetic recombination in mammals is mostly non-homologous, and the introduced DNA is inserted randomly at any position of the chromosome. Thus, the selection of only the clones wherein the target endogenous APP gene is inserted by homologous recombination cannot be efficiently performed by selection, such as the detection of expression of a drug resistance gene, and confirmation of the integrated site of all selected clones by the Southern blot method or PCR method will be necessary. Consequently, if a negative selection marker gene, for example, the herpes simplex virus derived thymidine kinase (HSV-tk) gene that gives gancyclovir sensitivity, is ligated outside the region homologous to the target sequence of the targeting vector, the cell in which the vector was randomly inserted will not be able to grow in gancyclovir containing medium because it has the HSV-tk gene, but the cell in which endogenous APP gene locus was targeted by homologous recombination will become gancyclovir resistant because it does not have the HSV-tk gene, and therefore will be selected. Alternatively, if, for example, the diphtheria toxin (DT) gene, is ligated in place of the HSV-tk gene, the cell in which the vector is randomly inserted will die by the toxin produced by itself, and the homologous recombinant can be selected in the absence of any agent. The resistant colonies that emerged are transferred respectively to culture plates, and after repeating trypsin treatment and medium replacement, a part thereof is left for cultivation, while the rest is used for PCR or Southern blot to confirm the presence of the introduced DNA.

*Escherichia coli*-derived plasmid, *Bacillus subtilis*-derived plasmid, yeast-derived plasmid, bacteriophage such as λ phage, for example, animal or insect virus retroviruses such as Moloney leukemia virus, lentivirus, adeno-associated virus, vaccinia virus or baculovirus and the like can be used as vectors to carry the human APP gene fragment, terminator, 5' and 3' arms homologous to the target sequence, and positive and negative selection marker genes. Among them, plasmid (preferably *Escherichia coli*-derived, *Bacillus subtilis*-derived or yeast-derived, particularly *Escherichia coli*-derived plasmid) and animal virus (preferably retrovirus, lentivirus) are preferable.

The above-mentioned human APP gene fragment, terminator, 5' and 3' arm homologous to the target sequence, and positive and negative selection marker genes and the like, can be inserted in the correct arrangement in the above-mentioned vector by general genetic engineering procedures that use appropriate restriction enzymes and DNA ligase and the like.

ES cells refer to cells which are derived from inner cell mass (ICM) of fertilized eggs of blastocyst stage, and can be maintained while keeping the undifferentiated state in vitro. The cells of ICM are cells that will form the embryo body in the future, and are the stem cells that will be the source of all tissues including the reproductive cells. Already established cell lines can be used as ES cells, or, the ES cells can be newly established ones according to the method of Evans and Kaufman (Nature, vol. 292, page 154, (1981)). For example, in the case of mouse ES cells, currently, 129-strain mouse-derived ES cells are generally used, but since the immunological background is not clear, for example, ES cells established from $BDF_1$ mouse ($F_1$ of C57BL/6 and DBA/2) which have been improved over the low egg collection number of the C57BL/6 mouse and C57BL/6 by crossbreeding with DBA/2, can be satisfactorily used, for example, for the purpose of obtaining ES cells of other pure strains and having an immunologically clear genetic background. In addition to the advantage in that the $BDF_1$ mouse has a large egg collection number and strong eggs, since the $BDF_1$ mouse has C57BL/6 mouse as the background, they can be advantageously used from the point that when a disease-model mouse is produced with ES cells derived from the $BDF_1$ mouse, its genetic background can be changed to a C57BL/6 mouse by back-crossing with a C57BL/6 mouse.

Preparation of ES Cells can be Performed, for Example, in the following way. Blastocyst stage embryo is collected from the uterus of postcoitus female non-human mammal [e.g., when a mouse (preferably inbred mouse such as C57BL/6J (B6), $F_1$ of B6 and other inbred strain, and the like) is used, approximately about 8 to about 10-week-old female mouse (about 3.5 days of pregnancy) which was mated with about 2-months-old or older male mouse is preferably used] (or after collecting the early embryo of morula stage or before from the fallopian tube, it can be cultivated in an embryo culture medium until blastocyst stage in the same manner as above), and cultivating it on a layer of appropriate feeder cells (e.g., in case of mouse, primary fibroblast prepared from mouse fetus or known STO fibroblast strain, etc.) causes a part of the cell of the blastocyst to come together and form an ICM which differentiates into an embryo in the future. ES cells are obtained by dissociating this inner cell mass into single cells by trypsin treatment, maintaining the appropriate cell density, and repeating dissociation and passage while performing medium replacement.

Either male or female ES cells can be used, but male ES cells are generally preferable for preparing germ line chimera. Furthermore, to reduce the labor of troublesome cultivation, it is desirable to distinguish the sex as early as possible. As one example of a sex determination method of ES cells, the method of amplifying the gene of the sex determination region on the Y chromosome by PCR method and detecting it can be used. Using this method, since karyotype analysis can be performed using only an ES cell number (about 50 cells) nearly equal to 1 colony, in contrast to about $10^6$ cells for conventional karyotype analysis, the primary selection of ES cells in the primary stage of cultivation can be performed by sex distinguishment. Thus, selection of male cells at an early stage affords a drastic reduction of the labor of primary stage cultivation.

Furthermore, as secondary selection, for example, confirmation of chromosome number by the G-banding method, and the like, can be performed. While the chromosome number of the obtained ES cells is desirably 100% of the normal number, if it is difficult to achieve due to the physical operation etc. for establishing the cell line, the chromosome is desirably cloned again to normal cells (e.g., cells having chromosome number of 2n=40 for mouse) after gene transfer to ES cells.

The ES cell line obtained in such a way should be carefully passage-cultured to maintain the properties of an undifferentiated stem cell. For example, it is cultivated by a method such as cultivation on an appropriate feeder cell such as an STO fibroblast, within carbon dioxide gas incubator (preferably, 5% carbon dioxide gas/95% air or 5% oxygen/5% carbon dioxide gas/90% air) at about 37° C. in the presence of LIF (1-10,000 U/ml) which is known to be a differentiation suppressor, and when passaging, for example, methods are taken such as causing them to become single cells by trypsin/EDTA solution (generally 0.001-0.5% trypsin/0.1-5 mM EDTA, preferably about 0.1% trypsin/1 mM EDTA) treatment, and seeding them onto newly prepared feeder cells. Such passaging is generally performed every 1-3 days, during which the cells are to be observed, and when morphological abnormality is observed, the cultured cells are desirably discarded.

Under suitable conditions, it is possible to cause ES cells to differentiate into various types of cells such as parietal muscle, visceral muscle, and myocardial cells by either performing single layer cultivation until it reaches a high density, or suspension culturing until it forms a cell clump [M. J. Evans and M. H. Kaufman, Nature, vol. 292, page 154, (1981); G. R. Martin, Proceedings of National Academy of Sciences U.S.A. (Proc. Natl. Acad. Sci. U.S.A.), vol. 78, page 7634, (1981); T. C. Doetschman et al., Journal of Embryology and Experimental Morphology, vol. 87, page 27, (1985)]. A non-human mammalian cell expressing the chimera APP gene obtained by differentiating the ES cell transferred with a targeting vector is useful in cell biological investigation of the human Aβ in vitro.

Any of the calcium phosphate co-precipitation method, electroporation method, lipofection method, retrovirus infection method, agglutination method, microinjection method, gene gun (particle gun) method, DEAE-dextran method, and the like can be used for gene transferring to ES cells, but the electroporation method is generally selected from the point that it enables convenient treatment of a large number of cells, and the like. The conditions used for gene transfer to normal animal cells can be used for electroporation, for example, after trypsin treatment of ES cells in the logarithmic growth phase and dispersion into single cells, they are suspended in a medium to be $10^6$-$10^8$ cell/ml and transferred to a cuvette, then 10-100 μg of targeting vector is added, and electric pulse of 200-600 V/cm can be applied.

ES cells, in which the introduced DNA has been integrated into the genome, can also be assayed by screening by Southern blot or PCR method of the chromosome DNA separated and extracted from the colony obtained by cultivating single cells on the feeder cell. The greatest advantage of the transgenic system using ES cells is that a transformant can be selected during the cell stage using the expression of drug resistance genes or reporter genes as an index. On the other hand, confirmation of integration by homologous recombination can be performed by selection using negative selection marker genes such as the above-mentioned HSV-tk and DT genes. For example, when a vector comprising the nptII gene as the positive selection marker gene and the HSV-tk gene as the negative selection marker gene is used, the presence of introduced DNA is confirmed by culturing ES cells that are gene transferred in a medium containing neomycin antibiotics such as G418 and gancyclovir, transferring the emerging resistant colonies to respective culture plates, and repeating trypsin treatment and medium replacement, and then leaving a part thereof for cultivation, and using the rest for PCR or Southern blot.

When the ES cell that has been confirmed of the integration of the introduced DNA is put back into the embryo derived from an allogenic non-human mammal, it is incorporated into the ICM of the host embryo and a chimera embryo is formed. A chimera KI animal is obtained by transplanting this to a foster parent (embryo recipient female) and allowing further continuation of the development. When the ES cell contributes to the formation of the primordial germ cell which differentiates in the future into ovum or spermatozoa, the germ line chimera will be obtained, and the KI animal which has the introduced DNA genetically fixed can be produced by mating them.

The production method of chimera embryo includes the method of aggregating the early embryo up to the morula stage by adhering them with each other (aggregation chimera method), and the method of microinjecting the cell into the blastocoel of the blastocyst (injection chimera method). In producing the chimera embryo by ES cells, the latter is heretofore widely performed, but recently, the method of making aggregation chimera by injecting ES cells into the zona pellucida of the 8-cell embryo, and as a micromanipulator-free and easily operatable method, the method of producing aggregation chimera by co-cultivating the ES cell mass and the 8-cell embryo with its zona pellucida removed and coagulating them, is also performed.

In both cases, the host embryo can be collected in the same manner from a non-human mammal that can be used as a female for egg collection in gene transferring into fertilized egg, but for example, in case of mouse, it is preferable that the host embryo is collected from a strain of mouse whose coat color differs from that of the strain that the ES cell is derived from such that the contribution rate of ES cells to chimeric mouse formation can be determined by coat color. For example, if the ES cells are derived from 129 strain mouse (coat color:aguti), then C57BL/6 mouse (coat color:black) or ICR mouse (coat color:albino) can be used as the female for egg collection, and if the ES cells are derived from C57BL/6 or $DBF_1$ mouse (coat color:black) or TT2 cells (derived from $F_1$ of C57BL/6 and CBA (coat color:agouti)), then ICR mouse or BALB/c mouse (coat color:albino) can be used as the female for egg collection.

Also, since the germ line chimera formation ability depends greatly on the combination of the ES cell and the host embryo, it is more preferable to select the combination leading to high germ line chimera formation ability. For example, in case of mouse, it is preferable to use C57BL/6 strain derived host embryo and the like for 129 strain derived ES cells, and it is preferable to use BALB/c strain derived host embryo and the like for C57BL/6 strain derived ES cells.

Approximately about 4 to about 6-week-old mice are preferable as the female mice for egg collection, and approximately about 2 to about 8-month-old mice of the same strain are preferable as the male mice for mating. Mating can be by natural mating, but it is preferable that it is performed after induction of superovulation by administration of gonadotropin (follicle stimulating hormone, followed by luteinizing hormone).

If the blastodisc injection method is used, blastocyst stage embryo (for example, in the case of mouse, about 3.5 days after mating) is collected from the uterus of the female for egg collection (or after collecting the early embryo of morula stage or before from the fallopian tube, it can be cultivated until blastocyst stage in the aforementioned embryo culture medium), ES cells (about 10 to about 15 cells) comprising the chimera APP gene are injected into the blastocoel of the blastocyst using a micromanipulator, followed by transplant into the uterus of a pseudopregnant recipient female non-human mammal. A non-human mammal that can also be used as a recipient female for gene transfer into a fertilized egg can be used in the same manner as the recipient female mouse.

If the co-culturing method is used, 8-cell embryo and morula (for example, in case of mouse, about 2.5 days after mating) are collected from the fallopian tube and the uterus of the female for egg collection (or after collecting the early embryo of 8-cell phase or before from the fallopian tube, it can be cultivated until 8-cell phase or morula stage in the aforementioned embryo culture medium) and the zona pellucida is dissolved in acidic Tyrode's solution, followed by putting the ES cell mass (cell number from about 10 to about 15) comprising the chimera APP gene into the microdroplet of the embryo culture medium with mineral oil layered, and further putting the above-mentioned 8-cell embryo or morula (preferably 2) and co-cultivating them overnight. The morula or blastocyst obtained is transplanted into the uterus of the recipient female non-human mammal in the same manner as mentioned above.

If the transplanted embryo is successfully implanted and the recipient female becomes pregnant, chimera non-human mammal is obtained by natural delivery or Caesarian section. A recipient female that gave natural delivery should be kept feeding, and when birth is given by Caesarian section, the baby can be fed by a separately arranged female for feeding (female non-human mammal that has normally mated and delivered).

If the sex of the ES cell is distinguished in advance, the selection of the germ line chimera is done by selecting a chimeric mouse with the same sex as the ES cell (generally, since a male ES cell is used, a male chimeric mouse is selected), and then selecting a chimeric mouse with a high ES cell contribution rate (e.g., 50% or more) by the phenotype such as the coat color. For example, in the case of a chimera mouse obtained from a chimera embryo of D3 cell which is a 129 strain mouse-derived male ES cell, and C57BL/6 mouse-derived host embryo, it is preferable to select a male mouse with a high ratio of agouti coat color. The confirmation of whether the selected chimera non-human mammal is a germ line chimera or not can be performed based on the phenotype of the $F_1$ animal obtained by crossbreeding with a suitable strain of the animal of the same race. For example, in the case of the above-mentioned chimeric mouse, since agouti is dominant to black, when it is crossbred with female C57BL/6 mouse, if the selected male mouse is a germ line chimera, then the coat color of the $F_1$ obtained will be agouti.

The germline chimera non-human mammal which comprises a chimera APP gene (founder) that is obtained in the above-mentioned way is, generally, obtained as a heterozygote that has an introduced DNA in only one of the homologous chromosomes. In order to obtain a homozygote that comprises the chimera APP gene in both homologous chromosomes, the littermates of the $F_1$ animal obtained in the above-mentioned way, which is a heterozygote that has an introduced DNA on only one of the homologous chromosomes, should be crossbred. The selection of the heterozygote can be tested by, for example, screening the chromosome DNA which was isolated and extracted from the tail of the $F_1$ animal, by Southern blot or the PCR method. ¼ of the $F_2$ animal obtained will be a homozygote.

In one embodiment of using a virus as the expression vector, a method can be used in which an ES cell of a non-human mammal is infected with a virus comprising the introduced DNA (e.g., see Proc. Natl. Acad. Sci. USA, vol. 99, 4, page 2140-2145, (2002)). For example, when retrovirus or lentivirus is used, the cell is plated on a suitable incubator such as a dish (it is preferable to remove the zona pellucida of fertilized eggs), a virus vector is added to the culture medium (polybrene can coexist if desired), and after cultivation for 1 to 2 days, in the case of early embryo, it is transplanted into the fallopian tube or the uterus of the pseudopregnant recipient female non-human mammal as mentioned above, and in the case of ES cells, a selective pharmaceutical agent such as G418 or hygromycin and gancyclovir is added as mentioned above, cultivation is continued, and the cells that have the vector integrated are selected.

Furthermore, as it is described in Proc. Natl. Acad. Sci. USA, vol. 98, page 13090-13095, (2001), by infection of spermatogonium that is collected from male non-human mammal with a virus vector while co-cultivating with STO feeder cells, followed by its injection into a seminiferous tubule of a male infertile non-human mammal and mating with a female non-human mammal, a chimera APP hetero KI(+/−) baby can be efficiently obtained.

The AD model animal of the present invention is characterized in that the Aβ42/Aβ40 ratio at 8-weeks-old is about 7-fold or more compared to a corresponding wild-type animal. The phenotype, in which the Aβ42/Aβ40 ratio is about 7-fold or more even at 8-weeks-old, has not been found in any conventionally known AD model mouse, and the AD model animal of the present invention is useful in that it is able to reproduce from an extremely early stage, and has the accumulation of human Aβ (particularly Aβ42) which is an initial hallmark in human AD pathology.

Particularly, in a chimera-APP-gene-KI-animal which has a mutation that promotes the excision and release of Aβ (particularly Aβ42) (preferably the Swedish mutation and the I716F mutation), which is particularly preferable embodiment of the present invention, the Aβ42/Aβ40 ratio at 8-weeks-old is about 7-fold higher compared to a wild-type animal even in a heterozygote, and when it is a homozygote, the Aβ42/Aβ40 ratio at 8-weeks-old is about 140-fold or more (e.g., about 145-fold or more, about 150-fold or more, about 155-fold or more, about 160-fold or more, about 165-fold or more, or about 170-fold or more) that of the wild-type animal. This value in a homozygote is equal to the Aβ42/Aβ40 ratio in a normal brain of a human in their 70's to 80's. Considering that it is suggested from studies and the like on abnormalities of neprilysin gene, which is an Aβ-degrading enzyme, and presenilin (PS)1 gene, which is a component of Aβ production enzyme, that there is a possibility that a slight rise in the brain Aβ42 level (e.g., 1.5-fold) determines the onset age of AD, it should be clear that the AD model animal of the present invention has a nonconventional superior property.

Additionally, the AD model animal of the present invention, particularly the chimera-APP-gene-KI-animal, is different from the conventionally known APP Tg animal which has a multiple copy number of APP gene integrated randomly into the chromosome, in that it has the Aβ coding region of endogenous APP gene of the recipient animal substituted with the human Aβ coding region, and does not have changes in the APP gene copy number, and since the APP gene expression is controlled by an endogenous promoter, the APP expression level is substantially equal to the corresponding wild-type animal, without significant difference. For this reason, there are no concerns that the artifact that accompanies the APP overexpression of a conventionally known APP Tg mouse (e.g., neuroprotective action by a sAPP fragment and the influence of axonal transport by APP itself, etc.) would be produced, and the Aβ42 accumulation can directly reflect the brain pathology. Therefore, it is anticipated that the AD pathology that was not sufficiently reproduced in a conventionally known AD model mouse, such as neurofibrillary tangle (tau accumulation) and neurodegeneration, can be reproduced in the AD model animal of the present invention.

The present invention also provides a non-human mammal or a part of its biological body, which comprises the above-mentioned chimera APP gene which can produce a human Aβ, as well as having a modification of a gene related to a neurodegenerative disease, which is other than the APP gene.

"A modification of a gene related to a neurodegenerative disease, which is other than the APP gene" includes, for example, spontaneous mutations or genetic polymorphisms such as mutations of the PS1 and PS2 genes identified in FAD, ApoE4 genetic polymorphism in apolipoprotein E (ApoE), deletion or mutation of the neprilysin gene, mutation of the tau gene, as well as Tg of KI of those genes, KO of genes that act protectively on neurodegeneration, knock-down (Tg animal in which gene expression has decreased to be undetectable or ignorable, by the introduction of antisense DNA or DNA encoding a neutralization antibody) or the introduction of a dominant negative mutation, etc.

The method of introducing a modification of a gene related to a neurodegenerative disease, which is other than the APP gene, to an animal which can produce a human Aβ and that comprises a chimera APP gene, is not particularly limited. For example, the method includes (1) the method of crossbreeding a non-human mammal comprising a chimera APP gene and a non-human mammal of the same race which has a modification of a gene related to a neurodegenerative disease, which is other than the APP gene; (2) the method of obtaining a KI non-human mammal by introducing a chimera APP gene that can produce human Aβ by the aforementioned method into an ES cell of a non-human mammal that has a modification of a gene related to a neurodegenerative disease, which is other than the APP gene; (3) the method of introducing a modification of a gene related to a neurodegenerative disease, which is other than the APP gene, into the early embryo or ES cells of a non-human mammal in which the chimera APP gene that can produce human Aβ was introduced, and the like. If a non-human mammal that has a modification of a gene related to a neurodegenerative disease, which is other than the APP gene preexists, the method of crossbreeding by the above-mentioned (1) is preferable considering its convenience.

A known disease model which has a modification of a gene related to a neurodegenerative disease, which is other than the APP gene, includes, but is not limited to, for example, the mouse described in the above-mentioned [Nature, 383: 710-3 (1996), and Neuron, 17: 181-90 (1996)], ApoE KO(−/−) mouse, neprilysin KO mouse, and the like.

When crossbreeding a non-human mammal which comprises a chimera APP gene that can produce human Aβ, and a disease model non-human mammal of the same race that has a modification of a gene related to a neurodegenerative disease, which is other than the APP gene, it is preferable to crossbreed homozygotes with each other. For example, the $F_1$ obtained by crossbreeding a homozygote KI mouse which comprises chimera APP gene, and an FAD mutant PS1 homozygote KI mouse are hetero regarding both genes. The $F_2$ individual obtained by mating littermates of $F_1$ with each other will be chimera APP(+/+)×mutant PS1(+/+) in 1/16 chance.

The present invention also provides a screening method utilizing the AD model animal or a part of its biological body for a substance which suppresses the accumulation of Aβ, suppresses the neurofibrillary tangle, and/or suppresses brain lesion such as neurodegeneration and inflammatory reaction, and accordingly is an AD prophylactic or a therapeutic drug. The screening method is characterized by the application of a test substance to the AD model animal of the present invention or a part of its biological body, and testing the brain Aβ accumulation, detecting the brain neurofibrillary tangle, or detecting brain lesion such as neurodegeneration and inflammatory reactions.

Specifically, in the screening method of the present invention, a test substance is administered to an AD model animal of the present invention. Other than known synthetic compounds, a peptide, protein, DNA library and the like, tissue extract or cell culture supernatant or the like of a mammal (e.g., mouse, rat, pig, cattle, sheep, monkey, human or the like), extract or cultured product or the like from a plant or a microorganism, or their mixture can be used as a test substance. The activity of a test substance can be tested by, for example, isolating the brain of the animal, and (1) homogenizing it using a suitable buffer such as phosphate-buffered saline and obtaining the soluble fraction and the insoluble fraction, performing immunoassay respectively using anti-Aβ antibodies (e.g., human β amyloid (1-42) ELISA kit Wako (manufactured by Wako Pure Chemical Industries, Ltd.) and the like can be used), measuring the Aβ42 and Aβ40 contents, calculating the Aβ42/Aβ40 ratio, or (2) preparing a frozen section or a paraffin-embedded section of the brain according to the conventional method, evaluating the amyloid deposition (e.g., by immunostaining with anti-Aβ antibody or thioflavin staining) or synapse abnormality (e.g., immunostaining of marker protein of presynapse, dendrite), morphological abnormality of cell skeleton protein (e.g., immunostaining by anti-phosphorylated tau antibody), neuronal cell death (e.g., Nissl body staining or HE staining) and the like, using histochemical procedures known per se (e.g., see Am. J. Pathol., vol. 165, pages 1289-1300, (2004), etc.), and comparing between the test substance administered group and the non-administered group. If the total Aβ level, Aβ42 level, and Aβ42/Aβ40 ratio decreases in the brain derived from the test substance administered group compared to the non-administered group, the test substance can be selected as a substance that suppresses the accumulation of Aβ (particularly Aβ42). Additionally, if as a result of histochemical analysis, (a) amyloid deposition, (b) neurofibrillary tangle, or (c) synapse abnormality (collapse) or neuronal cell death, inflammatory reaction or the like are significantly decreased in a brain derived from a test substance administered group, compared to a non-administered group, the test substance can be selected as a (a) substance that suppresses the accumulation of Aβ, (b) substance that suppresses neurofibrillary tangle, (c) substance that suppresses brain lesion such as neurodegeneration and inflammatory reaction.

Alternatively, the difference in learning and memory abilities and synaptic function can be compared between the administered group and the non-administered group by the animals' behavioral analysis or the like. If a significant improvement in learning and memory disorder is observed in the test substance administered group compared to the non-administered group, the test substance can be selected as a learning and memory disorder improvement drug.

In addition to the above-mentioned screening in vivo, a substance that suppresses accumulation of Aβ, a substance that suppresses neurofibrillary tangle, and a substance that suppresses brain lesion such as neurodegeneration, inflammatory reaction and the like can also be screened for by culturing a living part derived from the model animal of AD of the present invention, preferably a tissue piece or cell (e.g., neuronal cells etc.) of the brain regions corresponding to the lesion of AD or parts thereof (e.g., olfactory bulb, amygdaloid nucleus, basal ganglia, hippocampus, thalamus, hypothalamus, cerebral cortex, medulla oblongata, cerebellum etc.) in a suitable medium, adding a test substance, incubating the mixture for a given time (e.g., about 0.5-about 168 hr), treating a part of the tissue or cell in the same manner as the brain in the above-mentioned in vivo screening, and comparing a test substance administration group and a non-administration group. Such an in vitro assay system is useful for screening for a hit compound from a large number of candidate compounds in a high through-put manner in the primary screening in an initial stage of drug development and the like.

A substance obtained in this way is useful as a candidate drug for the prophylaxis or treatment of AD, because it suppressively acts on the characteristic pathology of AD such as accumulation of Aβ, formation of neurofibrillary tangle, neurodegeneration or inflammatory response and the like. The substance can be used, for example, orally as a sugar-coated tablet as necessary, capsule, elixir, microcapsule and the like, or parenterally in the route of an injection such as a sterile solution or a suspension with water or other pharmaceutically acceptable solution, and the like. The substance can be formulated by being admixed with a physiologically acceptable carrier, flavor, excipient, vehicle, preservative, stabilizer, binder and the like in the form of a unit dose required for application of a preparation. The amount of the active ingredient in such preparation can be appropriately selected in consideration of the dose mentioned below.

As the additives that can be contained in tablet, capsule and the like, for example, binders such as gelatin, cornstarch, tragacanth and gum arabic, excipients such as crystalline cellulose, swelling agents such as cornstarch, gelatin, alginic acid and the like, lubricants such as magnesium stearate, sweetening agents such as sucrose, lactose and saccharin, flavors such as peppermint, Gaultheria adenothrix oil and cherry, and the like can be used. When the unit dosage form of a preparation is a capsule, a liquid carrier such as fats and oils can be added to the aforementioned types of materials. An aseptic composition for injection can be formulated according to the conventional application of a preparation such as dissolution or suspension of the active substance, a naturally-occurring vegetable oil such as sesame oil, coconut oil etc., and the like in a vehicle such as water for injection and the like.

As the aqueous solution for injection, for example, saline, an isotonic solution (e.g., D-sorbitol, D-mannitol, sodium chloride and the like) containing glucose and other auxiliary agents, and the like can be used, and a suitable solubilizing agent, such as alcohol (e.g., ethanol and the like), polyalcohol (e.g., propylene glycol, polyethylene glycol and the like), a non-ionic surfactant (e.g., polysorbate 80™, HCO-50 and the like) and the like can be used in combination. As the oil, for example, sesame oil, soy bean oil and the like can be used, and benzyl benzoate, benzyl alcohol and the like can be used in combination as a solubilizing agent. In addition, a buffer (e.g., phosphate buffer, sodium acetate buffer and the like), a soothing agent (e.g., benzalkonium chloride, procaine hydrochloride and the like), a stabilizer (e.g., human serum albumin, polyethylene glycol and the like), a preservative (e.g., benzyl alcohol, phenol and the like), an antioxidant and the like can be added. The prepared injection is generally filled in a suitable ampoule.

Since the preparation obtained in this way is safe and has lower toxicity, for example, it can be administered to a mammal (e.g., human, rat, mouse, guinea pig, rabbit, sheep, swine, bovine, horse, cat, dog, monkey and the like), preferably human.

While the dose of the substance varies depending on the age, body weight, administration route, severity, drug acceptability, polymorphism of genes related to drug metabolism and the like of the subject of administration, it is within the range of, for example, about 0.0008-about 2.5 mg/kg, preferably about 0.008-about 0.025 mg/kg, in the amount of the active ingredient per day for an adult, which can be administered at once or in several portions.

In addition, the screening method of the present invention can also be used as an efficacy evaluation system for evaluating whether or not a candidate compound already suggested to be effective as a prophylactic or therapeutic drug for AD is actually effective for the prophylaxis and/or treatment of AD. Since such use is mostly necessary in a comparatively later stage of drug development, particularly a pre-clinical trial stage, an in vivo screening system using an individual animal is more desirable.

Moreover, the present invention provides a screening method for a substance having affinity for AD, which is characterized by applying a test substance to an AD model animal of the present invention or a living part thereof and determining the presence of the test substance in an area where Aβ is accumulated.

With the goal of enabling an early diagnosis of AD, compounds having affinity for amyloid to be used for magnetic resonance imaging (MRI) and positron emission computerized-tomography (PET) and single photon emission computed tomography (SPECT) have been developed. For example, amyloid detection probes containing various dyes such as alkaline congo red, thioflavin and the like and a radioactive nuclide such as $^{11}C$, $^{18}F$, $^{123}I$, $^{99m}Tc$ and the like in combination have been reported, but none of them have been put to practical use.

The AD model animal of the present invention and a tissue or cell (e.g., brain tissue fragment or neuronal cell) derived therefrom can be useful tools for the evaluation of the effect of candidate amyloid detection probes. To be specific, a test substance is added to a part of the body (e.g., a part of brain tissue or neuronal cell) taken from the AD model animal of the present invention, and an immunostaining image of amyloid is compared with the accumulation of the test substance, or a test substance is administered to the AD model animal of the present invention, an image is photographed by MRI, PET, SPECT and the like, and the obtained image is compared with an immunohistochemical staining image of a section prepared from the isolated brain of the animal, whereby the effectiveness of the test substance as an amyloid detection probe can be evaluated.

The present invention also provides a method of screening for biomarkers of various pathologies of AD using the AD model animal of the present invention or a part of the body thereof. The method is characterized in that a suitable specimen, for example, an RNA-containing specimen, a protein-containing specimen, a metabolite-containing specimen and the like is taken from an animal before and after the expression of a certain pathology of AD (e.g., Aβ accumulation, neurofibrillary tangle, morphologically or functionally abnormal (collapsed) synapse, neuronal cell death, or impairment of memory and learning function and the like), a gene transcription product (transcriptome), a gene translation product (proteome) or a metabolite (metabolome) is comprehensively assayed, and a substance that changes before and after the expression of the pathology is identified. Examples of the specimen include, but are not limited to, body fluids such as blood, plasma, serum, urine, sweat, tear, saliva, semen, cerebral spinal fluid and the like.

In a transcriptome analysis, for example, gene expression can be comprehensively analyzed using a commercially available DNA microarray suitable for the animal species. For a proteome analysis, a method including a two-dimensional gel electrophoresis and a time-of-flight mass spectrometry (TOF-MS) or an electronspray ionization mass spectrometry (ESI-MS) in combination with capillary HPLC/MS (LC/MS) or LC/MS/MS is known, and for a metabolome analysis, NMR, capillary electrophoresis, a method by LC/MS, LC/MS/MS and the like are known, and they can be appropriately combined and put to practical use.

Once a substance showing a significant change of expression before and after the development of a certain pathology of AD is identified, it can be utilized as a biomarker of AD for an early diagnosis, particularly a preclinical diagnosis, of AD. Once a particular biomarker is identified, a subsequent marker detection method (i.e., AD diagnosis method) is preferably performed by a method suitable and specific for each marker (e.g., when the marker is sugar, lipid, biological substance, protein or peptide, an immunoassay using an antibody specific therefor, or when the marker is a gene transcription product, Northern blot analysis or RT-PCR using a probe complementary to RNA or a primer capable of amplifying a part of the RNA).

EXAMPLES

The present invention is explained in detail in the following by referring to Examples, which are not to be construed as limitative.

Example 1

Construction of a Targeting Vector

A genome DNA clone of mouse APP was isolated from mouse 129/Sv strain obtained from a Bacterial Artificial Chromosome library. A targeting vector was prepared based on the pBluescript II KS (+) vector (Stratagene) using the following DNA fragments:

1) from Hind III site in intron 14 to 6.6 kb APP gene fragment in intron 15 (as 5' arm)

2) a fragment spanning exons 16 to 18 derived from human APP cDNA with the objective mutation introduced 3) 3 tandem repeats of 250 bp SV40 early mRNA polyadenylation signal which terminates the transcription (Maxwell et al., 1989, Biotechniques 7, p. 276-280)

4) 4.6 kb BamHI-SacI APP gene fragment spanning intron 16 to intron 17 (as 3' arm)

5) 2.0 kb pgk-neo gene cassette (for positive selection)

6) 1.2 kb Xho I diphtheria toxin A-fragment derived from pMC1DT-ApA (for negative selection) (Yagi et al., 1990, Proc. Natl. Acad. Sci. USA 87, p. 9918-9922; Gomi et al., 1995, Neuron 17, p. 29-41).

The above mentioned fragments were ligated in order of 1), 2), 3), 5), 4), and inserted into pBluescript II KS (+) vector. The above-mentioned fragment of 6) was inserted into pBluescript II KS (+) vector at its Xho I site.

Example 2

Production of a Human Aβ-Producing Chimeric APP Gene KI Mouse

An E14 cell derived from mouse blastocyst strain 129/O1a was used as the ES cell system (Hooper et al., 1987, Nature 326, p. 292-295). Cell culture and targeting experiments were performed as reported (Itohara et al., 1993, Cell 72, p. 337-348). In summary, 30 μg of the targeting vector linearized by SacI treatment was introduced into the ES cells by electroporation with a Gene Pulser (0.4 cm of electrode distance, at 800 V and 3 mF, Bio-Rad). Genomic DNA derived from a clone selected by 150 μg/ml of G418 was digested by XbaI, and then screened by the southern hybridization method with 5' external probe. Next, genomic DNA of a clone in which the introduction of the mutation had been confirmed was digested by StuI, and then identified by the southern hybridization method with 3' external probe.

A chimeric mouse was created according to a method described in a report by Bradley et al. (1984, Nature 309, p. 255-256). ES cells were microinjected into a C57BL/6J blastocyst 3.5 days after mating. After injection, the embryo was transferred into the uterus of a pseudopregnant ICR mouse. The obtained chimeric mouse was further crossbred with a C57BL/6J mouse to create a heterozygote mouse.

The genotype of the mouse was determined by Southern blot analysis of genomic DNA prepared from the tail. Next, the heterozygote mouse was backcrossed 5 to 6 times with C57BL/6 mouse. To obtain a homozygote, the obtained heterozygotes were crossbred with each other. Thus, a knock-out mouse of the present invention was obtained.

All mice were maintained by Research Resources Center of RIKEN Brain Science Institute, and all animal experiments were performed according to Guideline for Animal Experiment of RIKEN.

Example 3

Production of Aβ in human Aβ producing chimeric APP Gene KI Mouse

Figure 3:
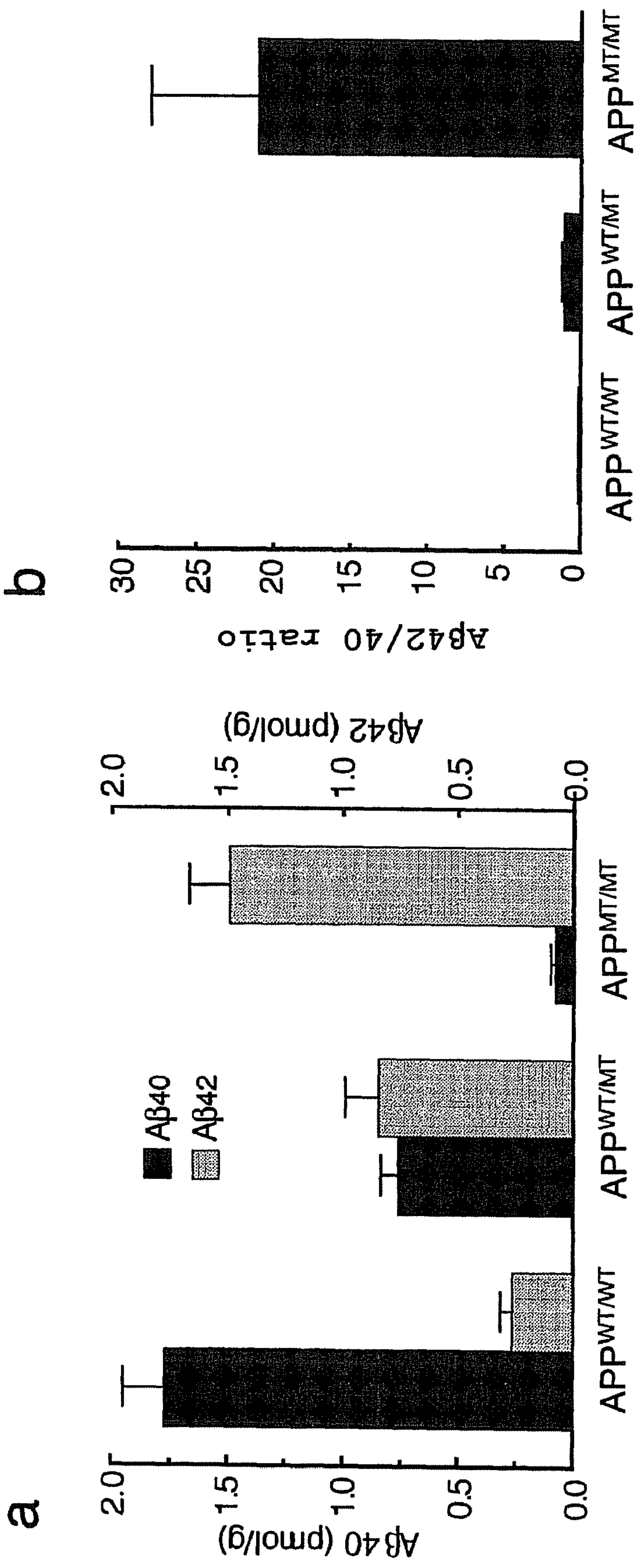
FIG. 3 shows comparison of production of Aβ42 and Aβ40 at 8-weeks-old between APP KI mouse and wild-type mouse. (a) The respective amount of Aβ42 and Aβ40 are shown. (b) Aβ42/Aβ40 ratio is shown. $APP^{WT/WT}$:wild-type mouse; $APP^{WT/MT}$:heterozygote; $APP^{MT/MT}$:homozygote.

APP KI mice (heterozygote $APP^{WT/MT}$ and homozygote $APP^{MT/MT}$) and wild-type mouse ($APP^{WT/WT}$) (3 to 4 mice each) were deprived of blood from the right atrium of the mice by PBS perfusion under pentobarbital anesthesia, and then brains were isolated from the mice. The isolated brains were homogenized with tris buffered saline, and subjected to ultracentrifugation. After that, the supernatant was obtained as a soluble fraction, and the pellet was solubilized by guanidine hydrochloride or formic acid to get an insoluble fraction. For each fraction, Aβ42 and Aβ40 content were measured by the sandwich ELISA method using Human β Amyloid (1-40) and (1-42) ELISA Kit Wako (from Wako Pure Chemical Industries, Ltd.). A sum of the measured values of each fraction was calculated as amounts of Aβs. The results are shown in FIG. 3. In the brains of wild-type mice, the Aβ42/Aβ40 ratio was generally about 0.2, while in the brains of APP KI mice, the Aβ42/Aβ40 ratio was 1.4 in heterozygotes at 8-weeks-old and increased by about 7-fold or more compared to wild-type (FIG. 3C). In homozygotes, the Aβ42/Aβ40 ratio was increased as great as 140-fold or more (FIG. 3C). Here, total Aβ amounts were not significantly different between heterozygotes and homozygotes, but slightly less than wild-type mice (FIG. 3*b*).

INDUSTRIAL APPLICABILITY

In the model animal of AD of the present invention, even at 8-weeks-old, the Aβ42/Aβ40 ratio increases by about 7-fold or more, and in homozygotes by about 140-fold or more, as compared to the corresponding wild-type animals, causing the accumulation of Aβ42 at a very early stage. Moreover, since the level of APP expression in the model animal of AD of the present invention is not significantly different from that of the wild-type animal, an influence of overproduction of sAPP fragments on the neuroprotective action and the like can be excluded, and therefore, AD pathologies such as neurofibrillary tangle and neurodegeneration, which could not be sufficiently reproduced in known model animals of AD can be reproduced. Accordingly, the animal is extremely useful as a superior model of AD disease, and as a research tool for the development of a prophylactic and/or therapeutic drug for AD and for the establishment of a method for an early pre-clinical diagnosis of AD.

The invention claimed is:

1. A transgenic mouse or living part thereof comprising a chimeric APP gene encoding a human Aβ having a FAD mutation and differing from the human APP gene of SEQ ID NO: 1 in that the Ile at amino acid 716 in the human APP gene of SEQ ID NO: 1 is substituted with an amino acid that is different than Ile, wherein the mouse or living part thereof has an Aβ42/Aβ40 ratio at 8-weeks-old that is about 7-fold or more higher than that of a corresponding wild-type mouse.

2. The mouse or living part thereof of claim 1, which is a heterozygote for the chimeric APP gene.

3. The mouse or living part thereof of claim 1, which is a homozygote for the chimeric APP gene.

4. The mouse or living part thereof of claim 1, wherein the mouse or living part thereof is a homozygote for the chimeric APP gene and has an Aβ42/Aβ40 ratio at 8-weeks-old that is about 140-fold or more higher than that of a corresponding wild-type mouse.

5. The mouse or a living part thereof of claim 1, which is a knock-in mouse, wherein an Aβ coding sequence of the endogenous APP gene is substituted with a human Aβ coding sequence.

6. The mouse or a living part thereof of claim 1, wherein the chimeric APP gene comprises at least one mutation that promotes production of Aβ42.

7. The mouse or a living part thereof of claim 1, wherein the mutation is a Swedish mutation.

8. A mouse or a living part thereof produced by breeding the mouse of claim 1 and a model mouse with a neurodegenerative disease comprising a modification in a gene other than the APP gene.

9. A method of screening for a substance suppressing a brain accumulation of Aβ, which comprises:

applying a test substance to the mouse or a living part thereof of claim 1, and determining the accumulation of Aβ.

10. A method of screening for a substance suppressing a brain neurofibrillary tangle, which comprises:

applying a test substance to the mouse or a living part thereof of claim 1, and detecting the neurofibrillary tangle.

11. A method of screening for a substance that improves learning and memory function or synaptic function of a mouse, which comprises:

applying a test substance to the mouse or a living part thereof of claim 1, and determining whether the test substance improves learning and memory function or synaptic function of the mouse.

12. A method of screening for a substance suppressing a brain lesion, which comprises:

applying a test substance to the mouse or a living part thereof of claim 1, and detecting the lesion.

13. The method of claim 12, wherein the brain lesion is a neurodegeneration or an inflammation reaction.

14. The method of claim 9, which is used for screening for a prophylactic and/or therapeutic drug for AD.

15. The method of claim 9, which is used for evaluating the efficacy of a prophylactic and/or therapeutic drug for AD.

16. A method of screening for a substance having an affinity for Aβ, which comprises:

applying a test substance to the mouse or a living part thereof of claim 1, and determining the presence of the test substance at a site of accumulation of Aβ.

17. A method of screening for a biomarker of an AD pathology, which comprises:

measuring cyclopaedically a gene transcription product, a gene translation product or a metabolite in a sample obtained from the mouse or a living part thereof of claim 1 before and after expression of the AD pathology, and identifying a substance that changes before and after the expression.

18. A knock-in mouse or living part thereof comprising a chimeric APP gene that encodes human Aβ having a Swedish mutation and differs from the human APP gene of SEQ ID NO: 1 in that the Ile at amino acid position 716 in the human APP gene of SEQ ID NO: 1 is substituted with Phe, and having the following properties:

(a) Aβ42/Aβ40 ratio at 8-weeks-old is about 7-fold or more higher than that of a corresponding wild-type mouse, when the mouse is a heterozygote for the chimeric APP gene, and (b) Aβ42/Aβ40 ratio at 8-weeks-old is about 140-fold or more higher than that of a corresponding wild-type mouse, when the mouse is a homozygote for the chimeric APP gene.

19. The knock-in mouse of claim 18, wherein the chimeric gene consists of SEQ ID NO: 1 except for the substitution of the Ile at amino acid position 716 with Phe.

* * * * *

SEQUENCE LISTING

```
<160> NUMBER OF SEQ ID NOS: 1

<210> SEQ ID NO 1
<211> LENGTH: 218241
<212> TYPE: DNA
<213> ORGANISM: Mus musculus
<220> FEATURE:
<221> NAME/KEY: exon
<222> LOCATION: (1)..(57)
<220> FEATURE:
<221> NAME/KEY: exon
<222> LOCATION: (52862)..(53029)
<220> FEATURE:
<221> NAME/KEY: exon
<222> LOCATION: (70224)..(70353)
<220> FEATURE:
<221> NAME/KEY: exon
<222> LOCATION: (90671)..(90783)
<220> FEATURE:
<221> NAME/KEY: exon
```

-continued

```
<222> LOCATION: (93526)..(93719)
<220> FEATURE:
<221> NAME/KEY: exon
<222> LOCATION: (117040)..(117242)
<220> FEATURE:
<221> NAME/KEY: exon
<222> LOCATION: (129823)..(129990)
<220> FEATURE:
<221> NAME/KEY: exon
<222> LOCATION: (133259)..(133315)
<220> FEATURE:
<221> NAME/KEY: exon
<222> LOCATION: (143201)..(143334)
<220> FEATURE:
<221> NAME/KEY: exon
<222> LOCATION: (148069)..(148143)
<220> FEATURE:
<221> NAME/KEY: exon
<222> LOCATION: (148555)..(148713)
<220> FEATURE:
<221> NAME/KEY: exon
<222> LOCATION: (158207)..(158335)
<220> FEATURE:
<221> NAME/KEY: exon
<222> LOCATION: (159841)..(159940)
<220> FEATURE:
<221> NAME/KEY: exon
<222> LOCATION: (195290)..(195511)
<220> FEATURE:
<221> NAME/KEY: exon
<222> LOCATION: (202114)..(202167)
<220> FEATURE:
<221> NAME/KEY: exon
<222> LOCATION: (207805)..(207905)
<220> FEATURE:
<221> NAME/KEY: exon
<222> LOCATION: (210707)..(210853)
<220> FEATURE:
<221> NAME/KEY: exon
<222> LOCATION: (218143)..(218241)

<400> SEQUENCE: 1

atg ctg ccc agc ttg gca ctg ctc ctg ctg gcc gcc tgg acg gtt cgg       48
Met Leu Pro Ser Leu Ala Leu Leu Leu Leu Ala Ala Trp Thr Val Arg
1               5                   10                  15

gct ctg gag gtgggtgccg cgccttggga acgagactgg ggaggcgggc               97
Ala Leu Glu

gccgggagga cgcgatcctc cccaccgagg agcttgaatc tcgagacgtg gggggctgtc    157

acgggtagac cgctcctcgc cgccccccgcc tgcgggcgcc ctgcgcttcg gcggctctgg    217

cccaaccctg cccggggacg cgctgcccga gcgatgaaga gggaatgggt tagggcgctg    277

gggtccccat atccgtgcca gcctagggct ggaaggcgag gggacgagcc tgaacgcaga    337

ccctgactcc tccctgcgtt gagagctgga ctccgggatg cgagagacac ccagttcgag    397

ggggaaggga cacgtgtgga aaaccgaaag cgtagcgtct caggattcag tgccctgcga    457

ggaaatcgcc gcccttcccc ttccttgggg tcctgggttg gaatgggggc agctctggat    517

gctggggagc gcctggctca cactcccttc ccacccccgc ctgtcttgac tgcgaagctg    577

ggctttgctc ctggcggccg cgggcggcgg ctgcctgcgc agcgaccctc tcccgagtcg    637

gtgcggggtc gcgcaccgcc gccttccttt tgcaaacttt gtgcattttc gtgtctccct    697

tttgtgtaag ttccaagtga tgggagggat cggaaagtgc ggccacccgg caccgtccct    757

caacctggac gtccaggact cttcagtgca cctccagttt ctccctgagt ctgagaaggt    817

ccccgggaac aaaagccgcg acaccccgcc ctcgccgtcc agggcgcggt ggcggagccc    877

tggtagttgg tgcgccaccg ccgttccttt ccccgagctg cgcgtctgcc cccgagggcc    937

tagaggtgct gctagggccc cgcggtctcc cacccccgca tcaccaccac ctactggcaa    997
```

-continued

```
tcctgtgagg gactgcaaag tcctgagaga gagagagaga gagagagaga gagagagaga   1057
gagagagaga gagagagaga gagagagagc gagccgggag tgaggcgtgc gtctgggaag   1117
ggcagtgcct ggtggtgggg aggctgaggc tccagggcat caaaggaggc gtttgtctga   1177
ttaaggtgcg gcctcctatg gggcagattt gggaactcta gcttagtcac cctggggggg   1237
acacaggatg ctggggaggg tcctcagggt tccttttttt tttaaaaaaa aaaaaaaagg   1297
ggtgcagata aaaggattga atagggtgaa gattaagacg gagaagatgg cgcctctgca   1357
gtgcagcaaa gaaaagctgt gtggaggctg cagcctgtga aatccaccca ccactaggtg   1417
tataacaagt cttccccatt catccaactc tccagcatgc agcacaaggc ttgttttcct   1477
ttttatccag agatgcctgg aagttgtttg cgtggcagct ggttttattt ctcttcattt   1537
gtaccctctt caccatctaa gcatttgcta atagcccttc ctcgtcgtcc tcctctttcc   1597
cctctacctc ataggaattt tcccaaaaag caatttccgg gcgagtgttt tcctgcaatt   1657
ttgtggggat tggctaggct atcacactag tatgagtttt tatttattta atttttttta   1717
gctcttaatt tacaaggtca ttgaactttt agcccctctg aatttttttt ttttttttaa   1777
cccacaagtg gcttcagaat ctgtaagtca cctcagactg gttaaaacag gtcttcgaag   1837
agtcttaaga atttagtgtt ccattttttt ttttcaaagc catttaatca agggaattct   1897
gatttctctg acgacctaag aatttaattg tatagtcatt cggtttttct aattgttttg   1957
ctgtgcagaa acacgactaa gtaattaaag gaataacttt aatttttgga gcattttact   2017
tttcttgagc atttttttta acttgtataa aaagagtcac agtgtaggcc aagatgaact   2077
ggatttatgt tttggcttgt gcgattgcat atcctttttc tgccgaacat ttggagatgc   2137
tcctgcagtt atcatcacct ttaaagggtt actgggagca ctacattcgt gcctttggtg   2197
agtcactgga aggataggta attcatcctg atgaggtttg acacactttg cagttctgcg   2257
tccactgaag ccacagaatt atgagttggc tgcgttttgt aaatcacaga aaatccgtct   2317
gctgcaggtg gctctgcaaa aagaacccgt gtgatggagg gtgctgatga tggggccatg   2377
agggtactga tgctggggtc tcgagggtgc tgatgctggg gcctccaggg tactgatgct   2437
ggggcctcgt cttccagggc gtcggcattt cctggtttgg ttttattttc ctggtatgtt   2497
gaacagaggc atgcgtttag caaaccgtga tggactcatc ttgtttgctt gtatagagct   2557
gataactatc aacttgcctc ggtagtggtg gctccttcac tgtctgcgac tgctgcccgg   2617
tagtgcctct ctgatggtag aagcctactc atagaacagc gaagctgaca ttcttttttt   2677
gacagggatc catcgggagt caccggttac tgcttgtcag tgggaagcca tgatactggc   2737
agactataaa tgcttctttc ttatcacccc caagggatag cgtccctcat tacacttgta   2797
aggctgcaag caattaaaag atggaaccga ggaaatgaaa aggtatatac aggatcacaa   2857
aactaaactg gaaaattcaa gatttaagat taaataggag aaaaatagga tcaatgggct   2917
actggtttga aggaaggtga agttactttt acggctaagg tttttaagtt tttagtttac   2977
tgtttatgac acgccaattt tctatatctc tgtgttaaag attatctgtc agtcatcctg   3037
catatagacg tgaagaaggt gcttaataaa atattatgcg ttatttttgc agaggtgttg   3097
tcgtgggatt tacagggcat ctttgactaa tacatttctt ttctaatctc tgccttttat   3157
gtcaagatgg acctgcacaa acatacttta aatatcaagc tcatgtttac ttgactgtat   3217
atattttatt gccttctccc acactgggta cagaagtatg cagggtgaat aaagcatgca   3277
cataattata aaataggagt gttgcgtacc aaaaaagaaa gtacagatta ggcaaagaaa   3337
```

-continued

```
aaaaagaaag gacacagaaa gtggggtact cagaaagtgt agcaggataa agacctagaa   3397
ttaaaaagag taaaggaaca agagaacacg ataatcctgg gatgtttcct gggtgaaagt   3457
ctccagccag gtttgtgtcc tggtctgtg aatggaggtt aagtatttgc atggattgta   3517
tttgctcacg cacagacact agagcctaca tgcaaggcct ttgtcttatc tgtcttccct   3577
gctctcgatt tccagccagg cacagataag gttttacata atgaaggcga gaacaagtgt   3637
ggagttccat ttgattcatg gcctcgtctg ttcatttggg acaatttgat tgattgattt   3697
ttaggccaaa tcgtgtctct cagctctgat cacctttatg taaacccccca taagtggaag   3757
cttatggagc gtccactcat ccaggcaaga caggaaataa acagaaactg tggcaggtgt   3817
aggccagact ctggagctgg gtgaagaact ggaagaagga gaccaaggct gaaagcagcc   3877
tgggaagtat ccctagcacc atcttgacca ggggaggtaa ggacaaaaag cttcacccac   3937
catgcaaact tccaggaggg aagggagaag caaattttca aagtgcttcc ataaggaacg   3997
ttagccaaga gttgtcatcc tcctttacac atcagggtca cagagtgtct ctgccttcct   4057
ccctccctcc ctccctccct cccttccttc ccccctctct cccttccttc ctgtgtttgt   4117
gtatgtgatg ttgggatttc atatggagac ttaggcatga tggacaaatg cctgctgcac   4177
tacatcccca tcccaaggaa tcatgaagat gaaaacaaaa ccagaagcag aaaagttcca   4237
gagtgttgtc agagttccac ccagtacatc agaaagagaa tcccggaagc aaggcctgga   4297
cattggcatt aagggaagaa aaaaacaaaa aattctccgg gcaattttaa aatagaaact   4357
gtgatttttg agggcagtta cagatggacc aatttgaacc acattcagga ttcatcaagc   4417
tgttctgaaa ccaaacgagc caagtaatgg catggaagct agtagctgtg caggaaaaca   4477
gggaggaggg cagaggaaag ctcgggtctg tttgcagcct cgtcatctct ccttaaggct   4537
gctgtggctt gacattacct ctctgtagcc aggactgcag tcacattcca ccccctgggc   4597
tagatgacct tgtggccttt tgggaaactt gcctcacaga gcacacacct gcgtttgtga   4657
aggcctggca ggcagccagc acgctcagct cccaagccct aacctggtta ttattttttt   4717
tttctttctg ttcttgtttg tttcttgatg caactgtgac atcttttcct tctcatagtg   4777
ggatcctaga tacaaaccgt ggagtgcaga gtgataatca atactgtctg atgcaagagc   4837
tcctgagtgc tgtaacctcc tgcatcttac cttccgtgac ctaccctcat gagtgcgtgg   4897
gaaagaggac aggctaaggt gggggagtga gcatgctccc tggatgagta gcaaggataa   4957
gcaactatac atattatatt tcagtcacag tttgcccatg gaggtattat tccaggagag   5017
atgttacata gctctttcct taacatggat tgcttttgag agagacgaat atttattatg   5077
aaaaaaaatg ttgggtgaat tttcttttct tcagattgtt ctacctagga ggtttgactg   5137
gtaccatctt tgggacagga aatgctccca agaatgctgg attagaatga ctgctgtagt   5197
aatttattta aaatgaggtt ttgtttgttt gtttgtttgt tttttgtttt tttttgctac   5257
tagttttaaa gaaagcattc atcaagaaat agctataaaa gagattacgg ggaacttggg   5317
ttcacataca ttcagtccta gcttcagtac tgggtaaaga agatatttta tttacattta   5377
tttatatgga aactgttttt attttttgag atggggatct gttttgatta ctttttgtta   5437
acttgacaga gactaaagtc acctgggaag agggaccctc aagtgagaat tgcctttatc   5497
agattggcct gcaggggtgg ggcattctct tgatttatga ttattgtggg ttggcctaga   5557
caactatggg cggggccacc cctgagcagg tagtccttgg atgtataaga aagcaggctg   5617
agccaaccct ggagacagcc agccagcaaa cacccccttct gttttagttc ctgcctctgg   5677
tccctatttg agctcatatc cttggctgtc cttgatggac tgtaacgtgt aagatgtaat   5737
```

-continued

```
aaacccttc ctcccaggtt actcttggcc ataccttaaa tattgtatta tcattttaaa   5797
attatgtcta tatgtgtggc tatgtgcaca tgagtacagt tacctgtgga gaatacaggc   5857
cttggatctc ccggaagtta gaatttacag gtgtctgtga atcaactgaa ttggaagaac   5917
caaagtgctc ttagtcccct cagcccctaa gaagacagaa ctggagtgaa catttgtaat   5977
actgattttg atgtcaggtg tattgttagg tcagtaattt gaaccattga gtgtttctca   6037
gatgtctaga aaaggccagc atttcacatt gctttctgtt gctgtgacac aatacctgag   6097
acagccaact taaaaagaag aaaggtttat cttggtttat agtttgggag gtttaagtct   6157
atgattggtt ggccccataa ttatgggcct gttgtgaggc agcatattat ggccagctgt   6217
tcctgtcatg gtggtctgcc tggaagcaaa caggagaaaa gaagagacca acttgtcaga   6277
ttcccacaca atccccacct ttaacgacag gggccttcag aaggctaagc ctttgaccca   6337
ctggcctttg ggtcatactt atgatttaag ctataacaaa catggatcca gaaaccaaat   6397
gggggcaagg ttgcttgagc atgtgctcag gataatgtgt accctgagat actggccatg   6457
ggtaaatttc tgtgcttctg taaaatgtag ctagtagtat ttaatgttgt caaggattaa   6517
tttaatatat aaggtcctta caagtagata aatcgatatg tattaatatg tacttgatgt   6577
atgatcgtaa ctaggtgtcg ctacttttat aggagggtag aaaattaata tgtttttctc   6637
acgcatagtt acagaaatct aaataatctt catgatattt cacttattag aataattgac   6697
tcacttagtg tctaattatg agtaagaaga acttggcagt ttgttttctg taaggttgaa   6757
tgaatttacc caagcatggc ttagacctgt aatcccagca ctataggaga catgagtgga   6817
ggatcacagg ttcaaggtca gattgggcta tgtgaaaaaa aaaaaagatt taaatacagc   6877
acaggtaaaa ggggtttggt ttctggtttt gtttgttttt tgtttgtaaa atatcattta   6937
tgtgattttc tatttcagtt ggatttttag aaattttaga atgattcgtg ttcactgaaa   6997
aaaattaaac agtagagaag tgtgcagggt ttgtacaaat agagaatgtt catttttttaa   7057
tgctgtgcat accagcagtt ttccatgtgt ttaatattaa accagtttat gcgctggctt   7117
gattattaac acaattattt attagttaga catcttcggg tttgtgtgag gacctgggga   7177
caggcttagt tttgtcttca gctaaacctt ttcaataaaa atgaataatc aggctttgtc   7237
atcagaacag atatagaaga atcaaatgcc agccaaagaa tgttggtcct agtgtagacg   7297
gctgcaacag cttcactcaa gacagggcat gaaggcagcc ttcctgtaag gaaatcagac   7357
tcaaaataaa atgagtttat ataactgttg tgctaggctc tcaggtcttt tacctacata   7417
tcagttaaaa atacacgcag aaaacaccag cagggttgct catgtgccat tttctctctg   7477
tgtgtcaaaa ttagtctaat gatatctgaa acttttagta atgatatttt aatgatattt   7537
aaaacttagg actctgtgat taaattctgg ttgcaaacag cacggaagga tcaagaagca   7597
aaggccttag ggttccaagt gggtttttgt taaccagccg tgtatttatt tagtatttgg   7657
atggaggtcg gttttggtct ggctgggagt acagaatcca tttttaggac tcaccctact   7717
cagggatgtt acacggagga aggccagatg gtctcagggc cccgagtgca gggccagtga   7777
acccacatga gaaatgagga aagggaacac attagagatg cttttgtaga ccgtgggtcc   7837
tgaacctagt acagcaatgg gcacggaaca ggacaggagt cccctcattt tcagatggcc   7897
tgggtttttt ttcctctcca gttcaaaaga tatttcaggt taaaaatttc gctcagaaac   7957
aataaaaaat ttactttgtt tttggtgatt tcccagttat gaagctgttc tttgtctgat   8017
gtttttcccc ctcagggaat caaatttgta ctatgtcctc ggtttctaga gagccacata   8077
```

-continued

```
ctgtctttat cttcaccgaa aacagtgggg ctttctaaat gatagtgaca aattactctt   8137
cccgcctctc tggacactta ggagagtaag agatccgtca tggaaagtca tttgtgttaa   8197
gtgaagaaat gctttatcgt tcctgtcgcc ttgctaaatt tcaaagcttt aatgacactc   8257
atatatcttc gccccacaga gacatttttg caggacaata aacatgaggt ttaatcttac   8317
cctggaggta tgtttgtgtg ttttaagatg tgccctttca ggcctggtta ccaaaaatct   8377
catttgttca gctttgcttt gtctgcacaa tcttctgttt gacattaatt aaatttaaaa   8437
ttaatgtttt ataaatacat tccttagtta tttaaaaatt atagctggat aagtttcaat   8497
gtgtatattt actgtgcaca ggcctctgct gcatgaggac attttcatgc aagtatatgc   8557
tgtatgctga ggatactctc ccctgccctg ccctgccctg ccctgccctg ccctgccctg   8617
ccctcccctc ccctcccctc ccttcccttc ccttcctctt ctctcccctt cccttcctct   8677
tctctcccct tccctctcct tccttctttc cccttctctc cccttccctt ctttcccctt   8737
ctctcccctc ccctcccttc ccttccttct tcttctctcc ccttcccttc ccttcccttc   8797
ccttccctcc cctcccttc ccttcccttc cctcccctcc cctcccctcc ccttcccttc   8857
ccttcccttc cctcccctcc cctcccctcc cctcccctcc cctcccctcc cctcccctcc   8917
cttcccctcc cttcccttcc cttcccttcc ctcccttctc ttcccagttt cttccagtta   8977
gcttccttat ttcccctaga gcgtttcact tctactttca tatcccacat acttactttt   9037
tatgtatcta cataagatct gggaaccaca aatgagaatg catacaaaaa aagaaaaaaa   9097
tccatctttc tgaaattggc ctgattagtg tacggtgatt attttcagtt tcttcttcgt   9157
ttattatttc aagcaatata atttcattct ttacgatggg aaatactcca ctgtgcatac   9217
acactacatt ttctttaccc actcctctgt tggaccctag attggtttca taacttgtat   9277
tattatgggc atttcaacat tgcttagtta ttatgaacat atctaaacat cgatatgtct   9337
gcatatactt aattggtatt ttacagtaaa atgaatgaag caatatacat ttatttttgt   9397
ggttgttttc tgtgctttgg attaaactca ggccatgtgc atcctaggta ggtactgtac   9457
cactgagcca cacacatctc tggcattaat ctttttaaag gatcgatcgt tggagttaga   9517
atacagtcca ttgagtctca tctggtgtgg tcatagctgt gtgcctcatt tgttcctcta   9577
ctcaggggaa caaaacccca ctgcatttca tttttaaaag aaaatagaat gttattatct   9637
ctcaagactt tgtggttaat cctagtatgt tccagttatt gaatgaagtt tcaaaagcat   9697
aattactttt ttttttaca aatgtatcaa taacttaagt tgtagagtat gatttataca   9757
caaaagttac catggtaaat aagcaccatt tctcagccca atggagtttt taaagcattt   9817
gaaaatgtcc atcttttttt tttttaaagt gatacaacgt ttttgaaatc tcagcttagc   9877
attttggaga gtgatactac aatttaccat atgaaacatc acattttata gcaaatattc   9937
cccattctga tagttaatcg cttgtcatag catgcttgta acaagtataa ttttaccgcc   9997
acaatatatt aatttgagat gaaaagttct tcagacactc caatagaaat gaaaagttca  10057
aatacgaaga ttaattttaa gaatatttaa ttcttagata cttgtctgtt aagtaaacca  10117
catttaatat taaaatctaa tttcttcaga gaagttactg gctaattttt cttacctggt  10177
gcattagtta catttttgtt gctgtgacaa aatactggac gaaggcaact taagaaagga  10237
agaccccccc cccaattccc acccctccac ttcccacccc cacccccctag tgctgggtat  10297
tgaacccagg gtcagggtca tgcatattag acatgaaggc aaatgctctt caaactgagt  10357
gtcaaactca gttttatatc ggctcacagg ttgagggtac aaacaaagcc tcatgactca  10417
taaagtcagg gtcctgggga cacaagactg ctgatctgct tgcacccata gtcaggaaag  10477
```

-continued

```
caggagatga aggccggtgc tcatctggcc tttttttttt cctgtcaccg tggcatggca  10537
accattcact gctaccaccc acttgagaat gggtcttcct tcctctttac actccctgga  10597
agcacacaca tagacacacc cagagttata cttcccgatc actctagatc ctgtcaagta  10657
gacgtggaga ttaaccgtca cttgcagaga agcctggatt cagactggga tatttagaca  10717
aggagaatca gctttttcct tgttccccag gaagcagcag gtggtcagtt gaataaacgt  10777
gggggtaaga gctaaaggag aattctacat ggaagtgtgc tgtgtgctaa tattttaggt  10837
aatatatata tatattacca atatactctt gtatatatta ccatgcatat atatacatac  10897
atatgtgtgt gtgtgtgtgt gtgtgtgtgt caggtagtgt gcatcactac cctgaggtaa  10957
actgaggtat ctgaactatt cacagtaaca tgaaagaaca actgtgaact ggggtctgct  11017
ttgaggcagt taaatattac aaatgaaagt ggaactagga gaatactagg aatattaatc  11077
tttgtgtcac tagggacaat accttgaatc cagatttatc cagtacttga taaatacttt  11137
tggtgagcac tgtagaaatt ctacagtgca ttgatcaagg gttgcatggt ttggtgcatg  11197
gtagacggtt tagcagggag agtgatttct gttcaagctg gatctgagtg tccatgccca  11257
gaacccatgt gaaagcatgg cacataactg tgacccccat gctggaaggg taggagaatt  11317
ctggagatgt actggccagc agaaatggga gctacggggt cagcgagtga ccctgcctca  11377
aaaataatga ggacatgata gaagaacatc actgccacct gacattgatc tctgatctct  11437
acacaagcat acagggtttg ttctctctct ctctctctct ctctctctct ctctctctct  11497
ctctctctct ctctctctct ctccacacac acacacacac acacacacac atacttagag  11557
acagagagag acagagagac agagagagag aagaaagaag aaaaaagagg aggagggggg  11617
aggaggagga ggaggaggag gaggagaaga ggaagaggaa gaagaagaag aagaggagga  11677
gaagaagaag aagaagaaga ataagaagaa gaggaggagg aggaggagga gaagaagaag  11737
aagaagaaga agaagaagaa gaagaagaag aagaagaaga cgaagaagaa gaagaagaag  11797
aagaagaaga agaagaagaa gaagaagaag aagaagaaga agaagaagaa gaagaagaag  11857
aagaagaaga agaagagaag gaggaggagg aggaagagga agaagaggaa gaagaggaag  11917
aaggaagaag aagaggagga agaggaggag gaggaggagg agaagaagga gaaggagaag  11977
gagaaggaga aggagaagaa gaagaagaag aagaagaaga agaagaagaa gaagaagaag  12037
aagaagaaga agaagaagaa gaagaagaag aagaagaaga aaagaagaag aagaaagaaa  12097
actgtacttt ccaacagctg aaagccagca ctactttatg ccattccaaa gccagcacta  12157
ctttatgcca ttctattgac aggcattaaa aatcttgctg aggtcattat ctttctcctg  12217
tttgctcagg cttgattttt aatgttttat gtcaagtgtt aaatcattct acaccaaagg  12277
gttcaggaaa tttaagtttg ctagaagtaa gctgaatttt aagataatgt agttgtgttg  12337
ggtggggaag tttctggaac aaccaataaa aacttttttt ctctcttttt tttttgagat  12397
tgttttacta tgtagttctg actgttctgg ataggactcc tatctatcta tctatctatc  12457
tatctatcta tctatctatc tatctatcta tctatccata catacataca tacatatata  12517
ccagtctggt ttcaaaggca cagagatcag cctgcctttg cctcctgagt gctgggatta  12577
aaggcatgtt ccactacaac ccagcctaat aaaatctctt gatgtgaaag tagcttacat  12637
cttgctgtta gtagacgaac tgcaaagggc cctacttaca ggactatatt ggtaatacta  12697
tagtgttatt tagtgaaaga tgagaggcag gaatccctga gggaagccaa agcaatttca  12757
gtatggctta aatagttgaa gggaagcttg caggatggac agagatgtgc ctaccactga  12817
```

-continued

```
gtagtttatt aacatggctg tcagaaacgt ccaggaccaa gataatgaag gatgagggtt  12877
cctagagggt atatgaagtt tatttattta ctttgcagat gctcctctgt tttagtata   12937
tttttaccag ttgttgggga atttcatacc tgactacaat gtttttagtt tttgtttttt  12997
ttaatcatat tcaccatgtc ttcctctcct aacttctccc agatctacac ccccttcttt  13057
cccacccctc ccaactttat gtcctcttta tagcaataaa aacaccaagt acactttggg  13117
ccagccctat actcatggat gtggggccat cccctggaat gtcatctgcc tgctaggggc  13177
cactccctta aagaaaacaa actctccctc ctccagaagc catctactgt caataactct  13237
tcagccagga atggggatca ccgcccctcc ccctccagta ctggaatgtc gactggcttg  13297
atcatgtgca cttcttttac aagcattcat gcctgctatg tgttaaggtt gcaccaggcc  13357
tgccatgttt agagggcacc atttaacttt ggtccttcaa aacccctggc tattaaaacc  13417
cttttgatcc ccttctgtag ttggtcccaa gccttggcat gagtgaagat gatagggata  13477
ttctatttgt ggcagaacac tattctggga ttttaatata gactgggga tcagattcct   13537
ctgttccttt gtatttgtgt tgcattgttg agcttttatg aactgggctc agaggttctt  13597
tcgtgaactt ctgagggtca tgttggaagg acacagatga caagagttca gtgggttgac  13657
agtatttctc ctatgtgtgt gtgtttttag ttgtatttat tgacttcata aataactgat  13717
aagatgagga aaatgtcatt accaacctcc ttcctggaga agaacagaca ttcgataaaa  13777
tatccaaggg tttattgtca catattaaaa tgtttgcaat tttgaagtaa tggcgtgttg  13837
actcattgct cattggctca ttcatatcag agtttgaata tatacaatcc agtcccaagt  13897
ccctgattct gttgtcagcc atggagctgg ggtaaatgct gaaattttaa cgggatttta  13957
gggtttgggg tgtcacatgg ttctatacct acttcacaat ctcttaggga atttgagcat  14017
ttcattgatg ctgatagtga tcggaagtta tgatgttttt ataactaatt tactgcacat  14077
tgcttttcct tctttgatca catttttaaa aagttaattc ctgagcatgt acaagatggc  14137
ttatgtttca acaggagccc attctgtcat ctctgtgatg ctgtatatgg agaggtagtt  14197
cctgctgtac cttgtcaatt tcacagtcta atgtagaagg aaaatgcagg aaaataatta  14257
cgcatactat gtcaaaggct acaataaaag cctatgtaaa ctcttcacag atatggctga  14317
gagcctttgg gcaggacttc aagggtaaat ggaagttggt cagagcagag tggggttcct  14377
agagatgaag aacacacagc caggggggtaa agggttaaaa gtagaagcct tagcatctgt  14437
gggatgggat gcgggtgtgt gtggaggggt aactgggaag gggatatta tttgaaatgt   14497
agacaaataa aataattaat aaaaaaagta gaagctgttg ttatgtggat atgagactca  14557
gggtttcaga agcccttgat gaatctgaac ttcattttct gaacaacagt gcacttttac  14617
atgttctaga aacagcagtg gtcactgata actataattc atctagattt aggagcttta  14677
atgaaagatc ttgttaatgt ctgcttaagc ttgtcattaa gcttgtcaca cctagctgca  14737
agggaatcag gtaaatgtgt tttattagcc aagtattctg tagccaggaa agccatttca  14797
ggatctatca ttagggttat tatttgtttt gatttgattt atttaaaata gggcctccct  14857
atgtagtatt ggctaccccg gaactcatta tgtagactat tctcgtcttc aactcacaga  14917
aatccttttg cctctgcttc ccacgttctg cacttaaagg catgcaccac catgcccaac  14977
aggctctatt cttaaggaca gaggagtcaa atacttggca acaggctaac attctgtatt  15037
gtaaaggtag gagaggaaaa tgagatgacc aatacatgtt ctccattaac gcattattct  15097
tcctgagcaa ttagagggca gttttggaat gttcctccca cctttcttac ctgctggctg  15157
accacatgga aaatatttgt gggatgatgg aagaggaggt ggggaatgct tctcgtctgt  15217
```

-continued

```
atgtgaaatc gcccaagagt caagctcatt ggactcagag tgtgttcaga tgcctgggga  15277
atacttccaa cgaaaatact gaggggttgg gggggtgggg gtgggggagg agtaatttca  15337
ggttctggaa agaaatgaca gcatcagttt cctttcccca ttggtaaact tttatttcat  15397
ctagaaactt tgttgttgaa cttttacttt gaaaggacta gcaggcgaaa tgggctttga  15457
ggcttttaga aaggagcaca gtatttagga cctcgtctga gccagatctg cccattatat  15517
aaaatcactt ttctgccacg acagagcttt ttcacatctg tttatactta gtctctctta  15577
cccagagtgg aaagatttat gtaaaaggag aaaagaactc tgaatgtatg tctcgcatca  15637
gtgaaagcgg ggcctccggc ttaacatcca tttgaagtac gtagctactg tctaatcatt  15697
tcagttattg tagaagtagc caaatgaagc tatgtccctg gaaattagag atgaagatgt  15757
ggggaaaacc tacaggtcta agaaggcttg acaagatcat caacattagg gagcgtgtga  15817
agggtctgcc atagacattt ggaatgcagg caaaggtttc atttaaaatg tctcaatgat  15877
tcgtgacata ctgcacctgg atctgtataa taataaatgt ctatcatggt tcctcaatag  15937
tttctcttcg ttttattttc taagttagtt gcagtttttc cttctcttaa gtgcagacga  15997
aagccatagg aacccgtcta aagacgtatt tagggcacac acacacacac acacacacac  16057
actatatcta gatagataga tagatagata gatagataga tagatagata gatagataga  16117
tagatagata gatagattag atagatataa agtggaaata gaagttccaa gtccactgtg  16177
aggagccagg gatggcactg ttccatgtaa gtgttccctg gagacatttg atctctacag  16237
ttgtctggcc tggccctctt agactgcact gtccaataaa actattgtag aactgtttaa  16297
atccaatttg aaatttcaaa tagccacata aaaatgtaaa agaagataaa gtcagaggta  16357
gagtgcaagt ttagcattta taatactctg ggttctatca ccagcacaga ctatcagatg  16417
ataaatgata gatgatagat gatagataga tagatagata gatagataga tagatagata  16477
gatagatatt cattcctttt tagtaagttc aaatagtctt tgaacatgta atccacataa  16537
agctaattac aaaataaata tattacatgg atttttatat catgtcttta aagttttatc  16597
tgttgtgcat attttaattc agatcagtca taagtagctg ccatattgga cagtggagcc  16657
ttacaagact gacccttccc gctgccttcc aaaacatgtt cacatttaga ggatggactc  16717
tgccaacact gcctaagccc cttcatttta caggtgaaga tgaccagatc tagagatgct  16777
gggttgctta gaatcccata gccattcaca tcagaagccc caccctttg tctgacttca  16837
attgctttca tcattctttc tttccttaga tttgtgttgc tgcaactact cactgtgaga  16897
ctgttgctgt tggttaaata ttgagccagg agtcttaaaa acatttggtc cactcagtaa  16957
agccactgtt tgatttggtg gaaactgttt tgagcagagt aggtagaact accaggcaca  17017
ttgacagttc tccatgagat agtaatagga ggtgataatg gggacagggg tgactttatg  17077
cttgttggtg ttgctgtggg cattatagga gtatgtgact tcaaattttg aaatgctagc  17137
tgcctgctta caggaaggga gatgagctgt tcccatgcaa agtttattgt ctagttgtat  17197
gtataagcct acacatgatg aatatcttaa tgcttaactc tctctggaaa tggcagggtt  17257
aagcttttat atttcatatt tttttcttgt attaggaacg tgtgtgtgtg tgtgtgtgtg  17317
tgtgtgtgtg tgtgtgtgtg tgtgtgtgta tgtgtgtgtg tgtgaatgta ctcctatttc  17377
tcactcagtt atacttaaag tgtgatgatt tttgacaagt taatcccagt acactcctgg  17437
catgtaaagt attttcagaa tgtaagccca tgtggaaatt cgttggcttg gtatgacggg  17497
ttcgggcagg ggaggcatag tgtgatcccg tggagtgttc ggagctgcca agtatttgtt  17557
```

-continued

```
cttcggtgtg aaagcgtgct tgacgggtgg actttcctag ctggaaggtg ctttgttcat  17617
ccttcctaaa acatttatca gcacggatgt tgtagatcgt gtaagagagt cccctttatt  17677
catgtgactt agttcagtga tcttagattt agagttaagt ttttgtgttc cagggttggg  17737
actaattccc agccatggcc cagctttacc cacaaaggaa ctaccgacct gtaaggatat  17797
tcatttgatg cgtttgcttt tgttcctggt gccagtcatt ggattttgcc tatagtgctt  17857
tatgtggcta tacttagaag ttttatagct tgtagcaatc aggtgaaagt acagggatat  17917
ggctgagtac tgtaacttgc gtctgtaatc ccagccagag gcaggaggat caccagtcca  17977
gggcaatttg agctacagag gcaaactgaa aaaggaaaag aaaaaaaaaa agagattcct  18037
ttatttcctt tggccttcat acacaaatat ttaaattctt aatgtacggt tttaagtcag  18097
ccccctacct cccccacctt ggtagtttgc atagtacaca ttagcatttg aaacaaaagt  18157
tttgagctat aagatgctca tgggagtcat tctgaaatat gtttaaggtg gattgattcg  18217
gaaaggatgc aaatccaagt taggctggct gaggcctccc cgcttcttta gagggtgata  18277
cggaaggttt gaggacccag tctgcttcgg tcggagtgtg gacagccagt gagggcagtg  18337
cagcaaaacc gtgtctcaga atcagaaagt taaaaaaaaa aaaagagggc agaggttata  18397
gtggagagac agggcatttg cttagcattc gtgaggcctt ccatttaaga tctctagtac  18457
cctgggagaa taaaaaatag tcgtaagttc attgtgggaa agtgagaaaa agtgtataag  18517
tgcttgtgtt ctatccacga ttgcttttgt tgttgttgtt gttgttacat catatttaaa  18577
agcatttttg taattatgcc atagattcca tttcatatct ggtttgttct ttttatggtt  18637
aaattccatc cctcataaat tctttgtaat tataacattt aaagggtgca ttcatttgtt  18697
taaagcaacc agagctactc acttgtacgt gtggggcttt gctttgtttg tttgcttgtt  18757
agttatttaa tattttaaca gagggggacg tctatgtgct aagtaagtgg tgatactcat  18817
ttgtcgagtg atctaaactg ctgctgcgct cacacttcgc tataatatgt gcttaaaaaa  18877
atgagatgaa cagatatcat acagatcaac agggatttat aaatcccccct gccaaccccc  18937
caaaaaaagc aagcaaaaaa tctggtctgc tgattgaaag aagcgatacc ccccacttaa  18997
cagctctatc ggcactcgtg aaggtagaag tttgtctgta agaagctgtt agacttgaca  19057
ggcaaaccta gctgcgcctt cggcatacac gttagtgata ttgtgccatc agcttactgg  19117
agcaactcag tgggaacagg attgggttgt atgatttcac aaatgtaaat agaacatcct  19177
cttcctcgtt tccttgctgc taatgtctct cttggtatta tgtggataaa gagaaaatta  19237
taactattaa ttctcgggag ttcccaaagg taagactcga aagccaccaa agagtactat  19297
atttatcttt aaattcaaca atgaggtgaa atgctctttt cagaggtcac cgtgtagaat  19357
ctggagccca cttagccaga cccacgtcag ctttattaag ggctgcccta catgcccagc  19417
tttatactac tgcgtgttgt tgtttactta tttattctgc tggatactgt agttgtgttc  19477
tgccactgag ctacaccccc aggtccatgt tcatttttaa taagataata ctataaacat  19537
atagtgaata aatgccagta cagcacacga tagataaatt aataaaactg aagttccata  19597
ccatcagcag aacaggaatt ataaaagatg acttcagtgt aagaggcaaa gtcatttgtt  19657
gagccccaac tctacgtgaa gaagaactca tattcaacca tggggggaaa aatgaaaaga  19717
catgaaatgc ctgatctctc caaacttctg cactactgag tagatagcaa gccaaactca  19777
ccaatcgata tatcctgtga cactggggat tagtctgtgg aggggagggg cgctacgtaa  19837
gcaagtgaag ggctcaagag acaagtcaga gtcagtacga gtgttcatgg gaacagagac  19897
caggcacttt gctgtatgga ttcttttgac ccgaaggcaa cggagaaata gcagacactt  19957
```

-continued

```
gaggctttta cccactcctc tctgcctaca tgtggatcaa tttccatctt tgatggtgtg  20017
agctgtatca ggaaggagtt tatcactgat cccgtggaca tggcactgac cttagtctac  20077
agaagcaaac ccctggtttc ttccatcttt tttttctttg ccaccagtag ctgctcttag  20137
cagctccagg tctcttagac tgtgaatcat tagccttccc tttgcatgtc aacatttagg  20197
atagtgagga atactggact atcttatagc catttcagag tctctggggg gaataggaaa  20257
aggaaagaat ttgcattaaa agtcagctga tctgtcatgt cagaggtgtg atttgttagt  20317
tttgggaaga ccattattct ttatggtaca tgtgaaaata ctgactgtgt aaagaagccc  20377
cttatccgtg gtgagaacaa tggtaattaa tagcagatag accttctaga agtcagttgt  20437
gcccagaagt gtgtttcatg taatccccg ctgaatggga atttaagatt ggaccacatg  20497
aacaatctgt ccttggtgcc tcctgagcca cctctgcact gcctacgtga atgatgggtg  20557
ggactgagct agtgggtcct gtcgggccag acatcctctc cttgaggaag acagccttgg  20617
ggtgggatgg actgataaga aggcagactg ggagtttgtt aagccatcag ccagttctca  20677
actgctctgg accctccctg cagcaggagg gatgctgagg agtaagacct cctcccacct  20737
ccactcacac tcgctccttg gtgtcttctc tgcctctctc tgctcgcatc accttttttcc  20797
tagtcgtcta agtcagcggt tctcaacctg tgggttgtga ccccattgaa ggttgggcaa  20857
gagatttttt tttttttttt tttgcagggg ttgcctaaga acatcgggga agtacagaca  20917
cttacgttat gattcataac atttgcaaaa tcatagttag gaagcggcaa ggaaaataac  20977
ttgacggttg gctcaccaca gcatgaggag ctggttggag tctccttctc tttatcacag  21037
ctccaaataa gggaaccctc agaagatctg ggggtcactc agaacatggg tctgcagatc  21097
atgcaagatc cagattatga atttgggtcc tgacttggca cagcccagta gaaacgcggc  21157
tgtagaggaa ttattaactt tcttaagctt ccatttccat atctacagag tatttgttaa  21217
tagtgctgtt aggagccatg ctgaattaat aagaactaca aagataacat gtggaaggta  21277
ctgaatgaag gattaacatg gctcttcttg tcatttcttg gccccttcgt aacagctctt  21337
ttctgacctt tctatacagt cctgactgta caggccagtg ctgcgtcccc tttttacaaa  21397
tgcaggggct gagaagagcc catttgccca aggttcttgt cttctgtttc agctgctgtc  21457
aaacagccgg aaggcttccg ttctaggcga attccctccc tgactgtacc tgagaccagg  21517
ttgttaagat tttccgcagg gcctttcttt ccttgcttat ccatccttgc agttcttgac  21577
cttcttgaac cctacaaaac cagcttagga aggaatctaa agcatgctgg tcacaacgag  21637
gaccatttcc ctgtccttcc ctctgattct ccacagttga ccaggcgccg gtgacagcct  21697
tggctgcttg aaccagctag agagagccac ggaattccag gctgcttgct ttcaaagggc  21757
tccactaacc cctctgaaaa caaagggttg tttatcacat atcaaagcat accgggcagg  21817
gataattgag agatcttctg ataggtcatg tggtttgtag tctctgccca ggcttctgga  21877
gtgggtgggc cgtgctcctg cctcaggtag cagtgacttc tgtctgccag gattagttct  21937
gtgtgactgt cctgtaggtg tgcatagcat ccgctcacca tcaacacttt atatttctct  21997
gcctaggtcc ctagaaaata gattcacaaa gaaaaccgtc ttgtactttg tatggtttca  22057
ggtgactctg atatttcatg aattcacaaa acccgagttg aacacagcac cacctagtct  22117
ctggtctagg agaggtgttt tgttttttct tttcttttct tttcttttct tttcttttct  22177
tttcttttct tttcttttct tttcttttct tttctttcct ttcctttcct ttcctttcct  22237
ttcctttcct ttccttttct tttctttttt ttttttagaa tggaagtatc aacctgggtt  22297
```

-continued

```
gggttaaatg ttttcgagac aagccccagg ctgcaggagg gttttgctgt ttagactcta  22357
gaggaacaag ccttctcttc tcgccattgc tttgccctga ccctgcatgt gtcaggccct  22417
atcatatgtt cggctgtgtg atcctgtgac acccacatcc tgttgctgga tccaagcgct  22477
ttgaggctgt attaacgcag attaattgaa cagttgccct gtgaaaacag atgcccttcg  22537
ccgctcgttt ctaataaatt gtcaagccat ttaaaagact tccccttgaa gaagtcatat  22597
ctccccgaga agctgaagca aaagtggaat gtttatgtcc caaattagtg tgctatattt  22657
aaaaccagtg gcctcggcct gaccaggaca taatccttcg ccgcttaatg aaactgccat  22717
cctgtccctc tgtattatat agtgaagttg gttctacttt ctgtattcca aaccagaaag  22777
ccgttgtaaa gaactagcca gaataagaca ttagtcttca gctatttgat gttttcttta  22837
taaattaaaa ttataactga ctttgaaata ggaagctaag cctggcctcc cctgaaccaa  22897
aaactgaaat tttagtaaca ttttgcttac gggatattgt aataaaatgc tctttgctta  22957
agataaaggt atttgtccag tgacattctg agttacagaa aattgagaat gtattataga  23017
taatgtacta tgaaaccaga agaacattct ctctagttga caaagatatg cacaatacaa  23077
agatccaggt attgatctga tgctgttcag agatcgagaa aggccgagag caaatcctat  23137
ttcaaagtgc aattcaagta aaattagatt cagtgagact atatcattta cccacccttg  23197
tagtaaataa taaggtagag gtgcgagtct aagctgttac ctaaaggaag tgaaatgacc  23257
cagagagatg agcatcccat gacctcccaa atggaatcga agcagttgaa cttgcaagag  23317
tagacactag atgccagtgg atggggtaaa tgggagatgt tgttcaaagg gtaggaattc  23377
gcagttagac atgggtacat catagagagc tggagtatag atattgtcac tgtagttaat  23437
aataagtgtt atattcttga aataggtttt aagtgttcac acacatatag aacagtatgt  23497
gtggtgatag gtaacttcat tagttaattg ttatttaatt acttaaaatt atatatatgt  23557
gtatatatat atgtatgtat atatatgtgt gtgtatatat atatatatat atatatatat  23617
atatatatat atatatcaaa acattatctc gtgcatgttg gataagataa cttttatttg  23677
ctacttcttt ttcacaaacc caccttgcac ttcatttgta aagagaagtg aagtccctaa  23737
cctggagggt tacagtaaga atatcgtgta ggcttcagta agcatttgtc attactgatg  23797
ctgctgtaag ccagtgctca tgactggctc ctctcccctt cctctgccag atgttctcag  23857
tggctctctg ttgatgcatg cagctgtgtt tctgagggac accatggaat gtccttaacc  23917
ctctgtcttc aggatcagtg tttatcccac agtaaaagaa acaaatcacc atcaaggttg  23977
ctttgtagca acatacaaac ccccaaagct cacataatga ctatgtgaca ccatatgaat  24037
ggacaccata gccaccatgt aacggctgat gacagatact ttctccccgt tttagtaaca  24097
ctctgctgct tttctgtccc atcagagttc catgtctttg tattatgtgt ttattagatc  24157
ctaggcatga tgtatgcagt actggttgcc atcaaaatag attgtagagt ttaatgggaa  24217
gtctaggagt tgacatccgt accctacata aaaccaacca accaaccttt taaccttgct  24277
gattagctat cattgagtaa tagatttccc acctggacca ccacttatac tctactaatt  24337
ctaatccaga ttctgtagct ctgttgtctg tctaaatctg aattcttttc tcttgactcc  24397
atctgttttg tcagagccta gtgtagaagc ggtggacttt gagccttaca tggacccagg  24457
ccaacagttc ttctccccac atccggagac caggctttgc cttttacaag aaggaaactg  24517
cctctctgtt cccaagacaa agctccctcg actatagttg ctgcatgttt ggctcagagg  24577
tttgcacagt ctatgtgtat aggcaggcca tggccttgct gggcctgctg gaagatggct  24637
agctctcgct ggctaatagt tgactcactc accgtgggat ggaagctctg gcctggacca  24697
```

-continued gactctggtc agtgtctgtt gatctcaggg aacattccac agctgctgat gtaactcaaa 24757
tgactggagc caactcttct ggaccggtta gagggcttgc ctggaccagt tagatgactg 24817
gctgtcactc agtttatctg ggggaattct gtgaagtgag tgttactttc agttcctcca 24877
tggtaagggg aacttctctc ctcttatctt ctttttgcaa agtgtgtttt ttataaaacc 24937
aaagtagcat ctttgggact gtggtggtgc cccgattccc gattgggaag ccttgggaag 24997
aggctgcaga aggatccaga gttcaaaaca gactcagcta cagatgttcc aggccaggcc 25057
aggtgacatg aaacggtgtc tcaagaaccc tcaaaataaa atcatcaaaa atagagatgg 25117
agtttataaa cgatgtggct actatttcat ttggtaccct attcaacatg atcctcacag 25177
tgcttataac tccttttgct tgaacttttt ttttttctcc tgagctgggg ctcagaccag 25237
agccttgtgt actaagtaaa aagtactgta ccagtgagag ctatcccaag actgaaatat 25297
ctttttattg agagattcct catgaaatgc atactgaggc ttttgtttgt ttgcttgttt 25357
ttctaaatgt gattgcagaa ccagataatt tgtgagactg cccatggtat gaaaagatta 25417
gttttcctag tctgggtgtg ggccaagacc tattgttgtt tctgatgcaa acccaagacc 25477
aaggactgcg gttgcaaact tacttatatg actgccatgt tcctaaaaaa gatttttaga 25537
aacttaaatt aaaaaagctt caagcagccc aggcacagtg ggcacacctg tcacccccagt 25597
acctggaaag tcaaaatcag gagttccagg tcatcctctg ctaggtacaa aattccagag 25657
aaccctgggc tagctacctg agactgtttt aaaacctgca acaaacaaac acaaacaaac 25717
aaacaaacaa aaaactctca cataaaaatt agaccaatag aattaggaaa acaggccact 25777
agataccaac atacattttg ttactaattt taaaactatc ccttagatgc acagaagtac 25837
ttatcagata actgcagctt aggggtcgcc cgagtttact aggaagccat ctgtttatgg 25897
gacaaacatg tatctgctgt catcaggaag gtcactgggg tagctgtgac tcagatccac 25957
taagggaagg gacagaaata ggactcctat cttttgtatc tctgggatgg tgaccagaga 26017
ggtttatgtt gttgctatgt aggccctttt taaaaactcc aagctgtaaa tactgaattt 26077
tagaagcaca tcgtcatggc tttagaaaaa caacggtcta ggatttccga aggagcttgt 26137
ggctcctgca gctattcctg atttggtgtt aagtttctgt tcttaccagg tatcctgacc 26197
tccagtgtgg gcttctttca gaacacttca attaaaaatg taattattag tgtggcattc 26257
gtgagaacat gccctggtag agctttaggg atgagaagac aacgtttgaa aattgattgt 26317
ctccttctga catgttatcc caggttggaa ctcatgttcc catgcagctc aggttactag 26377
gggtgttgct aagtactttc acctgagtta tcttccctgc caccaatcag aactcttagc 26437
agtcaaaata aaagggggaa aaagggtttc atttagtttt taaaagtcat tgtgtttttt 26497
tcaagaaaaa tagagattag attaaaaaaa cacattataa agtaaatttt aaagccctct 26557
ttgtttttat tgaaacttgt atcaatttct ttatttggct taccttggga caccaggaaa 26617
agagccaagg tttcctagaa cacagcttga aatccagtgt tccaaaggcc ccctagtctg 26677
tgctttcatt ttggagcacc attttttaaa aaaataaacc cagatttgaa gatgaagaga 26737
taagctgact ggccttgaag ttagggccaa ggcctaacaa tagctttgaa accagtttta 26797
tgttttcaga aaccaccaaa ccagccaggc atactgacac atgactttaa tcctagcact 26857
caggagacag aggcaggtgg atctctttga gtttgaggcc ggcctggtct acaaaacaag 26917
gtccaataca gctagggctg ttacaaagag aaatccccct ccaaaaaaaa aaaaaaaatc 26977
aaaagaaaaa gaaagagaaa gagaaagaga aaaagaagca agcaaaagga aaggaagaaa 27037

-continued

```
gcaagccacc aagccagcct taggtccagt gtcgttgatc agacagttca tctgcgtttg  27097
tcaccacttt actttctggg aaggaaagca gggattatat atatatggtg gatagagata  27157
aatgagcagc tatttaaaat gccatttttt ttgtacttac ttataagtca aatctgtgta  27217
gatactaaag atgagttata gagaccagac ttctgtttta tacatcaaat ttcaattttt  27277
tcaacagtaa ccttattgag aacctacgtg atttacttaa atgaaaaaca gctttcccta  27337
gatcctcatg gctttaggat ggagcctagt ggttacacat ttctcactgc cttagttttc  27397
tgttccgtga tcggtgatcc ctgggagacc ttttgacctg tggcaaggca gcacagcatg  27457
gtgggagcgc atggctcatt cacctcatgg ctatgactgg gtagaaagaa gaagcaaaga  27517
ttggagtctc cacgtcttca ttaaggacac acgcccaaag acaggaagac ctgcaaggga  27577
aagatcacca gcgtggaact ctttctcaaa agttaatcca gatttcgcca tcaaagcctc  27637
tgccttcatg gtgaggcata tgcgacgtgc ctctgacttg gtagagctaa agacaggaaa  27697
ggagaaaagc agaggggttg cggggggagg ggcacttgta cttttcatgt cttccagcca  27757
agcgcttgca cttgccctct tatggaagac tcgccatccg gacaaaggag ggtagttacg  27817
gccaaagaat gaagttgctg agtaaaatgg ataccccttct ctattttttt tttccatttt  27877
atcctggtac ctggcaaaga aaatggaaaa atgaaaattt ggttggaaaa aagtcaaaga  27937
cgcgtgtaat tggattaggg ctggggattg tagcaccgtt cagatcactt ggctagcggt  27997
gccctcagtt tattcctcga cattggtggg ggcgggggca gggggagcag gaagggcata  28057
aagggcatgt gaaggcagaa atggtggggg ctgaggagat agcttaacag ttaaggtcgc  28117
tcttcgcata gtcaggagga gcagagtttg gatcccagtt catttcacag cccgggctta  28177
cacccatagc tgtaacttca attctaaggg tcagaggcaa gaagaccagt gagcattctt  28237
ctctccaccc cacccccacc cccagcacat aaaaagtctc agagccaaga aaggacagtg  28297
cctcaaagga ataggcagaa tggtggagga ggagggacct acagagcaca tggatgcatg  28357
tactcacaca gacagacaga caaacagaca cgaataaagt atgcatgtac tcacaccaac  28417
agtcatacaa ataaagtatg catctactca catgcataca tacatacaga cagacagaca  28477
gacagacaga cagacggatg gacagagaga cagaaaaaaa taaagaagtc ttttagcaga  28537
aagagaaatt gttgttcttg atgctggagg caggggggaat cacaagttta aggctagcct  28597
gggcttagat tctgtcttta aaaggaagag ggtgagatgg cttagtgaat agaggttatc  28657
gcctctaatt tacctctaag tcacaaaggt cataaggcat tcatatttat gtctggtttt  28717
caacttgaac ttcctagtag tttggtcaga tttttaattc ctgagtaaga agttggaagc  28777
ctctacaggt aatcgtatta gccagctcca ccttcatgag aagctaggat ctcgaggtag  28837
gctaatcttg gctttatccc tggcttacta agtgattata cacagagatt agttctaata  28897
agggatatct cttcctgact acaccttgga agcatgagtg caaaggtctt taaaactttg  28957
gagctaagca ttgcagtccg gtcagggagg cctgatggaa tgctaaggta ggctgattcc  29017
tagcaataat cttagtgaac gaagggcagt ccatttttac tctgagtcca ctgagtgcgt  29077
cagacttgaa gggtttatga aatgtcgaat tatcttgact ctgagaaaaa tggtcagtta  29137
tagttttaga ggaatcttta taaaatcctg ggttaaaaaa aatgtattct cagtttgcat  29197
tctgatttat tcacaataga tctgagtcac aggagataat cacccctgtt gtgtggggac  29257
ccaacggaga caagtgactg tgttcccctg gaatcacaga gaaacttagt atgaagagca  29317
tattgtttta taaaagaaaa taattatgct tcctgttata atgcctgaaa aatccatgga  29377
agaaagaatc caaggaaggc tactgaggat cggtgatgat agtagtagtt gtagtgatga  29437
```

-continued

```
ggtggaggaa aacattgcca acctcaccac gcaggctggg tggacaagct ggaagatgaa  29497
gcatgattga atgctattgg acacttgccc ttaagtctgt cacacattgt tgttctaagt  29557
ccacagggta agcacctatc ttcagcgagt tgtcatgaga agacaggatt ttatacagtg  29617
tgtacccctg tagattcaag tttcaagtgg gatttttttt ccctgccagt tttattagaa  29677
cctggccagt tgcctcttaa ctgctaaaca ctaatacttt ggaagttcct atgaaatata  29737
gaataaaaca aaaagcagaa gcaaaggtat aacaaaacaa aggatgggca gacacctgct  29797
cagtcctgtc ttcactgcat ttgaaagatc cctgccgtgt gactccaagt cagtggatta  29857
gagacagaaa cttccgcttt tcatgttcaa agtcaaggtc aacactaagt taaagttctg  29917
atgagggaca ggaagggaaa tttattatga gttatctatt taatacatag tcaaccagat  29977
cctactgggt ggtgaaagct ttctcttact agttatggtt ggtttttctc ttattttaat  30037
gcttaattag ttgctttagt ccaaaatatg tgtaacaaga tggagtctct aatctgttac  30097
tgattagatg agtctactga tacgtcccct gactaatcat acataacaag caattagcac  30157
actgaaaagc aatctggatc tagcattaca caaacaatta cgtcagttgc tgacatgaaa  30217
atcccagcta gagtggtaat aataactgaa tgtgtgaata ggttctctct ttctaggctg  30277
ccagtaagtt acaacctttt cttgagttgg gtttcagcaa tgaaatatag tgaacgtcta  30337
ttgtagatta gattgaagta ggaggaccag ttacctatct attttactgt tcttgacgtc  30397
aggcaatcct tagggtcact gcacaaatat ttaaaattag gtagagacac taaagggagg  30457
gatcttttct gagtcaccac agcttatttc tcttagaagt ggtttgaaga ttcaatgcaa  30517
agaactttgc gctgtggcct aatttagtgc tgctttcccc cttcaaacag aataggaata  30577
acccagtgtt tatgtgctct ttgggtaagc actaagccag aggattccgt acttatagaa  30637
atgagtaaat atggagatgc tgaacaagtc aggcagaaag cacaattgca tagcaggcct  30697
gtgggaaatg aacaatgggg gaccgagtct ataaatgtaa ggaagaactg ataataactt  30757
ttgaaaagaa tattttatac atccagataa tctaattcat tatattagga caatgttctt  30817
tttgtaggtt tttttgtttt gtcttttttt ttttttgtca tgaatgaacg acttgctgca  30877
atgtctaact aaggtatata tttcagcctg aactttattc agaacatgag catgtggcat  30937
tgctaataac ttctctgttc cctttaaatg gaagcttctt tgatgttcct taaatatcat  30997
atgtcaagca tagttttttt tttatgatga tataatgtct tatcttgatg agattccttt  31057
ctaaatgtcc ctgcttgcaa gaagaagcct tcctttagtg gctcgtcgca tcagattttt  31117
gataacccag acctggatgt cgtttcatct caaggtcata attatagatc gtgtttatgt  31177
tgcttctgct ccccttagga gagctgttgg atctttaaga tgacttgaat ttggtgacaa  31237
tattaagtcc atggccattg aattgctttt cgattcagag gggcttgctt tgattagggc  31297
tttttctcta gtttatcatt ccttttggct tgtataaaat attgtccctt catacttaca  31357
gttgtacata ccataatagg tactttcttt tttccataat gatttaggta cagacaaaac  31417
taataatgct agtttgtcaa ttttctctta gaaaaaagga gtcgacgtat ttaaatgcct  31477
tgctgaacac actgctttct gccctggtgt ctttaagaag ttgataagaa tccccatgaa  31537
ctggaatact gttatatttt tgctagtaag ccgtggcatt ggtaaatagt gcagtattct  31597
atttcatgga ccctttcact gttttattga tgacgtaaat ttttattgcc ccaagatagg  31657
tgtactcaaa ggggaaacca gagtttcttt ttggtagtaa attcccatct aagggatggt  31717
tttagctgct taagcagggt ccccccttacc cccaccccag gcttcagatt tgttgtttcc  31777
```

-continued

```
tatgatggtg aggaaggaag ggagggggac tgctactaaa aataagaatt gctcaatcaa  31837
ggtgaagtct ctgtttgggt gttttaagtt cacatacttg tgctgtccag actcgaatga  31897
atatggagac aggaattagc cttcagcgta gtcttggcca agcagctgag tcatttctgt  31957
atacatatct taatagtttg gaatatttta gtgaagtcag aatacctaga acagatattc  32017
ggagttccca gttgtataaa actcagggag gaccttgact ttgattctca gaactttcca  32077
agtgttaaag aagacattat gctggacgta gtggtcatgt ctgtaatgcc agcactgggg  32137
agtctgaggc agaaggattg gggttcggt tctagcctgg gctatttact gaacgtctat  32197
cttaaagtga aagaagggtt attagtttac gtgtgttgtt atagtcagct ccaagacaca  32257
cttgtgttgg gcaagctttt ctaaaggagt ggggagtgcc tccctcttct tttttctccc  32317
ctcccttgat cttccttgtg tctcctccct ctctggcccc cttttcattc ttccattctc  32377
tcctcctcgg ctccattccc atcactcccc tctctctttt ctttcaaagg ctcttgctat  32437
gtagcccatg ctagcccttt cctcatcccc ctgctttcct taacctccac agtacagtgc  32497
tgtgattcca ggaacatgcc cagcactgtg ccagcctctt gctttttttt tttctacagg  32557
aaaaattcct ttcctaattt tcctcttcgt ttccttcttt cccttcagtc accccattcc  32617
acactccgct ggggatcaaa cctagggcct gtacttaagt tctgttacca agcaacggag  32677
ggagcagcat ccccttgact ttgtcatctc acctgttctg tattttcttt attaattaat  32737
ttatttgctt tacatcctaa ttgtggctac cttcctgtcc tctcctctcc tcccctcccc  32797
tccccccttc cctcctatcc ccatgattct cctgtcctcc ctttctcctc aaaagagggg  32857
aggcctccta tggatatcaa cccaccttgg catgtcaagt tgcagtaaga ctagatggat  32917
cttctcctat tgaggttaga cagggcagcc cagttagggg aaagggatcc gaaggcagag  32977
agtagagtca gagacagccc ctgttcctgc tgttaagagt cccacatgaa gaccaagctg  33037
tacatctgtt acatacatgg agcagggcta ggtcagtcca atgcatgctc tctgtttggt  33097
cagtctttgt aggcccttat ggacctaggc tagttgattc tataagtttt cttgtggtgt  33157
cctttatctc tctggttcct tctatccttc ttctttgttt tgttttgttt tgttttgttt  33217
tgttttgttt tgttttgttt tgttttgttt tgttggttct agggctatgg cccaggactg  33277
cacacacata agtgtaccac cattgagagt ggctctcatt tctcatcaga gaagtttttc  33337
tctgcagaca attatagaaa atcacacttg gctaaaaggc agaaaacaag tgatcatgga  33397
gggctcagct ctaatggacc catctacaac ataatacata tcttgccccc aaggctcaag  33457
gaacctcttg gaacagtggc tagaaagaca gtaagagcca gaggaccaaa agcgtgaggt  33517
gagattgtgt ctcctagaac taacagagaa gctacaccca ggaaatgtca acagtatggt  33577
cacctgaaca gggatacggc cactagacat gataaggtgg aaggcagaaa tttcacagag  33637
gtcccatctt tagacaaata actgtagaca actaagggat gctaagaatg tgagatggag  33697
tcttcactag ccatgagcct cttaattagt catttcttgt cttttgcaag tcagtgccag  33757
gtaaatggaa agaaactctg tggtcctcaa ataatgtgtc tgtctttcac atgacttttt  33817
acaacatttg gctcgatatc ctttgtgacc atatgaaatg ccaccatccc caatcttttc  33877
catgcattaa acagcagtgt gtatcctgtg ttttaaacaa gacagagagg cgctctgcct  33937
gctcctaggg gtggagattt cctgcatttc actctgtcct tctttctaag gggaagttta  33997
gccggttggc cttggtatgg tattcaccat gtcatgtggt acccattagc atagcggtat  34057
ttaccaaata gtaagattct ggccattacg tcatcttttt acttagctgc tgcaggacat  34117
gcgtaacacg caacgctact ttgtaaagct ctctgaagcc ttctctttat aaaaggagcc  34177
```

-continued

```
tggcattcag gagtcaggct gacctcccctt acacagtgtg agacaggagg tgatttgtgt  34237
tctctactgt gaaatcagaa ggacctagtg ctctgtgttc gggatgcaaa gcaccagctc  34297
gtccctcccc gcaggagtgc acttcagcag attctggcat ctgagctcct gccctttctc  34357
ttcttgttct cattcactaa tcctctttcc ttgatgccat tttgttaaat tttgcaagtg  34417
tcattttgga acctagagat ggggtttgaa tatatgcatc tatcatcagt cattttatat  34477
ttattttgta aaatgaaaac ttttttttt ttggagaggg gaggcagtgt ctttctatac  34537
agaccaaccc agcctcaaat tcaacgttct ttctgaccct cagccttctg agtgctgaca  34597
tctgtgtgcc atccggtctc gctggaactt taaacaaact atctttgttc attttacctg  34657
tattgtctaa aaggcaaaac agacccagcc aaataataaa taaataaata aataaataaa  34717
taaatatcga gggttttttt gttttgtttt gttttgtttt ttgtccttgt aagttcctga  34777
attttattta catacacatt tgaaattctt gcgattgacc tctgaaatac cacaggcctt  34837
tgcaacctca gattttctca gcctgcttac ttcctgtctc ctctcctcgt ttggcatggt  34897
ggctctgcag gagttttata atagcactca ccacttctgt tccctggaag gattcttttg  34957
gttttatata ctttacttaa atactagtta agttacgatt ggtcacccgt ttcaaacgtc  35017
ctagcacgcc gtagcccgta agttacgatt ggtcacccgt ttcaaacgtc ctagcacgtc  35077
gtagcccgat gtttgcttta agtatggcta ttatttcaac ttcttaaaaa cttgttgctc  35137
tgtatggtag caagatatat gtgtacataa aagatacctt ctaaaactct ttaaacttgt  35197
ctctttataa aaggaacatg taacggaggg gtctgggtgg gctctgccct actgtgtaaa  35257
tggacctcct aggcgaatgc atttgagaaa gcttggttaa agtgacccaa cgcttctact  35317
ctccagacac ctaatgaagg agcttctccc cgtgtttgta aacagaatgc gtccccactc  35377
cttgaaatgg cattttctag aaaccatttt ttgagaacat tcatttagga attaagtaag  35437
gtctatagtc atacttttaa aattttccaa taccacttgg ctgttctcag tatagataac  35497
cacctaatga tagatttagc aatttagcat taataagttt atactaaaaa aaaatgggtc  35557
cataacagaa gttctttata agaaacaatt tttctttatt ctattatttt cagaatcttg  35617
gtatgttagc cttgaatcca tgccctcctg cctcagtttc aaaactacag acaccagtgg  35677
ctaccgtgcc cagacctagg acaaaaattg actgctgtag ctacctagat gaaccaagac  35737
agccttaaca gtttgaactg tgctccttca tctcatttag aattagtgat tcactgcgaa  35797
taagctgtca agaatgggag ttcatcaacc acgtattagc caccagagct cactttgccg  35857
ttcaactgtg aattaagggc tcggagatgg tttaaaatac cacacggcct tggtgagtca  35917
gctctgccac acacactgca cttgtcgctt cgtagccggg agtgacgaca tatgagctgc  35977
agtgtcctta ctcgtttgtc tcctggagac aacttggcag gcagacatct tgcagataaa  36037
tgaggaaaga ttgtctattt caagtggcat aagacattcc ttaaagcagt gtgtcatatc  36097
tgcttataca gtcagcattt tctgtggagc agaaaatctc ctctccggct ccctgggtac  36157
acagcaaaca tctttgtgtg ggtagcgtcc aggaggcttc agtggctctg ttgtctgtag  36217
atgggtcagg aaatttcttg tgcctgcata cacttctttt ttttcttctt cctgttgaat  36277
gcaagcttgg tcaatctggg tagctttttt aaatgctcac tatacatctc ctgtgtatta  36337
ctgaattgta atttaaggtc aggtattgag aactatttta gagagaggaa ctaaggatga  36397
aaatcaaaag gcttggttgg actggatgat tggctcagag gttaagagca ctgactgctc  36457
ttccagaggt ccagagttca attcctagca accacatggt ggctcacaac catctgtaat  36517
```

-continued

```
gggatccgat gccctcttct ggtgtgactg aagacagtta cagtgtactc atacacataa  36577
aataaataaa taattctttt tttttttttt tgatccttaa gacttttaat atgtcatcat  36637
ttagtctgtc atttctcaac atgctttaaa actacaaatt acatattttt aagatttatc  36697
tatgtaccta tgtacctatt tatctatgta tctatctata tatctatgta tctatgcatc  36757
tatgtattta tgtatctatg tatctatcta catctatcta tctatctatc tatctatctg  36817
tatgtatgta tatacatgca tgcatacata tgtacataca tacatacatt aaatagagaa  36877
ggaaaattta atcaattttt atgattatat tttcaactta aatatatata aataattctt  36937
ttaagaaaga aagaaagaaa gaaagaaaga aagaaagaaa gaaggagaga gagagaaaga  36997
gagagaatca aaaggctctc tcttcaaagt tataaatgct aaattctaaa taggaccttt  37057
tctcatgata caaacatacc catctcttct gtgatttgtt ttgttttcca gtccctagag  37117
caactctgaa ccaatactct gaattttcta gatataggca gtgatggatt agacttgact  37177
aaagatgcaa gacatgggga agtttctgga aacatttttt aattcataag tgttcataag  37237
ggttttgcat tgggtaatca aatgatacaa atggtatgtg tgcatatggt tgttatccca  37297
gaacagtcaa gacattattc aaatagtttc cagtgacgtc gcttctctga gttggtctaa  37357
ggcacttaaa gaaacaatga ctatttggaa gtctttagtg acaaagaaga ctccagctgg  37417
ctgtgttgat cttggaacca ggaaggacac tagaatgaga tcccgtggat gtgctcagaa  37477
gcagagacca gcccatcgcc tacagttatg tagggtggtt aagatcgcct gcacctgttc  37537
ttgactgata aattataagt tgatcttcac agaatgaaca caataaaggg gtgtgtccgt  37597
tactgtatat aacgtaatta tggcctatcc tgtgtgatca cacactgaag agattacctg  37657
gctttttaac ctgtgaattt ggatcattgg agtcagagtg gggcttcatc ctaatatatt  37717
tgtaatgttt tatccccctt tgtattgtat tgtaggattc acggttataa cgtcacattt  37777
tgtcttttga ttaattaatt attttggtat gtatgagaag cagagactcg tgggctcaac  37837
ctctgtttga gtacatgttg gtatttggtt ttcttgttgg aaattgacca ggatttattt  37897
catgcatgct ttacacgagc cttaccactc tacctaagac tcaaggccaa ttttgatgta  37957
ttctcttaga aacacagagg taaataataa atgagttttc tcctaaagat ttaaaagctt  38017
agttcagaat ttcaacgaac acactgttga gattttccag ccaagtactt cttaattctc  38077
tatttggaag ggtttcctgg gagaaggtgg cctgtggggg atccctgacg tcttcatggt  38137
aggtacaagc agggccaccc atattgtgat gaccaactat cccaatgacc ttggatttgc  38197
acatggaaac aattctggaa gcaaaatgac ttcagaacca tgtgagttag ccagtggaga  38257
gccactgcat ggttgaacta cacatgtgga agcagtggta agccttcact gaaaactaca  38317
ctgtgggtgt aaaaccgagt gtttgtgaga actgaaaagc catcttcctg agggtctgag  38377
aaggatgctc ttgctaatta ctgcctccat ttttttttta cttagaatga tatagaatca  38437
tgtagagaat agccccagga aagaaggagc catcgtaata catggtgcca tcattttaaa  38497
aatcacagct atgtgcattt tgattggttt attcaaacaa aagtggctgt atcagtatca  38557
gtgtggtgtg tgtgtgtgtg tgtgtgtgtg tgtgtgtgtg tgtgtgtgtg tgaacactct  38617
ctggatagat tgtgtagtag gacttaaatc ttcctatcac ctcttatact ccagagaacg  38677
atgtagcttg agccccatat cacatctcca tctccatttc aggacttagc ctctatagat  38737
ctgtcagaac atccctggag aacagggcgt acatggtgac agtggagttc cttctcctcc  38797
tcccccccac cccccgcctg tcataggata tggctggcat acccctcccc ctgaactctc  38857
cagtccaaag gctgggctac ccttctcctc tggctctttt ctgtatgatc caatggtcct  38917
```

-continued

```
tttgtggcct cctgtccttt tgttgtcctg atcttccctc tccctttatg gctctcctca  38977
cactgccggc ctcatcttta ctctgggctg tcccagatgt ttccatctct ggctatgctc  39037
tccctcatat ttacagtaaa ctttctcctc tactatacct aggagcagtt gtgtctgcca  39097
gtttcctttc ttacgttcct tctcctgcaa tacaattcac ttttgtaggg gctgagaagg  39157
ggcgggctca tcctcttaca ccaatgagcg tccttctctt ctggtttttg gctagggcag  39217
tagttccatg tgtcttcatt tagtatatac tcaaggctgc ctagctgctc gtcctgagat  39277
gtcgtgactc cttcccacac tctcctgtgc ttcttagctg ctgcagtcat caccgtgcct  39337
aatccataca agtgcccccg tcctgtggtg tgtccaatga gacaccacca tcctaccttt  39397
ctttattctt tcagcacttt ctgttctgag gtgagccttg tctgagcctg taccactggg  39457
ttggatctcc ccacagtcct tttctgtggc tatgcttact gccttggaaa tgtttacatg  39517
atcctaagtc accaaaccag aacttccctg aaacttcgcc tccgaccgac cgagacaatt  39577
ctgtcctgtc tactggaagt ggcaagggct ccgtagccat cagcaccgag tttgagtttg  39637
gcttatctgt cagcggttgg tttcccgcat catcctgaaa gtattttctg ttcactagtt  39697
cactagcctt tctttcactt caagtgttag gttaggagtg gaaatctctt gagaatccct  39757
ttgtgcagct gaaggcatct cagctgcaag aactaaaaca aaacaaagta gctgattggg  39817
tgcttcattc aggaagtatg gctggccact gtgtttgtgc aatcctggag cccagtggga  39877
caagcctatg ttactcctct caggaatgtg ctattcgagc accaggaagt gaaccgagct  39937
gcctggctca gaaatccccc ttgcgttttg agctgttgcc tttagaatgt tctaggaaga  39997
gcccgaggtc aggccaagtt cagctgcaat tggtaatggc ctaagagtga attctgtgct  40057
ttcttttctc cattggctcc cactgcgaaa atcttatata tccctaagtc ggggtttatt  40117
ttatatcgtt gcacagcttt gttaatatcg acaagttctt tgcattttga ttttaatgtt  40177
attatttttt tacgccgggc attctttagc tcttgtattt attgtgggag ggaggcaggc  40237
atgttgtaga gagcaaggaa gttgtcacag gaggtggagt cgcgtttatc ttgtttgtac  40297
tttacaaact aaacacaagc cttcgctctg cacttacaat gcttagctgg atgctagctg  40357
gcagtaaaga cttcactgct cttatcactt ttgacttcaa attgcccccct aacacaaaat  40417
agagtgttgt tatatccctt tcaaaattat agccccccacc ccaccccccc cccccccccag  40477
cactgtgttt ctgagagcct ttgttgccaa aggaatggca atttgaaaaa gtggtttttg  40537
ttttgctttt tggttttggt atggctgggg gccatgaaaa gggaggcatc tttgatagtg  40597
cctgactcta agttacttga gaaggatagt ctccctgttc ttatcaagca catagctgga  40657
aacagaaacc tttgagtatt ctttacaacc ccggagaaga aataatcttg gcttacccta  40717
agagagataa ggtaacagaa agcgactgga acaatggaca ggaatgctgt ttttaagtga  40777
tcaccaattt tcacatggac tcccgtattc gctctgagtc tttcttgtgc ccacaaggca  40837
gtttctgcta cacccagtgc ccctgtggta aaaatacaat accatgagag ttataaacgc  40897
aggggaacag ccgatgagcc aatgttatga agctttggaa agaattaaac caagggataa  40957
aatgtaaata tttgttctgc tcatgtaaaa aaaaaatgtt tcacgtcctc atcctgaagc  41017
attccctgtg actctggtac acatagaaag gtgacgtcct aaggccacag attgttgctt  41077
aagtgaaaac ccagattcac ttcagtcctg tctgagttgg tcactggtct cttggtatct  41137
ttacatgaat gtgtacatgc gcttctcaga ataatgtgtg gcaagaaccc tcactgggta  41197
tgccacaccc atttgagcat atattgcttt caccttggga accgtggcca tagtgacgtg  41257
```

-continued

```
tttgctgatg aaatctgtac acaactgacc acaagtagta caggatttcc tattcatata  41317

gctctaggta aagtgtgagt agagatatag tctacttgat aaacattgta tccacatttg  41377

aaatatttcc ttgtaagtat gtattggcca aaataaaata tatacagctg aaaaaccatc  41437

aggtggctaa atcgtgtctt tgcagaagtc tcaaagagaa agaatcagag gagggctatg  41497

taattagtca gagctagaac ttggtagcag ttgattgaca tctccctata ggcttcagtg  41557

ctgatgctta gaacaagact gcttctactt aggtttttca tccccagatc tgtgtgtaag  41617

aaccagcatc atatggtcca tacactatcg ctggtcctaa gtcctgtcat gcatcacata  41677

ctggacgttt acggcacttc tggcttagaa ggctgctatt caatgcggct agtagttgag  41737

attttcactt gccaagggaa ggtatttact gtgtatagtg aggcccaagg tctgatagaa  41797

aagatgggaa gcaaacctga aggtaaattt gcccaacaca agtcttcatt gttgtttatt  41857

ttcaagcaaa agtctattta taagcgaggt ctgttgtaat attttgactt ttagttgtga  41917

cactcattct ccccctcccc cccccccagg cttactttta atgatggttc ttaaatgctt  41977

taacctccct tttagccctc tacccaccag atatagtgga aagggatacg ggggaagtac  42037

atctgtttag aaatggttct ttggaacaag tccctttttgt gttgtctagc aatcagcagt  42097

tcagtttaca ggttaacagg gcagcttgac tcactcacaa acacttcacg gatacaccag  42157

cagtatagtt tggcaaagtc ggtatagcaa gcacgaatca gcagtggtgg cactacctat  42217

cagagacagc caggcctcca cctccacttg agtcagcagg agggaccaag gccaacagga  42277

acaccagcaa aagttctcag cctctctcag caaaacaaag atcagtgaag acaaaagacc  42337

aacaagcatt tcacagctag ctctataagg aagcctagct cagcctccgt cactgtccct  42397

tgagtcctat ttataggcta ggtgcggcag aaattgaggt tccccagcag caagtgtctt  42457

aaacaggggt ggggttcata taggttttat cttagaaggc ttgactttgg gggaaaatgc  42517

taacctcata tacgtcctat gcaatcagtc tcttttgaag tggcttgttt tttcatatta  42577

actactctta ttttcattat agtctcctaa aaaaaatggc ttgcctccag agtttcaatt  42637

gtttttgaca aattaccttc aagaatcaac ttcaaaggag ggtaaggttt atgttgggtc  42697

ttggatctgg tgctatagac gtgttgacac aatacatcat ggcgacccag acacaaaggg  42757

gtagaaccaa gtcttaacta gttgctattg tatctctttt ccctttcaga ggcatattga  42817

atgacttgac ttttagtacc tgttaagggt ttccctactt actggcagtg ccacaggctg  42877

gcagccaagc ctttgacatg gacatttagg ggacactcca gacccaaact atgaccgtta  42937

cattctctaa ctgtagtgtt tctctgaagt gaatgcatca ctgtagattc aacttgataa  42997

agtaagacag tgtagctgtc ttcagacaca caccagaaga gtgcatcaga tcccatatcc  43057

agatggttgt gagccaccat gtggttgctg ggaattgaac tcaggacctc tggtagaggg  43117

ggtcagtcag tgctcttaag tgctgagcca tctgtccttc ttgaggctgt cctaaacaac  43177

aaccacaaac tcaaatcctg aaaacagctc agcgagggcc agagaaccca tcaagaatgc  43237

actaggaatt atagaacaaa gagagttaga aatccaaggt atttaaaaaa tataccagta  43297

gaaaagttag gagagcagtt aaagccagcc gaagactctc aactacaacc tcccagtcca  43357

acctgataga tagcattcaa agtctttcca taggtggagg ataggttttt attaggttaa  43417

tacattccaa aagatttgat ttgctactcc agttcctagg tcaacaaaga tgggcaaggt  43477

ttggctcctt agctgggctt gagatagcct gaaaataata attaattgtc gtgttgaatc  43537

agcagcgttg caaactgaat ggagtcactg aagtttttat cagtgttatc agcctgtgta  43597

cagaggtgct ttccaggaat gttcctgtgc atcgagcagt tcaaattcta gtcttttttt  43657
```

-continued

```
ttaaagggta gtggggacct aaataggcat ttgttggatt gcaaactaac tttgaaccta  43717
atccttgggt tatctcacaa atacttctgt ttttgttttt tttttttaaa ttccaatttc  43777
taatccattt atagttggtt aagcagcagt ctgcctgcca gtctttgcta ggccttccta  43837
taatgcaagc tttcagcggc agttattaat ctcgtgggtg ttgaatgata aacgctgctg  43897
ctttcaatag acctcttggt ttcctgctgg gcatcagcag ggagcatgct tcagtagcct  43957
tgagatgggg cagagttttg gggtcagctg gagaacacct gtgtggccct catttgcaga  44017
gcatggcatc cacagaggcc aggaaaagct tctaagagcg ctgagttgta atttgaagct  44077
atgtcagcaa gtgactccaa agaatgacga gtttccaggt gtgaaaacta cctacattaa  44137
gtctgtgaga gcggttattt cccctcccct ccccccttctc tactcacttt tgtaacagat  44197
ccttctaggc tggaactcag gctggacatg gctatactgt aaaggtactg tgacttactg  44257
tgaccaccat gtgggtaatt tgaggagcag ggttctaaca gccgtcgtgg ttcacttttc  44317
tgtacgtgtt tggtgggcaa ttctatcctt tgtccccaca cacatatgca tctgcctttg  44377
acagacagtg gccaacttct ctctgcctct gacactctag ccatggatga aatcttagtc  44437
tagtcctgct tcaagttggc ctaaatgatc tttgcacttt ctttcctttc ctcgattgta  44497
atttaagccc tagtttcctg ttattgacga aacgatgctc tgcgtatgtt ctctgtggat  44557
gatgggttag agggaccctc cctcgcagag tcttgtcttt tggttggagt agcaaaattt  44617
gctcatagtg attattcatc cttaaaagga gctcacaggc aaacttccta gattgtcatt  44677
acggaaatca gttcatgacc tttgaaaggg gagaaggcgt tcagggttga atttaaaaga  44737
aacttggagt gtacagtgtg tgtgtgtgtg tgtgtgtgtg tgtgtgtgtg tgtgtgtgtg  44797
tgtgtgtaag taatgtaatt gaactgtgct caggttatga gcaagcaaat agtatttatg  44857
caaggaaaac caaggatagg atagaaatag aatccgtctg tttttttaag agcttataca  44917
agaatcccac caaagaagaa aaaaatacca aatactacac catacgagag agaattattc  44977
aggccagtga gaagcctgct tggatgtaga aaccagatgg tcttcattag ccagaaacct  45037
taaaacgaca taaatccact gatggggcca agcgatggat ccatgccccg tcttgccaag  45097
ctggcctttt taaccaggaa aacagagagc tccttgttca agcccctctt agctgggact  45157
ggggtgaaga atgctgccaa acccgttcta taaggaattc tgatcttgat aatgaaaagg  45217
agagaaagtt cctggagaga aggagcgccc tgtttgaaag gcagaaagag agcttgttcc  45277
agacgctgcc tcttcccttc attgtaaatg gtaggggttg gaggggtaga cttccccatt  45337
caccctctgc agatgggtcc aagtcaagtc catatgttta cctttatttt agctctgctg  45397
atttaaggcc aacatctagc tgcagtacca tgaggaaagt ccatggcatg tctttgctct  45457
ctgtgttgtg gctcaaggaa aaaaaaaaac aaactttttt gttttccctg atagcaaagg  45517
tttgtttcca aaaaggttag ccgtgttttt aagagtaata tttccgtggc tctagctcag  45577
cgttttttta agtagcctct ttgcttttga agccatggct gaacacctac tgtttcagct  45637
ggctgttttg tttgttggca ccgaacactg ttttcccatg ggaaaaatat ctccagtttc  45697
aggatggcgg cagcaatcca tacaggttat tttcatacgc agcctccaca aaaccacacg  45757
aaccacgcag agccacctgt gtacagtatg ggttctagcc cgcactgttg acttacattt  45817
ctgaaaaaaa taacctggtg gtgctaatcc cactggtgga gattaagacc actgaaagaa  45877
tttttttgatc caaatttgaa gcaagctttt aattaaatac tggccaggat gatgaactct  45937
ggcggggtcc attcttgggg tcccaggaaa cagtaaagag taaccttctg cagaggtttg  45997
```

-continued aaaaggccac cccaacaggc caccatgttt cccatcaggg ccatccagag caagtgtagg 46057 tccagacgta cttcctgctt gtgtacctcc tacctacatc catccaatct gggccaaagg 46117 tcctacatcc tgagataatt cctgtctgca tgcatctggt gcagttgagt caagcaaact 46177 tgtttaaggg agttgcttcc agcctctctg caaggatctg tccttgggca agggacttac 46237 aggttagagg cattgttgtt taatggatct cttaggcaca gtaattagaa catacctttg 46297 gctctcacgg cggttcagtg gagtggttat tccactgatc ataattctcc acttactaag 46357 cggcatctgt tgcttttcca agtagggaga tattttttag aagcgaggag tagatcttcc 46417 agttgacatt gagaggagaa gaggaatctg acagcaaata tgttctagga tagaaagact 46477 tcaattatat gaacgttcat actgtcaggc tctgagtaga acattgcatg ggatttatta 46537 agctttttct tagagacttt gttcaggaaa agaggtttga gtaaacctgt tcggactggc 46597 cgtgaggcag gaaaatctta cgttctgtgt ggccccattg tctgatgctg ctgctctctt 46657 cttggatgga ttctgaggct gggttgctta tagcaaccag catgttgaca gatgcaggtg 46717 aggatgctga gagttgtctt gtgctggtta acttaggcgg gctacaggaa ggattgaaag 46777 gcttctgatt cactttgtgt gtttgatcta attgcttctt caatatccag ctgcagctga 46837 tttggaaaag aattttccat tagagacatg gtttttttgtt ttttgctttt gtttttcctt 46897 ttaagtacac atttgtaaaa ggtagcaaaa tgttaaataa aaccaattct gctgttccta 46957 gttcagtaat ctattataat tttggaggga ctagagctga agttcccaaa ctggctctac 47017 tttatggaaa tataatatgt tgtttaaaac cttctctatc tatgtattgg ctttcatact 47077 taatatttgt atcagctgct tctcttgttg ctgagacaga acatctggca aaagcaattt 47137 aagtaaggca agctggctct ctctctgagg gtagcatcca tcatggtggg gatgtcatgg 47197 aagcaggagg atgaagagct ggttgtgtca gatacatagt caggaagagg agagagatga 47257 atcctagcga ccaatttgtt ctctcctttt tttactatgc ctgtggtccc agcccatacg 47317 atgaacctgt tggtattcag ggagggtctt tactcttcag ttaaacctgg gtggaacaac 47377 ccacacagat tgttcacaag ttgaccacag acacacccca ggttcgtttc cacggagatt 47437 ctaaatgcag ccaagttgat gatgacgata accactacaa cattaactcc ccttgcacag 47497 aaaacccgaa gggaacatag gcatatattt tctagtttaa actcactttg ctgagctcac 47557 aacatcatca gaagactaca gggccgtagt cagtttcttt gaagagatat ggaaaagatc 47617 accacctttt gtcagcacat gtattctaca aacagatggc attaaaataa ttttaaaggt 47677 aagagggagg gtggcataga gaagtatgaa agacagaaaa acgaagttca ggaatcacac 47737 ttaggaaaat aaagcataat ttatttgata ggtttaatta aaaaaaaaaa aggtcaggta 47797 gtatgacagt tgtggaaagg acttgactgg ttttagctgc tccacctgta caatactagg 47857 cttgtcacca gtgtcatgga tgtgaggagc ctcctgtgct gacctattgt taaccattgg 47917 attgcgtgag gtgcgaaaga gaagatcatt tattgtcatc ggttgtgcat cagactatgg 47977 gaccaatggg cttctacagc tagttccaag cctgtagcta tgcagatggc ccgggatagc 48037 ttaaaatcaa tgaggaataa agcaaagcaa actgtcatga atgtggggaa ggggcttgta 48097 gagaggaggg gaaaggacag gagtgggagg agcattacag agggtctcta ttgctgtgaa 48157 aagacactat caccatagca actcttagaa aggaagacat taaacaggag ctggcttcca 48217 ggttcagagg tttagtccac tatcatcatg gtcagaagta tggtggtaca caggcagacc 48277 cggtgctggt aaaggaccca agagttctac atctggttcg tctgacagca ggaagagaga 48337 gtgtgtcact gggcctggct tgagtatctg aaacctcaaa gcctactccc agtgacacat 48397

-continued

```
ttcctccaac aaggccgcat cttctaacag agacactcct ggtgaccaag cgttcaagtg  48457
tatgcaccta tggggaccat tcttattcaa gctgccacag gagatgaaag taagcagtag  48517
acacttcata cacgtgtgaa tgtgtcaaag aacaaattta gtccattaaa aaacaaatcc  48577
aaggaacaaa aacctcaaat tactcttctg atggttccat tgaattcctt gatccccaca  48637
gtacaccacc agctagtgtt gttctgacgt aattgtgtat gtgcagaaaa gggaagggct  48697
ctttaggcgg aagggaacaa cagctctgtc attaggatgt cctcagctgt gggtggaatt  48757
ggaggatagg actcagaaag ggggtgatta gggaacaact gtgacatttc atggtgacag  48817
aagccaaaag gcagagactg ctaaggaaga aggattcaca tgttgcgaat aaggccagtg  48877
gggacacagg tactaagggc atcctctttg gtttctcaca ttgcagtcat atggaacctt  48937
tgagaggcag acaggtcagg gtgagatgag taaaccaggt tacaggggcc ttaaggaaca  48997
agtgaatgga ccggcgagat ggctgagcag ataaaggcgc caacaagcct gacaacctga  49057
gtttgattcc ctgggaccca catgatggga gaaatcgttt tcgcctacaa gttgttcttt  49117
aacttcaaca tattcgccag ggcagttagt tgtccaccac ccccgcccca cacacctctt  49177
atcctcacaa catacacaaa ataaataaaa attttaaaaa gcaagtggaa aatgttagcg  49237
gccagtgttt aaaatcacaa gatgatttaa agtttgtgac cagtggaaaa aaaatatgcg  49297
gacggacagg gtggagttgg ctatgtcgga tttactgcct gctttgtaca tacagttctg  49357
gatgggggaa agccttcatt ccttcgaatg ttgttaaagg ccctttctcc tatagcacga  49417
gccttaaata cgtactagcc ggtcctttca gggagctctc tgacccctga ctgtagaagc  49477
atgggcaaaa gtgaggaagt gtttgttcct cgtttggtgt gttcagcaga agagctcaga  49537
ggctgttgaa gagcagagca agagctgtta gtgtttcttg ctgtgtgaca ggttgcctca  49597
aacttactag cttaaaacga caagtggttc catttcagct tctgtgagtg aggaacttag  49657
gagtccttct aggtgctctg cctctggatc tctctcaaag ccacattctt tttttttttt  49717
tttcctgtgt tggtaacttt ttctttccat ttttattagg tatttagctc atttacattt  49777
ccaatgctat accaaaagtc ccccataccc acccaccccc actcccctac ccacccactc  49837
cccctttttg gccctggcgt tcccctgtac tggggcatat aaagtttgca tgtccaatgg  49897
gcctctcttt ccagtgatgg ccgactaggc catcttttgg tacatatgca gctagagtca  49957
agagctccgg ggtactggtt agttcataat gttgttccac ctatagggtt gcagatccct  50017
ttagctcctt gggtactttc tctagctcct ccattgggag ccctgtgatc catccattag  50077
ctgactgtga gcatccactt ctgtgtttgc taggccccgg catagtctca caagaaacag  50137
ctacatctgg gtccttttga taaaatcttg ctagtgtatg caatggtgtc agcgtttgga  50197
tgctgattat ggggtggatc cctggatatg gcagtctcta catggtccat cctttcatct  50257
cagctccaaa ctttgtctct gtaactcctt ccatgggtgt tttgttccca cttctaagga  50317
ggggcatagt gtccacactt cagtcttcat ttttcttgag tttcatgtgt ttaggaaatt  50377
gtatcttata tcttgggtat cctaggtttt gggctaatat ccacttatca gtgagtacat  50437
attgtgtgag ttcctttgtg aatgtgttac ctcactcagg atgatgccct ccaggtccat  50497
ccatttggct aggaatttca taaattcatt ctttttaata gctgagtagt actccattgt  50557
gtagatgtac cacattttct gtatccattc ctctgttgag ggcatctgg gttctttcca  50617
gcttctggct attataaata aggctgctat gaacatagtg gagcatgtgt ccttcttacc  50677
agttgggaca tcttctagat atatgcccag gagaggtatt gcttcaaagc cacattctta  50737
```

-continued

```
tggtcaccca tggctgtagc cagatgtcat tggtgtcact gaggtgtggc ttatgtctaa  50797

acttgctggt gtggctctga acgaggtcgg accttcttat tcttgggatt cagacctgga  50857

acaaacagat gaggtgcata tttaaccaag tggacctgac ctccagattc tcccagaatc  50917

cctcagtccg tgtttattac agggcatggc tggcataccc tgcctctgtg ctgaactttc  50977

cagcccaggg gaggggcttg ctctccccccc agaaggaggt cttccctaca caatccagat  51037

attttggtca gtctctttcc ccctccatcc ttctttccct ctctccctcc ctccatccct  51097

tcctcctttt ttccctcccc actccccccc cctctctccc tccctctctg catgcacaga  51157

ttctttctct tccccccccc ccctcctcta tctccctata aatggtgaca tccctggctt  51217

cattccttgg ggccagtgaa ctcacccaag agctgccctg ccaataccca tttttatact  51277

ttaatttggc ttgaactggc tctttttgtc agcagagata acctatcact taagattgcc  51337

caacaatgag tgagccgcaa tgtcatgacc ttacttttga acttgcacat ccccatttct  51397

gacaagcatt gtctgctgca tagacagact aatgcattat gggaaaggac tgcccaaggt  51457

cgtgatttcc aggaagcaga caggatcgtg gcgtctttct tgggctttga ctatcccagg  51517

agagaacttg ttacttaaat tctctttgca gaaggaaaca gtctctcctg catttgcgtt  51577

cagtgagagg tggtgagctc acctggcctg tgggagtgaa gaggctgtga ggctcttact  51637

gagggaaatg gtcctcaagg tgaggatggg attcttttga tgatagattc accaacttcc  51697

agtgaaagtt ctgtaactcc tctttggtta gggataagat ggcaaggtgt gctaaccgtg  51757

gaaatctttg ggacagagta gggctcacaa taaggtttgc agtgaccaca aacaagcccc  51817

cccttagcct ccacgccagg gatttcccca caggtggctg actatgattt gactttcttt  51877

aacttccctg ccctgttacc cacctgctta tttcagtaaa attggcaaga tgtacatttt  51937

gatctctaag atccgggctt tgaatttcct tcaaactctc gggtgagcgg ctaagatcaa  51997

gttcacagaa cattctgttt gggacacaac tttgcctctg gtggagaatg agacttccag  52057

tttcctggat tggtgggaga tgacaggggc ctcctgtgga agagttgagc ggccgcaaca  52117

tcgaagggag ttcttgtttg tttgtatgtt ttgttttatt tcaaaatggt taattctcca  52177

gtggaatttt ctaacgaaaa ctcagataca agctggccta gtggcacacg cctgtaatcc  52237

cagcactcag gaggcacagg caagtgatct ctgagtttga agtcacgctg gtctatacag  52297

tgaattccag gccaggcagg gctacacagt ggattctagg acagcttaag gctacataga  52357

gagatcctgt ttcgaaataa aacaaaacat aaaaactaac aaaaactcaa tgcagccagt  52417

ggctcagcat tgaggcactc tgatgacatc atgctgtcac ctctagtcta ggccttgtca  52477

tcaagcaggg actggcattg tgctgtgtgt gagcagctgc gggatatgag aatgtgggtt  52537

cttccacggg gcttatattt atgttagaaa cccctcttta ttgttagaac tttccaacag  52597

atactgcaaa atcttctatg gcaaaactaa agaattattg aatgagcaaa tgtccttcaa  52657

tactcttagt gccttccttt aaatactctg ttaaagaaca cgctgtcttc cgtaggttat  52717

tttctgagtc tgtagcatgt atattagccc aacaatgctg atgccgggtt gctgtgtgac  52777

tgaagagcac taggcatcac catcatattt tctgttcttc gtggagctgt ggattctgtt  52837

actaactagg acttattctc ttag gta ccc act gat ggc aac gcc ggg ctg     52888
                           Val Pro Thr Asp Gly Asn Ala Gly Leu
                           20                  25

ctg gca gaa ccc cag atc gcc atg ttc tgt ggt aaa ctc aac atg cac    52936
Leu Ala Glu Pro Gln Ile Ala Met Phe Cys Gly Lys Leu Asn Met His
    30                  35                  40

atg aat gtg cag aat gga aag tgg gag tca gac ccg tca ggg acc aaa    52984
```

-continued

```
Met Asn Val Gln Asn Gly Lys Trp Glu Ser Asp Pro Ser Gly Thr Lys
45                  50                  55                  60

acc tgc att ggc acc aag gag ggc atc ttg cag tac tgc caa gag        53029
Thr Cys Ile Gly Thr Lys Glu Gly Ile Leu Gln Tyr Cys Gln Glu
                65                  70                  75

gtaagtccct agtggtgcat caccggcatt cactaaaagt atttactttc ttacatctta  53089

tatttatatt ttctctcata ataaaaatcc tggttcctaa tgatccacta tacctttcat  53149

acagttttc tttactctgc agttcacaca gttacatact gctctgtgct atgaccatca  53209

ataaactggg taaaatttaa gttttcacag tttactatgt tctactgtgc ctgtgtaata  53269

aagggataaa ggaattaaaa gtgctagatt taattattta tttttgttca acctctttga  53329

catattttag tacaactaca acttgatatt tttctagctt tttttctcct gtaatattgt  53389

atctttgaag taaacattta tgctgataac tctagaaagt atacagaagg tcacttccac  53449

ttcatcccat gctgatgaat atttttattc tttaaaacgt acatttttat ttcttgtata  53509

tggatgcttg ttttgcctgg gtacatgtct gtgtaccacg agtgaggctg atgcctaagg  53569

aggctccaga agaggttgtc acatctcttg ggactggaat taccaaagta cagttgtgag  53629

ctttcatatg gggcttgga gggaggattg aagtttcctt ttctgaaatg cttgtgttca  53689

gagtattttg gattttatag aatttgaagt attcgaaagg tcatgttgag ctgctttgtg  53749

gatgggaccc aagtgaacat gaaattctta tctacttcct gtatccctca cactcacaac  53809

tgtaaggtca ttttctgtgg tgcttttcgt ttgagctcct tttggactgc agcctgtccc  53869

atgagatcag gtaggaattt cccacatata gattcagagc agctttccaa aaagtgcctg  53929

gttttggaac atttccaatg tcctgtgttt ggaccagaga tgctcagttt ccgtcttctt  53989

tgcctttctc actagccctt tttgaaagta agccacagtt gtcaaggact tttcctgccg  54049

ctctatgaca tgggaaggaa gctgtctctt caggtagcta cctgtctgta ccctaagttt  54109

cccatgattc caaagtgcta gcagtgactg actattccag tagacttcag cagaggccag  54169

taggaaggct ggacacacgc tttgtccgtg atggtgcctt ctgaatttct atgtgaatgg  54229

ttgttagtac ctgtggatca tcccgtaagc ccgtgttttc cacaaatgac cacatgtttt  54289

taagcctatg aatattgatc ctacaaagat tattttcctt gactgggaag agccctcact  54349

tcctgctgcc ctgagcccag tcatgcctgg gtagcttcat tttctgtttt agtttgtggc  54409

ttgtgcaggg atgagccaca gactggttct ttccactcca gactgcctgc ttgcgggtag  54469

ccatggggga ggagcagggg aaagcctttt ggcagatttc ttctttctgc cgctaatgta  54529

gcattcatct ctccttgctc atcacctgca gtccattgga caagaaaggg ctaacatatc  54589

aagggtttgc gagccatttt catgaatttg gtccgcatcc tataacaatg aaaagccact  54649

gaagccattc gttggcttaa tttttgaaga agaggagaga ctacgttgga atttcagagt  54709

caaccctatc cagtatatat cactgtagaa cattccagac acctggtccc aagcccatgt  54769

gacggagttt ccagtcccta tgctttttgt acagcttgag cacttgaaat gtggccagtt  54829

agatctgtac tgttgagata aatgtcatgt ttcagaaatg taataccaac aaaggcatac  54889

aacatagatt tcattttgaa gtgactatat tgtgtgtagt tattaaggat gtcataagga  54949

tgttacagtc aaactatatg gggttaaagt tgatttcacc tctttgtggt tttttttgt  55009

tttgtttttt tcatgaagct ggaaaaaaac ttgaatgtcc actggccact tgtttgtatt  55069

tccactcagc agtgctctcg gcttgtccag tgtcactgtg acagggtcgt aatcaattca  55129

ttatccggtc atctgaagca taagagagaa atgagctggg gagtccccac agattgccac  55189
```

-continued

```
tcagaaggtt cttggaagcc tttaaatcac attgttcaat ctgggtgtgg tggctctctc  55249
ctgtaatcct tacactggca aatctgagcc ttagctatag aatgaaatgt ctcaaaagca  55309
caaatgaggg agatagagag atggcagagg gagatagaga gatggcaaag cagcttagag  55369
cacttgtccg tctctcaaaa catgctggtc tgattcccag tcccacttgg tggctcagaa  55429
ccaaggatag ataactctag ttcctgatgt ttgcataccc tcttgtggat tgcatgggca  55489
gcaggcaccc atgtgggtgc acatacatac acatgcatac atgtgggaaa aacacagatg  55549
atataaaaat aaataaatat aaattagtat ctttaaaaga aagaaaatca tcttactaga  55609
atgtttcaag gtgtggagaa gatataagag ccagtgtctt cctctttgag acatttgcct  55669
ctggatggta agatctccgt gtagacccac taattaacat aagaggagca cagctccaga  55729
cccaaggtct tagtgctgta aattgacagg gcagaggtga tgatgtcacc acttgtaatc  55789
ccttttcatt cttaacaaag cctcagcctc agggccaagt gcttctgtcc ctttaaccca  55849
cttagtgaca cttctggaaa ggagccttgg aatagacctt ggggaaatgc aacatttaag  55909
gggaacaaag agatgctatg aagtggccag agacaggacc agaactggca tgtgtcatgt  55969
gctgggagac aagctaagtt aattgctaaa cagagaaaaa tgatgagaca agtatggtca  56029
aaaatgagag cgactgaagt gtgattttta gcaaggtcag cgtgtgcctc catgaaaact  56089
gaccacatgc caaaagcagg tcttcagtgc acttcttaag gggagaagag tgtaagcttt  56149
tcagactggc ccaggttgac ttggataggg gtagattctt agcacgtttc aattgcatgg  56209
atgtgaacag ggatcaccag caattatttc cataggctag gaagcattga cattgctcac  56269
agggtctgtg cccataagcc tataaaatca ccactcaact ctaaaacagt atccctcaaa  56329
tcaaatcatc tttctccgac tagctttggg tactggacag ccacatctat ctgcctttta  56389
ctggctggat actgcctttt attaggcaga aaggttgtct tttcttcttt cttcctttct  56449
ttctttcttt ctttctttct ttctttcttt ctttctttct ttctttcctt tcttccttcc  56509
ttccttcctt ccttctcttc ctttttgttt gagaaaatta attttgacaa aggacattac  56569
ccttaataga gacaagccta attgctacaa atatgacatg accaagtggc gaggataatt  56629
atcactctga ggaaaaaaaa atctagataa agagcttgag gtgaacagag gcaaaggaaa  56689
ccatcttcgc tttagtattt atttattttt tgtttgtttg tttggttggt tggttgattg  56749
gtttttaatg atggcaactt aagccaaagg agactgaagc caaatcaagg gaagcatagt  56809
tgtccatcat aaatctcagg tgtgtgcaga ggaggaggct agatattgca ttggacacag  56869
ctatgctgtc cagtacctgg gaggctaagg caaaaggatt aaaagtcaga ggccatactt  56929
ggctacactg tgagattctg tgtccaaaga gagagtaggg tgagccgaaa gatctgaagg  56989
tgaaaggaga ctccgctgaa tctggtgagt tttggaaatg gcaaagaatg accttttttcc  57049
aagaaacggt taactaggta ggttctgttg cccagagaca aaaccaatgg aacagcccat  57109
gtgtgtggaa gagggtttct cctacataga gaaaaaccct gggctgaagg cagctttcaa  57169
agggaggaag caggactagg tcctgtgttg gagtgttgga gcagagaact attcccaagt  57229
gctacttctc ctgttaatgc cgttctttgt tctgccttta ctcctcttct ggtgctaaga  57289
tgggtgcccc ttggggctca ggaaggtcgg aagctggcag ccagtgcttc tgggagtggc  57349
atcccaactt tgtttgccat tgtgtattgt aattccaggg agaagggatt ctgagtggct  57409
tcgtgttgac cacacaaaga tttggcgcct gcaccagggt acttacccat gtggctgtgt  57469
ggtctggcaa cccacaaggc atggaagaat ggctgctcac agaagaggga gagaaatgca  57529
caaggccaaa acggaatgac tgtggccctg tgtacagtgg cgacagagct gggtagttct  57589
```

-continued

```
tttggctgaa agtgctggct gggatccaca ttgggtcttg actttaactg gcacagagaa  57649
aatggcagag tggctggaga tgaccacttg gggccgttaa atgtagtttg acattgccta  57709
caagatcttt cattagtgtt ttagtgttta gtgtttagtg tttccctgcc acttcccaca  57769
ttgtagctac tcctggtatt tttaataaat agctctgatt tatagatctg aatttttttgt  57829
atattttgct agaatacatt tctttgcttt tattccttct ttaactatgt ttatatatta  57889
agtgacattg attgactcat tgcatgaaat gaaaaggaaa ataatactca acaatttttg  57949
ctaaattata atatttttat atttttaagg ttgaatatta aggtatgttc tgttgcagga  58009
attcccatgt cagatatttc ttttcaacag gacttgttta gagctaatgc ttccagccat  58069
gttctaattt ctgtattact tattaggctg ttatactgtt attattattt tgatgacttt  58129
tgccttaatt agtcatttgc aataattttg cttagtacca taaaggtgat ctcctttttg  58189
ccatctctca ttgcacagat tcctttgaag aattctttgc aaccctgaga ccagagttct  58249
acccccagaa ctcattgtag aaaaagctac atgtgaagta caattataac cctagtgttg  58309
gggagccaga gacagacaac tggtcaacct atcttactta gcgcattcta ggagaatgag  58369
aaaccctttt caaggggggaa aaaaatcaaa agatgaatgg catgtgatga atgacaccca  58429
aagttgtcct ttggccaccg cacacatgag cacacacaca cacacaccag aaatgatctc  58489
tacttattac cagtaacagg actaaacagt taatggtttt ttgtctccct gtaatggtga  58549
ctttatttta tgcatggact ctaacctccc aagactgaga cacagatgtt ttagaagcaa  58609
tctgctgagt cagagaggca gctgttagca gtctgagcct agggcagaca ggaggagctg  58669
aactcatgac tataacctca ttttgacctt ttgctaacca actgaatttt cctgctaaat  58729
atatctgtaa tagatgcctt taactgtttg ctggtgctta gcccagggtg gtatcttaat  58789
attgatcctt ttatggggaa ttaggtatta actagtttat gtcctctgat ctctctcact  58849
cttcttggct tatcttccct gctattgact tgatttggaa gtctataaga gtggcattta  58909
tgtccctttg gttcctttgg agctatcctt ggtcaaggga aagaccgagg agaaacagta  58969
atggctgaat attttacctc tactcctagg tacacataag gccttatgaa gtttgattga  59029
gaaaatagtt ttgattgtat gacctaatgt gtatgtttgt tttagccaca tgttgaccag  59089
gtcttccaaa tgtttgatgt ctatatattt ccttctgtcc ccagtcatag tagtttttct  59149
tctacccagt cattgttgaa gtacatgtct ctctctttta tttctatgct ttttattagc  59209
tccatgtaca gtttttcttc agctccttat caagcacata ttgagtgctg ttaaccaact  59269
gaacaattct gcattcccaa agttcatagg ttaggctaac tctctttaga taggttttgg  59329
agacacagtc tttcagagat gactagtatt gatgacgtca tgagggcaga gccctccaga  59389
tggtattgat gcccttacag aaactgcaga gagccagctc tctttacttc ctcatacaaa  59449
ggggtcatgt gaggatgcag tgtgaaaata gaaaaatgtc ctcagcagca cattcggact  59509
tggttttgtc actttcctga actgtgacaa aatagatttc cattgttaga gttgcccagg  59569
gtgtggtatt ttactgtagc atgtccacca ggaccccatt atgtctcctg taggtaaagg  59629
ctctagaaac ccatggtgct acagagagtg acatttttag ggtcatgatt cacaaagcat  59689
tttatctgac aactgaagca tgctggtggc catttggtaa tgctggtgga tgactttgtt  59749
agcatgagac tgtagtagga tgggcagagg catccttgtc tatcctgagg gagagttccc  59809
tgcaggagca cctgtggttt ctgcctgagg ggccattctg ttctactgtt cctggtttta  59869
aagttgttag acaagagtca tgggattgca cagatttggc ctcattttat atacccaaca  59929
```

-continued

```
aaaagtgcaa tgagaggacc tgcaacctta gagagaaaca cagagtgtag ctttaaaatg  59989
ctttaatatt gtctgtgact ctttgatgga ggaaaatagc cttttctatg atcaatacta  60049
gaagcagagt gctaacatgg agaaagatac ttaaatgtaa cttcataaat ttaacaatat  60109
aacaatagcc atttgtgcta atgagctgtt ggggtaccat ggcaaatgtt atggctgaag  60169
aaatgtcaaa atagaaaaag cctcagagaa acaaatatta tgtattttct atttgtggtt  60229
cctatgcatt gtatagattc ataaaatcat gtctgtctat atgacatgat ggtatcaatg  60289
agatgtctaa gggaacaaga ggtgacagtg ggtggtatag ggtagggtaa ggtagggaaa  60349
gctatggagg agaatatatt cattgtactg tttaaactta tgtgagagct ctttatgcat  60409
ctgagtgcca tgtacaatgg atggacacac tcaaagctgt agaaatatta aaaataagag  60469
atcaaaaacc attaaaattt agggtcagaa aatgagactt attaggtttc attgcatggc  60529
tttcaggtga aatgatattt ttttaaaaaa aaaatatatt gtttcatgta caccaaaggc  60589
ttcagggtgt gtttagttcc acgtctcaag actttatttc tttactttta agccaggcaa  60649
ccctggccag cgtagctaaa gactaccgag gatagggctt tgtgtcagac aatgcctttc  60709
ctggcttaca aggggtgcaa acatgctctg ttccatcaga ttgagaataa aacctagaaa  60769
atggagacag tggtaggtag caaggagggt cttgatggtg atgtggagac tctggatcca  60829
ggttttgaga gatggaagcc aggggatgtg ttagtatgag tgcttttagt gagacatttc  60889
agtagtgtgt ttcaaaggtt gggctgactg gggagagaat ttattttaca aacagaggtg  60949
ggaaaatgga tgtgaaagat catcctctga attctgtcag tgaccccatg gtccagtgta  61009
tgaagtacca tgattcaggg caatccacaa acaatgtctc agactgtgtc cttcctgtgt  61069
aaccgggaca ggcagatgtt atgaaagcca gttgttatga gaaatcatat acagccttga  61129
tcctcctctg tccccctctg gtcttaagca cacaggaagg acttttgcta ggcaaagctt  61189
cctgaaggaa gggttggctc tttgagcatc cacttggagc cagcctgtgg aggctggctg  61249
aggatgggaa aagtttcaag tgtaggtagt cagatggacg cacttggctt tttgcatttc  61309
ctctactctt agattattca cacattctta agtaagtcct ttatattcat gacaatgtct  61369
gtgatttctt tatccttgtt cctctatttg agtgctttct ttgggattaa caggccctca  61429
aaacaaagta gtcctgtgca gaagcaaaca aacaaacaaa agctggctat atgaattgaa  61489
aacagctctt tcttttccct aactttctat tctaaaattt attatataac ccaatgtggg  61549
attcccagga agagttattt ctctttctgt tgtcattctt cattaatagg aaacaaaatt  61609
gttaaaaaga caaaaacagt ttgtcctcat caatctaact gtctttcagg gttgccctgt  61669
gataaacagc atccccgaaa taaacttggt ttgtttcagt tcacacgtta cagtccatca  61729
ctgagggaaa ctaaggtagg aggaacataa ggcaggaatc tagaagtagg aactgaagca  61789
gatctgggcc atggaaaagt atgggttact ggctggcttg ctccaggctc ctgttcagct  61849
acttttcttg tctagcccag gcccacctgc ctagggatgg tactgcccac agttccaggg  61909
tccccctgta tcatttaaca gtgaaaaaaa tgcccataga catgcctaca ggccagtgtg  61969
ttggaggcac ctctttagtg gaagttcctt cttttccagt tcctaggttt gttacaaatg  62029
gatagcagat gctataggag tgtattctat atactgttgt ttctctctgg tcactttatg  62089
tgctcaaaat taacccacag atcataagcg tcatagtcct gatacttaaa aggtccaaga  62149
attcatatta agtaaagcag ttttttgaat cggtggatca taatttttga atatgagtac  62209
tggtgtatat tctgcatcga tggtctattt ggattcaagg actacttgga acttagggct  62269
aaaagagatg aagtcagtct aaatattgta acataagaat tatagtgagg gtgtgtgtct  62329
```

-continued

```
tagtaagcct tctgctgctg tgataaaacc ctgaccaaat ccaactaggg ggaagaaagg  62389
gcatatttga tattatactc ccaggtccca ctccatcact gaaggaagat aggtagggca  62449
ggaacttcag taggacctga agcaaaaacc atgcagtatc gctgtttgcc ggcttgcttt  62509
ccctggctgg tgctcagcca actttcttag acaacccagg acctctttcc tacctggggt  62569
tgcatcaacc acatcaatca acattcaaga tggttcccca cagaccagtc agtcaggcag  62629
gcctgggcaa tccctccagc gagcctccct cttctccagt gattcttggt tgtgtcaagt  62689
tagcaataag aactgacaga gagaaaactg atgtctgaat gaggccatgt gtgtacgcat  62749
gtgtctttgt tttcacatct gtgacgtgcc ttacacgcta ggcatcccct ctttgctttt  62809
ctcatgagtg ctttggaaag gcagcggcat accagccaaa ccaggctcct ccgtgccttc  62869
ccgcaccaag tgtgaatgtg cggctagaac aacacattaa tatgcagtgt cacatgcaga  62929
attgggccaa atggttggga aacacactct tgccttgcag cgctttgcct tctgcctcgt  62989
gcaaggcatc cttgtgagag cagggcccac tctgctcccc tctctctgac attgcagacg  63049
tgtttcatca gctgcctgtg cctctcagca cctcattaag tcacgagcag ccgccacttt  63109
tcggcttcca tttctctttc tcaactgaat tagatgttct gttttctata tcccctctca  63169
ttagcagaat cgaggcggaa aacagtttta agatgcagtt ttttcatcag gttctagaaa  63229
ctttaaagtg tgtcacttaa atctggaaac agaaatgtat tctcttccgc acaccccagt  63289
cttggcttac acacaccaaa gtttaagcag cgaagcgcgt gctgttaatg tggtctccgt  63349
gtgcttagaa aaggcacctg cgatagttgt caatccgctg tgacatgctg cccaggagat  63409
gtttgcagtg atgtctgcca ttggggaaac ctttattatg atctggtttt attttcttct  63469
tgagcattct cttcgtatgg ttcaacctca tggaccacat cagttctgga cgccatagtt  63529
tgctatgcct acctgtgagc taaatgtctt gaaggaagca tcacaggtta catatggggt  63589
tctggtgtac agacttaaca gttcctgaca ttaaaaaatg atagagaaac atcctttaag  63649
atagtactgc atcctttaag atattttatt ttaagaataa aaaccctgac taccgatatc  63709
atctttttgg gttgttttgg ttgatttttt tttttttttt gagataggtt tcccctgtgt  63769
agctctgact gttccagaac tcactctgta gaccaggctg gccttgaact cgggtatcca  63829
cctgcctctg tctcctgagt gctgagatta aagctgtgtg ataccacctt gctgctacca  63889
ctttttatag ggaacccaag atggtttcta catgaccatt tttctggctt ttggtatttt  63949
ggaatttttt caattctcta tttaaaaata attttataga ctgatactta atcctttaat  64009
gatatggcat gattctagga ccaggtaaat gggcctttaa aaaaaattgt ggatttaatt  64069
cttccaacag ttcatcttca gctgtgtatt attgttagct tatttcaacc caagatacta  64129
ttagaagtat aacctaccac ctctgtttag aagaacaaca ttgagagaat tatttttctc  64189
aaaaagcata aaaccaagta gctgtcttat agtcattggg cctagcagat aggtgtgtga  64249
tgcccagcaa gagtgtaaga catgtaaacc atttccatat tgaattgtat caggacttaa  64309
ccagaaataa cattaaatat ttgtcagaca ttactgtgct ggcatagtgg gaggggtggt  64369
gggtggggac tccaactgca ccgcatggct cttgccttca agaaggacat gttccagcag  64429
gtgtctagga ggtaggacac ggtcagttgc caggtgttgt cagtgataat agccatggca  64489
tgaagtggcc ttgttccaga aaaagaagga ttcgtggagg ggcatttgtg aaaccagcaa  64549
ataaaggggt ccatttctac tcagctgaaa ggaacatagc actaggtttt aatgtatctg  64609
agggagatat actgtaaagg ggtgtttcct agaagctgag tgcccttgtt ttgagtttcg  64669
```

-continued gaggctcggt gctcttctgc agcttctctc tctgcacctc ttcctattta cctcccctgg 64729 attgccctgg ctcctgctgg gcaccgtaca cctatccacc aagcccaata ctatagccag 64789 ctacttgctt ttatgctttt tgaaaaaaag cattgtcatc ctgatgactg gcttccccgc 64849 ctttgctctg gcttccccgc ctttgctctg gcttccccga atacccagaa ctggaaccac 64909 aggtgttttc cagctaccat gttgatacta ggaaaggaac ctgggtctcc tgtaagatgc 64969 aagtgctctt aactgctgag atatctttat ctgcacccat caagtccatg attttcatca 65029 agaaagcaac cgtacacaca aaacgtagca aagaaaggac cacaaacaag gatttttttat 65089 gtctgttata ctagcgttct ggtacataca tcattagtga cagttgtccc actaacagca 65149 tattttcgaa tgtaaagtac ttgcaaatta catgtaattt gtaatgcatg tgagaattga 65209 ggactaatgt ccaaagtttt tctttaactt ctaacaactt cctgctgttt aggatggcaa 65269 aatattattc tttttggcga ttccagatta ataatccttc atctctgagt aaaagtgact 65329 gagtcaggtt gaagttgctg catccatgtc acagatcagg gaaatcagac aaactgcatg 65389 tgacatgact gacatatgcc agcagtcaca tacaggactg cacctgtaca cattatatat 65449 atatatatat atatatatat atatatatat acttaaacac acacatacac aaaactcatg 65509 gcatctttgc ttcctttatt aaaatttact gtgtcacaaa aatattaaat gttgtcctgt 65569 ttcttgtgat taaatatgat gaataattaa atattgttac aaggttattt acacattata 65629 attcacttaa tttttgtttt gttttgcttt tttgagacaa gtctttctat gtattcctgg 65689 tagtcctaaa accaggctag cctcaaactc atagacatcc tcttgcctct gccctcaagt 65749 gctgagatgt aagatgtgtg ccaccacacc cagataattc agtttttatt cttgactaag 65809 acagtgcatt atgtgatcta atctatcaac aaaaaatgca ccattgtctc tatagacttc 65869 ttctggagct acttaaacaa gcattcataa attttttttt gtaattttta aaaatatagg 65929 tgtttcgttg tgtatgtttg tctggcattg ctttgttggg gtttgtacct gtgcaaagtc 65989 atcacattac ctagctggcc attcagtact tcaaaaggaa atttactact ttaatttttt 66049 ttaaatcatc tttttcccct ttaaataaac ttcctgctat ttagaatggc aaaatattat 66109 tctctttggc gatcccaaat taataatcct tcatctctga gtaaaagtga ctgagtcaga 66169 ttgaagttgc tgcatccatg tcacggatca gggaaattag acaaactgca tgggctttat 66229 gcagttcggg ttttataatc tctcatcttt ctgcatatga acactgctgt cagagcatgg 66289 agggaggtgg agaagcccag ggagtcacat gtgtgtccta gattctctgg atagaattgg 66349 aaattaattg tctggctgat cgccattcaa agctctggta atctcaaggg agagccacat 66409 gttcacaggt ttggtctgtc agcttgccat cttctctgca cagacactgg gcaccgaaag 66469 atttactggt ccgctgcacc agatattatc ctaggagtct gatggtggtg tgtgagcaat 66529 gggagcaagg aggccccttc tcctgctggt ccatttgtaa actcaattcc ttggttgtaa 66589 tggaaaggaa ggaaatgtgg tgtgactgta ttagaggaat ttatagaaaa atgacgtcta 66649 agatgcgtct cgtaggggca gcatttctaa agtgccagct gggttccctt tagaaagatg 66709 cagtaactca cacttcactg cacataaagt cctatccccc agggcaaact ctcatgccat 66769 cgagtttatg actcacaagt gctgtttgtt tgtggtctaa taaacaagaa aaggtgggag 66829 aattatattt ctgtacacaa cgctacctgc cctccattat agagaataat gctatggggc 66889 tcttaaattt ttagtggcat tttcaagggg agcattgccc gggccttaaa tgcatgtact 66949 cacgggttgg agatacttaa gcacaaaacc aaatggagcg aaggtagctg tgccctttgc 67009 agctaaactg ctggtcgtgt ttgaagaaca gggctctgcc ttacagacga aactaattat 67069

-continued

```
tacattttga tgttctcttg tttgtgcacg catgtgagtg cgtctgggtg cacaggtgcc  67129
aacaggtgat tgctgaagat tgaactcagg ccagccggtg ccttcatcag ctgagccatc  67189
tcactgtccc cgacttgggt acttacgtat ttgtttagcc acatgattcc tctgattgat  67249
accttgtgtt ttattatttg agaatatagt tccttttttt ctttgaaaga gaagtcatac  67309
atttaccaaa aagcataaaa gacggcagag agatgcagta gatttctctt atcatgaaga  67369
tattctacca gaatgagcca gccctgacaa ggcatgaacc cacactgtca tgctttgtcg  67429
ctcacagtct atagttggtc ttagggcttg ctcttggtgt tgtagctcct atgggtcaga  67489
taggcgtgtg tgtgtgtgtg tgtgtgtgtg tgtgtgtgtg tacagggtta tacctacagg  67549
gatatgggca agcatggaca ccaactttga gtgtctattc ttcaagagcc atctcctttt  67609
tactttttgt aagatttatc ttattttgtc tgtgagaatg ttttgcctgt atagatatgc  67669
accatgtgtg gtgtctttta tatacaccgt gtgtgtgtgt ccggtgccca cagaggtccc  67729
aagggctgct agatggcatg acactgatgt taagaatgct aaccacaatg agggcgcttg  67789
taatcacaaa caattcctct gcaagaacaa taactgcttt ttgttagcct gagttgtcct  67849
tccaggctta tcaccttgtt ttatgagaca gggtctctta ggcaaggcca actgctcaac  67909
gagtctcagg gatctggctg tctccatctt cccagctctg taattacaca tgagcccccca  67969
acatgcacag ttacagggga ttcatctctg gctcataggc gagtgctttg tccagacact  68029
gatcgttttg ctgcctgtgt agagaattgt ctttatagac tgtcatgtct ttataggaag  68089
tcataacagt atggatcctt tatacactga tttctgccac ttaatggtag gcatttattt  68149
cagttccctc tgtgtatttt cttagctaga tggatcattt tggggggaga ggatactaaa  68209
tatttctgtg tccacaatgt aattatgtag tttttaaata tccattttca tcgtcctgtc  68269
tttcttcctt tcctttcctt tcctttcctt tcctttcctt tcctcccctc ccctcccctc  68329
ccgtcccctc ccctcccctc ccgtcccctc ccctcccctc ccctctcctc tcctctcctt  68389
atctttcctt tcctttcctt tcctttcctt tcctttcctt tcctttcctt tcccttccct  68449
tcccttccct tcccttccct ttcctttcct ttcctttcct ctttcctttc cttttctttc  68509
cccttccttc ctcccttcct cccttcctcc cttcctccct tcctcccttc ctcccttcct  68569
cccttcctcc cttcttttac aaacatcttt tacctcacaa agtaaggtga ggtaatcaag  68629
gcataagtaa tatcgtttta tagtatttca attagatgcc cccctccccc cataactgca  68689
atggacaaga tgtcagcatc ttaaatgaag acagggtcac tctgacaatc acaaacaaag  68749
taccgcggcg tatccacggc tcccaggtgg gcacggtgct ctagttcagg ttcctaggtt  68809
ttctcagcag tgtgcgcaga agctggggat gagtctgttc cgcatctcca gctccacacc  68869
cctccccctc cccccaaaac ccttaaacct gtctatgaac tctagtgctt tcagcctaga  68929
ctgtctttgt tgtctatgga tggagttgac cctgagccct actagcctgt ggtacgcacc  68989
ttcaatcttt gaagtcttct gcttctggct tcctgtcatc cattacaacc cttttgtagg  69049
ctgtagttat ctgggaggag tcagtgatac ctctggtact tccgtttctc aaacccacat  69109
catgaatcct tcagggacat tggcttcttt ttgttttgtt ttaattatct actccctttg  69169
atggccatat ttatattcct tgcgattacc aataattggg actttctcag attcctaatt  69229
ttaattccca aactctccca agcactagtc cttcctggct cactttctat aatatgtcta  69289
caccaaaccc tttagcccat tccagaattc gaatcctgtt gtcttacaac cttttgactg  69349
tgtccaattc ccttcatgtt ctcaccttca cctcctggat tcatcacctc cagttaaact  69409
```

-continued

```
atctgcttcc ttacagcctt tagtaaacta tttccctggt tatttatctc gcaaaatggc  69469

tcactttaga gccatattgt gtattgctat tcttctttca aatctctaac ccattattat  69529

tattacatag aagtggtttg atatttcaca aatacatttt ggttgattga gtttgacatt  69589

tcgttccaag tgatcagcaa acagcatgat tcatgagcag cagtcatcac agacagagat  69649

aagtagttta ttactgaagg aggagaattc ctgagtgccg tcctttaaat ggctctcttg  69709

aagatgcact taataaaata tttttgtgta aactgttttg aggacagagg ctgatttttt  69769

tgtgtgtgtg gaaaccatct atgtgccatg ctctgtgcat gaagtatttt tcagatagca  69829

gtgagttgaa tataagtaga gatgacaacc ttaagtatat cagtcccagg gtttctttag  69889

aatactacaa gctgtggtct tccctagcgg tttattttgc atagaaaatg acctcatgct  69949

ttcaagagtc tgtgctttcc catggttcta gtttaactct cctggacagt gtctgaaaag  70009

acagctcgat gcaagtcacc ttggagtgga atactaggta cagccgctca ggcattttcc  70069

tttgtatcag tgtccgtgct tggccagaag cagagcaact tggctcttag agaataacgg  70129

aacctttgaa taacagcgaa ggttcaacat gtactctgtg tgccagccag gctttgccaa  70189

gagtaatcat ttcctcttct cctgtgttcc ccag gtc tac cct gaa ctg cag atc  70244
                                     Val Tyr Pro Glu Leu Gln Ile
                                                         80

aca aac gtg gtg gaa gcc aac cag cca gtg acc atc cag aac tgg tgc    70292
Thr Asn Val Val Glu Ala Asn Gln Pro Val Thr Ile Gln Asn Trp Cys
        85                  90                  95

aag cgg ggc cgc aag cag tgc aag aca cac acc cac atc gtg att cct    70340
Lys Arg Gly Arg Lys Gln Cys Lys Thr His Thr His Ile Val Ile Pro
    100                 105                 110

tac cgt tgc cta g gtgagccggt tagccagcca cccccacagc tcgagctgag      70393
Tyr Arg Cys Leu
115

gggaggatgt tgtaattagg tcatattcat gcatgcacat tttatcagca tgtcactgcc  70453

aacatattgt tggtgccata cctttgagtt tcatatctgc agattcatcc aaagatgggt  70513

gggaaaaaaa aaatggaagt gcaaactcca aacagtcctg tgtctgtcct tatgtttcat  70573

ttaaattgca ttagatattg gaagtaagga gaggcgatgt atttgtttct tcattattta  70633

gtgtggtgat tgagaacaaa cataggactt tataaaggtt aggtgagcat tctattaata  70693

atgtgtatcc caagcctggg ggaggtgagt taaagtttgt aagcacttgt atgtaggctg  70753

taggagaata ctcattttct atgaggcttg aggttttagt gtccacaatg catgaaaggg  70813

cctccctccc tccccacaaa taccatggga gtgtatacta ctatagtttg gatggtgcag  70873

gtactgccct gtgttctttt aatacaagac cagcattcct tagctctctg cttctgaata  70933

gctttcctgt ctcccagcca gtccctggtc ttctgagtgg aaagtgtctg ctggtgaaac  70993

cccagagact tgcaagggat tctcgtttac actgtccagt gttacaaatg gcaggccttg  71053

tatatttcct cacaggattt cacaggaaga ctataatgtg aggtctccac actctagcta  71113

attcctcaga aagcccttcc ctagggcacc ccttgttcct acagttgaaa atgatcagga  71173

agtatgtttg ctggattgtt tgattttata tttattcaga tcgaaccgaa ggaaaccatg  71233

tgttcacaaa ggcctgaaaa ctctactttc atttttatct taaaaaatgg agtccttttt  71293

gtcttttgag aaagccatct taagtccatt ttcaatcttg tcacaccttc ttcctggcat  71353

ttcatgtgaa caagcctgcc atagctagcc ctgtttgatg tgataaatcc cacttgaatg  71413

tttccattgt tattgattaa taagaaggtt gtaagaatgg agatctttat atggatagtg  71473

atgactttga ataaagtcta aaagaaatct tttttagaga gtcaccgttc cccttccagg  71533
```

-continued

```
tacaaggagg tgagtttgca ttccaacact ttagctacaa gggctccaat caaaaccttg  71593
taaataaaga taaatactga agactctagg aacttgtata gttttgttta gctgtggatt  71653
ccatagagca tactggaagc tggtggaaca gctctgcagt taagagttct tgctgctctt  71713
ctgaagaacc tgaattcagt tcctggtact caggttggat gacacacaat tgcttgtagc  71773
tagctctagc tccaggagat ctgacaccct cttctagact tcaagggcac ttgcgctcaa  71833
atgcacctcc cactcctatt tttatatatt ctttcaagga catgctgacg tctgcttatt  71893
tgcgcatgta atttgagaca tcaacagaaa acatgggcca ttagaatgaa gatctcacct  71953
gtgtttcata ttcagtaagt taacaatgaa gacaatgttg aaccagatgc ttgaccattt  72013
gatagtctgt gtattctctt acactccctt attcctttaa tcccttatta gctctttaag  72073
tatggttgag aagtcaagat ttcataagag aataataaga gccagatttt acactgtggg  72133
cacataggaa ctatcaaaat cttagttttc attatgataa acctcattat atcattcagg  72193
gacagcctca ctaatttgcc ttttagtcct agtttatgta gcaaacacca attagtgacc  72253
tgccccctgc ttttccctca actgttagag aacgattttt cactggttga ggtttgtaga  72313
gatgtccata caggtcagac aggggtaaga gaaagtggag aggtgcctca aaattgtcca  72373
agagatcctg tgaggaaatg aggaagaccg aattccctgc tgcctctgtc ttcggcaagg  72433
accagatttc tcttttatct tctaaataga ttctgagctc ctttgatgtt gaagtacata  72493
attcaaggag gcaggccact tgtgacatgt ttagaaaatt tcccgggtct ggggcagcat  72553
ctgatctaaa tcagcacact gactctaact gttcctgact gctaatagac tagatgatca  72613
ttagatactc ccagcaggca tttggcctgt ttgaatcttt tattgtgttt ctcctataaa  72673
gtccctggtc ttttcccatt ggatctgaaa caaagggtca gttgacaggc agagcatacc  72733
tgtctcttgc tttgccaaag agcttagatt agaattaagc aatgtgaaca ttgtcaattt  72793
cttaggcagt ggcaaaattt ctacgtgtct cagatatgtt acacaaggca tataaaatgc  72853
gctgatgtgt atgtgtggtg tatcttcagt tttgagaaaa aggaattaca gaacacatat  72913
aactcatgtc tattgtttgc atgaacattg taagttgcac ctcttcacct actgtcttca  72973
ttccttccct ccctcttccc ctggcttcct gatctgtcct tcatcttgat gtcctgtcat  73033
tggtggcatg ggtcatccat tggaatggct atcccataag gttgactctg ttggcctccc  73093
ttcgggagta taagtgttca ttgctagaga agttggattt cttgatataa gtcacacagc  73153
catgatgtgt tcagatcagg accagagccc acaatttctt gatttcttat tatctgtatt  73213
ctttataatt tttttaaaag aattaggcct ggcagtggtg gtgtgtacct ttaataccag  73273
gacacagaag catgtggatc tcttgagttc aaggccagcc tggtctagag agtgagttct  73333
aggatagcca aggctacaca gagaaacctt gtctcaatgc ctgccacata gaaaaaaaaa  73393
gtattaaaac aactgtccac ttggtttgtt aattcaaatc atgcaagaaa ggttgtgaat  73453
ttgagacaat aaatattaaa atccacagta gatatcatgt tgataaaggt ggcaatttgg  73513
acctttggta aggaatgatt gggagttcaa atttttttctg ataattacag aggtagtcag  73573
tgacttcctt ctctataatt tgcttctgaa acaaagaatt cttgtttagc actaatctac  73633
aaactctctg agacttcccg ctgtatccaa atatatattt tagacaaagg agagttttac  73693
tggagttaat tcccacaaag acgtgaccta aaaacaagag taagattgtc ttagacattg  73753
ccatattgaa attcaaaaca aatctggaga gagacgcctg ccattcctgg cttgtgacct  73813
cctgaccgct gcctgtctca gatgaaggac cagaatggca tgagctgaat tccctctata  73873
```

-continued

```
ggggtgtttg cctcgggctc ttagctctgc actatctctc tttgctggtg agatggggaa  73933
gtgtatcatg ttacctttgg caccgttctc ccatggaatg gacggcttcc gtcccttggg  73993
aaggaaggct agctctcctt tcccttttta tttttcatac ttccagaagc agagtatagg  74053
atctgacttg atcaagtaaa catcttatca tgtgccatat gtgtaatcca aagcacatcg  74113
ttcatcgtcc ctcagggaag cggtcggttt ttgtttttgc tttttcgaac cttttccatt  74173
tcagtgactt ctctctttat gggataatgg atgcactatt gaagttggca cacttctgca  74233
cttgtgtctg actagtagtg ccacagtatg ttgcctaaga taaatcactg ttgcttttac  74293
agggccaaag tgcagttagt agtgtaatcc aaaagaggaa ttagaagttg aggaactacg  74353
aggcgacact gcggtatgcc cctgttgcta aggaagatac cccaaatttg caggttgtaa  74413
tggccttgtg cagaatgaga aattaaggtt ccattctctg cattttgaat tttataggtt  74473
taataacatt ataagacaag tctgccttag ttcctagatg gctgcttctc tgaagcatct  74533
atagccatct tggtcttctt taggtcaaat agtgtgtatt tgtttacttg atagataact  74593
gtacaacaga tgtgtcaact tatgctcaac agatttttgt tgttgttgtt gttattgttt  74653
gtttttttaa acatattagc caatggtaaa atgtttaaga gtaaaaatgt taccaaagtg  74713
tgaaagtagg aaagaggatg gaaaaacatt tgttttagac tttaaatatc ctttaaatgt  74773
ccagaaacct aaatgttgga ctccagagaa tttatagatt taacattttt tttcagtttt  74833
aatatgataa attagaaatt aggtaccgtt tttcctgata atgaatctac aaagtactca  74893
ttaaaaccac tttagttgtt ttaaaggtaa gaattttatc aagattactg aaattgaatt  74953
aatgaagata ttatacttga ctgataaaat actgctggcc agggtaggag atgataggct  75013
tttaaaatca ttatctaaaa aataacctca agaatataag aattaacatg acataacagt  75073
gaatctaaag ttcaagttaa aagacagttt agtatcaata tcagctatgg cccagcatgg  75133
tggcccaggc ctttaacacc aatactcagt aggcagtggc aggaagagct ctgtgaaata  75193
taggccaacc tggtctacat aatgaagtcg aggatagcca gggttgcaaa gtgagaccct  75253
ttctcaaaca aagaatcagg aaggaaggaa ggaaggaggg agggagggag ggagggaggg  75313
agggagggag ggagggaggg gggagggagg gagggaggga gggagggagg gagggaggga  75373
gggagggagg gaggaaggaa ggaaggaagg aaggaaggaa ggaaggaagg aaggaaggaa  75433
ggaaggaagg aaggaaggaa gattggttgg tttaaacata ggtacgtgca gaaggctctc  75493
attattttc tctacaatgg agagaaattc aggtcttttt ttttttaagg tcatggtagt  75553
tgccaagtag ctgattaaac attctgtttt tttacatacc ccttgatgaa tttcatatcc  75613
ccaatgatgt gtcccagggg ccccttctct gtccctcttc ctagttctct tttcctgtga  75673
gtcttcagct ttggctttga tccctaacag agaaggaaag tcccaacgca gcagctgggc  75733
agcagcagtc tggagagcaa cgagggaaga ttgcagaaga gtggagggca tcccagaagt  75793
ggggctcttg aggaagagat gacactgatg gatgacctgc tgtagagtcc cagcttggcc  75853
ccttgtgtgg ctttagagtc ctctcacaga gtttgggaaa ggtatagtgc cgaggaaaca  75913
taggaagtga agcaaatttt aaagtgtggg ctcttactac ttttggcaaa cgaaacacag  75973
aacataaaaa taaataaata aataaataaa taaataaata aataaataaa taaatacagc  76033
aaaaagttat tttattaaaa cacacagaca tcagtgtgaa cagctatgtc atctgtgttg  76093
ttggtaggct ttctgtggag ctccgaggac aaggctctta gtttagcgcg tgcagagttg  76153
gttggcccaa ttgttttgtg cctatggtga ggtaaggtgg tgataggaat acatggatta  76213
cctcatggcc agcaataaaa agtaatggga gaggaggaag ctaggggctt ctcacacctc  76273
```

-continued

```
tcttggaggg caaggccacc aatcacataa cctcctctca cctccaggct ccatctctca  76333
agcattctgt taccccttt agtacctgtc tcattggaga gacgttgaag atgtgatctt  76393
cactgcctgt cttgaggaag gtaccacatg aggctacgct ggtaacgttg gtgtgaagag  76453
aaggcaggag acttaagagg tggtatcacc tcccgctttg gggagactta aagtggagaa  76513
atcactaaag caggtcctta cccaagtcac cagcactaac ctgtccccgt ggaccccat  76573
agatcccttt cactggggtt gcttgtgcga gtatggatca gggcttgatg acgggagtct  76633
taccagtggc tacatcatta aagaaaatgt ctcatctccc cgtttgaatg gcagtcaact  76693
gtgagagcat cgtgtcagga aagtattaca tcagtgaatt ggcgaatctg cttagggaaa  76753
agaataattg cagggctata ttaggaataa atacttcatg gggcagaaga ttaacaatgc  76813
ttcctcgcca tgcttttgca ttcggagata attggtttct gtgtgaaata taagctcttt  76873
ggtgattagg acttttgttc gctcactgaa aactcccgag agcttagaac atgtcacagc  76933
cccttagttc ccgcttgtca ccatgtattg aaagaatgaa ctgaaggttt aaacgaatgg  76993
gagggacagg gagaaggagg gacatcactt gaaaggcaga agacagggag tggaacttct  77053
cctgccaaac acttcctaag gtgacagcag gcatcagtgt ccttatgtca gcctatgctg  77113
atagcagcat gactacagtc agccttccaa gaagctccct tggagtttac cagttgagtg  77173
atttgagctg ttttcatcaa ccgccatggc tcttatagta agattgtagt cagaattcga  77233
agttgagttt aaaatgtatg ggtaccaaat gcatccttgt attttttgaa aaagaaaaaa  77293
agaatctatt gtttggggct ggagagatta tagctcagta gctaagagct gttcttccag  77353
aggagctggg ttcaggtccc agtacccttt tggcagctta ctgctgtctg taactccaga  77413
tgtaaggtat ctgtctgaca ccctctttgg gcctctgggc attcctgcac gcatgtgctt  77473
cactggtaca catacacaca ctcaggcaca gagagagaga gagagagaca gagagagaga  77533
gagacagaga gagagacaga gacagagaca gagacagaga ggcagagaca gagaggcaga  77593
gacagagaga cagagacaca gacatacgca catagataga tagatagata gatagataga  77653
tagatagata ctatatatat atatacatat aaacaaataa atgtttttg aactgtaaga  77713
gaaaaaatat tactgtgtgc gcgcgtgcgt gcgtgcgtgc gtgcgtgtgt gtgtgtgtgt  77773
gtgtgtgtgt gtgcgcgtgt gtgttgtgtc atggtacaac tgtggaggtc agagaacaac  77833
tttctggagt cagttctccc cttttgttta ttacctaggt ttcttggtga gaatcgagtc  77893
gccaggcttg catggcaaac actttaagct cacgagctag gccttgagca ggccttgcag  77953
gcctgcgtgc atatatttc ctcgagatgt tctttagtct tctgtctccc ttttgacttg  78013
atgaagacct ttgccccacg gcccgtttga tttccgttat cactactgtg taggcttctc  78073
gggctttctt tgttcttcag agaactcttg gcttcgtgtc agtgtgctga tcgcatgcat  78133
ttcttgagca gacatctttg ctgtctgtcc ttcacagttc tgcctcctga tctggtggtt  78193
agaggtcata ggagggcctg ttagccttcg actcttttgc agtcaggcag catcaggagt  78253
ccatgtctcc agctccgttt atctgtggaa tcactgatgc tctgagcaca gattctcttg  78313
attgtagtct ttgccttgct gttccttctg tgcattcctt cattgttttc catcacaggc  78373
tctttttgta gacttcagaa atcctaacta ctggtgtttt tctacagcct ttctccctgg  78433
tcgttcattt tgtataactc acatgcttgc cagaaaattc catccatgct gtggtttccc  78493
taatagccgt cctgagttat catgcccaag gcaaggtttc ttctctagga agagtctcag  78553
atttggtgtg acctctggag tactggcaca tagctttctt ggacatttca ggagataccg  78613
```

-continued gtagatgcca gttccttatg aagaaatgct gggcagtggt cgagcatttg cctgccgtga 78673 gtgaggtcct gggttcgagc tccagcactg ccaaatgaaa cactactaat agatgataaa 78733 tttgagattt ttagattaaa ccgtgcttaa acagtatgct atttttatca cttaatttat 78793 tgctaaatac catttgcaat gattacaatt tgtcataaga gaggagtata gttattctca 78853 gccttctgaa aactatgcag ataggtatat ctgtgcacat gcatgaatgt atatgtgtgt 78913 gtgcatgtgt gtggtacata ctcacgagag agagagagaa ggggtagtta tgagagattg 78973 agaagggctg gagaaagcaa gaagggaggg tgtttgtgca tgtacacccc ctacgcctgt 79033 tcctttcttt tatcaaagtc tccaggactc ttggttcctt gcttaagaac taattaagtc 79093 catgtgaact aggagtcctg ctgccaatac ctggcaagca ttcatggcct gatttttaat 79153 atattttaaa gtggtactgt gtaattaaca cattcttaaa ttttgacttc taaaaagcat 79213 tttggaatac ttcggtataa atataagatt ggttgcaaag tattggttaa aaatatagat 79273 gtggtctcta gtttagaatg atgttatttt atgaggagaa tttaggactg tcctaaagct 79333 agggaccaag gatatggctc agtggataga gatgtttgtg cataggatgg gaaagctgag 79393 ttcagggccc acatcttgga gagaaatgac ctttgagagt tgtcctttga cctctacata 79453 tacttgcttg aattctctct ctctctctct ctctctctct ctctctctct ctctctctct 79513 ctctctcaca cacacacaca cacacacaca cacagagaga gagagagaga gagagagaga 79573 gagagagaga gagagagaga gagagagaga aatttaaaat tagagctgaa aagacgaaag 79633 ttaaatcatc tgcaagcaaa tgcagaggcc gcttgctgag ggaatgctaa ctagagttgc 79693 ctaatgaatc aaaaaaatgg caaatgctta aaattcagga aaatacagat aagacctatt 79753 atttattgtt gtagttgaat attctgttga gatgggactg gttatcaaag atgtcctttg 79813 tactctacgt ggcttttcga atgtcagctc tatttttctcg gagagatggg ctactgtgtc 79873 taggcttgga gatagccata tagcttgaat agaaccccag acgagctgat cgtgcagatg 79933 tcatgtggca tccactgagg tcaagaggaa ggagtggctt tgcctttatt ttctttattt 79993 tcctttctga tgaatgacct caagggcaca cttcatacaa ctttaagctt agaccagaga 80053 actcctatag tctgctaaag tggatgctgt tggaagggct gcctcactca cacttcttcc 80113 agaagattct gctacgtatt gtcagtttgc ctcagtgttt ttcctacacc acattcctgg 80173 ggtaaaacaa ctcagatctg aatgataact ttgcttgaat gcatgttcgt caacaagaaa 80233 ggcagaaatc ataccatctg aaagggggta tccccttttaa ttatttcaag ccttagtcac 80293 ataggtcctc cttctgattg tttaatataa aatgagagat gtaagttctc caaaaactct 80353 gcttgtatct tctattttttg agaaatgatt taagtgcatt taaaagctta gtctctgctt 80413 gcccagaatg cttgctcttc aaaatatctg ctccccggag aggtaaactc aagttagtct 80473 tttcatgtga ctctggatcg ttgacctgga agacttcggg gtaatggaat gggctttggc 80533 actgatcgct gttttctggt tgagtaccca gcctggaaag gaaggcgtga ctgagccatg 80593 tgcaaagggg gagggtgggt ggagtctaac gatgtttgaa gcatgagtac accttcattt 80653 gatgcctcga tttactgagg gagagaactc taaactgctg catccatgga tggatggaag 80713 tgcctcagct tgtaaggatg cttatttaaa tgattttgca tattcaaatg attctacagc 80773 caatcaaacg cattcattcc ctgcctggtg agtgaaaact gaatgacact tgtgctccct 80833 ctgaaaggaa cagacgtttt cattatcaaa ttcaaccaag cagaaaatct ggcgaaggga 80893 gcagaaatct ccatttattt acatctacca tcgactgttt ggtgatagga gattagtagg 80953 ttgaggaaga gccttgttct catttagcta tgtgacccta gacttttgtc tccttgaaaa 81013

-continued

```
tacttactta ggttatgagc atgaagccaa ccaaaagtct caaattgtgc atatatattt  81073
aattctctat agatatttct ggtgcttgtg ggcagagaga agtcctagtc acatattaac  81133
attctatgtc ttccttatac tttaaagcca ttgcttatca gctgtaaaag cttaactgct  81193
gcctttatgt tctgttagca gagtgtcccc atctgacttc cattttattt gcatcagccg  81253
gtgtagttca tcataaaagt ctgcattaga gaagtggatc agaaccctcc aggggaattt  81313
gctgccaaag catagttaga gatctacctt ttgaatcctc catataattc tttcttgccc  81373
aaacctttct ccgtacaagt ccaggaattc aattatttca gctctctgag gagcagtaag  81433
ctccagaaaa ttgatttgca ataatgaaac taagccttgt ttacaaatct gagtggcact  81493
ttcgaagact ggactggcat ggtgacagga ggagggtacg aatttatcta ggggctcacc  81553
ccctttgaaa agatcatgtt tgtggaaaca cggctggaaa ggatataggt aatttctaaa  81613
agaccttgat gggtcatgtt ttaatctgct tcctttttaa ttctattatc tcctgtgttg  81673
ctcatcccta ggtgtgctgc tgagagcgag tgctttaaga gagtgagtgc tgatagctga  81733
ccatagtgct ctgatgccca gttaaaagct gagccagttt caaggggtat ggcctcattt  81793
ctttgcagtt gacttgttaa gtgctgtgac atttttttcc cattctcttc tttctcccca  81853
taagatattt gacccagtga gaaatgggcc atttttcttt gcgtacatgg gatttgaaaa  81913
gctggttgga caccatgacg tctctatgtg tctagccggt gactagaaat gccaaaagag  81973
aggtcagcct tggaagagta gagaaagtga ctgaatcctt aggcccgagt ggtattcctg  82033
agtgacagtg gaaaatgagc agagggcaga gctttgtgca atcaggactg ttaaaaagtg  82093
ggtggggggg cggcactgag agtgagcttc acacagaaag cggagaacaa gagcggtctg  82153
gcttgcggag aagcgggagg agaggactga agctacaaga agacggtggt gtgatggagt  82213
ggtcagggaa cacggggact gagaccaaag catttggtgt tgaccttgaa cgaactgttg  82273
tcgatcgtca tgtgctgagc cacgtggaaa ggatcggaaa gattccggca aggtttagag  82333
aatgacggac ggactagagc tcgggcagaa actctctaag tgcctcttcc tgtcttgatt  82393
atagcctgcc tcacacaggg gtttctggat ctggcacatg gaagaccggg ctgtgtactt  82453
tttcttccca ctgtgatgtc aggttttgct aatgactggt ggttgtcgtg cctcactgta  82513
cctcagcctg gttggcgttt tgtaagtaat tatgtgggtt ttttttcttc tctttccttt  82573
tttttaaagc accgcatata actctaatta attacatctt ttttttttaa tctatgtggc  82633
tttgaaaaaa attttttttaa tgaggcagaa aaagaaaagc gtttggggaa agcggccagc  82693
gaggatattt gtgtttcagg agacaatgta atataggacg gtgtctctgc agggtccact  82753
ttttagctcc taggaaacaa gaatgagttt aaccaaagga ggctgaggcc tggtgggaac  82813
cgacgtcctt cggtttccat agcggagcta gtcacatatc ctataaatac aaaatataat  82873
aacagcagaa ctgtcgaaag tggaggaggg agaaaggcag gtatggtaag cactgattag  82933
ggtggtaaca aagcgaatcc tggaggcgca tctctcagca tctatgccgt ttacgctcac  82993
acgatgaaca gtatactcac atagtaaaac cgtgcagtat cagtggacag ttgcattcag  83053
atccagactc ctgttcctct actaacccct gtcttgggct tcacatgttc tcccaaaacc  83113
cctacctgtc cgaatttagc tcatgggtcc tcaaaagaaa ttcccgatct ttaaaatcct  83173
atggaaggtg tcttgtgctc actgccagcc accagccact agtggccata caatactgaa  83233
gacagctact ccagacagct ttgcaggtat aaaggcaaac cgtggagcaa aggaaaatac  83293
agcatgcttt aataagtatt tgtgcaatgg tttcacgttg aaaagacaaa atataggatg  83353
```

-continued

```
cataaataaa atatgttccc agagtgaatt tagtatatat tgagtatgga aaaatgcata  83413
ctgcttttta gaatgtgcct gaaaccacat atgtgagcta ctttttattt ctgttgggcc  83473
tgactgctct tggtgcacac tgcttgcata tgcctcattt ctcccatctt ctacggatac  83533
agctccagga caggttagca tttagtggta cccactgatg ttgagtagcc acttaaaatt  83593
gcatcacatc atgttagatt tcgatgttta ttttcattac tctttgaatt tctctggcca  83653
gtaagccttt tttagagtgt ctccactatg aaaaactgag cattcttatc ataaaacctg  83713
aaattccaaa agcttcataa ttggggactt tctagatgcc acatcctgcc ataaatggaa  83773
aatcctatac tgtaaaaact tgtttcttgt ccaaactatg aaaggaattg cagagggtca  83833
gtgtggcctc atgtgtaagc ccagcattct ggaagtagag acaggagggg ggagtattca  83893
agatactgaa aaaacaaaaa tgtggtaaaa ttgctggaga agtggccaat tttaagaacc  83953
gggcagtaga taaacaagaa gaccctacag catcttgtca gaatcataaa gtctgtgcag  84013
gggggtatgc ccgatgagta caggagacaa ctcccaatag ctaaaggtgg accaatttag  84073
gcacacaaac ataatatgta cactgtatgt gaaatataac acatatactc acacacacac  84133
tttcattttt aaagaaagtc attacacgga gcccacgact gggatggaga atcacgcccc  84193
acttttccta ggttagagtt tatatgtgta aagtatttag aattcttctg aataggagat  84253
tatctttttt tttcccagtg tttcatcact tagactaatg aattttccta ttatacgtcg  84313
atatttaatt ctgtcctgca cagtgtgtgt gtgtgtgtgt atgtgtgcac acacaagcac  84373
acatgctcac tttatataac ccctataaaa actttgtgat tccaacaaga tgctgtaggg  84433
ttgtccttta tcttctccac aaatctaaga atcaatcatt tctccagagt cctgtttcct  84493
tttgttggag aataatagaa agatccaata tctaggcttt gtgtgctcat tgctgctgaa  84553
gtgtctgctt tgttgctgat ggaccgagga agtccccttg ctactcctcg atcttatagt  84613
atggattcct gtagatattt ctgtagctct ctgtgtctca attagcatcc ctaggagctc  84673
accctgttga tccctctatc acccactgga ctgttctact tcccgtgctt gtctgtaaac  84733
tctcacccca ctgtgagcat ctgccttcca cccaccttcc tttgcctcca ccatttaatt  84793
cagaatgctc tgatgacaac atcacaatta cagtacttta aattgtgaaa gctctttaaa  84853
aaatcctaaa attgttagcc attgttgatc actatacttt gaaaaaatat cattattatt  84913
tcaaaacaat tattgttaac agagaggtac aggtagtctg tttctcttga acacccatct  84973
cacggttagt gtgttcacga acgtgagcac atctgcgtgt ggtatgtatg tgaggcagaa  85033
ctctcctcac ctgaatgagt ctgaaagact taaaggaaac ttttagtgct cacttcttgg  85093
cttgcagctt gcttgaaaca ttcactcagc ttctgccatc tgccaaattg ttctctgaag  85153
aaacccagct gccagctgtt attgtaatag ttacggtgac actcggggtg acagcacagc  85213
cactttacag aaccgagtca tttactcatg tgttcctgag aacccagagg tgaccctcac  85273
catgaagcaa aactctgcct catgccgagc cagttgagag gcattttggt gaaatacact  85333
tctgaaaaca ttctttccac acaaatgcct cccggagccg tttgccagct ggttgtcagc  85393
gtgcgccact tatagggcgt cagtccatct aacgtgctga aacaaaatat atatatatat  85453
ttaaataaat tttccaagta aatatgagta aacatttctt cggtctgtag ctatcacttt  85513
ggtatgtaca tatgcagtgt gaactaaagc gcacataaat ctagagtggg tatttgtacg  85573
tttgcgaatt tatggggaca tgtgagacac atctgatcct gggcatctcc atccggtgtg  85633
aagtggcttc tagtttgtga ggcaggagta ggcaggcttt gtttctttcc tcccggatct  85693
tttcagtttg acttccattc taaactcttc atcctagtct gaggtggtgt cacttttccc  85753
```

-continued

```
gtggataagg tcaacagcac cagcctagtc agctatgatg ctaatgacag gcgaacatgc  85813
ccatctccct gtgttcctca aaagtgctga ccagatttgt agctgaacac tgtgtagcct  85873
gccctcaccc acccatgagc tcatgcaaat tgctcttctc tgagaattca ccccctcctg  85933
tttttgtctg gattcatagg catgcgtttg ctagggactt ctgtaccctg ttgctctgtg  85993
gctggaatgt cttctgtcaa cgtaggatgt ttttctcttc ccttttctcg ctttctccag  86053
cgcattctca acctattcgc tctcacgacc cagtaaagtt ctccaccttg tctctcagat  86113
tagtccctac tccagttcct ccactttttc tccatcatat ttctcaccag ccaacagttt  86173
ctttcttatt atcatgttcc tctagagtgc tactttattg catctcttgt cggtttcctg  86233
gattctcagc cctaggagaa atgtaaataa cttgcaatga agacttgtgt taggggtgga  86293
ctgaggttct tgggagaggt gtttgaagat acccagactt ctcttaagaa ccaccatcat  86353
cgtgagactt ggaggctcac tgctctcatc ctgggcctct gcctccctct gcagagctct  86413
accggagctg ttatctagca tacgtgatgt tcaaatgtac aacgcaccac ttcatctgtg  86473
aggctccaca gagctccaca gaatagctat aataaacgtg gttctcttgc ttgcagcttt  86533
tcctttgaaa tcattttatt caaaaaccca ttctgactgt ccaaaaacagt cctagttctg  86593
agaaaaaaat ttctcaattg tctcacactg gttccttctt attttcccct gtggggcgaa  86653
ctggtggggg tcccctcatg tttctgatag tggatgttta tactcctaat actacctcat  86713
tgctgggatc ttttttctgt aaagtcacaa tataataatt agaagtgcat ccctgccctt  86773
gaatgcacgg tactgcagaa tctacctttc acaggtttca tagccaccat tccctctcct  86833
tttctcaaac gttctcttgt gtaagggaac cttatacagt aagctcactg gcaaatactt  86893
tctgctcact tccattgcaa ctcaattcga gcagctaaga cagtgggtaa aaatgcagcc  86953
cgttggcggg ggatcacttg gagggagagt ctccctccct ggtaacaccg ggaaactgca  87013
gagcaggaaa ccgcccatcc ttgctccatt ccgccgggag cgtgaccgtg aggttatagg  87073
ttcccatgga cagtctatct tgtgactaca gagcccggtg tcacacagtc gcactgtgtt  87133
caagtcactg ttcgatgggt tctaactgat gcagcagaat gcattcccgg cccgttcatt  87193
tggatgactg gacattttag tctcattctt ttctaatggc cagactgatc agatcataac  87253
attaaaatat ttcacgggct taggataaat cattttctta tatcaaagcc aagggagatt  87313
ggccatgtaa accatggtga cccgagtttc aatgagtcaa ggtatctctg gaaggccaga  87373
gagcagggac acgtgaaatt tcagctcagc tctgctgcct gctggccctg tgagcgaacc  87433
actgacctgc acttcttcct gcccatctac aaaatgaggt aattcaggtt agaggtctgt  87493
tctccccgac accagagcca gcactgcacg cctgcagggg ccctgttgat ttccacatct  87553
ttgttttctt gccaagacat cagccaagtg tgcattttat ctactttaaa aaccctctct  87613
cctctgaaat ttgcatatgt gctttaaata tgaaattctt tttttctttc acataaaaac  87673
agtttgcatg gctaccaaaa aacatgccca gtgtgtattg gagaattttt ctgtttagag  87733
taaacgttgc cttatttccc acaatatgta gacgcggtga gcacagcttc tccttccgat  87793
tctctgttta atttgaacat tggctgcctt catctgaatt ctgttaagaa atgctcgctc  87853
ttgaagcatg agtccacata aacaggttta tttccaaacc caaagcaccc atccttgtgt  87913
atggaaaccc caggttatac ctatcataga ctttttaaaa aaaaaaatca ataaattttg  87973
atttacatat tactctcagt ctatatcaaa acatccatct ttcccgtaaa actaaactat  88033
gttctagcat agactttgtt aaaaaattaa tttttaacaa aattcaatcc tctcaattct  88093
```

-continued

```
taaagaattt ttttgctatt tatttccatc tttaattgta ttatgtggat aattctcagt  88153
aggacaatct gtgcacgaat gcagatattc acagttgtca gaggtgtcgg gtcgcaacgg  88213
agcaggacat actggatgct agggactgaa ctcaacaaca gtagccctct taactcctga  88273
gccatctctc caggctctct ctctctctct ctctctctct ctctctctct ctctgggaga  88333
gatttttata atttagcctt ctaaccttct tgatgagtgg cattctaata tgctttccca  88393
accctcaggg gacgataaga aaggctgtcc actggtaaat ttcactttaa tgatagggca  88453
cagtgagctt ccattttgcc ctttgtcctg aggcctttta aagtagctcg tgttaatcct  88513
ttgctagagc aatttttcgt tagctatagg caataccagc aacttacagt taagtaaaat  88573
aatttgcaaa ttaaaaattc cagtatcctt ttaaaataga atgaacagtt gttagactgt  88633
aagcatctct cagtgactgg ctcagcactg tcatcgagcc ctggacagac gaaaaccgat  88693
ggatttgatt ttgtttcttg gcaccagttt ttctatttgt acccccaaga actcatttag  88753
gccatggacc agaacatctt atgtttctt ttgatattct aaaaatggat tcaatattaa  88813
cagtcagcat ttaataatag gccagcattt aatctgtcca ataattactt atgaaacagg  88873
aaaacatcac agatgcaaat atggctgacc atgttaacta aggagggtgg ctatattaag  88933
ggttgtggtc acttttgtct tcctataccc tattttcctg aaatacctca gtgaataggc  88993
atttcctggc cgccaggatt ggttacctga cttcctcaga cagcctgagt agttcacctg  89053
ggaacggtcc ttcctcatag atggtatctg tttagctctg gaactaggtt acaacctcct  89113
gtggtccaca ctgccttagg caggtttctt tgcagaggtt tctcactagg gaagtggatt  89173
tgtaggagat gacatcatgg ctctgtgtgg agtaagatgc atgatgcagc tgcagaagtg  89233
ggaagttttg aagtgccctt tgcccttccc ttcctccagt acaagcatgc ttgccagagc  89293
tgtgtcaggg gtagggatgg aatagtctga tggccagcat taatccacag aatctagaat  89353
cacctgggag attggcctat gagcatgcct gtggttgatt atcttattat gttaactagg  89413
atggaacaag tggcccactg tgggtggcac cattcccttg ccgggatcct gtgctgcatg  89473
tgtggaacag gggagcagag gagcctgttg tattccacat tctctgcttc ctggtagtgg  89533
atgtcacagc tgtgtgagag actgtctttc tttcccacca tgatggaccc tatgtgccct  89593
tggatcctaa gacagagtca gctctttctc ccttaggtca tatttgtcag agagttttta  89653
tttttacagc agggaaaatc agatgataaa tgaggtgctg tccatacatt gtgaaactta  89713
tcttcatgac ctactctacc catccactta gactaacctt tagtgatatt tctacctgaa  89773
gacattcccc tgtgcacccg gtcagattca ttcactgtat tgacctagga cttgcttcat  89833
tctggtatga aaagaaatct cttcattctt caacagacat tcattgtcta gtagatgcag  89893
actttgtgct gaagcagagg aatgccacaa tggacaaaac caagagcaac taatttcaca  89953
gcttatgtta tttttcactg tcaatctttt accctcatga ctatgtatga acatgcatga  90013
acatgtatgt atgtgtatac aggaagggtg atatgtaaca ttcctaaccc tggagtacca  90073
gtcaggctta ggagcctttc tcatgagatg taagttcaaa gaaaacaaga ttccataatt  90133
tgaatgaatt actctttcca gagtgttttt atataaacac atatataata cacattgtgt  90193
atgtacagat tggagcttaa catttaaaaa tgctgcagtc tctaacaatt tgcaagcagt  90253
ttaaatttac aaaatacaga aacagacatt ggtgttgaca gtgctcaaat taaagctatc  90313
tgtttttgta ctgtaatcct taatgacaac gaatgtcagt ggctacttgt gcagctgcta  90373
tatggatgca gaaactgaaa ttaattcaag gagaaggcac tgggaatata tagggaacat  90433
acagccatca aggatgcatg catagggaat gtatggacat aaggtcttca tggtagcaag  90493
```

-continued

```
gcagtcggtt gtttaaagag gctgacccac catgctaaag gtagtgtagc ctttgtgggg  90553

tttttcgtgc attgaaagtt ctgggtaagt tctctgacct ccgtcgagcc cgtgtgtgtc  90613

catggtgaaa tcagctgtca tacgcgaatg atacaggtcc actctcctct ctttcag     90670

tt  ggt gag ttt gtg agc gac gcc ctt ctc gtg ccc gac aag tgc aag    90717
Val Gly Glu Phe Val Ser Asp Ala Leu Leu Val Pro Asp Lys Cys Lys
    120                 125                 130

ttc cta cac cag gag cgg atg gat gtt tgt gag acc cat ctt cac tgg    90765
Phe Leu His Gln Glu Arg Met Asp Val Cys Glu Thr His Leu His Trp
135                 140                 145                 150

cac acc gtc gcc aaa gag gtaccaatct gtgcccgctt tcctgcagag           90813
His Thr Val Ala Lys Glu
                155

cgatctcctt gggggagggg ggaatacaaa gatgttttta gagggttgtt gaaggcagta  90873

agttcttggt ggtttttttgt ttttgttttt gtttttcgag acagggcttc tctgtatagc  90933

cctggctgtc ctggtactca ctctgtagac caggctggcc tcgaactcag aaatccacct  90993

gcctctgcct cctgagtgct gggattaaag gcgagtgcta ccatgcccgg tggcagaaag  91053

ttctttatgg aagcaatgtt caagcatttt aaaactgaat ttactttttta aagtaatttt  91113

attttttttgg caaggtcacc actgaacaga aagtctaatg agctaccctg aaccatgtct  91173

gtacacgttt gtgcttctct atccatgaac agccctcatg gtcagcaata gctctcatta  91233

gatacatctc tgggctacat cttacagatg aacataaagc tgtcatgttt aataggcata  91293

tgtaacctta cattgagcat ctttctctat ttattttcta ccatcgctct tgtcccatgt  91353

ggtttgcata atttaactag ctactggtga atgagctggt agaacaagga agccacatgt  91413

tcaaggccac ctgaggccac agtcgttaaa gtcataccct ctcctgccac cttcctttcc  91473

acggtgagcg catctggggt agcacgcgca gccctttgct agcctctgct ttgggctaag  91533

tcagtggaat attaaggaca atagaatgta gtgaatcgtc acccttagaa ccgcactgta  91593

ccctccatat aattataatg cttttctcct aagtagttat gtcaagatgg gggagccagt  91653

gttctagaat tagggtcctt tatctagctc aggagttcac taccagcgtc agttttgtac  91713

ccctgttcct tcctaggaac atttttgctt gtctgacctg tagaggcact accactggca  91773

ggtaacagtc aaagaccaac agctaaaaac cctcccagga acagggtaga ctccacctgg  91833

cgacgtttct tttccacatt aatcccatgg aggctgagct ataatagccc tctgagctat  91893

atccaaggcc ttgtttctaa agtgcttctg agatccaaag tagagtcttg ctaaggggct  91953

cactttggtc ttgatattgc actataattc aatcaggcca tgaacttgcc acagccttcc  92013

aagtagccag aattatagac tagatgcact aggcctggct cctcagcaaa ttaatttagt  92073

ccaaaatatc aaatacgttg gttgacgaat taaagggaga aaaagggttt aacttgactt  92133

ttatatttca tgaaagagtg tgctctgatt cactgtaaaa acaaaacttt ctttatctaa  92193

aaatgatttt ggaagtggaa tagctgcctg agcttacagt agactacatc ctttgaagcc  92253

cagcttccca aatgataacc tcactttgcg cttcctctga gtttgcaaag gaagactccc  92313

ttgctactac gaaacaacaa actggtgatt cctgtggggt taaaatgcat ctataatact  92373

tttactgttt ccctaggcat gttgaattat taatttttttt tctctgtcac ggggaaatag  92433

tttctcagtt tttctcttcg tgccgatttc tgcaaaatta acagatccca ggcaatcaaa  92493

aagatactga aagagaaatc agggctgtgg agggcagttt cttccttcct gggactggga  92553

ctctgagata tgagccaaga gacaccattt ccagaataag atgcaactaa ctgcctataa  92613
```

-continued

```
aaaaaaattc tatatctggg gtagagaaaa gaggggatag gcaaatgtag acggagcctt  92673

caattcctga aaagccatca cagcccaaaa cgtaaatcat ttcctgatat ttgtccccgt  92733

gtttagcttt ctggaacctg ctttcttttc atgtttactt tgtaaacata atacattaaa  92793

aaatgttttt aggtatattt atttcatttt atgtatatat tgtatatatt gcctgcatat  92853

atgtatatgc acaggtctgt ggctggtgcc cataggccag agtcaaaatt gggtattaga  92913

tccatggacc tggcggtggg tacggttcta aaccatgggt caggggtctg ctacaagaac  92973

aacaaatgcc tttaaccact taggccatct ctcaacccca cctaccaaga aaacaatata  93033

aagatagaat accaggcagc ccttgctgaa caccgggtta gaaacgagtt cagacagcaa  93093

gccgccctta ccttctggag taggctccaa atctatctgt ccatgctgat tttcctggct  93153

gtgacggcgg ttcaattgtt ccagctgtgg ttgtgttcga ttatctgcgc agtgactgcg  93213

tttgattgtt ccagctgtgg cagtgttcga ttgtctggtc tgtggctgtg ttctattgtt  93273

ccaactgtgg cgtgttcgat tgcccgggct gtggctgtgt tcgattgtgt ggaccatggc  93333

tgctgtccga ctcttctagc tgtggttcga ttgtccgggc tgtggctgtg ttcgattgtc  93393

cgggctgtgg ctgtgttcga ttgtctgggc tgtggctgta gtccgactgt ccttgctgcg  93453

gttccattgt cctggctgcg gctgcggtcc gcttgcctct gtgcccacac tgactcctcc  93513

ttccttttgt ag aca tgc agc gag aag agc act aac ttg cac gac tat ggc  93564
              Thr Cys Ser Glu Lys Ser Thr Asn Leu His Asp Tyr Gly
                          160                 165

atg ctg ctg ccc tgc ggc atc gac aag ttc cga ggg gta gag ttt gta    93612
Met Leu Leu Pro Cys Gly Ile Asp Lys Phe Arg Gly Val Glu Phe Val
170                 175                 180                 185

tgc tgc ccg ttg gcc gag gaa agc gac agc gtg gat tct gcg gat gca    93660
Cys Cys Pro Leu Ala Glu Glu Ser Asp Ser Val Asp Ser Ala Asp Ala
                190                 195                 200

gag gag gat gac tct gat gtc tgg tgg ggt gga gcg gac aca gac tac    93708
Glu Glu Asp Asp Ser Asp Val Trp Trp Gly Gly Ala Asp Thr Asp Tyr
            205                 210                 215

gct gat ggc gg  gtaaggcggc ttttgagatg ggtctcagat tggctgagcc        93759
Ala Asp Gly Gly
        220

atctcgtctc ttacagtttt tgtattctct gagtgtgtct ctctgtctca cagtggaaag  93819

agacctctca ctccagttat atttgataat accagaaaaa tctaaccctg aagggctgct  93879

ctgattcttg tatgccactt actgttagtg ttactgataa accttcatga agtcattgga  93939

ccacgtttga atgtcaggaa tactgatcag actccactca gagctgctcc tcagtaggtc  93999

taccaggaag ctagtagatt tgagctcagc actctggcat gccattttgt cctgccattt  94059

ggaaatattt ttttattaga taatttcttt atttacattt caaatgttat ctcctttcct  94119

ggtttcccct ccgaaaaccc cctatccctt ccaccctccc cctgctcacc aacccaccca  94179

ctcccacttc cctgtcctgt cattcctcta cactggggca tagagccttc acaggaccaa  94239

gggcctctct gcccattgat gtccaacaag gccatagtct gctacatagg cagctggagc  94299

catgggtccc tccatgtgtg ctctttggtt ggtggtttag tccctggaag ctctgggggt  94359

attggttagt tcatattgtt gttcctccta tggggctgca aaccccttca gctctttggg  94419

tcctttctct agctccttca ttggggacct tgtgctcagt ccaatggttg gctgagagca  94479

tccacctctg tatttgtcag gcactggcag agcctgtcac gagacagccc catcagactc  94539

ctgttagcaa gcacttcttg atatccacaa tagtgtctgg gtttagtgac tggcctctct  94599

ccctatctat tcaataccgt acttaaaaat acttttaaac actctttcgt gaactcaata  94659
```

-continued

```
caaattttg gttaaggaag acatggtttg tgtttgtata tttactctta aggatttcct  94719
tcttctttgc ttttggtttg gttttggatg ggtgggtaga cccctcccct caaccatctt  94779
tttcctttgt gtagtgagca acactaataa atgtttgcgg aagttcttta actatctcca  94839
gttgcgtgat tgctggttga cattttttttt ttgcctcatt ttccttggga tcttaacccc  94899
ttcgttaatt ttctgactct tttcacttgt gcacaaatat ccatattcaa atcataagtc  94959
tatgaagcca gaatttttga gttagaccta tgacccggtt tgttgatgaa tccaggctat  95019
cctatccctg aaatgtaagg ctcgggcttt cctgccaagg tcctctcagc tgttcctcag  95079
ggttttctag ctcaaacgga acaccaacca aaaatcacaa aacttactat cagtaagatg  95139
aggcttcatt ttagtactag ctgcctgagt ttatcaggac gtgtgtgtgt gtgtgtgtgc  95199
gcgcgcgtgt gttacagtct tttatatccc ctctttacca tttactttca tccatctatc  95259
tatttgagtc aggatagagg ctacatagag aggatacata caggatagag gctgcatgta  95319
gccctggctg gccaggacta gctatgtaga ataggctggc ccagaactaa gagctctagc  95379
tgccactgcc ttctgggtgt tggaattaaa ggcttgcact acttactaca tccaggtaat  95439
tgtcttgctc ccccacctct caaaataatt acatttgatc tagcttgaca tagagccaag  95499
gaaactgaaa aaaagatttt cagatacttc tcggtgatgt aaaagttcac cacctatgca  95559
taagtctcgt gtttcccagg caagaagtct ccgggaagca gaatttgctt ctgagatttc  95619
tgtcatctaa tgagttaggg gttccccata atggcttgac aacccacccc ctatacttct  95679
gttctatgta ccacatgtgg gacaggaatg ggttaaactt aattatctct ctctcttttt  95739
agaaacgagg tggcctagtt ctcccttatt aagcccactc ctaccctcct tggccacatc  95799
tagatttgaa cgtttcagag gcttcggaaa caaatcccat ccttaggcgt ctgatcacag  95859
aaccagtaca accagcattc ctaaaggaaa atctagttac ttagcctgga cgttgtctgt  95919
tttcataagc tactggatat ttgatttgct aatttccagt gagtaacctg actatggatt  95979
gagaaagtat gcagaatggt atttaaactt ggaaacttcc atggctggtg ttaaaactct  96039
aaggcactag atatgtattt gtaaccatct tgttaaccat caaccttgtg ctgatgtcac  96099
agggaacatg tgtatgtgtg tgtgtgtgtg tgtagagttt agagttcaac actgagtgtt  96159
tttctcaact atcctccacc taattttttt tatacttaga caccaaggct caaactcagg  96219
ctgtcaagca tttaatcaaa cccctacctc ccagccccag cagggacttt ttaaatttta  96279
aaatgattat ttttattttc ttgaaagcca ccagcctctg ccaagcttct tccacatgta  96339
agacatgttc tatgcctcgt aaaaccttct ttttaagatg ggtccagttt tcctcaggtt  96399
ttgatctttt catcctacac ttttttctga gatactgaca ccattgccac ggtatcagtg  96459
gccctttctc ctgctgctgg aaactgatcc cggcagatgg ctttgcattc tgacccaggt  96519
ctctagtcta ttcaccacgt cactgggtaa ttgtaccttc ttgataccca tctctgagtc  96579
tatgacttct tttagttctc actgttacaa ctcccaagct aggagacatt tgttttcctc  96639
ctttgaatgt gctgtgtttg aatgtgctat gctacctcct agagaagggg tatagtatgt  96699
tatctaaacc agagagaaca ctcagacccc agccaccccc tgcgtgggta atatggtcac  96759
cctgtcatca tcatcaactt gaaatgcaag ctggctcctc tcctaattat cttcctttgt  96819
attctgtctc atgttccaac tccctcatcc cttggagacg gtgcacgctt agtattccca  96879
accattacat ctgaaccact caccgggtct tgctgccttt cagactcatc atcacagcag  96939
cagcatgcaa cccgtcgacc tttcctttct tttgcccatg atcaatccgg acagactgaa  96999
```

-continued

```
ccactcacat ataccccaca catcctagac ttgcagagat gttcacattt cccaaatata  97059
ttttggtcag ttctcaatgc cggggaaaac ttaacttctt cctgtaacca cttccgaatt  97119
tcctgagcta tcgagttgtg taactgagcc ggttgattcc acgtcgtaac agcagctgaa  97179
accttaatgt ttctggatgc tcctgattac tgtccccatt tgaggacaga tcatcgtcta  97239
ccaagccatc aatccaaacc aactgccttg gtccctagca tcacctttct tccttgctgt  97299
atctatgacc ctttcatagc taacctctgt ggatgtctag agcaaggtac ctggcatttg  97359
gtggacactc atgtgcaagt ctcctttgct acctaaatat ctcctgtccc ttattcttct  97419
agcctggatt cctggttacc ccccaccccc caactccctc cattaccctt tccatctcac  97479
tggctccacc tcctttacct ctaaacctgc tctttctgga atgattattc tctggtactc  97539
ccttccttat tttgggagca caccaatgaa agtggtgatc tcgtactgtc ccatccttct  97599
cggcaggccc atcactgctc catttttagg tttctggggt ttatttggaa tagttagcga  97659
atgacggtga catacttctt gggatgtcaa aataagaaaa tgtcgtaacc taggaaaact  97719
gaggtcagga ccctgcatgt gtcctggatg tacgatacgt tacggtggac ttgtatgata  97779
actgtacaat aaaatgagtt ttgcttaatt attattattt ttctccaaga aagagttaaa  97839
gttcagaaat actattcctt cttagagtta cttacactgc tcagaaaggt agcaagtgct  97899
gggattccaa gagttaacag cccatcagtt cctgagagtt tgtcacttgg caagtggaaa  97959
cacctggcat aattgtgtaa acattaggtg ctcaacaaat atttgagtag aattggagtg  98019
gccctgacat caaatccgta cagaggcgca gtcattgtca ccaaaggtca gcacatatac  98079
acaaagtgat tggtataaag aaaaaggaaa acccaaacaa acagcagagg aacatcattc  98139
ttggtaggca atgattacat gaaattgcat cagaaatccc tgaagctaga aattgtattg  98199
aaaaatgtac tgagaccaaa ggaaaattaa tcctttctta atgaccttta atgtggagcc  98259
tacatgaata cctcattcaa aaaagtgtga taaagttaga aataaagaca agattacttt  98319
tcttagaccc tagggtaaaa gtcagtttgt gtttgtgttt ggtttggttt gtgtgtttgg  98379
caggaccaac cattgtacct aaagctaggg tgggggtgct ttaccaccga cgttcagcat  98439
ttgccctttt attactattt gtttttaatt tccgctggcg acagactctc cctctgcagt  98499
acagggagcc ttcggctttc tgtacacttg catcagcttc cggattagcc aggattattg  98559
gggctgtgca accacactgg ctcctgaagt ccattcttag acaaacttct tcctttggaa  98619
tcagtaagtt ccttttgttt ctgtcaactt ggagtgctta aaaaaaaatc aaacaaacaa  98679
acaaaacctg taggtaaaat cccagtaaat acaagttata tgcatgggac taccagctgt  98739
tggcaagcat tctgtgattt gagaaacaaa cttcagtgaa gagcagtatt tcccaatggt  98799
gaacgatttt cactcaaggg gcatctggaa atgtctgccg gcagtttgag ttgtcacagt  98859
gtgggtagtg tgagagaaat gtcattgtca tcaagggggc tagggatgat gacactgcca  98919
aacatcccac agtgtatagg acatccctat gacattgtgg agtgtgctgg ggttaagggc  98979
ccccaatttg gaggcaagaa agatgctcca aggccaagag tacatgttgc tcttgcagag  99039
gacttgggtt tggttccgag catccgcatg gcagggcaca ggcatctgta actctagttc  99099
cagggcctct gccatcctca tttagcttcc atgggcacta catgcatacg ctgtgcacac  99159
atacatgcag gcaaaacatt gtacacatag aaaaatatat atcaatctaa attaaaacca  99219
gttttttttc cccaagtgtc agggttcata cctatagacc cagcgcttgg gagacaaaca  99279
caggagtttt ctgggagttc aaggttacct gggccacaga gcttgttcta ggccagccaa  99339
gactgcataa taagactcca tccaacaaaa caaaacaaaa caaaacaaaa caaaacaaaa  99399
```

-continued

```
caggggggggg aaaacctcta tttgaaggtt tgtttaccat ttaactttta gggaacctac  99459
tctccattca aggctctgcc tctaattctg catggacaaa gaagcaacca tctacccacc  99519
ttgagagtct tcctctaaag tacagtttgg ggattttttt atccctccct ctctctctcc  99579
ttcgttctct ctctcccttc cttcttccct cccttcctcc tctcttcttc ctctctcctt  99639
cctattctct ccctgctcct tcccattctc cctctgttcc tccttccctc cctccctccc  99699
tccctccctc cctccctccc tccctccctc cctccctcct tccttccttc cctccttccc  99759
tccctccctc ccttccgtcc atccatctaa ataaaccttc ctagcctcag ctgcagcctt  99819
aaaattctgt catcaaaatg tgcttaagtg cagggaactt ttattgagac ttctcatttg  99879
taccaaatta ttttatgaat ctatgatctc agttttgcta ctgtaaacta ccattatact  99939
ttgggagggg gtgttgtagc ttaagatatt cagtgaattt taaaagcatg agagagggag  99999
aaaaaaaaaa gcatgagaga atcttaatga ccattgcatt ccatttgaat tttttaaag 100059
ctgtcagatg aggggcaaat tattatggtt tgatctgatt gtaagttttg gtccatatag 100119
atttacttat agctaaaaca aaaactttaa tcctaaagta ttaccatcat gtactttgca 100179
ttcaaagtct tactgtttac tccttgagtt ctgtttatta tggttcatcg tctgttttta 100239
tcccactgtg agatgttaca caggtggtca atgcagagca cagacttcca tgaactcttc 100299
cttaatcacc ccttgtaggc aggataggaa gttcacatta aggacttgtt tgtaaagcag 100359
cactctgcta ggtatagtga ctgaaaaatc actgtcatta tggcctctgt accccaagat 100419
cctctcagac attaatagcc acatgacttt atagagtaag ttttatttga ccatctatct 100479
tctcctttat atctgtggag tccaagttct tagaatagtc ttgttcagtt tctgccttgg 100539
gctttaagaa aaggctactc aaggctgacg ggagaagaaa acaccacgga tgttagacgg 100599
acaccaagtg aatcacacaa atgatgaacg aaggtctgga gtctttgtca gtggatgagt 100659
cgagtctgaa tggaaccgat gaagcagcgc atggctttgc gatgtgactg tcacagtgct 100719
ggcttggcag cttccagagc tgggctgggc tgtctgcctc tggtctgaat aaaggaacta 100779
acttgacaat gatgacgagg agaattgcag agacttgtac ttgcccttga ggacactggc 100839
cgccactacc aaggccttat tagaaatgct gtctctaaag ttaataaact tggatcgcat 100899
atacattcag aaaaaaaaaa acaaatcacg ttaatagtct tcaccggatt ccagacgatg 100959
tgaggccaag ccagtggggt ttgtttcggt ttctgagcag gagatggcag agagaagagc 101019
gtttttcctg tataggactt ggctgctggt atctgaggta cagttggtac tgcattgagc 101079
acaaggtgcc cactaataga aagtcatctg atgacataac ccacactctt ggaagtgtta 101139
ttttaagggc tgggttattc agtgatggtg atttcaggac cgtggtccac ggtcagagag 101199
taagacaaga gaagaagata tagattcttg ttgttttgac tggatacagt gactcgcacc 101259
cacaagagct aatttcctga tgaagctggg atcaagataa tgtcatctct agagtaaaat 101319
cccttgtttg tatggaattt atcaccgtct catgtcaaag tcatgacatt taaaatcttt 101379
aatttacgta ttaagttgtt atggcaaaag atatttctct tactagaact acacggcatg 101439
aagcggtgcc aatcgctttc tgtaagaaac tcagcaaaat gtgaaagcat gtagttcggt 101499
agaaggaagt cagtctttag gcaagtgtga aaccacatcc tctcacttcc catatttatg 101559
aactaacatt ttaagggaac cggtgaaatt aattgtgaaa ctagagatgg tgggcatgcc 101619
caattttgtt gaagccagga catgagtgtg tccaagtaga tgaggaaagg ggagccctgt 101679
tagcaaataa gatcgtctgg ctttgcaatc gatgaccctt agacagagag actcacacgg 101739
```

-continued

```
ggcgaatcgc agagaagaag agaccgtagt gttcagccat aaatgacatc tgtgccatgc 101799
tcccatggct cagggatcat cacagaacgt ataagagcca aaggttgcag agcactactt 101859
caagaaaggg ttcctttgga catcataggc ttcgctgccc atgtgaaccc atagcagctg 101919
tgactacatg cagaagacct gtgtaagatc aagccagtca gaactctaat gtagggactg 101979
gaaggactca ggaagcccca ctcctagttg aacagctatt gacaatggaa aacttcactg 102039
agagggtgtg tcagttttct tcaggggtgc aggccagggt aggctgccca tgcaccagtg 102099
gctggcccta tgcttaggca cataccagca gcaccgcacc agctagactg cctggttaat 102159
atgttaataa atagcaagca catgaagttg tgaggtagct ttggaaggaa gagacataag 102219
agggggcaga gaggtaagat ggtctgaatt tcatcaagac attataaaca tggatgaaaa 102279
tctcaaagaa taatttaaaa tatacatttt tttaaaacat gctttaaccc tagcatatct 102339
gtttgcgcct ctttcctctg acaggggtaa tgttagataa cttgtatcac agtgcttttt 102399
ggtctactga ctaatgtacg gacacattta taacgtgtag actggatccc gaagggaggt 102459
aaacccctat ggagctgatc tgtagaccac cccaccccaa ccctgtctcg ttctgccaaa 102519
ttataaaagc actcttcggg gtgtggagcc cagtgtccta catctgctca ataatcatga 102579
ccagtatact gtgttcttct ctcagtcgac tcttaaggct ttgtcactgt tgtaactgat 102639
actgagagat gagcacatct cagacctctt gtcttagatg aggctgagaa catcttaaag 102699
cagctgttgg tagcaagcga gtgatgatac tcctttttta tatgcctgtt ttatctctta 102759
aatatccaag aattatttta aagatgcaaa aaaaggacca aaatataaga ttccctatga 102819
ctggaaattg cccattaaat tagttgtggt tgactttggt tctcttggat atttttaaat 102879
agaaacttaa tgactgttta aactttcaat ttccacatct gaaaaccttc cattttatat 102939
ctcagttata tatttccgaa atagagaaga attgcaagta agagcagatt aagtttttaa 102999
tcttctgccc cctggaatat gctgttcatc ggcttcccat tgtagaaccg ttgattgtca 103059
tgttaatcgg ccttcagcag aattttatag ccagtgttgt tagagctgga gctgagttgt 103119
acaagtatca gatgtagtaa tgaaagactt tggctttatg aaaatgtgtg tccagggtat 103179
tcctgggaca gcggcacctc atttaattga ggagtatgca ggtcctaagt ccattgacac 103239
agcattgcca ggcacctatc ccacaaggct ccagacccat ccactactca tgcaatactc 103299
atgcaatact catgctgaca ctcccttagc aatgcaggac atagagcatc tgaaaccggg 103359
aggccttcta agtcccttca gcttgacagt attgtttcta cccatgcaaa ttgggaattg 103419
accatatagc cattttagat acacatttat gacatccata gtctctgatt taacccccta 103479
cattgaatgg ggatttttgt tgttgttggt tttttttttt tttttgtttt ttgtttttgt 103539
tttttttctc tgtcatcaac acaagtgaca ggcttttcct tggattccct ggattttaac 103599
cgtcaggtac cagtacatgc acacacaggc ccaggcatct gtgggcacag gagttcgagc 103659
aaccatagca gaccacggaa agcttagaag gtccttggaa tcctttattt cctctccata 103719
tctgacttac ctatcctact attaccagcc tgctcttctt gtgtgctctt cagtcaaggc 103779
attgattggg tcttttgttt attggattat aactacctgc tctctctttt tgtctttgat 103839
tgtaaatatt agttaaggca aatagttcaa gacttacttc tgtagcctgg aagacctcgt 103899
tattttacag ataaatgaat tccagtgcat acgggtgttg ttattggctg ctggccccca 103959
gccccagttg ggttccgtga tatctgttct atctttagaa acactccttg aagtattaga 104019
gcccagggct ctgcactgtt acttctgcaa attctgccag gtttgcttca cctaatctgt 104079
ttatcctgtc caaatacaat cttagtctaa agtaccttaa aagacaacca aaattagtac 104139
```

-continued

```
cctcctaaag tcttatcatt aactttctcc tatgcattca tacttcttca acatacagat 104199
tgaaagctta tagcctctat agagcagcta cagtgtggaa cacgtgaata cataaccctg 104259
atgtagaact ccccaacatg ctttggtgag ttcccaacat actaaagagc caatatgcag 104319
ggtgaatgca gggaagtctt gcttgaagca atgtaagtgg atacagttac agagattgtt 104379
tttgtgccaa gccctcatgt aatctatgat tctgtgtgtg tgtgttcctg ttgtatatat 104439
gcaggtgaat gtatgtgtgc atatgtatgt ggaaaccaga gaacaaattt ggctattgtt 104499
cctcaagtgc tgtcaacctt gtttttagag acaggctacc actggcgtag agctcatcga 104559
ataagctgag ctggccagtc tgtgagcccc agagatcatt tgatcctaac ctccccactc 104619
tgagattata aatgtggagc accattccca gccatacata tatatgtatg taaacattac 104679
atacatatgc tgggatttga ggagggaaat ccttcccttg agagggaaac accttctggg 104739
tgtcagccct ctatttcctc cccaaccccc cacttcccca cacatatcaa gtctctgcag 104799
gactaggcac agcctttccc actgaggcca ggtaaggctg tccatttagg gatgcaggat 104859
ctataggcag gcaagcagac aacaggctca ggaacagcct ctgccccagt tgtttagggg 104919
tcccacatga ataccaagct gctcatctgc tacatatgta tgggggagag aagggggcta 104979
ggtccagcct gtgctcatgc tttagttggt caatctctgg gagctctcaa ggatccaggt 105039
tagttgactg ttggtcttcc tgtggagtct ctgtcctctg tggctctccc aacatttctc 105099
ccaactcttc cataagactc ctcaagctcc atctcatgtt tggatgtgag tttctgcatc 105159
tcttcccatt ggctgctggg tggagcctgt tagagaaagt tatgctaggc tcctgtctgc 105219
aagcataatg tcagttagtt agtaatgtca gggattggtt cttgcccctg ggatgggact 105279
caagttgagg cagtttggtt acctattccc gcagtctctg ttacctttgt ccctgcacat 105339
cctgtaggca ggacatattt tgggtcaaag gctttgtggg tgagttgctg cccctatccc 105399
tccactgggg atagttgcct agttacagga agtagcaata tcagaatcca ttcacagcta 105459
gagttgcccc cttagaccct ctgaggcttc tcccatcgta ggtctctggc acttcctaga 105519
gatcgcccct gccctcagct gatctctgtt ccctctccct tcttctccct acatatgacc 105579
tagccccact cccctcccac aggaacagac aagtctccct gcctgtagtc ctcttcccct 105639
gacaggctca tggccagttt ggtgttttgt tttgttttgt tttgttttgt tttgttttgt 105699
tttgttttgt tttgtttttg tcttggatat cagctccttg tttcacagaa atgaaaggag 105759
tcaccctttt cagaagatcc aggcttcact atttcagtct tggcatcccg tctgtgtgtc 105819
ctgacactga ccccgcgctt cagcatttta tttgctcctt gtctttttct cctccagtgg 105879
aatgcgcacc atgaggaggg gcaacttact ctccttgtcc ctttgggaac ctcatatctg 105939
actcaagttc tagcgcacgt tatccaccgg ctaacgttat ccatcttctt gtgtccattg 105999
tctgtggttt tggcttccac gatctaaaaa tattagttgg aagtatctaa aaataagatt 106059
cgtaaacttt tcagttgcgt gctgctttga gtagcatggt gacatttggc gccatctgct 106119
cccttctgct caggacatga gccacccttt cccaacagat ccacactgtg tatgggtctt 106179
gcctgttaat agttgtctca gttctgcaac cgaaagttgt ggtattataa tgcttatgga 106239
tttttaaaag catttgttta ataatggttg taaagggcaa agatgatgct gacagctttt 106299
atatttgttt gtttattgtc aagagaagcc ataaaatatc atcttacacc gtcacataag 106359
gtactgttca ataacatact gtggaaaaga gaccagattc atacaatgtc tattatggga 106419
cattgttcta attgcttttt gtagttatta gtttcttact atgtctggtt tataaaagta 106479
```

-continued

```
aattttatga gacatagatg tgcgcaaggg ataaaatcta taatatgtat ggagttcagt 106539
gctctctaca gttccaggag ccctctgggg ggccttggga tgtctcctca cacataatgc 106599
tgtttaaaac attgttccca attaataaaa tgggatattt actgttgaat aaaacctata 106659
aggcatctca aaatctttct catagatctc tgaattgaca gcagtcgtga aatacgttcc 106719
tgggttgatc agggacagaa acaagagctg tacaattaga cttcagaagg ccagtctctg 106779
tttctactcc aggtgataat gtaaatggtc catgttagcc atgcacaaag tgaggggcca 106839
tctgctccac tatcagtggt ctttcaggaa ttgtacctct tcattttttt ttcaatgctg 106899
tgtatttaag agtcataaga aggccaattc aaacagactg tattcgtggc ccaaatttct 106959
ggcccttcat ttctagctgt ctgttgatga tccttttcca atagtatctg tcagcatgtc 107019
aaatccatca tgatcaaagc cggatccatt aacgtctgct ccttgccact gggccttcct 107079
gctgtatccc gttgccatta gtaaccatcc ctaccctttc tccatcttga agcacaagat 107139
tcatcttccc actaaccccg ccccatccag acggccacca gttctgttat tctctgaaac 107199
ccctcatggt ttctcagcct ccttggctgt gcttctcctg aaccttctcc acacagcccc 107259
tgtcactctg tcacctgtct gacccccatg ccgcttccag cgcacgaatg tcgatgtgtg 107319
accgctcttc catcctttga cttaaagttt gtttattaca cgctgggttc ctgtgcataa 107379
ggatccagat gagtcttcag ccggtgaaaa caaactcttt catagtacag ccatggcctg 107439
ccttctgttt tctgtgaaca ctcactcgtg ttctgcagcc tacagagctc ttggccctct 107499
gttgtcccct ttcccatgtg ctctttcctg tagcttcgta ctcatatatt gcttcccact 107559
ttattatatt ttgattctgt tcttaagtct gccttctcca gatcttgtct ctctctctat 107619
atatatgcaa atatatttat aaattgttat atattgctta tatactttat atatgtattg 107679
ttttatatat tgtttttata tgtttatatt tattatttat atatagaaac aaaaatgttt 107739
gatttatata gtaaactgat aataaatagg gtgaacaata actagtagta aaacagggcc 107799
attatatcag gttgtggcaa taaaagctag tcaaaatgca tgaattgttt ctctcagaaa 107859
cttttcacaa aatattttaa gtccgaggcc gacccgaagg agagtaactg aagccacatc 107919
taatgaggtg acttactgtg tacttagtgt catctgtctt cctgatagaa caaagcactc 107979
acagaagcag ctgttgtcag ggacttcacc taaaacacaa gatgtggcca cactgagcgc 108039
actacatgtg actctccatc tacccttgct gcactgtgta aggaacactg gtgtcctgtg 108099
tgctgactct gagttttcca gatacttctt gagaaaattc ttatcaaggc aagaaactgg 108159
ccttgctggt aaaggaaaaa aaaaattacc cacagtggaa aagccctttt cctatctaaa 108219
cacgcattcc tcagttttct ggctaccgag tcctttcatg atgcagtagt gataggctta 108279
aatttatatc acctctagtt tatatccaat tgaaaagact cccttactca cttcaaaccc 108339
tcagaaacaa aaagaagtgg ggtatgtgag gatccctggt gtagcttcct ttcttgctat 108399
tttttccggg atgagacaac aagacatgtc tggtctttcc ggaaaggctc tcctgagagc 108459
ataggtgcaa ccagcatccc aggggttctg ccctttctta gaagaagggt tgcaggttcc 108519
tatggctacg tcacgtatga aaccaatgtg gctttcatac aagcaggaag cttccctttc 108579
tccttctcct ttccgaggtc gtgtgtgtgt gtgtgtgtgt gtgtgtgtgt gtgtgtgaga 108639
gagagagaga gagagagaga gagagagagg cttgattagt ttctcacttt aagacagtcc 108699
tagaaagctg gataagcatt tagctcacag atcacctgca gttttatgct tgttaaaaga 108759
aagcagaaga gaagactggg cacagtgtcc ctcagatgct tgtgttcatg gtgtcttctc 108819
cagctgcctt cattcaatac ttttctcacg gctgggagca aacaccagga caggctataa 108879
```

-continued cctaaagctt cccgtgaaag acccacttct ttttttttat attagatatt ttcttcactt 108939
acatttcaaa tgccatcatg aaagtcccat agaccatccc ccaccatgat cccctaccca 108999
ccctctccca cttattggcc atggctttcc cctgtactgg ggcatataaa gtttgcaaga 109059
ccaaggggtc tctcttccca atgatggctg gctaggccat cttctgatac atatgcagct 109119
agagatacga gctctggggg tactggttag ttcatattgt tccacctata gggttgcaga 109179
tcccttcagc tccttgggta ctttctctag ctcctccatt gggaaccctg tgatccatcc 109239
tataggtgac tgtgagcatc cacttctgta tttgccaggc actggcatag tatcataaga 109299
gacagctata ccagggtcct ttcagcaaaa tcttgctggc atatgcaata gtgtctgggt 109359
ttggtggctg attatgggat ggacccccag gtggggcagt ctctagatgg tccatccttt 109419
catcttagct ccaaactttg tctgtacaac tccttccatg ggtattttgt tccctattct 109479
agggaggaat aaagtatccg atgcgttccg gtcttccttc gttgcatttt ctatgtgttt 109539
ttggaaattg tatcttggat attctaggtt tctgggctaa tatccactta tcattgagtg 109599
catatcaagt gacttctttt atgattgtgt taccttactc aggatgatat cctccggata 109659
catccatttg cctaacaatt tcataaattt attgttttta atagctgagt agtactccat 109719
tatgtaaatg taccacattt tctgtatcca ttcctctgtt gagggacatc tgggttcttt 109779
ccagcttctg gctattataa acaaggctgc ctatgaacat agtggagcat gtgttcttct 109839
tactggttgg aatatcttct gggtatatgc ccaggagagg tattgctgga tcttctggta 109899
gtactatgtc cagttttctg aggaaccacc agactgattt ccagagtggt tgtacaagct 109959
tgcaatccca ccagcaatgg aggagtgttc ctctttctcc acatcctaga cagcatctgc 110019
tgtcacctga atttttatc ctagccattc tgactggtgt gaggtggaat cttaaggctt 110079
ctcggcctcc tgaaacagtg ctaccaccta ggaaccaagg gttccataca cgagtgtttg 110139
ggaaatgcct ctcacgcagg ccatagcaca gctttggaca gtccaaatgc tcatccctta 110199
gtcatccctg cctgtcctag atagtgttcc tgagttcagt tccccttttg tgctcatcac 110259
cttggactgt gccagtagac caccatttct tcagttcgta gtctttttg gtctatagga 110319
tgtgcgtacc aggagggcag agacattctc tgatttgttt ctcgcaatgt cccccagatt 110379
ttgaacatgc ccccaaactt agtatgaagc ctattgtcca aatggataga gatcatggat 110439
tccctgatct ccatttgcaa tctgcacacg gtcggtcacc catactcacc aagaccctga 110499
tcttcaggaa tttgttcctt cagaggtttc tggcatagcc tctgatgaac caggattttg 110559
ttttctcaca tcaagaattt agaatggttc taggactttt ttttctttct cactgcaggt 110619
gcttctactt aatcctgcac ggatcataaa gctgtcagga caatgtactt tatattatat 110679
atcacttttc ttacttccaa gatagccttg gggggaagaa aagcacttta gtcttttact 110739
gtaattatag tccagattta gaagccttgc cagaatatca ttctaccaca ctttttatg 110799
atgctgaaat attttaaaga aaagttcagt taagagcata ctaactaaat atgtctgtac 110859
atctctaaaa ctgctgctct gcagaacaca ctgataccct ctcacccaca aaattaataa 110919
aaaaagaaaa attgatacca ggaagtacta agttcacaga tttgtctaaa ctgtttttca 110979
tggtttattt tttatataac agatccttcc taacaacaga ggtttttttt ttcaaaaata 111039
ttttatggtt ggggtgtttt tggtttttgt attttacctg catgtatatc tgtacaccac 111099
atagacctac ccgacacccc atgcagtgtc caacctttga acttccagtc cttcctgcct 111159
gttgtccact ccattagcaa gatcaaacaa gtaaaaaacg tctctgggta tgtgaagtat 111219

-continued taatatgcta atgagcaggt aggatgtgtg ttctggagac catgagagaa tttcaagtgc 111279
agtgtccatg agtgaccctg agcaagtcag aagatgccat aactactgaa tggcaaagag 111339
tatagtctaa tggaggcatt caaggttgga tgaatggctg cattgcctat ttattcatta 111399
atttacattg aacctgccta gatctcattt acatccacat ttaaccacta aggaaaaagc 111459
cctggtttcc ttctgtcttt cctctccatt aaaactcagt gtccctgtga acttttgttg 111519
ggatcatcgt tatttgcata ttgttcccaa ttgcataatg aatgcatatt cctgactcat 111579
cccaactgcc cagtggcctc tggcctgtgc cagtcacttt ctccttggaa tttctgaagc 111639
gagtgttatg caagtcccct gttgctcact gagccattag tagagactct ctcacccaga 111699
ataggcatta ctaaatgtgt gatgacgact cagtccaatt tcaaaccaag gttgggaccg 111759
gcagctcact cttaattgcc tgagtcatgc agttttgatg tctcagtctt taagttaagg 111819
ctccagctgg gtttgagatc cttcctcagc aaggaatact ttagctgcaa atgtcaaaaa 111879
tcgccaggat tggttcagag tctttccagt gagctgtgct taactgatgg tccactttga 111939
taaatctaat gccatccgct cgtagctggc aggggcttct gcctttcggg tggtcacaga 111999
agctaggagt aacaaggcaa agaaacaaag acacaggggc taccttttca tctggatgtg 112059
acttctccat gaagtacagg catgtagcct ggcttctggt tgtttagaaa ttgccggttg 112119
caaggccttc tagctgcaag ggatgcagca atgtggacta atgggctatt tggttcttat 112179
ccatctcctg tcaagggagg ggaggaagga cttgagaatg accttgggta acttacacag 112239
tatctgctac aaggagttta tgctttcttc ccaagggaaa catacatcgg attttgtttt 112299
ggaaaacttc taactgaaaa tttgatatgc cttgctagct agcatgtgtc accaaggcaa 112359
ctactcccct atctgcagga gatacggcct atagggttct gtcatcacta cattgtgtat 112419
atactttttg ttgctttcct tctgtagagt gtgcactcat ccacagaaag aggtcattga 112479
cagattatca acagatcatg aaaaagatgg agtgatcata acgatagtgt actaagaatt 112539
acttaaaggt tatgaattgt ttctggattt tccactagat agtttttag acggtgtttg 112599
accaggtaat tcagagtgtc atcacagtat tgtagaataa aataggaact acattttaag 112659
tctatagtca aaagaagact tttgtgtat gtagatctga attgatgaag taatcagtgt 112719
agaggataat ttgcctcgtt caacctgatt cagtgatgcc atgacaaaag gtactataga 112779
tatgaaaagt catagccgtg tttttgcttt cttttgttat aattaccttt attgtacttg 112839
taatagggtt cttggaagag ggaatatgtt tgcaaattgc aggccctcaa atggcagttt 112899
tgctactgag agtttttatg ccagatcaac ccacaagtat ttataagaaa agttgtttgt 112959
tacattagga aaatctactt caagtctttt ttttttctg aaaaaggggt gtgcattaac 113019
aaagaactca taacacaact ctacagcttt gcctaatttt taaaaccaaa aatgacctga 113079
tagtctaaat cagaacacct acccttacca gccaccctct cctgcaatcc aggtttcttc 113139
tcaccagatc ctacaactcc tgaattcatc tgcttgaaca tttgcctata ttcattgttt 113199
ctgtaagtga gtgggacatg gttcatgtca gtaaggacac catttaggag gccgaggcaa 113259
aaggttccta atgatatcaa ggtcatctta ggctgctgac cggaaccttc tctcaaacca 113319
gtataaacaa atgagtaaag aaataggcta agagtgacct tgtgtgttta cttttggaat 113379
gggagtgttc ttgacttcac cttccttggg ctgtcctttg ttgacgattt cctggggacc 113439
acagaaaaca agcttacctt cttccgtgtt tcttcatgtt ctctgcaagt aacaacaatg 113499
atctcagaca ttgcttttct ttggaacaca ctgacttact cagttggaga actctgaatc 113559
caacgaaggg gaaaacatct gttcatctca ggttgttttc ttgtgttatt ggtgcattgg 113619

-continued cgtttgtttg tttgtttgtt tgtttgttgt ttctgtcttc atggctgtat tttctctgtg 113679 tctctcactt tgattctggg aatctctcac agacgcttct gtcttcctct tcttcccgta 113739 catcggcatg cataggtctg agccccatct tttttcagtc atgctcctct ggcctcttat 113799 tggtcacaac atgttgggaa ctggcttttg gttattttta tcactgctga agtggaggcc 113859 agatagtaga tcgcattctc gtacccatga atatcagaac atctctctgc catttctttt 113919 ctccggtttc tatgatagca ggaagaaaga aaaacaaact aaatgtttac aggctgtgaa 113979 acaacaaata aaacttctaa aggtccttta ttcatttaat tgggcaggag gtaccaacac 114039 attcaattat cccttacttc gtgacttcaa accccctacca ttgtgcccaa cagaggaata 114099 catgtggccc ccactatcct atcatgcaga atagcttcac agaccaaagg accctcaatg 114159 aactgtgagt tcactcctcc ctgagcctcc accccacagc cactgatctt tttactccag 114219 cctttggccg tacatggaat gtcagagaat gcaaatggca aaacactttg cttgactttc 114279 aaaacaagga atgaaagctg gtgtgtgaat cctgctgcct aaggagactc ccaggtggca 114339 gcatcatatg caattatgtc aggttcagcc tcgtgggaaa tggcgatcca ccttcatggt 114399 agcctttatc ctccagcaaa gtacaacctt tcactgtgtc actggtgact cactgcacct 114459 cctcactgca ctcagatact cttaggatgg ccaggagctc ctgtttcctt agtatttctt 114519 agtatttctc actttaaaac ctagagaaag cattggtaat atgtaagctg acggcctttg 114579 cagttggggg atgggatgag agtgttctgc catcttatca tctttctgtg actgtttctt 114639 gcccggcttg tgaagaaatg gctctgcctc acattttcac agacttctcc ccgcccttct 114699 gttttctgtt gctgtgctca gctttacaca cccatctcac ctttcttaca tcacagaaga 114759 aactaactgg cctttcagct ggtggcagaa aaacatcttt cccgcctgct aatgcttcct 114819 gttagcccta aaagctccaa ttagaagtcg taagagggac acgttcaaga ttctcggaga 114879 agatgcagcc tcattaaaac acaattgtgt gcttctgctt taaatagtgt ccaaatagat 114939 aagtgaattc aggtccgcct aaatttaatt ccagaaatca aagccacagc aataagaact 114999 ggacctgagt tctcttaggg caagtaattt aatttctcag ccagttgaac tattatgcat 115059 ctcagttctt agttattatg acagtaaatt atgccgacag aggcggtgag gggtgatgtg 115119 catataattt cttcttttc ctggctaagc acacaccaga atgcagatgt cttaaacagc 115179 ttttccctca gccaaggctt ccgtttggag ctttaaaagc agtgtttacg taataacgga 115239 agatggatag acacctcagg gaatccagct gtgtatatgc ttcaccctac ctgacagccc 115299 agggctaacc aaatcctgga ctgtatacca gtgatgaaca ctgtcacaac agtcatggag 115359 tgagatcatg ggtaattcat ggtttataga gaatcctggc ctggacttag cttttctccc 115419 tgccattgct tttgcattac cactgacagt ggagaaacaa agggaattgt gactgattcg 115479 attggacaaa gaggggattc cagacacaat caattcagga atctaccacc cttcactaga 115539 aaaacagcct tgagattaag taaaagaccc caagtcaaat ctgcgccagc tgtaggttta 115599 gtttggaaat acgccatcgg tgctagatgt gtgcacagag agttttgtgc aggcaatcaa 115659 gaaatcaatt agtttaccct atttatatct aggcagatgg aggcttatcc tatctgatta 115719 tccatttctc acctatttct tcatggtctt gatgagaatg tgaaaatcag ttatagtctc 115779 ctacctatca acacattatg cattagcact tcactaaatt attcatctta ataatttctt 115839 ctgtacattt tagtcaaacg tttcagaata tgttgtgttt ttcatcgtat ttcaccagag 115899 ttggggaaat gtccccttga agagcccaac atagttttat aggatttttt caagtcctgc 115959

-continued

```
atcctgggct tgcacccaag ggcctgctat gcatcattca ttacagaacc tgtacaaagt 116019

atccctggag ttggaggaaa ccacaccggt cccttggtgc tacatccatc tccttggatt 116079

tcctttccct ttcattttca ggacagcatc tcactgctac gctgtcagac actgactgtg 116139

agagtctttc aacctctgga agcatgtgag atcacagctg ggaccattcc agtctctagc 116199

tcacatgata cagtctatga cactggacgc acactccttt agagctgagc tgtgtccttc 116259

ctcaacacat ccagagcatc atggtgtcac agctcataca acctccagat ttccattgcc 116319

tttcccaatg gaaaagcaca ctccttcttg ctggccacac tccacttcgg ggtgatagtt 116379

tccgtgtgcc ctgtttgttg gtggggacac tgacctggcc atggcctctt ttccactctc 116439

ttgtgtagtg cttctcattt gacacaactg ggccagagag tctcagtctc agctgtttgt 116499

cttgtgttgg ctttttgatg tggtccagca tgtctctgtc ctttcccagt aggcaataca 116559

gggtaggctc tccctgcttt tatcttcatc cgtgtgctct tggccaagct ggcattggca 116619

gccagttgct ttccgcacag gttccttagt agttccttaa attgtgtcct agacatgtcc 116679

tttcacgatt ttatcttgcc aattgctacc tgacctgtgt gtgttggtac atagatgttt 116739

acagccatat tatctctcaa cagtctacat aattttgcct tgaccgaagc gtcatataat 116799

tggagtcaga gtatcttctt tctgcaacca ttaaacgaag agctatgtcc acttgtgaaa 116859

cattttgtgg acctcagata gagttcctac ttaacagcat tttgaccttc ctagtgtttt 116919

ttcatcaatc ccatactccc tcacgcatta ccaaagtccc ttgattcttt ttcttcttca 116979

ctttcctaaa ctttcattca gccgagtctc tcacagctat ttttttatct gttcttccag 117039

t gaa gac aaa gta gta gaa gtc gcc gaa gag gag gaa gtg gct gat gtt 117088
  Glu Asp Lys Val Val Glu Val Ala Glu Glu Glu Glu Val Ala Asp Val
              225                 230                 235

gag gaa gag gaa gct gat gat gat gag gat gtg gag gat ggg gac gag   117136
Glu Glu Glu Glu Ala Asp Asp Asp Glu Asp Val Glu Asp Gly Asp Glu
        240                 245                 250

gtg gag gag gag gcc gag gag ccc tac gaa gag gcc acc gag aga aca   117184
Val Glu Glu Glu Ala Glu Glu Pro Tyr Glu Glu Ala Thr Glu Arg Thr
    255                 260                 265

acc agc act gcc acc acc acc aca acc acc act gag tcc gtg gag gag   117232
Thr Ser Thr Ala Thr Thr Thr Thr Thr Thr Thr Glu Ser Val Glu Glu
270                 275                 280                 285

gtg gtc cga g gtaagccgct gttggattgc tatttaactg ccctgggata         117282
Val Val Arg

agagatttca atcagtgctt cccttctcca gccccctgcc ctcacctccc tcccaccact 117342

cccccaaaat cacaaggctt cttcctcttg gtttattgct ggtgttggtt tggttgctat 117402

aacaagccgt ccagcagtcc atttaaacta aaacaaatct cgcttgcata gtcacttcta 117462

tgccttgtgt atgctgttga aggagtccta gactatattt atataagacc ccacctagcc 117522

agaaggcatc aaatttgaaa agtgctgaat catgccctgg tggtgggcct tcattgttca 117582

gcactgcccg ttgcatcttg gacccctgag actgggaact ccttgattgg aagaactgta 117642

gtttgggtca ttcactgtgc tggacttata gacaattcca atgaagtttg ctcgtgtgaa 117702

tagcttttta ttagatttta ctaattttac taaatctatt ttctttttgt ttactgagtc 117762

aaacttttaa tatgatttgg taagaatcac tttatttcgt gctgtgaagt tcaacatggg 117822

caatttgtgt tacttgttta atcgggacgt atgtcggcac cttcttcaaa acaggtgtaa 117882

ttcccatgcc tcagcgaatg cccctcccga gaatgttgta aaccaaagaa atgaagaaga 117942

cttttcatct ccaggaagtg aaagcaaata ctttgattat gttaaacaaa ccaaatgtta 118002
```

-continued

```
tgccaactag tgtgtttggg ggttggggaa tttaaatggg tatgtgttgg tttttttttcc 118062
ccacagtaaa atctgcctct agatctagac tgagtgaaca tgggttgact tcattttagt 118122
gtaatgcaga tgatgttagc tttcgtccac aaatgttaaa aacgcagtaa gatttccttc 118182
ctttttgatt atggtgtaat gattacagct cattagagtt taatatgaga cactgtccaa 118242
cccaaggaca tcgctaatta ttattactag ccctccctct ccctttgctg cattttaaag 118302
aactttattg aggtaagatt ttatatatca taatattaac tcattttcaa tatataagag 118362
agtgacttta ataaatttac tcagttgttt aatatcacgg taatctcgcc cagggccttc 118422
cagcacccta atgagatccc ttctgcccac tcacagactt ggtcctcgct catgcccata 118482
aatggctggg ctactttggc ctccattgag ttgcctttct ctgaatactt aatccataac 118542
tgaggttgta cccggcacag cttaatggct gacttgtgtc ccttaacagt gttttctgtt 118602
tttcacttgg agtttttggt tagtgacgaa ttgaacactt agatctaatg gaagtattct 118662
atattgttta ggaagagagt ccagtttcag gtagatggtt tagttttatc gtttccctac 118722
ttaagacagc atgtgcaaat agaggtatcc ttgatctgaa tgaaatgctc ttcttcaaat 118782
gcccaaggca tctttttcca aagaaatttt caaatgtctc tggaggccat gactggtaga 118842
tctggcctaa tgaatttttt agccctgatt tttctcagca aggaaagagg tgtttttttgt 118902
tttttgttt tgttttttttg ttttgttttg ttttgtttgt ttttggtttt tttgtttttg 118962
tttttttttat ttccccactc tgggtttctt ttcttggagt cacatcacag tgactgataa 119022
tctgcaatga agtgaggtct tcagaagtag aggacacttg ttggctgcct gtaagtctga 119082
atggcacagg tgaagaccac acacagcctc atgatgacca tgagcgctga gatctaggat 119142
gaaatcaaag ccaaagaaat gcaaaacctt ctactctgta aattaagaac acagagccta 119202
cttcagaaca agcttccagg ttggctaaca aaggttctta agtagatggc atttaagcaa 119262
ggcaggggaa gtgtcgccag gtaaattttg ttatgacgca cacacatcac agtcagtcgg 119322
aaagagcaaa caaaccctgt gctctggtgg aagataaggg gcatgcttgg gagacaggac 119382
tagttggtac tctgtggaaa agaatctgga aaaactgggt tgggacagat gctgagaatg 119442
atgggaaatg gagtgaattt gaccgtcatg agtcacaggg gaacacggag tggtgatctt 119502
aggcttatat tctaatcaag atggaatttt ctcgagatct gtgatctcgt taactttcaa 119562
gtcttgttat ttttctgaat tagttcttcc ctttctcagt ttcacgagta cctttgaatt 119622
ttagatgttt agttttagta tacagttttc catgtaaggt gtaattttta gatcttcaga 119682
cagaacatat aaagacatga acactatgga atttttctct agaaagcctc aagttcaagt 119742
gagaactaca agagatctct aagcaagatg tttataagaa aaatctaaag caagcactaa 119802
ttttaaagat aagcaggagc tggggattgg cacaggagat agagtacttg ctacaaaggt 119862
aggaagagct tagttcaaac cctcagagcc cgatgtaaaa aggcaagcat ggttatgcaa 119922
gcctgcaacc cagagctgag gacacaggaa gtttgttggg ggatattgtt ggatgttctg 119982
tagaagactc tgtgtggaga aaataagaca gtgttaaagc aagacatcca acatcctatt 120042
ctggaaaata cagacgaaca tacaacacac acatgcacaa acacacacac acacacaaac 120102
acacacacac acacacatta atgctataaa aaggtttttt tttaaatgtg agcacattca 120162
ctctatgtaa ggcttatgga gttcaccaac gacataaatt caggcaaatc tttccgagat 120222
gttagaggat gctcattaat gatgcagatg taggattaag gcagacgacc cttccctgtg 120282
tattcctagt gtagaaggcg actgctaatt cttctcctta gtaggagccc cagcaatggc 120342
agagccgatc gcacactttg taaaaccctc cctgcaaagc cggcttccgt gcctgggaag 120402
```

-continued caaacactac ctgcagagaa cagattagta ttgcactctt attatcaacg tcaatgtttt 120462 cgcctctgaa aggacatgaa tgtgatttac caccattcat agaaagaaaa atcatttcac 120522 catttcaaga ctccggcaac taagccgagt ccttactggg cttcttaaga actcggtcct 120582 ttcatagccc attggctcct gagaggacta agcagaggga aggaagcaga agatattttt 120642 acctgatcat agaacttcta accccagctg cctgttctgc attactgagt tcagagagaa 120702 ggcaattctt tggaggtaag ctcgttactg caaaatccat ctggttgcta agctttgcta 120762 attaggaaga tgttggatat cagtcaaatg cctcaagttg ttaccagtta agggaagcaa 120822 cagtcttaga ctcttgttct catttttttc agatcataag tccgagatgt gagggttttc 120882 ttttctgaag tgtgaatgtt gtaggaattg gctcagcttt ggcttttgaa cccaattctg 120942 cctgtccaga aaaacgtttt ccttatggtt atttattcag taaatattct ttgtgccctg 121002 ctgctggcta aagtctttgc tgctgtagaa agcatagcag ggctagcaca gacaggcttc 121062 cacctgctag aagcatccac gttggagttc tttagaactt agaagtgctc tggctcaccg 121122 tttcccttgt tctttaaagc catgtcttag tcagggtttc tattcctgca caaacatcat 121182 gaccaagaag caagttgggg aggaaagggt ttattcagct tacacttcca cattgctgtt 121242 catcaccaaa ggaagtcagg attggaactc aagcaggtca ggaagcagga gctgatgcag 121302 aggccatgga gggatgtttc ttactggctt gattcccccg gcttactcag cctgctctct 121362 tatagaaccc aggacctcca gcccagggat ggcaccactc acagtgggcc ctcccagcct 121422 tgatcactaa ttgagaaaat gccttacagc tggatctcat ggaggcattt cctcaaggga 121482 ggctcctttc tctgtgataa ctccagctta tgtcaagttg acacacaaaa ccagccagta 121542 taggctgtaa ttctcctttt aagccttata gctgtagtat gcagtagaaa agttatttcc 121602 cctatttgaa gtcagggcaa ttatgactta gggaaacttt aaacatacat tagtcatata 121662 agtagtaatt gatgaagcca ggatttgggt ccacatgagc taggctattt cagtttcgtt 121722 aatgcccaaa tgatattttc acttttcttt ctaaatacat actcttctgt ttaacttgca 121782 cctcctgtaa gtgcctgttc atttgctatg gacatggatg catcttttat ttctgtgccg 121842 tacattcctg gaattttctg tttttaaatt aaacaatagt aatgatcagg tgtcaatgat 121902 cagtaataca tgactagtgg tcacaatact atatatatat tccagggacc acaagtagca 121962 tgttacctat tttttaagac aaaggttttc ctgggagaca ctcaacccca cttatttaga 122022 tgttgtctct ggctatgttc acgctataaa agcagaatat agagctgagg agatggataa 122082 ttacaaagga gattatactg tcagaaaaga ccaaggtata tactgtttct taatctcaga 122142 tattgttcaa agaaagaatt ctacttacta aaatcaagtt gatttcagtg tgtgtatgtg 122202 tgtgcgtgcg tgtgtatgcc catgtgtatg caggtacata tgcatacatg tggatgtgtg 122262 tgtagaattc ataggacaac ctcattcatg catgtagata tgtgtgtaga actcatagga 122322 caacctcatt catgcatgca aatatgtgtg taaaaatcat aggacaacct caagtgttgt 122382 tcctcgggtg gtcccaacca ccttttcttg tttctagact ttaggcagtg atgggaggca 122442 gggcctttca ctggccaaga actgatccag tagactaggc tacatgacca acaagtccca 122502 catatgtttg gaatggtaag cggtcccgcc ttgcctggct ttttcttaat gtgaatattg 122562 aactcgggtc ttcatgtttg tgcagcaaag agtttatgga ctaagccatc cccctcccct 122622 cagctccatc tgtagtattt actggagaca tttatcattt tatggccttg ggccagtcga 122682 gtaacctgct ttttatttgc ctaacataag tgctgacgtt gccttgcatg ttttaagagt 122742

-continued gactttacat gatctatgat aagcgcttac ctaggaagac ttagacttag ttgctcaagt 122802 acaggttgct cagatttgaa tcctacttag ccctgcagcc tgggaactgc aaaatcctgc 122862 acgatgcagc aatgcaagta gtcctgcatc ctcgtatgtc tctgtaaaac tggggttgat 122922 atctagccac tctgtgagaa gcaagtggct cctagtaacc cctgggaacc attgagccca 122982 gtttctgaca gacaggaagt cctcagcctg gagcgtgtgg tcactgcggt tgtagtcatc 123042 attccaatac cttggtagat tcagaacatt agacaactag tgtttactac cagtcagacg 123102 tattaaaggt aaaccaacag attgacattt taattgcagt gtgatgcatc tctgaactgt 123162 tggtacaaca gagctggggt ttgtagacag cattctgtta ccattaaaat gcagcatgaa 123222 ctgggtctcc tgcttaaaat agttttgtgt gtgaatctat tcccacatat caagatattt 123282 gcaattaaac tttatatcta gcggcaaatt gaacaagatg gtactgaatg tcacgtttca 123342 agatcgactg tttattcctt ccatccattt tatgccccgt gggaggaaat tcatcagtaa 123402 ggggacagag agagagacac ggacacaggt gactttttaa acacttgtgt ttgtgaagct 123462 aaaatctccg gtctaaaccc tggctggctt atgttagctg gctgatcttg tgaagttatt 123522 gctcctctgt ggataattac tgagaagcag cagacaagta tcaggaattg acatgaagac 123582 atccccaaca gtgatgaggc acatttacac actgggcaca gcattattct ctcggggccc 123642 agggatatga acccaggtag ctcaggtctg tccatccaga tctgcgtagc ctcttttcac 123702 cctgtgtgga aaagggcatc cgtatcctgt ggacgttttg acccactgac agagcatcag 123762 aagtaatgca tctaacaagc ttcataaata aagccatgtt gctctgtagg gtataaaaga 123822 gacgaagctt atgtttctcc cccatctcca ttggtatggc tcaataaagg catgacacaa 123882 gcagcctgga actcatgggt tcttgctttg tctgtcatgc tcagcttttt cagactccgg 123942 agaaacagta aacatggctt gctgtgagtg tgccaaggag ctcaaagctc taaagtgtgt 124002 ttgggggttg agggggtagg aaaaagaaca gtagtatgtt cgttcttcaa gagccagcca 124062 taggctttta cctctgctct aactaaggca gagaatgcat tcacacattc gaaccaaggt 124122 gtggcacccc ctttaatgtc gggaaaactg gtgtcagcac tggccatgta ggtgacaggt 124182 ggcagcctgt tattttgtgc cctgtggcat aacagtcact gattctaagc cattccatgc 124242 atgctttgct tgggctgagg ggtccatgta actgttgctt aactgtccta atctggaaag 124302 cctactgtag caattagtgt gcttaagaca caggactggg gaatgaggtt tacagagaca 124362 gagagagaga gtatacatat atgtggtttt cttagtttta gtaagaactt cattgacata 124422 atttcctatc gacaaagttt agtaaattca caaagatctg tttgccataa gaaaattttt 124482 gtgccttaag taatgattat gtgtctactt aacagtttat atcgtaaaaa caaaaaaata 124542 agttccttaa aatgtaatgc aacaaattag agagcaggta acatgattat gtatgtatac 124602 attttcgcct tttcaattaa tcattaactc cagcagagtg ttgttgtctc aggtaacaaa 124662 gctctggttc ttcgtggaaa tatttagttc ccttaatata agtgtccaga actttaaaag 124722 tggggtggat tgcaaccaaa atatctgttt ctgttggttt tcagcaatcc cgcccttctg 124782 aagatccgtc tgtgacttcc aggcatgtat cagagtagcg tgtctatcat tttgtgtttt 124842 tattaggaga atacggagaa ttccagaaga gatgagactg aataagtctc aatgtgtgtg 124902 tgtgtgtgtg tgtgtgtgtg tgtgtgtgtg tgtgtgtgtg tgtgtgtgtt tatgtatgct 124962 gaaacacaaa agactcattg tatgacttta aacttgatct ctctgtgtct tggttgcttg 125022 tgctaggatc agcagcctgc accatccctg gtttgacact cctactatgt aagcagtgac 125082 atgtggagga aactcttctc tgatcgggtg tttcctcttc caaaggaatc cattctccct 125142

-continued aatacactga ggtgaaaggc aaaccctggt catgggacag actttaagta ggaatgatgc 125202
tgttctcagt ttgaatctta attcttctct gttagagact atggaaggaa gccagccact 125262
gtggaaaggt gggcatgccc tgtcttcctc agacagaaac gtgtttccag accccagctc 125322
actggaagtg ttcttttgtt ctcaaaagtg ttgatgccat ctcgaatgtc ttcccaggaa 125382
aacgctgtga aaagttaggt tccaagtttg ctttagttca ttccttgatt ttttaaaaat 125442
ttttttcagc attattttca aaataacaaa ataataataa tataatatga aaataaaagc 125502
tgtagtgtgg aagtcgaaga gggccactag aggtcatatt tctgagaagt gacgttttta 125562
taggtttaaa tataagagaa ctattatctc agtattgatt aaggcagaag tgttgtggtg 125622
tttttaaaaa cagttaattg tatagagtag gaaaaatatg tattggcaat ctgtttaaaa 125682
acagttcatc tgttatcttt ctgtattttt tattctaaga ctcttctcat ttcccacatg 125742
aaccaaacgt tttccaattt ttaccagttc ctcccctctc gtcctaaggt gcgactgtgt 125802
ctctatattt ttaatataac acatttcaac tacatttaat aagttagttg ggcatggtgg 125862
cacacacctg cagtctttga atttgggaat cagactggag gattgatcat aggggtttac 125922
tgtgtacatg agccacgtca tgtgaccttg cttctctaaa cacaggctag aaagccacac 125982
cctcccacac tcgctacagc ctttcaaggt gcttagcatc ctttgcagtt cttctccagg 126042
cacctatggc tttcactgag cctacacagg agagaggggc gtggctggtc agagagagag 126102
agagagagag gcgtggctgg tcatggagcg tactttgatg aaattttagc accatttctt 126162
gccttctgtg ttttgaggat ttgggcatgg agacaggaaa tttgaaactt aaggggaaag 126222
ctttcttttt ctggtagctt tccattcgtg cctgtgtttt cctggtgtgg cactgtcaga 126282
tccctactgg gctgtgaaaa ctaattatta ctgtagtgag gaattttggg agtcataacc 126342
actacagctt gaaataccag tcgtgggagt tttacctaga aaatagccaa atgctacaat 126402
gtatttatct tcccagatac acacaatttt ttaaagcaaa ttcttccatc tcattcggtt 126462
agaaaagaaa atatttcccc tatgacacaa ggtacgcctt atccttaccc tgttctaggt 126522
ttaaacgtgt tgaaaacatg ttgtgtgtcc aattaaccac agctgacagg aagtcaaggt 126582
tcttgaagca tcatagtggt ctctgagctc gattgcagca gtctcagggg cactgactgg 126642
tgtaaaaccc attttacaga cccatctcct tcaggtgcta ttttataaga aacctttctg 126702
catagggagg tgtgagaatc aggtcaagtg taattacaat gacagagaac tgcacatctc 126762
aatacaaagc ccagccagct tgaggctacc tgctacactg ggtctcaatc tggtggttgt 126822
gacccctttg ggtttgaat aactctttga caggggttgc ctaagatgat tggaaaacac 126882
agatatttgc attgcgattc ataacagtgg caaagactac aatatgaaat agcaatgaag 126942
atgttaatgg ttgtaaattt aatggtaata attttaatag taattttaat gttgggggt 127002
caccataaca tgaagaacta tgctaaaggt tgtagctttc cattaggaat gcagccttag 127062
gaacactgag gaccattgtg ctggagactt ctataaaaaa ttcacacaca tcgtccttct 127122
gagtctatga cttcaataat gtgcacagct gctcgtgtga tttgctgata tttcaacctg 127182
tatttggaac atgagatttc atctccagct tgctggccta atttgcatga ttatatttag 127242
cacaacatga ttactagata ataaatattt gatcatttat ttcctggtaa agattaattt 127302
tcttatcgtt tttatgacta cttgttagca ttcacaatgc atgatgaatg tgatttctgc 127362
tagaagtatg tgattgtagc attggagtta acacgttctt taaaaaagga accacttggg 127422
ctggtgagat ggctcagtga gtaagagcac ccgactgctc ttccgaaggt ccgaagttca 127482

-continued

```
aatcccagca accacatggt ggctcacaac catcggtaac aagatctgac tccctcttct 127542
ggtgtgtctg aagatagcta cagtgtactt acatataata ataaataaat ctttaaaaaa 127602
aaaaaaaaaa ggaaccactt ttctaatgtg ttgttttaaa ttttgcttca tctatgaaaa 127662
ccaaacgaat atttacctat agaatatagt ttttgttcag ataaattagg ctcttggaat 127722
gttgctatat tgcaattgtt aaatttgtag caataactta attgggattt ttaaaaaata 127782
gtttttttcat gcttatttta ttaggaatat aattcttttg tttgtttgct tgcttgcttg 127842
cttgtttctt cttcttgtcg ctgatagttt agaacttgct ctgtagacta gactagcctt 127902
gagcctgtca atatagtcct gtctctgttt cccaggtact ggaattggcg ggtattcacc 127962
gccacatctt gatcatggtt gttttaaagg acactgacat cagagttttc cattattatg 128022
gttgaatgta gaccacaatt tatttgaatg aagtattgat gatcaacaca ctgtagtaca 128082
acttgaatgt ctttaccttt taagctttat ttcactgtta agttagatag caaagctgta 128142
tttgtctttg ttctctacaa ttagagacta aaattacaaa aacggggttt taaaagaggt 128202
acatttatat tatgtatgtc tctgtattgt gtttaattta gcatgtttca cagaacatgg 128262
agaaaatcat gctttgggaa tgtttttctc cgcattctga gaatctgcat ctcctaattt 128322
tatccatcaa accctagtat cggaaggcgc tccatccagt ggctgtctgc cggatgctaa 128382
agggaggggc tcacttttgt ccagttcttc caggctcaca cagacccatc ccatcccctc 128442
tcccacacat tatgcatttg ccactgttta attccattac ctcacctgtg cccgagttct 128502
ggctctgtta ttcagtgagt gggagagact ctgaggacac gccccttgta ccagagccga 128562
caaggatgga ttttgctgac agtctctgtt gactgaaggt ggtgccagtg gatccaaaac 128622
ttctgttcct cttgtggcca cactacaaac ccagtgcagg acactgctgt ccaatcttgg 128682
cattgataaa accgaagaag agactactga aaagtaatat cacgttagga acaaacgagg 128742
gtgctataaa gcatgtacag tcccagccct caaaaggaac aggaggaggc ccacagtagg 128802
aataccagtg gggaatgctg gaatcacgtg attcctccta gaaactggaa aagtcagaat 128862
tgtttcagat gcttgtcaca tggagtggat tcccatggag ttctgtttga ggctctccag 128922
ggttagaaac ccccaaataa gagatggagc tattgttctc cttgcaacaa aaacagacat 128982
gtggaaagtc tatagagctc taccttctaa tagggaggaa cctttaaaat gcaagtgagt 129042
gggttgctgc tttttaaacc aatggggata tggaactgat ttggggagac aggggcaaga 129102
tagactgaca agtaaggtgt gttttaatgt aagataatgt gtggtatata ttaataaatt 129162
tgaatgtgtt agctgtatat gttactgttt ggagcatgac gggctaaggg tcagaaaaaa 129222
atacacgaat agataatttc ttagagttac catggttgac tgtcagtcac tcttgcagat 129282
gttacgtacg ttttcaggtt tagtccgtgg acaggctgga aacattaaac ataaatgtga 129342
ttacttatgc atgagtctag gcgatcattt actaagaaaa acagtcagaa gttggagaga 129402
acgtaaattt tggcatcaca tcccgagaaa tcctttttttt tttttttttt ttttaaacat 129462
cagagttgac tcaaggttgt tttagaagat gccttttttt tttaagagaa atttttgatg 129522
tgcagagaga gagacttttt atctttaaat tgagaaaaca acctttttcac ttctagccca 129582
aatcctgtag ctgctactgc atcctacaca ttaaacaagc cgagaatgtc ttgttttgtg 129642
gaagaggtga ctctgaagtc tgagtgggtc aattcagtcc ctcaaggaag acttaaagta 129702
gctgcttcct ccgttcagcc caggtcacca ctgggaggat cagggcttaa gttgagtaag 129762
tatgtatgtg aacagccaga agatgtcttt tctcgctaaa tgtggttccc ctctgattag 129822
ag  gtg tgc tct gaa caa gcc gag acc ggg cca tgc cgc gca atg atc   129869
```

-continued

```
Glu Val Cys Ser Glu Gln Ala Glu Thr Gly Pro Cys Arg Ala Met Ile
    290                 295                 300

tcc cgc tgg tac ttt gat gtc act gaa ggg aag tgt gtc cca ttc ttt   129917
Ser Arg Trp Tyr Phe Asp Val Thr Glu Gly Lys Cys Val Pro Phe Phe
305                 310                 315                 320

tac ggc gga tgt ggc ggc aac agg aac aac ttt gac acg gaa gag tac   129965
Tyr Gly Gly Cys Gly Gly Asn Arg Asn Asn Phe Asp Thr Glu Glu Tyr
                325                 330                 335

tgc atg gcg gtg tgt ggc agc gtg t gtaagtggat ccttcctcca           130010
Cys Met Ala Val Cys Gly Ser Val
            340

gcctggccac ctcttgtctt tctcgccact ggctctgctc tttgtaacag atcgagtttc 130070

cctcttgttc ttgggaatgg gcccactgtt gctaccacta accacatgcc tgtcaatttc 130130

tctaattacc agaagcctcc tccaccacgg tatgtccagt catgagcgta tctctccgtc 130190

tatctctaat aaagcatggc cttggatgta ttctgtagta gtcatcatag agtcttcttt 130250

caactcctag gaacttctga ctgcttctct ttacacaagg gctagagtgg cttttgtctt 130310

cttcagtcct tcctgcagat gcatagacat ctgtgtctgt ctatgttctt acatgtcttc 130370

gtgtttctgc atgtgcacat gggcagtagc ctctcactgg tagctggctt atggcactgt 130430

cttgataaga ttgctataga gaattcctct tatttcatca tggttttttt tttttttaac 130490

ttcattctga taatgacatt taattgaatt gagctcatgt cacctcaggt gctatcatgg 130550

tgtttcattg ctgtgaagag acaccatggc cacagcaact cttataaagg acaacatgta 130610

attggggatg gattatagtt cagaggttta gcccttatca tcatggtggg aaccatggga 130670

cacatagtta gacatggtgc tggacaggca gctgagagtt cttcacccgg atcggcaggc 130730

aacaagaaga agagaggtac tgggcctggc ttgagcatct gaaacctcaa agcccacccc 130790

cagtgacaga cttctccaac aaggacacac ctactccaat aaggtcatac tttctaataa 130850

tgccattctg taggggccta tgtggcccat tttcattcaa accattatac tatgggtgcc 130910

catgctgttc cctgaatgaa cctcgagcac atattcttgc caagttttc tttttttctc 130970

atgcaattag gtagacgaga aatagggatc gggaccattt aataaaaact cttgccatgc 131030

aactgtgagg acctgagttc aagtccccag aatgcacata aaacaaatgt gcagtctgtg 131090

cctatctaat gctagcactt gcaaaggggg atgggaggca gtggctggag aagcacctga 131150

agactgggac cagctagcct ggcctatgta gttgaagtag actgttccaa acaaggtaga 131210

aagcttgtga cctgtgacta tcacatgggc tccgtggcgt gtcacacatg aatgtgtaca 131270

ttcatgtgca cacaaagaaa agaataatgc tagcaacttt cagtggcaca aggctgaagg 131330

aaataactta cagtgtctct caggaaacat ccaactgtct ctactgtggg agataatgat 131390

gtgaagtcct gatgacttca gtgtaaaatg aagtattccc cgcagagagt cagtccccaa 131450

gaagccatgt ctcagatata tggaatatct gcttctatta gtagcctttc aagcaaagtc 131510

cttagttgta tttgtttatt cttgatcaca agttggctat atgaattatt caagggtctt 131570

agtgacagtg catgcctttc ttgagagatt cttgcatttt aattcttgaa tttgcaggga 131630

gacatatccc ttccctttcc ctggatatct gggaacattc tggcaatttt ccaaccaaat 131690

cccagaacca agcaaaacaa agacttgctc tcttaagacc tcacactgtg aggtagctaa 131750

tatctgtttg ggacctagaa aggtcttatt ggtctcctag gagataactc cacttaagta 131810

ctctgaggaa actagtagtg gagaggctct gacttcaatt ggatgattgt agctcctagt 131870

tgaagatacc caagctcatt ttcacctaga ggttaattgg gttagataac tgaaacacaa 131930
```

-continued

```
taaaggagtc tggtgcctgg agcctttgga acaaagggcc tttgttacct cggctctaaa 131990

gggtttagct gctaggtcag gatttcctgg caaagttctc aggtttcccc ccctttccct 132050

aaggtagggt tagtttctgg aatatcatat tctagcgatc aggaagtttg ctttatatta 132110

ttagcagaga acaattcaac tcaagttttg gacactgtct tcttacccac cctagtgtaa 132170

acccccctca tctcccttcc acttgattac tctgtgcagg gagtataaaa cattatatac 132230

cttcaccagg ggttggagca tgcatacact ttatagatgg atttgtaaaa atccagtgcc 132290

ttcaacaggg tcttatgaga gaaggtctgt agtcctgatt tcatttttac agagtcgggt 132350

tacaaggtat caaggaagca aaggcacagc tgggtaccag actctggtct gattctcaga 132410

acctttggag gaataaggca ggggatggga aggctggaga gatgcttcag tcttctttta 132470

aaaaaaaaga aagagaaaat ttcaataaaa gcaagagaac cagcgttcag gtctccagca 132530

cctgttgagc gtggtattgt tagcacttag aaggcaggga caggagcatc cctggggctt 132590

gctaggcagc cactgtagcc aaccagcaag ctccatgttc actgagaaac tttgtctcaa 132650

acaatatggc gagcaatggt tggaaaagat ctatctgctc tccacacgca tgaatgtgta 132710

accctgtgca cataagcatt acaaacacat acactacgca cagtaataca acttttaaaa 132770

gaaggaaagg gaagaatagg gttgaaggtc aggttagacg ggtggatagt gaagaatgga 132830

agcctcatca catatctgag ccagacctca gaagcgtccc cgtgaacaag tgacatatgc 132890

ggagctactg ctgaggaagg cgcagagaga aatgagggtc attggtgcta atgagggaaa 132950

agagacccct aagtcctcct gtagatttcc cagtgtcctg tcagtggcag aatgggcagc 133010

aatttcacaa tactgatctt tactggtaac aaatctcacc tgcatttcct tggttctttg 133070

tttaggtttt aattttagtt tcatgatttc cctcccagcc ctcaattttg tttgattgct 133130

tttgagtcct gtgggtgtgt ttctgccatc attcccacct ttctgttgtt ggggtttttt 133190

tttgtttgtt tgtttgtttt gttttgtttt gttttgtttt tagttatgtt ctctcgtttt 133250

ctccatag ca  acc caa agt tta ctc aag act acc agt gaa cct ctt ccc  133299
         Ser Thr Gln Ser Leu Leu Lys Thr Thr Ser Glu Pro Leu Pro
         345                 350                 355

caa gat cct gat aaa c gtatgttgtc actgacttgg gggaggggca aggggaagac 133355
Gln Asp Pro Asp Lys
    360

tatgttgcat gactgaatgt gtccttccct tgcatcatct gcttggcatg ggttttgtgt 133415

gattattgac caggaacctt ttgatagata ctattttccc attgtcttgc gtgtcatttc 133475

atccggtttt tactaggcaa cttcagatgt tgggcagaga gcatctactt aaaccattta 133535

cacttctgaa caaattcctt tctgatttgt gttgttctgt gaaataccac acatagagta 133595

tttcttgatt tggcagaact ttttttttta atttcccgaa agctgtcaac atgccataat 133655

ttaatgaaat catatttgat agtacaggta accccctccc taaaaatgta atattgctta 133715

ttcaagacaa ttttgtgtgc acatttcaag gttcctgtgt taaatgataa ctgtgcagca 133775

ttgggaggtg aaaggtgagc cacatagatt tcaggactcc cctcctcccc ctcccagagt 133835

gcacactggt tggtgtgcta tcaggtcttc cacttaggga acttaatgga atttcctata 133895

aaaagacatt gcttcaacca tataatatac tcttggtctt aacagcgtct tgctttctgg 133955

ttgcccaatc agtctaattt cattttcaaa tgtcatatct aacacatcca tattcgcttt 134015

taaaattcag tctgtattta gaaatggatc ccccctctcc agggatggtc tatattgttg 134075

gtacttactg aggcttgaag aggaaaccca atttcagttg gaaatgagat gattaaaatt 134135

cgcctttgtc acgattatcc tggaggggat ggggggatcc taacctcaaa actaataaga 134195
```

-continued

```
aaatgatttt taaaaaatgt agtgtagatg attacatcat cctatactgt tattcttcag 134255
gggcctccat aagatattac tgttaattca aataatggga tgatatttga aagatgtggg 134315
tttttttatt gacacaataa gcccatgtcc tgatattgtg aaattgttcc tctaaaacct 134375
taagtctggc aagtgggtgg tagaggacta gggaaagtct ccgagcgtca cacccaaaga 134435
ctaggaaaac atcatttgtg tgtgtgtcgc gttgttccca gggttttcaa agattgcaga 134495
tctccttctg acacacttgt gtaccttttc cttgcatctt tggtgcctat gagaaaatcc 134555
gaggcctaac gctctctgtg cgttgtctgc aggcatcaaa caccagaggg ccgtgtctga 134615
aacctaaggg cactctggct gggctccaca ccaaatggct ccacactggg ttctgacatt 134675
ttctaggtta gacagtttcc aaggttcaga aagcacattt tcaaaaaata taagaaacca 134735
cacaaaactg gaaaatgcta acatacctcc ccaacaaggt cacacgtatg aatagtaggc 134795
atttctcatc ctgtcttgaa aacgatggta attggttctc ttccatttta tttcctttca 134855
gtatgtaaaa ggctgttggt tttcactctt cttcattgat tagaattaaa cattatttga 134915
taatttattt ttataaagta tacataaggt tttccagaca gatcctggag gcgtcccttt 134975
ctcctcccat ctgcggtgtg gtacagaccc taacatcctt ccatcccggg gggatgaggt 135035
gatttttgtc agctttattt cttgtctccc tacagagact attcaatcac agcaagtgaa 135095
gggttttgca gtgctagtac caacatacgg gagaaagcat ataatttcta gttatttata 135155
gctgtgtggt tgtgctgcct gccttattta tagctaagcc acacatttga attgaaaaag 135215
tcatggtcac ctggaggtca aatgcagatc gcagcctcga ttctgaggaa atgtgtgcag 135275
aatgagaaga ggagcaggca gcctgttcca ctggaaaacc caggcttatg cacggcgtct 135335
tcacccactt agagttaatt gaatggcatc tctttgctcg gaggtgattg gttctacaga 135395
tgctctgtct gaagtgctgc tagtgggaga ataaatgcta agtaagctag aaaaggccct 135455
tccactgaac tgctttaaga ctttacatac agagaactgt gcactgggac cgcatcatga 135515
atcatttcct gacaagtctt aatgctctaa ccaggcactg ctagatttta acttctcccc 135575
cacaaacacc aacactgaaa agcaccacaa ttttcaggac acttatttgt cgtgactgct 135635
ctcccagaga cctctgcacc acagggacag cgagaggcct gagactgaag agtggtctta 135695
ttcctaacca tgggttccta tctctttgaa aaccctttcc atctgaggtg aagaacctcc 135755
tgtgtctcag cagcttcgga cgtcagttct gcatctattt gacttaatac acaggcctca 135815
cctccaggcc ctcaatgcag ttcttgtaaa atagtaaagt tattaggtaa agatttgacc 135875
agcttatatt tcgaaggtga ggagagcgtt gcctgtctgt gtgctatctc catcagacct 135935
catttcaaaa gcaggcagat aaactccatg atgaagacaa agaacattac accatttttt 135995
tttctgattt atttttattt ttattttatt ttatttttat tatttagtat agaataaagt 136055
ttattcaggg catggggagg ggagacaaga gggtagtaga ggcagagaaa ggcagaaaga 136115
gtagagaagt agaagagtgg aggccggcca tgagcacatg gagagagggg gaagggaatg 136175
gggagagagg acggaagggg caaggggaaa gagagggaac aagaagaaaa gagaacaaga 136235
gggcaagagc tacttattta tttatgtatg tgagtgctct atctgcattt atgcctgcag 136295
gatagaagaa ggcatcagat cccagtaaag gtggctgtga gtcactgcat gcttgctggg 136355
aatccaaccc agaacctcag tgagtgagcg ctccagggat ctaccaggcg ctcccacttt 136415
tccaccatgg tgcagtatac cacagtacca agatgtacct ctgttccagt ctagtattct 136475
cttcacccct gacctgactg agagtggaac tacgttcata tatagatttg tgggtcacag 136535
```

-continued

```
atgggagatc ctgttaaagt ataaggatgc ctgaagccgc agatgtttat gaccctgtta 136595
gaccaacttc ctagatccca gatgctgttg ttctttgact acaagatcag atgtctcagt 136655
gttttttttct aatgtattgt aagctacggt ggatacagaa ggtagaccag caagctctgt 136715
taatcatggt ttacccgcat acccctcccc acttccccgt ttgtttcatc ctggtttcca 136775
ttaacctggc tatctgtaga gatgctggag acccttgctt cttgtttacc tctatcttgg 136835
cattgtgttt ctggtcttag gtccatgatt acagcatatc agggggagat atggccccat 136895
acatggttaa aacaggggaa gagatggctt tgtccacaca ttgtgtgatc cagtagtccc 136955
gaagtagttt tttgtatcag aaggttatga tttgcaaaca gtagctgact catgccaaca 137015
tgaatagggt ctaccagtgt taccctcagc cattgtcctt ggctagtttt gggctattgt 137075
tttaaattat tcttcatttg ttcttctagc tgtgaaataa tagccatcaa tttgttagca 137135
catcatggaa tactaataat ggaactatgc tattctctta gactgccaaa ctatagtaaa 137195
aacaattatt tggctaggca tggttggcgc acttctttaa ccccagaact caagaggaag 137255
aagctaatgg atttctgcaa ggctgaggcc aagctgggct ccagagttac ttccaggcta 137315
gtcagagcta tataatggga cctatttcaa aataataata ataattatta ttattgttgt 137375
ttaaataatt cttgcacaga tatgtactcc ttccatcagc tacttgataa aggcatggaa 137435
gtgcatccat tttattaaag ggattgggcg tgcttttctg tcaggccgta gagtcactat 137495
cctatctaca cactgctgca accacagata gtaaattagt aggtagtcat gactgtgtgg 137555
ttgccatggc agccagcgtc ctaggagagg cctctgttgg tgatgtacct gctatgcaag 137615
catgaggacc tgaatttgaa aatttgaacc cccagcattc gaatgcgggg actgcaacac 137675
aggaggagtc tggaaccctg gtgctagggt agaatggtga agccagacta gccaatgggc 137735
ttgctccaag ttagtgaaag acctgccttt aaaacaaaca aaaacaaaaa caaacaagca 137795
ggtaaataaa agagggagtg gccgaggaag gcaccttaca gtggcttcta gcctttgcat 137855
acatctacat aaaatggaaa gcagctagca gcaacatgtc tactttaata cacagagagg 137915
ttacttttat tagcccagag tgtgagaatg ctaccactat gcctcttgag agactcggca 137975
ggataatgta agcaggccac attcagtaat ttacttacag gatcagagat gtggtcggaa 138035
ggattaaatc tcagcatatg agtgaattgg gaaaggttgc tctggaaggc tgtggtaaat 138095
ttacattcgc tgtatcttta aggctttaag aagttaagga tccatcagcg ctcactatca 138155
gagtttttgt gatacgactg gtagtgaaga ctggcgttct gaactcatct gttaaatatt 138215
gagtagttat gactgttcat gtctttgtga gccactgcta atgaagtcaa ggaagcttcc 138275
agcaaactaa gaagaaacaa caccctacgg ctaagcgagt ctgacttcca gttactatta 138335
ctctcatttt atgtctttct gcctggtggt tgttcgtatt caggctaaag atagcattta 138395
agtgcaggga atatagctat gaataaaaat tatgctaaca ttcattcttc tacattcatc 138455
gcacatatct gataaaaaaa aatgtcccat gtcagtacaa gttcatagac ataaaaaaga 138515
aatgtagctt gactggtgaa gagtaaacag agcgtagatt acatttttat tgccttctgt 138575
ccacgtagga cattcatagt gttctccagc aactgtgttc gaactggccg taaaagaaga 138635
gaggctcaag aacacacctc tttaaaatcc agtgtgctgt tgaaagatca ctcgcttcta 138695
ttttcctgtt catccaactc agacttggta ggggtggccg ctatttaggt tttgagtgga 138755
atgtactaag agttttagct agtttgaaat tagagagatg aaggaaactt tatattaaaa 138815
aaatgtttta agtggagatg gcagtttgaa agccttgtca cgtggagatt aaaatttcct 138875
ataaagtcct tctttatagg tttacagttc actcatacat aaattactca cgctgtcata 138935
```

-continued

```
gcccataact cgtagccatt tcaagggacc gcattactag ctctcaatca aatagaattt 138995
tcaatgataa ggcagtgagt tacataagtc ttcactgtta tctttgcttg ccattgttgt 139055
atagataagc tgcattctgc caggggtggg ggatatatca aatagatgct atccgtgggg 139115
aattttgtct aggaatcact cccttgtgtt gtagtttaga tggtcaaggg cattacacct 139175
gacccccacc acacacacac acacacacac acacacacac acacacacac acacactaac 139235
acacataccc agcatacaca aaacaaaata agtaaatcta aaactaatat taaaagaaat 139295
ggtgtcacct tgcaaattga ggagtcaaat ggatatgaaa actgtaggga ttttttttta 139355
atatcttaat tgtcggtgtg aggatcgact ggagcccagt cagtcctcag tctccttatc 139415
tatgcattca agcaaccatg agtcaaaaat gaatgcctct gtactgagca tatacaagct 139475
tttttttctc gtttctcaaa caatacagga agaaaaacca ctccctttaa tgtttgcatt 139535
atcttcagta atataaacag tctgaaaaag gacagtgtag acattagata ctccaaacta 139595
tatacaaata tacaaaaggg aggtgggcaa actggagttt gctctctata gcgaaccctg 139655
gaaccaaccg cctctgcaca cacccaggca cagttagcct gcagggagct gaaatcacag 139715
tgagggaaat tggtgtatga agagtcgggc tcgatcatgc ctgtctgtga accctctgag 139775
ctgcatagtg acttcagcca ctcccaggaa cctcagtggg tttcactttt ttttcttttt 139835
ttttttaatg atgttttttt attagatatt ttcttcattt acatttcaaa tgctatcccg 139895
gaagtcccct ataccctccc cctgccctgc tcccctaccc acccactcct acttcctggc 139955
cctggcattc ccctgtactg gggcatatga tcttcacaag atcaaaggcc tctcttccca 140015
gtgatggcca actaggccat cttctgctac atatgcagtt agagacatga gctctgggga 140075
ttactgatta gttcatattg ttgttcctcc tatagggttt catacccctt cagctcctag 140135
ggtactttct ctagctcctc cattgggggt cctgtgttcc catccaatag ctgactgtga 140195
gcatccagta agttcctcac gtagtaaggc ctttcccagg ggacagcaac tacagaaaat 140255
ggtgtcgtgt tctcaggata gtgtttttttg tgagagacca tgcatcatga agactcagaa 140315
atccgaagta agcctgttcc ccaccaacca gaaaatagac gtccagtgga tcttaagaag 140375
acctaagact gtacagcggg tactgtgacc agcactggtg aaatggactc tcacatgaaa 140435
cttactctca taatattcat cttcctgggc tttaggttta ggtagcgtag ttttattatg 140495
agaaaacaga cacacccgtg tcccttcgtg tatgtgacca gcagaggagg gagactgcag 140555
aagacgtgtg tgtgtgtgtg tgtgtgtgtg tgtgtgttag cgctcgcagg agcacgcata 140615
cacatataca tatacattta tataaagaat tctactctga ggaatttact tctgtgatgt 140675
ttgtggatac tggtaagtac acgattgact ccaagccatg ggaatcagaa tgttccctgt 140735
ccatgggcaa agaccagtgt ctcagacaag aatccaaaag cacacatacc tcctttggcc 140795
tttttgttag gttcaagctc ttggagaagc gcctgaagag atcttcagat ccagtagcca 140855
atcttataca gaaacaccct tgcatgccta caccaaaatg acgattgact ctggcacgct 140915
gtaactcatt caaattggca catgaaatga gctagcatag cgctatacct tcatgaagca 140975
gagtaaatgg taataacacc atgtgttcat ttccatgttc ctgtaagaaa tctatttgaa 141035
ataaccctga tacccgtaaa cataccccac ttgctcgtat cctgattatt attttattct 141095
tatttttgca ggcctacatt ttcacttagc ccaatcaagg caggttttgc taaggggaac 141155
cataatcaga tagtacttac agcagattct gtctgtgcct gtgcgttccc accgtatgga 141215
acagaaagtg caggttgcct ggtcacctcc gcctgttgct attctattta ctagtgttta 141275
```

-continued

```
ctgtagcttc tcattttcac tctgccagta agagggaaaa aatggttagg tccatgggaa 141335

gcaagttttg ataaggcggt taggaaacac gtgtgtattg atttgcttga ggttgtgcaa 141395

agcaaatata tttgtctttg gtatcttttc tgttacagac agtacttaaa attgcagatc 141455

atttttcagt cattcaggat aagaaaccat atattttatt tacgtccatg ttctgtgtgg 141515

actatatata agttgaattt ttctggggtt tgtttgtttg tttgtttgtt tgttttctgg 141575

aaaatgtgtt gcttttcctg taggtgacat tgcatagtcc tgtgttctaa cttattttca 141635

gtgaattaga agtaaatata tctgattttt ccccaaggtt agcataaaag atttctgtag 141695

gacataatgg taggcaataa aggcaccggc gtgcgtggag ttaccctgtg tgactaacac 141755

ttaattgtag gatgcaaggc atgttatcac cactagataa aaatcctggg atgcagagtg 141815

ctcgggtcac ttgccctggg taccagctgg tgtaaaaaca ttgttcacac ctagctgggc 141875

ctaatttcca agtcctgagt ggaccttcct tccctctcgc cattgggcaa gtgttccctt 141935

ttttatcagc tagatgagga cagttgtttg aggttccaag aataagcctt tgcctccctc 141995

cttctgctcg aaagccacac ctgggcagac atctcggctg ctgttaggtt tttgaaaagt 142055

tatgattaac cagtgaccac agaaaaagga aagacatcag aatgcatgcc tctcgtgttt 142115

attgaaacgc actctggttt ctgttaacat ggtcaaacct ttgattctaa tgccagtcat 142175

tttcttaaat atatagacaa ggtactatct ccatgtgacc tagctgtgac ttctcatcta 142235

tttgccattg gagatactgc atcccaagcc tctttactcc aagaatttga tgaacagtgt 142295

gaagagaata tgcgaaacag tggttgatat tgttgaatga acattgaaag tgatttgaga 142355

aggatgatat catttcctga taagggggaa accttttaaa aactgtctct ttcctctctg 142415

tctttcttga ctcgcttaaa tacttccaat tcttgcaaac cactactcgt tcgtgagtta 142475

gaatattctt gttttatagt tcagtcttcg gttttcggag catccccgtt gccaggtaac 142535

atcacagtga gtgtggcaat tcagatactg cctggcagta ttgaattgaa agagaaatca 142595

ctgtctattt gacgaacctt gcgatgaatt acagactgtt gccaagtgtg tgaaggctga 142655

atgtccttgc gtggtttcga aactgcactt gttgatgttt atgtgacttc ctgtggtgtt 142715

ctagctctct catgaaaggt agcgtcgtaa ttaggctgtc taaaacacaa tgtgcggaat 142775

tcccatctcg ccgagatgcc tcgattttgc gatcgccttc ttctcagatt ccatttgtgt 142835

ctgcgggact ttacaatgat gctggtgata ccattagcta ttctgcagat tacaaaatag 142895

ccaagccgag catgaggatt tgatgaaaca tggccatatt aagcagtgga tgctggagga 142955

atgcctgtct gggaaaggca tttttaatgc tatagctttt aaatgtgctt ttcttgctat 143015

gttctacaga ggtgaaactt gctcctgcca tggtaaaatg tctctgggtg cttctttcgg 143075

ctgcattggc atctactgtg tgctcctctt tcacacgatt tctctgtcct gggaaatgac 143135

tggctttctt acaaaggttg ggcaccctgt gtctcttctc aacttgcctc ccatctcctt 143195

tctag tt  ccc acg aca gca gcc agc acc ccc gac gcc gtc gac aag tac 143244
      Leu Pro Thr Thr Ala Ala Ser Thr Pro Asp Ala Val Asp Lys Tyr
          365                 370                 375

ctg gag aca ccc ggg gac gag aac gag cat gcc cat ttc cag aaa gcc   143292
Leu Glu Thr Pro Gly Asp Glu Asn Glu His Ala His Phe Gln Lys Ala
    380                 385                 390

aaa gag agg ctg gaa gcc aag cac cga gag aga atg tcc cag           143334
Lys Glu Arg Leu Glu Ala Lys His Arg Glu Arg Met Ser Gln
395                 400                 405

gtagggagga atcttccatc ctctgttgtt ttgttatata gggaaatctg cgctcgcctc 143394

tgcctcagct gggtagacat aaagtttaat ttaaatgttt gctgcaaggc cacagattcc 143454
```

-continued ccccacatct atccctgtgc acggtcacat caagtaaagg caagtacaag aggattttga 143514
agcacaggtc caactctctg cgaaagagag gaattctgtg aagatggtga ggtgagggct 143574
gttaattgat acattgtagg aaactttatc ttgtgtgtga gtctcatgat aggctgtgta 143634
ctttaaatgt gcgttgtaag atatacttaa agaataaaaa ggagtagttc aaatcagtaa 143694
actagttcct attgcccact aagctcgagg acctgagttt gattcccaga acacacattt 143754
aaaaagccag accttgtggc ctctgttttt aatccagggc tgtgggggca gaagacaggc 143814
agcctgtcta atctgtctgg agaggtccag ccccatgacg taagccgttt cccaggaagt 143874
gtgaggtact agaggaagaa caccgacacc tttaagctat gccttattcc ttgggccaaa 143934
tcctagctaa cttctttatc aggctttggg ttccaggctc caaccctgca acaggcacta 143994
ttgctttgtg aaatctcccc atgccataga actactgccc agctgagcca accaaactag 144054
ttattcctaa gctggcttac ctcaagtctt tactcctgcc cctaaataca ttctaaggtg 144114
ttgctcagtc ctcccgtcta tcctcccgtc agtcctccca tcagttctct gcctgagatt 144174
ggccctggcc ctgtgtccct gtaaatcatt gagtcttctt catagaactc atctcctggg 144234
ctgttggcat cccaaacaac aagaaaaccc tcattttaag cagaactaac gatgtatctc 144294
aaaaagcagg acaaggttgc tatttcttca aagacgacta gcaataaaag atgactagct 144354
ataacacttg gccctactct gcagttgtaa ccctgagaga aaaggtttta caactacact 144414
gaaccacaat aatcctggcc atgaactatc acttacatcc taccagttgg ccatgagcta 144474
tcattcgaat cctaccagtt gcccatgggg aaagcctgaa agccagttga gctagaaagc 144534
caactgaatg gaacaggcaa ctaaaagcaa tcctctggaa aactagaact tttcacattt 144594
ttttttcatt agaaaagtca tttaggccag gcagtggtag cctttaatcc cagcacttgg 144654
gaggcagaga caggcagatt tctgagttca aggccaacct ggtctacaga gtgagtttca 144714
agacagccag ggctacacag agaaaccctg tctcgaaaga aagaaaaaaa aaaaaaaaag 144774
aaacaagaaa agtcatttag gaaggtgtgg aattgggaat tactacaatt ccttcctttt 144834
tagactcaag actgatctca ttttctgaag ctttcagagg ctgccctggg cacataatgg 144894
ggcagaaggc cagaggaagt gtaataaaca ctgagcgctc ccgtgatgtt tccagcccct 144954
gccagggcac cctgatgcca gccttgcctc cagctggaag ctcctcccct ctccggctcc 145014
tctcctctct ggcctcactt tgctcttgac attggcttac tttagaagtg cctttcttct 145074
tcttcttctt cttcttcttc ttcttcttct tcttcttctt cttcccaccc acaaatctca 145134
gcagatccgc tgctgcacat cttgcttgac tcagggcaag tggttactcg aacctttat 145194
ttgattctaa agatttatat aatagtttac ttattggtgg tttctatatc atatgttcta 145254
ctacactcta attcctttta aatcatacaa aattatataa ggcataccaa ctttatattt 145314
cctccttaaa tccatgtgaa tcattttttta aaatattttc actttctcca agatattttt 145374
atgtaattaa gaaaattagt ttcaagtagt gtgttagctt ctgacatgat atgttgtgga 145434
aataagaaca ctggtgagca tctatttaat ccagggctta gttcatagat ttccgggaga 145494
ctttctccat cttcacatcc cagatcaggg actacttagc tgtagtcatt cctagagcag 145554
agaatgcacc tggtagtccc cagtgttaca gcgttagctg ccatctctca ccatagtctc 145614
tgctgctcaa ttctagggac tttttgactt tgaacttgtc tgtctcttaa atctctactt 145674
agtaatcgtc attttctctg catgacatag ccaggcctct aaagaactgt aaatcctgat 145734
agaattggtg cctctctgca cacagtgaaa aactgctgga cagggaccca cagtgcagcc 145794

-continued

```
ctgaagttca gattcagaga acttcaggtt ttcaaattcg gagccttcca acttgacttt 145854

tgttgtagct ttcaattagt tttctgggtt agccccccca aataatggac ctcatctctt 145914

tccactgcag gggcaggggg ttagggaaga tgatatttgt attgatgttg atggcctggt 145974

gatctgaaga tcttggttac agtgtgactg gcatgtgtca gatgcagata agcacacatg 146034

caaaacccaa gcgcttcatc actgtattag tgacttcttg gtatgccaag caacctgaga 146094

agagcaacct aagaaaggaa gcctttgtgt gggtgtagaa ttccagggta cagtccagag 146154

tgacacagtg agcatggtgt gaggcaggag cttgaggcag cagcaggtca catggcacct 146214

gcagtcaggc agcagagtgc atggcctgct ctctcctttg cctcctgtcc agaaacccca 146274

gccacagccc agtgcttctt aaatttaggg tgagtctccc cacatcaact aacctaatcc 146334

agaaaatccc tgcccctgac atttccagag acttggttcc ctaaatccca tcaggctggc 146394

gagcaagatc attggtcaca cttacttcta tatctagtcc atttagtgtg catgcagaat 146454

gaagtccttc aaaacaaaaa cttgcccgat gctgagtttt ttaatatatt cagtggcatc 146514

ttagggacag ctactggtac tgacccttga cttgcctgta gatagatctg cagcagcaca 146574

ctgggccagg aggatagtag gctcatcatc actcctcgtc cattggttac tctcacagct 146634

ttcttaaaca ggtctgtaga gtaagattac tgagtacaga gcctgctgta atcaggcatc 146694

aattaaacca gacagatttt gtaaagcact ttacccagta atattatcta ttaccagtgc 146754

accctagtaa aagccactgg ttaaggggt aaatcttctg cctacagcgt gtctgtaagt 146814

agtccttcag tgacgacata ggccatggat gtgtgagagt agaagatgtt tgctaaatta 146874

ttctgaaaag tcaacattca agttcattta tatagtaatg catattttca atacattacc 146934

taggtaaatc ttaattattt catggatctg caattccaag agggtgatcc aggttccgaa 146994

tgtctaagat aagatgatag caaagataca taatgcaggg gaatcggttt tcatgcccca 147054

gtaagacatt tagtttctat ctcaaactaa ttttgagatg tcttgcctga ggaattctcc 147114

ttagaacatc gccactcggg aacgttccct tccatacagg aaattgaaac atttttcttc 147174

ccaggctcat ctataaagcg aagcatctct tcaatatctt ttcgtccaac gctgcccttt 147234

attagctaat agaaatactc aagtacctgg aacagtttgt acattttcca tgtatcttgt 147294

tctcaagaaa ctaatttaaa aaaaaaaaat ccaactcacg tgctgatcgg ataagacctt 147354

ataagcctgg ttttcctcac agattcggga gatggattaa aaagtccacg aggacctact 147414

ctgtaatcaa ctttgtatat tgcttcatct tcctccatta ggcttacatt acagcaggct 147474

ggcctgcttc ctcaactagt gtcttacctt tcaccacatt caggagatta taatgcatac 147534

tttctggggc tttctgggtg gatttggaat aatccccttg ctactcatga cttagttact 147594

gaacaggaag agtccactct tcatttgtgc aaggaataga ctttggcatt gtattcctgg 147654

tttacacata cacattccca aaacatacca cttggaatgc tttgacttga tgtcgtaaaa 147714

ggttaaaatc aatgtcttag tttattgatg ggagacttcg ctcagatggc atacgccttt 147774

tatgggtaat cagtgtttac tcacgtcaag taaaatgact ttccgacagt tctcaaggaa 147834

aatggaaaga tgaaccaacc ttatttcggg agactgcaat acatgtaggc atttatattc 147894

accataccgc tggcataaat tatttatatt cttgtaggac aaatattagt cacattggga 147954

ggggcatgtg atgttttttt aataggaaac atattgtcgt ataagccact gtgttaaatc 148014

tgtatttgaa aggacaatgg gggattttca tattgcctta tgtcctcttt atag gtc   148071
                                                             Val

atg aga gaa tgg gaa gag gca gag cgt caa gcc aag aac ttg ccc aaa   148119
Met Arg Glu Trp Glu Glu Ala Glu Arg Gln Ala Lys Asn Leu Pro Lys
```

-continued

```
410                 415                 420                 425

gct gac aag aag gcc gtt atc cag gtaacacccc ggtcccacct acaccagaca  148173
Ala Asp Lys Lys Ala Val Ile Gln
                430

gaacatgcca ctctcagcca tcaggacctc caggaatctg ctggaaaccc ctgttttata 148233

tattttcatg accttcactt gttcttcact tcttgtctta gtaataagtt gcttccctta 148293

cattttctcc aactatttaa aattagaact aatcacccca aatatattct atggcttgca 148353

atcttctttc cattaatgat acatcttttg agagactgaa gttttcagct cctccagtaa 148413

ccttggaaaa tttaagtgag attaggaatt taggactaaa cccagtctac acatgacctc 148473

gtacaaacag agagaaacta tctttgcact aatcgttatg ttaagaaaca aatatgtttg 148533

tgtgtgtttt tatcatatca g cat ttc cag gag aaa gtg gaa tct ctg gaa   148584
                        His Phe Gln Glu Lys Val Glu Ser Leu Glu
                            435                 440

cag gaa gca gcc aat gag aga cag cag ctt gta gag aca cac atg gcc   148632
Gln Glu Ala Ala Asn Glu Arg Gln Gln Leu Val Glu Thr His Met Ala
    445                 450                 455

aga gtt gaa gcc atg ctc aat gac cgc cgc cgc ctg gcc ctc gag aat   148680
Arg Val Glu Ala Met Leu Asn Asp Arg Arg Arg Leu Ala Leu Glu Asn
460                 465                 470                 475

tac atc act gca ctg cag gcg gtg ccc cca agg gtaagtcata ttgatttgtc 148733
Tyr Ile Thr Ala Leu Gln Ala Val Pro Pro Arg
                480                 485

acttcaggtc acagcatcaa tgatggtgtc cagacagtgg agactggagg ccgcagggaa 148793

gaagctagga gaaatgccac aagcacttta tttgtagatg tgacttaggt acattgtatc 148853

ctaaagacat ggggtaatag accagtgttg gccctccctc tcttaactct tttggcagtt 148913

acctttatac tgatttccat gctgcattct tatttttctt taagccatca ttttttaaaa 148973

tctttttat ctaatgagga actattatac ttttttgcct aatatagtca tgagttttca 149033

tagtcatatt ctctgttcac atttaccatg tatcattttt cttcttgggc atcctttatg 149093

ttttcaagtg cagatgaaat gaagtttgaa ttctttgggt tacaatgtgt ataagctagt 149153

gatttattta tgcctgaaaa acaccttaac tttaccattg gttttaaaag atatttttgc 149213

tgggtataga attatcagtc gaagtgattt tcttttacta ctttaatgat gtttgctgtt 149273

ttcaacagac cattcttatc acctctacag ataatctttt gtttgatctg gctgtgctag 149333

aggtttttct cttttcacag tagctatttt atccatgtaa aacgatggaa ttccatctgt 149393

ccttagtctc ttatgaccat cccttcatct catacttaag attatgtttg atattttcgt 149453

gcataaattt ttattggcta tcataaacta tgaaatgttg ttggtgctag gtacttttgt 149513

ataactatga atatattcag actttgattt gaaatctagc tagttttcct agaagcagct 149573

tcaccctttc gcattttgct ctttttagat atgttaggtg gagtgactct tcttgtaact 149633

tgttatttcc attttcaaat caggatcctt aatagtctac catgaactct gagtttcaaa 149693

ttggattgac aagaaccagg cagtcatgtg tctgtgggac ttcaggcact attacctcta 149753

atcttctggg taccttttac ctctagcctc tgtttcttat accagcaggc actgaatagt 149813

cctcagctac agtcagttag taggataacc tgcagatctc ttatagagca cctgtcctgt 149873

aaagtctagc cacctgggtt tccaatgctc tttccttctt ggggtccact gcctgagagc 149933

cctaccttgt acagtcaggg aagctcaggg accatggttg ctgacagttg taggacctca 149993

ccttgtgtat ctcctcttcc tctctggtcc atggtccgta ctctgcagaa actgttcctg 150053

ttatgtagtc catctattcc ttttctctgg caggagggtg aaattttggt cttcttagca 150113
```

-continued gatcttgacc agaagtggag atttgtccac attatgtaag ggaacccaaa ctccacccac 150173
ccacttgtgc tgatttccct caccacactg atagtccttt ctcagttaag gagctcctgg 150233
cattcctccg ggtatcgaga ggacactggt tcttttgtac tgatgacatc actgtgatct 150293
cggaggatgg ggtggctggt tcagggtgat accagtagtc atggacagag aaagctgaga 150353
gtcagttgcc tgctgcagtg tctcttctct gggtcacact tcctccctga acaaacagct 150413
tctgacaata agatgtctat attagcattt tgttttctgt gagcaatctc tgtctttccc 150473
aggcagtact tagtgaaatc ctgcttatat ctctttgcag atgacaaggt tctgggttac 150533
tctttcttta gagagcatgc tttggtgagg agagttgtgg gggtcatttg tccaggcaag 150593
agctgctagg tagattttta agccgcaggc ctgagtcttg gggcactgac tcctgtgcat 150653
aaagttaccg accttgagtt atttaaattt ggactcagcc actgcagata gctctgtatt 150713
tttgaaaggt gttagaaaac tctctcttcc cgattgcctt tgtgcaaatc tctaaaaaga 150773
tataaatcaa gagttttcat taaatcttgt aattcgatct acaaactgtg tttggatatg 150833
ctgcttataa caaccacaga gccataacag gtgatgagaa atatgactta aatgtgcgct 150893
gactatttga acacaaaatt aaaagtcaaa aggttttttt ctcttttaaa acagtttaat 150953
cttattctaa atgtttgcca agcttcatag acagatcttc ctcaagacca gtgagaaata 151013
cgtgaccagg ggcatatgtg tcctagtttt aattaattca aacagaaaat taaggaataa 151073
gcttggaagc tttcctgttt ctcaaaatgt attccttaac atgttccctc cagagaggag 151133
ctgccctccg gcacttcctt ctgggcacgt cttcacgggc agctgtccgc acctgcagtg 151193
ctgggatgct ctgtggacca ttcctggggt gctaatatct gctttttttct tttatctttg 151253
aaagtgaaaa aattactatg aaattacaag tgtttagata cttaaaaaca ttttattgca 151313
cacaaatgaa aagtgattgt taccagagtt tgccctagag agcagggagt tggtaagatg 151373
gcctctctct ctttctcttt ctctctctct ctttctctct ctctctctct cgctctctct 151433
ctctctctct ctctctctct ctctctctct ctctctctct cacacacaca cacacacacc 151493
actcttaaaa ccatttccag gggtacattt gcttgtttaa atttaacatg cattctcatc 151553
gagtaataat aataagtgtc agaataagag tgacttgaaa taaaatataa aatataatca 151613
gttcagttgc agagaaagtt atgataagga gaatttgtaa gctaactagt atggaaatat 151673
aaagtttctg atatgtaact tttttctttt tttaaatgat tttggctgac tattaatatt 151733
agtggtagta accaagctgt gagaatgatt agtggtgtgg atgaggggtc tgagggaaac 151793
ataattgaga aatttaggcc attttcgtcg tttttgtgat aacagtggta ggctaaggag 151853
acttactaag aagctataag aggttacgtt tgttcagggt attttttttgg atgattgtga 151913
taatcaagtt aatgggagaa gtattagtga tggtaaaata atttttagca ttgtagaagg 151973
ttagggtttt gtacatagtc tgttccatac aaactcatca gttataactg gattctaaga 152033
agtcttactt tagttttatt atataagtgt ttttaattaa aaagaaaaaa aaaacagaaa 152093
agaactttcc gttgtttcac aacagtgtag gcgttggaaa ggagggaatg tagtttaagc 152153
agcctaggtt cattcaacct tggattgttg cttcattaga gagcgtttga agaaagagca 152213
gaggatctca aatgcgaata tgcaaaatta aaacagattg ttgtaagtca ccctgaaaaa 152273
agtcaagaat atgtcacagg tggcatttgt tggatggcca gacctcttgg caaacctttc 152333
ccggggtctg tgttgcttta aaacatcttt tgttgactaa ttcatgctta ctctgtaggc 152393
tctgccttct gggttgtgtt attaagcctg tttatccccg gagagcttcg gtctgtttgg 152453

-continued

```
tttgacaaaa caaggcttaa agatgcagaa gtccatatca gacctggcct ttcagtgctg 152513
tggggttgga gggggttagc tctgtcccca gtgtctgtac agctaacatt tagctgaagg 152573
catgggcttc atcgcagagc tgtgggcaag ggctaaatct cagtctaaac cgaatgtcat 152633
tgacaaaggt cgctggtttg tgggagagga ctgcaatcag tctgttttcc aaaggttctg 152693
gtgttatata aagacctgtg tttaatggcc aagatagcca tttaatctgt aactagggac 152753
aagttactta acaaaggaat tcttcctccc cagtctgcaa atcggggtta aattttcaac 152813
attgttgaaa cagcaactag cgtgtttcta gcgttgactg gccataattc aaaaccagaa 152873
ggattcactg aaggttgaga caggactgta gagagtacaa agatgtcttc cttcccaagg 152933
ggtctgcgag gtggtatgga acacatggag gctttggtga ctgtccagtt gggaaggttt 152993
gcttcttagt taaagaggag ccaatgggcg atgacgtatc ggaactcctt gcatgtgcga 153053
catgtctgct ctagcagtgt gaaccctgca caaaagacag attatgcaaa acctttccat 153113
gtaacacatc attattatct gaacagaaag aagcctccaa gaataatcta ttgccatttt 153173
ctctactcag tggaatttgt gtttgaccta cctagatagt tttctaaaga aaaagattat 153233
agatacattt tatatcaggc tttaaatttt ttcactcaat cactaaactt aactgcaaaa 153293
gaaaacctta ttttctaaaa tttgcaatgt aagtttcccc aatcggtttt gatttgtttc 153353
cttggtttat ttttgtttgc gttcatgttc ctggggtctc cttctggatt tcttctcctg 153413
tgacattgag aatatgtata caaggttgat ggcaaaatcg ggaatcaaac tcagtaggag 153473
acagcacaag gtgtagctct ctcaagtgtg tctttaaacc accacacagt tgtttcatac 153533
agttcatgtc atatgctgaa tactttttgt actctaagat taagactgca aaaatctgtg 153593
gccttataaa aacaggagaa agttactttt tttcctgcag agctaaagtt caaggtttca 153653
gaagccatta gcatgcaatt taatgtttca gaaagggttt ttatactatt taaacaggga 153713
caggtcatgg tttccttcca ttttgtggac accagcctgg tatcaacatg ttataaagac 153773
aatggataga tatcttttgg aattagtgaa atgagcctca ttaagagaaa aattggatat 153833
atctggactc tgttaggtat tttctgggac gattgaccac ttcaaacacc ttcttaaatg 153893
gatggggata ctgagtaaat acaccaagtg ggtttggaat ttcagtgtgg tctatgaaca 153953
ttgggagact gtttttctca tctgagagat attcacttgc atgaataaga tacaaaggat 154013
agtttacagg ccagaaacac tgctgaaatt atacttggct ctgagtcacg catcagttta 154073
attaacagta aattattagc agctacattg agccaggaac tatgctggga ggcaggaata 154133
ggccatgcct ttgttcctat ctcagaatgt gtgcattctg ctttgccgtg agttcttgtc 154193
ttctgtgctc tcattgtgga cgtcatctaa tccgtttcct tactgcgtat ccctcatctt 154253
tccagaaatt aatttttaaa tgcctctttt aaaaggcagt gtgatcccaa ggtgaaggag 154313
gtgacaattg aaagggccac atcagctgca gagagaatgc agttacggga caaagatgca 154373
cacagaaaca atgaagatga taataagggg gctgggtata attggtccca atggggcaga 154433
tctgtttctt tattcttaac catgagtttt agatcccacc cattgccagt ataaccaaat 154493
tgcagtatta atacttaact gaaataagaa tttccaagta aaatacacat gaacacatac 154553
atgtacacac atacagcaca tacattgcac acacaaacaa tatgcacaaa cacacataca 154613
tgtctgtata tgtgtgtata tagagagatg catatagatg tgtgtgtgtg tataaatatg 154673
tgtgtatata tatatgtgtg tgtgtgtgtg tgtcactagt tagagaaaat ttcaagactt 154733
aatgttaatg aatattaaat tatttattat caacatattt ataatgagcc actgaatttt 154793
tgcttgttct gtgaacaatt ccattttgaa tgtgagtaac atcaggctaa cagttattaa 154853
```

-continued caacaattac tttaaggcaa tttacttgtg agctctctat atagacacag tagagatacc 154913
aggcattctt tttttctacc attcttaagt ggacattttt tcttttttt aattagaatt 154973
taccaaattc atctttgtcc cggcataatc aaatgaagat ccctagacaa cgatggttgc 155033
tcattactcg acaatggatt atatagctct agaaataact atcgtccacc ttggagaatt 155093
gtggctgaaa gttgtaaaga gggctgtccc tctttacatt tcatttcttt tcttttcttt 155153
tctttttgga aggaaatgcg catgaatcat atgccaaagc caagccgttt tctttgtaac 155213
aaatgaaaac ataataatgt ggggaaatgc tgcttgtttt ttaattcttt atctacacac 155273
actgtctgtc ctctatgagg tccggacaca caccatttta agtggtttgt ctgcttgttc 155333
tccaacgtag agattgatct atctaacttt ttaactttct aaacacgatc cttgcaaatt 155393
gccagctcag agcaaccaag cagaagccag cagctaggag catcttacgg tcttcagagt 155453
tatctgatgt cagcaggctt tgctcatggg ggtctccaga ctcacaggat gatgaggtca 155513
gagctcattc tgagccccca gggctcacgg cgcatacagg tctagggctg gggatcctc 155573
gaggcctgct gtgctattgc tctgtatcag gctctggggg attttcaggg aaagttagga 155633
atatctttcc aaaacacaca aagaagtagt ggtgttaagc gagataagag cttgaaacca 155693
tgtgaacaca ttctttcttt aattatcacc aggcttatta gaagataagg atgaattcag 155753
aaggcagacc catgaatatc ataaaagccc aacttgtacc taataccttg aatcactttt 155813
cagtaatctt ctaatgagat tgacagggga cgttcctatc ttctatttct cctttctgct 155873
tcagaccttt agcaaagtac agcctcctgc caagagccta ggaccagaaa tgagatacag 155933
taatctaaat ccagatcttc tcctctgtta aaaagaactg cagtcagagt gctccacaaa 155993
ttcagtcctg ttatctgccc tggccacagt ttcatttttg cacaatttta gtttcttatg 156053
gtcatcgctg tctcagaata ttaaatggaa aattccaagt gccagccata agtttttaat 156113
agcttttatt tcaccatatt gctgttgttt tattggggag tgttggtgtt ttactgacta 156173
atttataaat cagtcttcat catagacatg tgtgtatagt accaagcaca gtcaatgtac 156233
aatcggtacc tgtccctgag tttacagaac taggaattca gatgagaact cccagaacag 156293
tttttcactc tccagttgca tcattgtcaa gcctatctgc gccttgatag aaatctatca 156353
tgttaaattc taagatgggc tcacatagtg gccaagggta cagagctatg gaggcagaca 156413
gcttttgggg gaacactaag tgtctatgcc acctggactt gtgtgtccct tacatcatcc 156473
cttcaggcca agcattaaca tccaactagt caactgacga aactttttca tcctgaaatt 156533
cctactcccc ttctctctct ctctctctct ctctctctct ctctctctct ctctctctct 156593
ctctctctct cccccacccc cctggggacg gtttatgtcc attgtgtatg gctctgtttg 156653
tattctaagg cacaggaacg tggcctgtac cccgcatatt tcaagtacag agcaccaatg 156713
ccgggttggg caccatggat cggagctcct gatggagctc ctgatagaca ggaagtgaga 156773
tctaatctgg acctgtggct gtcactttga agagagggat ctagcataat aacggagtat 156833
actgaatgca actactgggt tttgaacagc aattcaaggt agaacagaga aagggcacca 156893
aattccactt agaattgcca ggagaatgcc tcaaagttat atatatgctt aataaaataa 156953
atatatatgt gtatatatat atatatatat atatatatat atatatatat atatatacaa 157013
attataatac acagtgtaca ttttggggcc gtgcacaaaa catgctaatt tgatatatat 157073
cacattacca gtgtttatat atatatgtgt gtgtgtgtgt gtgtgtgtca ctatatataa 157133
ccttgaagca ttatataata taatatatat aataatatat gataataata tactataaat 157193

-continued

```
tatatatagt ataataaaaa cactgtaatt caccctccta tttactccac atatacactc 157253

acatgtgcaa acatgtacat agcacatata ctggttcata tatgcatata cgcatgcata 157313

tgtacttaac atacatagtt tctggtaata agttccatac catccaactg tttctctagg 157373

tgttgaacac acattattta atagctgtat ttgtctaaac attcctggca tgtcttcgtg 157433

aaggatgtat acccttgtgc atcatcgtct gaaatcctag gcaggatacc aacagcagca 157493

gaattgctcg agacaaagga aacttaaatc ctttttaaaa aatgtcttca tgtaaaacct 157553

gaataaattg aagtagaacc agttagaata aaaacacacc caagaagcac ctaagaaaaa 157613

acttaattgt ttctgggagt tttagcatct gattgtttga aaagagctta attcaatttc 157673

aaagtaacat aactacagtt caatgagggc ctttgttctg ggaaagata atgtttcatg 157733

gggcttatca ggcattcctt gcccgacagt tgaagagtag ttagattgtc tgttattttc 157793

ttattttgat tattgcacca ctgtaagtta ctaatgaaag gattatttgg gaagcactaa 157853

ttctggtctt ggggctgtgc acaaacatgg taatgtaatc tcatgaacac tccatgaata 157913

tttctgtggt taaatagaag gatcttactg aaaactgaga aatccaaagc ttattctccc 157973

tctacagcag aaagcagcta tttagaaaga gcgtgctgat ttaggacagt gtcagaaata 158033

ctaaacacgc atataattcg taaagaggaa aaacaggctg ggtatccatt tatgaagaat 158093

tgggagaatt cccttgcagt gcacacatca tgggaccctt gaactcaatg ctagtggaag 158153

aagtgatgtt ttgctcacac ttgaaaccca tgttcttgcg gtttcctca cag cct    158209
                                                          Pro

cat cat gtg ttc aac atg ctg aag aag tac gtc cgt gcg gag cag aaa   158257
His His Val Phe Asn Met Leu Lys Lys Tyr Val Arg Ala Glu Gln Lys
        490                 495                 500

gac aga cag cac acc cta aag cat ttt gaa cat gtg cgc atg gtg gac   158305
Asp Arg Gln His Thr Leu Lys His Phe Glu His Val Arg Met Val Asp
    505                 510                 515

ccc aag aaa gct gct cag atc cgg tcc cag gtaagccctg agtgggggaa     158355
Pro Lys Lys Ala Ala Gln Ile Arg Ser Gln
520                 525

ccttctgcag cttacagtcc agttgttgct tcctcagttt gttgggaaga taattacctc 158415

cctctagagc acctatggtg agggtgttgt atctctttgt caagagttct ttaatatctg 158475

aaactctaaa agctaatctt cagaacacac agttctacaa ggcttaacat gtggaggcag 158535

aaggatggat agttcaaggc cagctcggct acttgagaga gatgctgtct caaagaggtg 158595

agaagcagag agatgactca ccagttaaga gtgcttgctc ttcttgctga ggacctgaag 158655

ttagtgccca gcccccacat ttcaccacca cttaaaactc taggttcagg ggatatgaca 158715

ctatcttctg gcttcctctg gttcctgcac aaatatctga gtgcacacaa acacacatac 158775

atacacacat acataaataa gctgaatctt ctacaaaagg aagggtgttt tagtactgtg 158835

tgccttgaca ttttcgaagt ttcccccagt aatatggaat ataaattctg aagtgttgag 158895

agcagccaaa atttttaatg ctagccattc atcatttaat gctagccacc aggtctggga 158955

agtggctcac agttgacaaa gtgggaacca gagtttggat gccactgagt gtggtaaccc 159015

accagtaatt ctagcactga ggaagctcag atgggatccg tggaacaagt tggttagcta 159075

acatagtcgt attagtgagc tctgggtccg actgagaggc tctgcctcag tgaacaaggt 159135

gcaaagcagt agaagaagat tctcagtgtg agcctcaagc ctctacacac tcccacttga 159195

gtgtgcatcc acgtgttcag ttaacacgca aacattcata catgcacaca tacatacata 159255

aataaacaaa aaataaaaga ataaagtcac caaaatggag aaaatgataa ctcagtaaac 159315
```

-continued

```
agaaagctgt gtactctaat cagtaaacta tgcccagtcc tggcaaactc cattgtaact 159375

accatgttta gggttgctag agtctagatg aagatttgta attattttct gctttctcat 159435

tcccagaggt tgaaaaacta gggtctgcct ccagaaatct aagattttaa attttctcaa 159495

atgaaataaa actaaaaatt gcatttgcct tctatacaaa atatccaatc aaattgaaat 159555

attcctatgt attagaaaat cttcaaaggt atttctgtag ggactagggt atttaggaag 159615

cttcagtggt cggagtgtgg tgactgatgt ggtcgttgaa atcgactgtt acaagcatgc 159675

aggctactgg taaatactga ggaatgagag aataaaaaag aggcaaagaa accaaaagcc 159735

cctttacttc agtgttccag ctgtgtgtgt gtgtgtgttg ggcgtggtct ttgtcactgt 159795

ttccttagca gagattgttc atgtggaggt gccatcttct aacag gtt atg aca cac 159852
                                                  Val Met Thr His
                                                  530

ctc cgt gtg atc tac gag cgc atg aac cag tct ctg tcc ctg ctc tac   159900
Leu Arg Val Ile Tyr Glu Arg Met Asn Gln Ser Leu Ser Leu Leu Tyr
    535                 540                 545

aat gtc cct gcg gtg gct gag gag att caa gat gaa gtc g gtaagtgagc  159950
Asn Val Pro Ala Val Ala Glu Glu Ile Gln Asp Glu Val
550                 555                 560

tgtccttcgg atgttctccg agagataggc ttacccccag aacacatcag ggctgagagt 160010

cttctgtgtc tgtcacctgt gcccaggtgc ctacgcgttg tacagtacat tttgtgggtt 160070

ggtggaggga ggggggggttt cacacgtgtg tgaatgagtc taaaatcctt cagtgcacat 160130

ggcaaccagg ggaaggaaga taccaggtgt tggaagatac taggtgttgg aagataccac 160190

caggtgttct actctatcac cccgttctca tgggacagtt gctatctgaa cctagagctt 160250

gggtggtggc cagcaaagcc ccgtgatttc ccttaatggt gctgggattc cggggccaca 160310

tgcttataca tggatgctga gggttgaagc atagctcctc tcatttacac agcaggcaat 160370

ctcgcccatt ctgccctctc tagccccaga tcgcctctta cagtgaatct caccttggct 160430

gctgcttcag ctcttaactt tcaatgcctg tgagacctaa agatgtaacc tggtatagag 160490

aagaccttga agtcttcaag cagtgaatca gttgttgaat cccatgtcaa cagtgatatt 160550

ctaatttatc caatcttgta ggtagatact cactaggctt ctctacttta taactaagca 160610

cagtagtttt agcctaccct gtgtatcgag agctcaactc cccatttgtt tttcacttcc 160670

ttaaatttct tgtgactgca cgtttcagtt atgtttggaa gacagagatc agtaataagt 160730

cctctatata agaagtcaag aactgggtac agtaatccat gcctgtaatt gtggcacttg 160790

tgaggctcaa acagggaatt gcttcaagtt caagtccagc tggtactacg gagtgagttc 160850

aagtccagtc taggatacac agtgaaacct atctcaagga aaagataaaa ataaaataaa 160910

tatatataaa tgaaaacaga tctccacaag ggagaaaaat tcaaaacata actcataatc 160970

ttactgaatt gaagttaaaa tttctagatg tgtgcattaa atgagtgtgc tttgtggtta 161030

gcgtcaccct cttatcctgt gtgacttaca ttaaggtagc attagcaata tcaaactata 161090

gaacaataag ccattagaaa ggaactgtac ctaaacccgc taattacagt tggcactctc 161150

tggtttctaa tttgctcttt gtagagcttc tcatttggca ttgtgctcct ctaaatatta 161210

gccacaagtg agtcggacag atggcgactc aaatccctca gtgctgcaaa atacccaaga 161270

acgggaccac ccagtaactt aaaatctcag tggcagagag atggttaact agaatcacac 161330

ttgggtttct gttctttctt tcaataaagt aagaaactgc catgggggta gatcaggaac 161390

aattacgtaa aaactaggac tggagggatg gctcagtgag taaagtgctt actggacgtt 161450

tagaagacct ggattgagat ccctcgcacc aacatttaaa aaaaaatgtc agtcatgatg 161510
```

-continued acatgtgcct gtaagcctac tgtaggggca aaagcaggtg gatcgcaggg gcttgctggc 161570
cagcgctact gcacctgtgt cagtcgataa ggagaagaag ccattgaaga aggcatccca 161630
acatcaacct atcagccttc gtgcacacac acacacacac acacacaaga ttcctgtcat 161690
tctacatata ctggagacca catacttaca gaaaatcttt ctaagatctt tctcttggaa 161750
tcctggatgc tatcatctta agatagttgt ttacatagga aaaaccactt gctgcaatga 161810
acacattaca gcctgtccac tacaggcctg tgtgcccttt aagctcctga cacaaaagct 161870
tgaggtacga gttcttcaag gacaatgggc ttccttggtt gtccttagtg ggcttcctga 161930
agaactgtga cacaaacaag caaatgaaca gccagtaaaa ctctccatca catcgatgca 161990
gacaaaccca aaatcggctc tgtatgctgc tcacaaaatc ctttatattt taatctcttt 162050
acttttgttc atatttgaag tattccataa tgaaagtgtg atttgtttgt tgttatccaa 162110
tgcaaagaag aacctcatag agtccttccg attggcacct tacagtagac acagtcgtct 162170
gtggattccg ttcacccacc atttttccct aagttatcaa acttgaggtt tgaatcagtt 162230
cggtatagat aaggagaaag ccacacttca gttggcagaa gggtgagatg ggaaatatag 162290
agatgctcgt gtgttttggg taaacgttgg cgcctttgtg cacctcaact aggataagct 162350
caattcagtc tacagcttgg aaagaatgca gcattctact gcttaacact catggttgct 162410
ttctgagtaa agggttttag gctgaggatc tgccagtatc agtttttctt taatgacaca 162470
ggtgtatctc tctcagtgaa ttatgcttcc aaccttaaat ctctattata ggccaaaatg 162530
ggtgagaagg gggccttaac tacaaagaag ttatgctgtg tggttggagg tggggactgg 162590
aatcaagcct gtaagaaaga ataaataaac aaaccaacca tactgactag gaatcatgct 162650
gccagggaat tctggccctg atcatgttac cccattgtgc ttccctgagg cagcccatct 162710
ggttaggcta cagccagctc tagtaaatcc caaatcggta gttctagtaa ccacacacat 162770
atgggtggcc ttccgtcatc cagcatcttg tgtgcctgag agactctgga ccagtccttc 162830
tcaaccttcc tgatgctgtg accctttaat acagttcctg atattatggt gacccccccc 162890
aaccatataa ttattttgtt cctatttcat aactgtaatt taatattatg aattataatg 162950
taagtatctg atatgcagga tatctgatat gcaacccccg caatgtggtc acaacccaca 163010
gtttgagaac cagcttcggt agactctgga accacacatt tgaccttgtc ctgcttccat 163070
ggtctcagga acttccggcc gaatatctga gcctttacct cgcattggcc gcctcaccca 163130
aattctccct ctggatggcc tgagcaggac aggtgtcctg tccttggaaa gtcgcatccc 163190
tcaggatcca actgaaagcc tcagcagctc tgtaaagtct tcaccgataa cctcagaggg 163250
cagagcagga agcaatggtt tgatgagctc agacgggtct gcccatgaca tcagtgtcta 163310
ggtatattgt gaaaggtcac cttggagtac tggaccagcg catatagaag gagcaggagg 163370
tctaggggag gagtccgggc cctcggtccc tcagacatta ggtgtgtcca cgttcagcaa 163430
ggttttcttg tattttgcac aaaggcggca tacgggctaa tatcaatggt gaagaattct 163490
gtggcagtat ctccagctca taattgaaga aactggatcc tagagaggcc acttaggatg 163550
atagtggagg aataaaactg actctgaggc cagggtcttg cctgaatccc acatctgtgt 163610
tctctctggc acccattgtc ttgcaccgtg agttctcttc tctttaacct tagggtctac 163670
acatagggtt taaacctggg aggccatact ctagcttgtg ttgatttcta tgtttctatc 163730
acagcaatgt ccaatccgct gagctctgct gccatccatg gtctttgact gtggttctag 163790
cagacagcct ggtgtgcttt agagatttcc gttgctgtag tctaggaatg aggcaaaccg 163850

-continued tcacgctttg aggtcgctgt cccttaaatt atgagatgat ctgtttcttg ataatgccca 163910
aacctccatg ctaagctcct tccttgaccc ctcccatacc cattgcacga agtacctccc 163970
tttctgctgt gacaatgttc cctaaagctg ttatggttga tctacccaac agaatgatgt 164030
catcgggcag tggcagcaaa gtaaagaata aagcagattt cccagaaccc ttttttaaca 164090
ctgtataagg aggtttgggt cgcagccttg acactgtgtc ctgtggtcat ctccagagtt 164150
tacacagtca catggttggt tgattggttg attaaccatg catctgattt ggttctccta 164210
agtattgtct aaactgctgt tagttctttt tacaaaaggc tgacctttta ttatcttgcc 164270
gtttttagtc cagcttaaat tattattcac aagtcccaaa gcacacatac tagttactat 164330
tttctttttc aaaggtttgc atgtaaatta tgaagctttc ttgttcagaa aggttgtaag 164390
aaatgttgat aaagagggga cattgcctta cgtcttctaa atcctgtcta ggaatgtgct 164450
gttcaattca gtgatgactg agttaccgtt ctgatgaaat gcagctgctc agagttcctg 164510
cccatgcaaa tcgtcgtcac ttcagtcccc acagctcttc agctcaacgc tgatttggcc 164570
cacttgccat tctaagccat tagatgtttt tgtcccttgt aatttccctt aagtccctta 164630
agtccttgct aaattggttc tggcattgag gaattttttt tatcattgtc cctcaagatt 164690
cttcagattg cagccacctc aaggctgtaa aactgtagca gcatttcatt ccgagatgtc 164750
tgtctcacac aaggctgtcc tgaccaattt atgagttaaa cagaaggaag gaaggaagga 164810
ggaaggcagc tctaattgtt tcacactggt ttatcattta aattaataaa aaaagtgaaa 164870
tactaaaaac cagaaagacc ggtgactggg taaatccgtg gttagtgggg ctggtatgga 164930
atgatgtgcc aaggagacaa gaaagccact ttcatggaag agtgcttact gttgttacaa 164990
ctttgctttt tattacaatt tcactgtggc ctcttgataa aaatgtccag cctccaggga 165050
aaaaaatcca gcatgtctat ttcagggaca gtgtctctgt tgtctgtgcc tatgtggagc 165110
tggttacaaa tccaaattgg gtttaaagtc gaatatttac aactcttctc agtctgacaa 165170
aatagaagag tgagttagta ctgcctgaga attatttacc atcccgtggg tacttgtcag 165230
ttaagagaga gcattagttt cggctccaaa ctttgtctct gtaagtcctt ccatgggtga 165290
ttgtttccaa ttctaaaaag gggcaaagtg tccacacttt ggtcttcatt cttcttcagt 165350
ttcatgtgtt ttgcaaattg tatcttatat ctcgggtata ctaagtttct gggctaatat 165410
ccacttatca gtgagtacat atcatttgag ttcctttatg attgctattg gatggagcac 165470 agcacccccca atggaggagc tagagaaagt atccaaggag ctaaagagat ctgcaaccct 165530
gtaggtgcaa caacattatg aactaaccag taccctggag ctcttgactc tagctgcata 165590
tgtatcaaaa gatggcctag tcggccatca ctggaaaaag aggcccattg gacatgcaaa 165650
ctttatatgc cccagtacag gggaatgcca gggccagaaa atgggaatgg gtgggtaggg 165710
aagtgggggg agggtatggg ggacttttgg gatagcattc taaatgtaac taaggaaaat 165770
acgtaataat aaaaaatatt tacaaaaaaa gagagaacat tactgagaga gagagagtgt 165830
gtgacgcccc aggagatgga gttcaagacc aacctggctg cctagctaga catcctggct 165890
tgttgagagt gagggaacca gagagataga gacgataaaa ttgttagtaa ataagacaga 165950
ggcactattt aatttattct gttcttactt gatttttaat aaaagtgact gctactcaca 166010
tgtaaagtct tacagctgaa ttaggcactc aaaaacaaca tgtgttcata tttcagacag 166070
acatgaggac cttcctttgg tgacttcatt atagtctcaa agccaatctg ttgttcccag 166130
tatcattaac tgagtgtttg ccttgcttgt agccaccctt atttaaatgg gtatctttga 166190
ctccccctga aaaaagacaa catttttgtt ttttgatttt ttttttcaa aataaagccc 166250

-continued ctagttccac gcatgaaaat gtctgggcta gtgcagaaat ccccagcaga agatagtagc 166310
cttcaaatta gatggtattc ccagttttct gacagagtga gactgggttg acgagtcccc 166370
agacagagag gttagcctcc tcagagtccc agccggtctt tacaacgtgg ggaagaggcc 166430
tttaacagat aaactcgccc aaactgccaa gtgctgttct ttatatacat tcctggctat 166490
catatagtat aaggtttcat tgtctgactc aggagttaaa ttagatcaat agattatacg 166550
tctttaggaa gatctgttaa agtgactgat aaggtcacat gaatgtgtca aacatccctc 166610
tagcatgatt ctcacataga tatttccagt gcacaatagt ggggaagcca gtctatacta 166670
gcaacaccca gaaagtgcac tgtccaagaa caaatgcgta ggcttggtgt ttctattggt 166730
ttggctttta tttttaacca atcagtctcc cctgtctaac cagaaaggca aattgttgac 166790
actgaaacct agaatgcagc gcagtgcatg gagctgtgtt cctgtccgtg gatgctggca 166850
gtcctcagct gaattaaacg tcatccacat tgtgctgact cactaccgat ctatctcttg 166910
gtttttttcc agataaagtg ttatcttctc aaatccttga accactttaa ttggtttctt 166970
tgctttttta ttattacggt tgagttgtgt gcgttctttg tatattctag gcactaactt 167030
atcacataca caacctgcaa atgtttttccc cattcaatgg gtgttttggt gggtttttta 167090
acttttgctt attttttatt agatattttc tttatttaca tttcaaatgt tattcccttt 167150
cctagattcc cctctgaaaa taagcctatc ccgttctgcc tccccctgct cccgaaccca 167210
cccactccca tttcctggcc ctggcattcc cctatactag ggaatagaac cttcacagga 167270
ccaaggacct cttctcccat ttatgaccaa ctaggccatc ctctgctaca tatgaagctg 167330
gagccatgag tcccaccatg tgttttcttt ggttggttta gtcccaggga gctctgtctg 167390
gggttactgg ttagttcgta ttgttgttcc tcctataggg ctgcaaaccc cttcagctcc 167450
ttgggtcctt tctttagctc cttcattggg gaccctgtgc tctgtccaat ggatggctat 167510
gagcatccac ttctgtattt gccaggcatt gctgttttta tctttacacg tgtttttttg 167570
ttgttgttgt tttgttttgt tttgttttga catgcagttt tagttgttct gtttttttaat 167630
tgtagacaaa gtctagcaga ttgattcttt attttttgtt tttgcactgt tgctttggta 167690
atagatagac aaagccactt gaattctgat tggattcatt ttgtatgggg cactaactag 167750
ttaagggtct cagtttacag attcctacca tgtgatgaag aagaggttct tcctaactaa 167810
aagacattgt accgtgtgca aattctgttg actgtagact tctataccct caatttcctg 167870
cctattcttc ggtccatact tctacactac tttgattact gtgactttgt ggttaagctt 167930
tgagattggc aggtatgggt tctgtacttt tggatttttt tggtgatggt cattgttgtt 167990
attgttttaa gattgctttg aacattctag ttacttttga atttctactt caattgtgat 168050
gtttttctca ggactgttta agagaatatg ggtttgtatt ttttttctca ttgctaagac 168110
aagttatctg ataagagcag ttgaaagagg ggtgtcttag tcagggtttc tattcctgca 168170
aacatcatga ccaagaagca agttggagag gaaagggttt tagtcagctt acacttccat 168230
actgctgttc atcaccaagg aagtcaggac tggaactcaa gcaggtcagg aagcaggagc 168290
tgatgcagag gccatggagg gatgttcatt actggcttgc ttcccctggc ttgctcagcc 168350
tgctctctta tagaaccaag actaccaggc aagggatggt cccacccaca aggggccttt 168410
ccccccttgat cactaattga gaaaattcct tgcagctgga tctcatggag gcatttcccc 168470
aactgaatga agctcctttc tctgtgataa ctccagccta tgtcaagttg acacaaaact 168530
agccagtaca attgacccct tgtcaacttg acacacaaac acatcactag taagcctcaa 168590

-continued

```
ccccttagttt cttattcatc cccaagatct aaataacttt aaaagtccca cagtctttac 168650
atattaaaag ttcaatccct ttcagagatc cagtatcttt taaaatccaa agacttttta 168710
caattaaaag tctcttaact gtgggctcca ctaaaaagct tccttcaaga gggaaaaaca 168770
tcagggcaca gtcacaatca aaaacaaaaa ttctgggatc cactcatgat cttctgggct 168830
cttccaaggg cttgggtcac ttctccattc ctttcctttg tagcacatgg cttgtcttct 168890
aggctccagc tgcctgtact ccgctgctgc tgctgttctt ggtggtcatc ttatggtact 168950
ggcatctcca aaaacactgc tgtcttccac tgtaacttgg cttcaacaat agcctcttat 169010
aggctctcat ggtaccaagc ctcaactcct ttgcatgacc ccttcagtcc ggggccatca 169070
attgcaactg aggttgcacc ttcaccaatg gccttccatg gcctctcaca gtgccgtgcc 169130
tcagctgctc tgcatgaccc cttcatgcct tcaaaaccag taccacctgg gtaactctta 169190
cacattacca agtccagcca cagcacaagg tacagccttg gctatctctg caacacagcc 169250
tctgtggtct cagaaaacac ttcccaggag atgtcacctc aatgatgctg gtctcttctt 169310
aattaaagtt aggttcttac ctccagataa ccagaatcaa tagtcaatag ttccagtaat 169370
gcaaaggttt tgctttagta gttctgatat cttgttaatc acagctgatt cttcagcccc 169430
agctaaccag aaccacagaa tcttcacaat caaaatagca atggccctga aaagactctt 169490
taatcttccc tctggaattt cacaagccag gcctccatct tctgcactgt actccacatt 169550
atcttccaag ctcctacaca acatctgaca gagctcttaa caatgaatgg atggatcttc 169610
tagcccaaag ttccaaaatc cttccacagt cctcccaaaa catggtcagg tttttacagg 169670
agtatgccac tgtgctggta ccaatttgtc ttagtcaggg tttctattcc tgcacaaaca 169730
tcatgaccaa gaagcaagtt ggggaggaaa gggtttattc agcttacact tccatactgc 169790
tgttcatcac caaggaagtc aggactggaa ctcaagcagg tcaggaagca ggagctgatg 169850
cagaggccat ggagggatgt tacttactgg cttgcttccc ctggcttgct cagcctgctc 169910
tcttatagaa ccaagactac cagcccaggg atggtaccac ccacaagggg cctttccccc 169970
ttgatcactc attgagaaaa tgccttgtag ctggatctcg tggaggcatt tccccaactg 170030
aaagctcctt tctctgtgat aactccagcc tgtgtcaagt tgacagaaaa ctagccagta 170090
caaggggttt acttcaattc atatgtatgc attcatgatg gctggaaagt tcccaaggta 170150
gtgggagcac aaggcagctg gcctcactgc tatccccagt tagttaggaa gcagtgtcag 170210
acaatcgctg gtgcccacct tgcattggcc tttccattcc tgtgaatatt ccagccctgg 170270
aagaactgct ctcacccaca tgtaaggtga gccttaccat cccagttaac tcaatctaga 170330
aacttcctta taaacttatc caaagtttat ctcctaggtc attctaggcc ctatcaagct 170390
gacaatacta ttcataatta gattataatg gctctctata tagatcagtt tgggaattat 170450
tgctgttatc acatttcccc tattttcagt gtatgtgaat gtgtttgagg cacagtggcc 170510
cacacgtgag tacatgcatt tatacacaca tgttgggtac acatgtggag gctggcagct 170570
gatgctgacc aacttttccc ctccattcta ctccatttac agttgttgct gtagggctgc 170630
cctctccacc ccgctggtac ttagatcctg ggaattcaaa ctccattcac acttccagaa 170690
agccttgtgc actgaaccat ctccccagac tcctgttata aagttttaaa taaggattaa 170750
ttaaacaaca ggatgctaca gcaggccgtg agaggattct agctgaggcc cactgtgaca 170810
aggcaagttc ttaaaattag tggaattcac gcttttggct ttcacgctat tattttagta 170870
aaattccaaa ggtttggtag tcctcttgtc aagatgtgct gtctctacta cctcagtagc 170930
ttctgtccgt tttcacacag tcacttactt tgcagtaagg agcatctcta ccagatgggt 170990
```

-continued gaggcttgag gcagcatctc ccaccccaag ctgctgattc tcatgaagat gcggggagtc 171050
attttcccag ctccccaact cttatgtgct gtagtttgaa acaaaaccta aagagaagcc 171110
ctagcaaaaa ctgagtaggg tgtgaaagca gaccacagcg gtggcaagat ggtttcctgg 171170
cacgaaacac tgcaacagat gtgtcctgat tccttttctt ttctacagtc ttgggaaaaa 171230
ccaatgattt tggacggtaa caagggctgg ttactctatt tttcacaagc agctgccttc 171290
aaggttcttt ttttaaaagg gaaaaaaaat gtagagatat ttgccaccca gaatatggaa 171350
atgaagccaa attaattttg aagtgtgctt ccacaaggat taactggaga tgagatgagc 171410
ttgtttgcat gtgagtcaga gttgggaacg aatgtaattt gcctcttgct gttcctctca 171470
gaaacaaatt ctgcaatgta gtcactgagg aagcctcatt attctttatt aatagctctt 171530
aggtagtgtg tcttgtgcag acactgttag ctaggaaatc ataaacaggg agggtgtgtc 171590
aacagggctg gagggatggc tcagcacata atgctcttag agaggtccca ggagaggttc 171650
ccagcaccca tgttggactg cttacagctt ctgtaacacc agctccaggc gatctaatgc 171710
cctcttctgg ccatcacagc catgcacaca caagaacaca cgtgagtgca ctcacacaca 171770
cacacacaca ttctcacaca cacacataca cacacacaag acttaatatt cttaattcat 171830
gggtcaacct gttgtgtttt atgagagaga gagaaagaga gagagagaga gagagagaga 171890
gagagagaga gagaaagaga gagagagaga gagtttggtg gaggcacagt atggtgtctg 171950
tggaaggggg tggctctgtg ggcccatgct gaggcatccc ttccccctga ggtaccagcc 172010
acagaaaggt atagtataga ataactttat gtgcctcagt acaggggaac gccagggcca 172070
agaaatggga ggggggaggg tatgggggac ttttgggata gcattggaaa tgtaaatgaa 172130
gaaaatacct aattaaataa aaaagaatag agtttattca cagaactgaa cacctcgttg 172190
tttctgaaga agggcctttt tttgggggag ggaggagaag cttggggcat aggggagcgg 172250
atgtgggagg ggagtggagg gaaggcaggc catgagcaca tggagaggtg gggggagagg 172310
ggcaagagga atggggagag aggggtaaga gggtaaggga acaagagcaa gaggagaaga 172370
gaagaaagtg aggaggggac aagcagtccc tttcatagtg aatcaggcac acatggccat 172430
taccagggaa ctgtggggtg gggcctagac gaaatgccaa cacaaccaat taacctattc 172490
tattatgagc gctgtccaga gaaacagtat tttgatatgt gtcaagacac tattcattca 172550
gggtatgtta gtatacacca aaaaccttat cacttgggag actgaaagag gagcaacttg 172610
agttcatggc tggccttgac tctaccagga aatcctatct ccaaaagaca agggattaaa 172670
aacaagcaaa caaataaaca agtagtattt gcaatgcctt tgttagtggg tagagtccag 172730
ttcatttcag ccactgctga tagatgatgt attagcaaag acaaagaatt tactagccat 172790
ttggtgcact gaactcgttg ttgctgactg gcatttgttc ataaaggtgt tagctacatc 172850
ttttgcttga aaaaaagcac ctggcctcta tgaaattacc ctatctctgc ctttgctttt 172910
ggtctgtgta gcatttagat gtgtcttccc gtcctgagac aaggctgtgt ccctaagtct 172970
gcaatgtccc ctattacact gaactctgta cggctgcgta agtaggccag ttgtgaaacc 173030
agacacatct ttggcctaaa caagggaagc aagctgggta gaatttcatt ctggtacaaa 173090
cactagcctg agcccttcta gccctggcac accagctgtg tctcctcttt ccgaggttgt 173150
aaccataagc ggaagttttg caggtgcctg ggttcctctt gcagccttgc ctcattaaga 173210
aggagcttcc aagtacagta gtgcaaagtt aagagtgtaa acgagagtgt agcacgttga 173270
taggatcatg cttacttgca ttctataatg tttttattta ggaaacagtg aaagcaaacc 173330

```
aagtttcaca ttctgaaata gtgggtgtgg aggcctcttt gtttggtttg tttttttaat  173390
gtgtgtgact gtttgcctat gtgtgtgtgt gtgtgtgtgt ctatcacatg tatgcctgat  173450
gcctgaggag gccagaagag tgccgaatcc tttggaactg aggtgatgga gggttgtgaa  173510
ctgccaaatg tatgttgaga actgagctct ggtcctcttc aagatcactg agtactcagg  173570
accaccgaag cttctctcgg gccccataca tgtttcctaa tgaaagtctg tgatttaaaa  173630
ttcaaagtta attgttagct ttaaatatag caaccttcat ttcataatta ctgagtctta  173690
ggaagcaact gagagttctc agatgatagc caatatcttc tctataaagg aaggttgcta  173750
cacatacttg tcctgtgata taggcatcct gtggcatgaa aatgaatcat tgtgtcatct  173810
ttctttgtta caataaaact tccctaggaa ctctagccaa atgaagtgct tattgctaga  173870
agttgtcaaa gataccaata aacagttctc cagagtttct atttgtgaaa tgtagtagtt  173930
gctagtatag ttttaagtgt agttttctaa tagtaaatat ctgttgccta atacaaagaa  173990
agtttagtgt tgccactgag gtagatgagt gacagttttc agacattatt attatctgaa  174050
aataatcttt gatgatttag gtatatacat tttacattat atatatgcat atatatatac  174110
acacatgtat ataatgcata tgtatatata catatatatg cacatatata cacattatta  174170
tacttttata tgactttcaa aaaataagat gtaggaaggc tgggtgtgac ttacttactt  174230
acataggaga gtgcttcata gcctgtatga agcctaggtt tcctcctccc acattgcaca  174290
aaacgtggta tgatggtgta atacctgcaa tctcagcaca caggtgatga agacagacaa  174350
atctaagacc ttggctactt agtacagcta ggcatgaaac actgtcttta aaaaaaatgt  174410
ctatccatgt acatacaccg ctatcatttg ccactgtgag taacaagaag atccaagaac  174470
taagcaagga tattcagcat cagtgaattg tttgttaaat acctacaata ctctgggact  174530
gttaaagatt cggggcacag tctttcttac tcaaataact tagaataatt tagaatttgc  174590
ttagagaccg cagatcatca gccaagacaa ggctctgttc tcaccgaggc agttgatgaa  174650
ggctgatctg atagcacgag gtggtcttgt ctaataacca cccttcctcc taaccacctc  174710
aagaagacta ctaagcaaga gggaagcttg cttttcaaca gctcaagcca cgttatttta  174770
taggttcaac taaggccata catcacatgt ggtcaataat ctaaggccat acctaacgcc  174830
tggtcaatag cctgcagact aacccgttcc attggtcttg atccaacggc actcacttag  174890
tgataatagc aaattcaagg ctgaatctgg gaataatatg ggcagcttca gcgtcctttc  174950
actgaacgtg ttacgcactg aagagttgtc tcaacagctt tgcacacata catctctgtt  175010
gatgtgttaa acattttgta ggacttgggg gccatgccac ctttctccat ttgatcggaa  175070
ctcatatgct gaagtatgag tcgctgacag ttccgtggac catgatatca taattcccca  175130
tgatgacttc accattgatt ctccgggacc agccatgcag gctagggctt tgccaatgtt  175190
tatggtcaga gacttctggc aaacagcatg gaagtggtgt attgttgctg gccattaaat  175250
cagacccatg aagtggcctc ccctgccagc agagcagatc gcttcttggt ttgttttttt  175310
ccactcaaat ttacaaagaa aggctaacag ataatttaat gaaaagctct gtatatgttt  175370
ttgtttctat tattgttatc ttcattttga tcacaaactt ttttttagtc tccctaagtc  175430
ttgcttaatc ctcaaaaaaa tccttgataa gcaaagtgta tggcttttcc cgtcatttat  175490
tacggtatta ctttatatgt tttggaaaca ggcctgtgta tgccaggctg ctctcattcg  175550
cagtccccct ggttcagcat ctcaggtgct aaggaacatg gtagtcgtct tcctttcttc  175610
tcttgctgag tctgacattg caggcaagct gacgtcctgc tctcagccct ggatacactg  175670
gcatatgttc tgcttatgtc tacagtgttg acttttttcag gtcgaatatg catttgtatc  175730
```

-continued tcttcacaaa aaaatatgcc cacagccaag ggatgattaa tagaaacagt tctcatcatg 175790
tggctttgga ccggcaacag cagcatcaat gagaaattgt tagaagtgtg cattccttgg 175850
cctcattccc agcctaataa tccagctatg tgtggaatag atgtgtcagc ttttatctct 175910
gtggctaaat acctaacata aataaactta aaagaccagc tttattttat aatatatcta 175970
tatttcagaa gtctgagtct atagtccatt ggccctattg ctttgggttt gtggcaacta 176030
tattatggcc agaagagctt cttagtttcc ggtgaccaga aggagaaagt aaagatggga 176090
agaagaagaa ctgaaacaag agaattctct gtaaagacaa atccctaact tccaagaggt 176150
cccatctctt aaagatcctg ctgccactca ttaccaactt gggctgcaga caagtccctt 176210
aaaacatgga cctttggagg aaatgtaaga tctagaagta attggtgctc agtctgtagt 176270
gatagtgctc agttagtact aaagttatga tgctcagtct atagtgatag tgctcagtta 176330
ctattataat aatgatgctc aatctacagt gatagtgctt agttagtatt acaatgatga 176390
tgctcagtct acagtgatag tacttagtat tatagtaatg atactcagac tacagtgatt 176450
gtacttagta ttatagtaat gatattcagc ctacagtgat agtgcacagt ctagactatg 176510
ttaatggtcc aaggtccaga tatagtaatg gatgtaaatg atacacagct tgtcttcaga 176570
gagagatgtt tttgctattg ttagatcttt tttaggggag gtggattggg aaaatgactc 176630
agtaggtaaa tcacaggctg cccaagcttg aagacctgag tttgaatctc tctcccctcc 176690
catgtaaaaa tggacatagc atcatctgta gtccctatac tcctacagga agatgggagg 176750
cagacacaaa aacctggaag ctcacagcat gagcaataaa caagagaccc tgtctcaaac 176810
aggttggaaa gcagagactg gagactgaca actgaggctg tcctgggacc tccacctaca 176870
caccaagttg tataaatgcc tgtactcaca tacaagcaca tgtacataca tcatacatac 176930
taatactctc tcttgagtga tgttgcctgt aaaactatag agctgtaaag gatggaagat 176990
attcaaagac tcgggttctc tctctcagac ccccctttag gctgcctacc ccagtgtcct 177050
tagactttag aacaaccgca gtacaaggtg ttggctgtga atactaaagt tcaggaacta 177110
ccggtggaaa tggttgggcc taagagaact atgagtgtga gatgatctgc tttcttcctc 177170
caggatatta cacgtgctca tgtgagctta gagctcttaa tttgtatgta actgggtaaa 177230
gggagaggac tatttcctaa tgtgctacct accatcttcc cctcggattt attagagtag 177290
gtgatgccag ataaaatggg ttcaaccaat tctttgagtt tctgtttgtt tctctgtact 177350
ttgtccggaa tcttttatcc aaagtccttg ggattggaaa tgtttcagat ttcagaattt 177410
ttcaaattcg gggcacaacg ctaccagtta taactagcta tcatcttcag tccaaagagc 177470
tgagattcgg aatgctttga aagctttagc tttcagaaca tcccacatgt agagtctgag 177530
agcaagccca tgcaatatag gtattcagaa tatatcagag agcaacagta accctcacgt 177590
ttactactga agaccaacct gagccgtttc cagtctgctg ctggcaatgt ctgtgatcct 177650
gagcaaaatg ggagaaagct gtctcaagaa aaagaggtgg aagccaaggg aagggctttg 177710
taatgtgttc aggcctatag gagtgcggtt agcgctgagc ctgtgtttac attccctcgt 177770
tcccttaggc agggagccag tgtcttgcac tgagtgtttt gttttctccc accttaagga 177830
gaagccttct tatacctaaa gcagaaagta cctccttcag gtgcaggagg gaaaacttaa 177890
gcaatctgtg gattgctcaa aacacagtct gtcctttgat aaaccaggca tcgccctgca 177950
agtcaaacat tgtatgaaaa tgtgagaggt ttggcagact gttctctttg atgtggagag 178010
agaaaagctg gcttcctttc ccacattcag ctcgggtctg catctaccct gctgctaaga 178070

-continued ggctcttcaa gggaacttga aagtggtgcc ggaccctcca gctttgcaga ttaaggatct 178130
agggtgatta actgatttga tcaaaatcag agactaaaac tggtcagggg tcgagggctt 178190
cttcacatct tgccagagtt cttcagaaat caaagtgagt tttaaatacc tggggtgtga 178250
ataaatgaga caattttctt ccattaaaga aaagtggcca cgaggaatgg ggaacccttt 178310
gtagacatca gagtgttcaa atatggcctt gtgtccaaca cggccttgtg tccaacacag 178370
ccttgtgccc ggagcttgcc acgagttgaa gcgagcatct aagctggcag gttccggtcc 178430
ctcgggagtt catcctgtca tttctgcatg tctgtccctt actccgctga cagtaaacag 178490
tgtctacatt tttcaggatc ttacttcagt tgctgtaaat acttcaacaa tctgaaagtc 178550
tcattcagaa gccacttagg aagaaaagtt actctcagtg gaaattggta tcctggaagt 178610
cactgtgtct caatgcatac ttgggaccaa gtaaagtata atgtggagga gttcttgttt 178670
aaaataccgg gtcttgaact cttcctcaca ctcagagaaa tcaactcatc ttctacttca 178730
aatgattctt gaataattca aaaggtttaa tgtttatatg tgctagtaaa aatacaagct 178790
tttgtagaaa attgagagtg tatttgtata tatctttgac ctaaaaaatt aaacattatt 178850
aatgtatcct acatgaagtt agaccagtct ttcccttcag tctctgattt acagtgttct 178910
gacttacaag attttctgac attgtagcga ggagaaagta atgtgttttg aatcataatc 178970
cgtccccggg tcactacatg tggtgccagc atacagcact gcgtggcagg tccttatctt 179030
agtcagggtt accactgtgc tcaaacacca tggccaaagc agcttgggga ggaaagggtt 179090
tgtttgatct acacctccac ttcactattt atcgtcaaag gaagtcggga caggaactca 179150
aaaagaggta ggagctgatg tggcggcctt ggagtggtgt tgcttactgg cctgctttct 179210
tatagaaccc agaatcacct gcccagggag ggccccaccc cacccccatc aatcactaat 179270
taagaaaatc tcccacatac aggcatgtgt gcaacctaat cttgtggagg cattttctca 179330
gctgagtttc cctcctctct ggtgacttta gcttgtgtca agtttcacat gatcaagata 179390
ataatcaaca atagccctca ctctctcatc ttgagctctg ctgttcagtg gactaggtgc 179450
agccgtggca tgtttgacta ggaatgttgt gtggaaggac catgaggcta tattcgcatc 179510
atgaaagaac acatgtattt ccaaggggcc actgcataaa atacttccgg gagatgacat 179570
ttactttgaa ggttgaatac agctctgtta agtaacacaa tgttgaggtt gcgcttaact 179630
tacccaagtc actggcataa actccttttc tctttgtttt tattgtgttc atgtgtgggc 179690
acacgcacat gtctaggcca gaggacagca aaaggttttg ttccttagct ctttacacca 179750
tctgtttgag gcaaggtctc tctttggtct gcaagtcacc caaatggact agactgatta 179810
gccaggagcc ccaaagatcc tcctgtctcc attctgaaat tataaaccca acaccacaca 179870
cagctatctc cctgtctccc tcttccccct ctgtgttttg gggggcagga caggttatat 179930
ccatacaact cagatcctgt gtgtgtgtgt atgtgtgtgt gtgtgtgtgt gtgtgtgtgt 179990
gtgtgtgtgt gtgagtgtgt gtgtgtctgt gtgtgtctgt gtctgtgtgt gtgtgtctgt 180050
gtgtctgtgt gttctgacca caaaactcag gtccttacct cctgacccac gcacaccccc 180110
caaacccgcc aacttaacca cttattaacc tcagtcactg ctcttgacag tgaacagtga 180170
aagcctgggg ctggtgggaa cttcttgcct agatgctgct ttccttggaa gttcagagcc 180230
tgctcgtctc tctgacagat ccttttcctc tctcagtcct gacccttcgc tctcctatca 180290
ctgattccac catagaaata ctccatggag gtggccttca aatccaagat gatactaact 180350
tcatcagagg caaaagagaa gattaatgct atgcccaggg tgaccagcat tgtagaggac 180410
attcatccga atctcggaca gttcactgac agcctagcat ccgctcagga agtatgtgtc 180470

-continued

```
cgatagtgaa cggacaaaac aagaacacga gaaaagctat gctggctgcc aacactagat 180530
gccagtcccc aggagggagc tcactgtgtc acacggtcac atgtgtatat tttagattac 180590
ataggaaaac cctctaaacc ccttttgtgg tttcctgaag tgacatggac tagaaatcaa 180650
ataccagctc ttcttttatt ccacaaacaa atagaccacc tgattggaca tgctccagaa 180710
atgtgggaaa gctatcattg gctattttcc ttcaacctgt ggtgaacaag gcatgtggaa 180770
atagaatgct taagaagaga gcaataaaaa ttaaaatcat ttccttgtct tctctgtgaa 180830
ggggatgtac gatcatttct ccctgtttag atatccaggc acatgcctgt aatctcaatg 180890
gttcccaagt tcaaaggcag gctagctaca tagtgagtcc cagaccagcc tgggctacat 180950
attaagactc tgtctcaaag gaaatgaaac aaaaagaagt atgtttttca aagccttttt 181010
cttgcgtatc cagagtgagc aggattaatt taccctcagc ctgcagctgt cacctttctt 181070
gaacacagag aagaaaggaa acagaatccc ttagagaaga catttagatc tcttcctttt 181130
gcctcagtct ggctagaaag gtgcagtagt gacctgggtt agagttctgt tcccatttgc 181190
cctctccaga ctctgtgtat aaaattgata gtgcgtacac atcacacaca cacacacaca 181250
cacacaccac ctgttacctc ataagcgata gtttattctg aagccaaatg cgtctggcag 181310
tggcctggaa cacagattta ttttctccaa attccatgtt cctacatgga agcatcttat 181370
agtaaccaaa caaagaaagc cataagtcaa gacactccgt aaaggcatcg gtggaaatat 181430
cagggtagac tggttgagga agagcagaga aaccccacct gtagtcctca ggtgccacct 181490
gatgacattc taagcttgct gactggttgg ctaactctag tttgtacatc cggagggatt 181550
tacctaatgg tcgaaaagga gctgggtcag gtataaagga gaacagtaca tgactgctgc 181610
aggggctatt gagggcccaa agctctacac ttgctgcctt ccagagtttc tggtctctgt 181670
ggttctcatc agttacatgg gcttacagaa gggtcagtgg aactttccag aatccccaag 181730
tgtatgtgtt aattgccttg aggtgcagtc tttgggtggc agttaggatt gggttccgtg 181790
tagctaagat cttcatatag aagcttgccg tggacactct gctctgtgat ggcccagtgg 181850
gagatccctt gctacatacg ggtaccctgc tctctctttt ttttatgtat tagaaagaga 181910
aggatttgta tggcttttgc ttcttttgtt ttgttttgtt ttgttttgta cactgagaag 181970
aaagcagtag acagaaacag aagaagcccc tgcagaaacc ccctttataa attattcatt 182030
ctctgatcct cagttatgac agaaaataga acagcctcaa gcttagggta atggcgcaaa 182090
cttatgattt cagccactca gcatactgaa acaggaagat cctgggttct gggcagacct 182150
gggctacatt gtgagatcct gtctcaagaa aatacagtgg tttgaatagc ttaaaaatga 182210
aagtgacttt tctcatgttt tttggagctc gtaaattcaa gatgatgggt atttaggaag 182270
gccttctcag tttctccatg atacaatttg tttcatcgta ttgggagcaa ggatccagat 182330
gttctagagg ctgcccctgg ggagttcctg ctatgctgga acaaagaact ggcccaggga 182390
cacgtggaca gtggtagaaa aagacatgat ttattaagaa aaagaaagcc attttcagga 182450
tggaactttg agagatttgg acacaggtgg gccacagttc aaaacactaa cggtcctggg 182510
ttcttgagcc tttttagatc atgtgtgtag cacccacctt cccccatctt aggagatcac 182570
agaggttttc tgtgtgtgca tgctgtttgg tcacatacag ccacaggaag tggaggttgt 182630
cttcctgcca tcggttgctt tcctgtgctg atcttgatgt ttcttcccat aaaacctgtc 182690
ttggaaggag caatctctct ggtttctccc cagcctcagc atccagtcac cctgggataa 182750
tatttagcgt cagtcttcac cttaaatggc tcttctcaag atgatgccct tgagggctaa 182810
```

-continued ggcctccatg gatttcatcg gggatccagt tcagcccaca ccacttagct gggtcagtcc 182870
tttggctagg tctaatgtcc tccctctctg ttgaccctta ccctttagcc acttacagcg 182930
catgtgctct ttattctaaa agctatacac agaagccatg acatatagta gtactcttaa 182990
tttttaattt tttgacatct tgaattggaa tagaattaca tcaattctcc aacccctctc 183050
agcatccctc cctcaatccc cttctatgct accccagtct taggttggta gtctcctctt 183110
caaatccaaa ataaatactc tggccaccat tttttttatg ttatgaagcc tgagagtcac 183170
aaacaaccca gcactgctcg ctaatcgtgc actccatggc ccaatctagt catcctataa 183230
aaacaacagc atgaccttca ggctttttga agatagtttt gtgcagaccc agtttgtcca 183290
gtgtgagccc taagttgaaa tcatcaggct aaattgcacg gcttcctcca gctgtcccgg 183350
cttctctaaa tggagtccct gggcttgagt gcagagtgca gttctcctgc ctctgtgatg 183410
gtggtgtcat cactctgagt gcagtaagat ctaaaactcg cctggtattt gccacatgtc 183470
ttggtgccag gcacaactca gcttctccgg ctccccagga aggaagtgac atagccgctg 183530
tgtacgaggt gcttgaatga ggctactcca ttttcctgct gacttgaaga atctgcagac 183590
acttccccca aatactccca tgtttaaatc aaacagctac atgtcttgaa tcttcaccct 183650
acacgtgaaa aaaaaaagat taatttccat attacgaaac tgtaaaaggt tttaagcgcc 183710
tttccttcct gtgaggctga taaaggagtg aatttgtaaa ctgcggctgg gttaattagc 183770
cagggttaat taatgtttac cacactggga cgatgaaaag aggtgtgtaa atgcacagta 183830
atgcgggtca tttttcaatt tattgttgaa gcttacggtg tgtgtgagtg aggacaacat 183890
aaagcgcatg cgtgtttcag agggctactg atgctctgcg gtaattatga ggcgtaggct 183950
tctaagtgga ttaattacat gttcctgaag acgatcacag gctaatagtg tttatttagg 184010
gacaggctgc tgtttcaagt tgaactattt ggagagctgg gtgaggtgag gagaggctaa 184070
ctgtgtgggc atgaaaacag cattttaaag taacctttaa aaataaataa tagatagatt 184130
tctagagtcg tgtattttca agagagccca aagagtctta ggtgaagtcc tggattaaag 184190
ctgggaagta cagatactag aagcagtttg aagagattgg aatataatct cctatgaact 184250
gggtagatat ccctcagtgt tgggagttta ggaccagatt ccaggacacg cccacctcag 184310
gaatccccaa attcatggat gctccaactc cttatataga cagtttgtat ttgtatagga 184370
cttatgagca tcttcttggg ggctggagtg atggctcagt ggttcagagc actgactact 184430
cttccagagg tcctgagttc agatcccagc aagtacatgg tggctcacaa ccatctgcaa 184490
tgagatctga tgccctcttc tgatgtgtct gaagacagct acagtgtact tcctgagcat 184550
cttcttgtgt gctgctcata aaacctaatc cattgccact gctcagtcaa cactcactac 184610
cctgtaatgt tttgaaaaca gcatggtaaa agccctattt gtgttcaata cagacacagt 184670
gagtgttttc ccattaactt ttgatctgag tgccggagag ttggcttagt ggataaagtc 184730
tttgctatga acacgtgaag acctgcgttc tgatccccag ggccgtgtca aaagcaggaa 184790
tgacagcatg cacctataat ccgggcccta aatgatggaa agagaagtgt ctgaggaata 184850
ggacatccta gtgcttgtgt gggtcctttc ctgtcagcct tgagttcttt gcatgcgaag 184910
aaattgagtt agttatttct ggcactggtc tggaaatatc gacaaatgag tatcagtgag 184970
ctcaccacgt aactcgtttg agtctccttg ttccagattc ttacagggat ttcttcccac 185030
tcctcacctc tgtgcactga gtgccttcct gaaggcaggt cgattccacc cctggccaaa 185090
cccctaacgc ttagcacttg ccatttccag gcttggatgc tatcttactt tttctgttgc 185150
tgagataaag taccctgacc aaagcagctt aagggagaaa ggctctatct ccgcttgcag 185210

-continued tccaaggaca caatggatca aagcagagca gccaaagctg caggtcactt gacatccagg 185270
acgaggaagt ggagggtggt gattggtcgg ttcttgttaa tttccctctt tggcctagta 185330
ggacccaagc agagaaaggt gtgacccaca tttagggtag gtctaccttc tgttaaccta 185390
atgaaaccga tccctcctag gcaggcatgg aggctaactt aatctaaata atcctttgtc 185450
tccttggtta ctccagagcc tatcaagttg ccagttggcg ttattcttca tcacagtctc 185510
ctgggcctcg ttaagggacc atgtgaatga gtttctgctg gagagaaagg gccatcgcca 185570
tagctaggaa agcaagattt cgttaaagac aaacaggcca gtgtacagaa gagcatactg 185630
gatgtgttta gggtttctaa aatatgcata cattagcatt taaatgagcg gtcatgccta 185690
cagagatgta ttgtgtataa ggaacatagc cctccattgt gatgacctgt gtatttaggc 185750
acattttcca cactgagccc ttatttatca gcatatcttt tagggtctcc ccatgaaatt 185810
gtctacagat gttggcatct tcctttctac cacgagctca ccatcttttg acccagtttt 185870
ttcatccccc tgaatatagt agttgtccgt ccctcatcaa ctggaactgt actgagctct 185930
cttcctggcc cagcagtgtg tgattcccat tccatacatc tgctgtggtc ttgagcaggc 185990
caggcagggt tctcttccaa gtctgaggga gagcacttga gagcctgggc cactgcatag 186050
ctacagttgt ataagtcgca caggaccctg ctataacgga cagcagtcat ggaaaccaca 186110
gtgaagagtt gtctgcagct gcacagccat gaacagcagt cctgtggcca tgccagcatg 186170
gccacccgcc cctgcttctc tctctgatgt gtttgaagac gcacaccatt gctgaagtcc 186230
aaagcacgtg tggcagagcc agtcatgggc tgtgcatgtg actcactcgc ctcaaagaaa 186290
atgttatgtc catttgtaag gagagaggtt gatttcctta ccagctgtct cagaggtggc 186350
tcggagctca agtggggatg aaagaacccc aagtaatgat gcccagaaca ccctacagga 186410
gccgagaagg agccacggga ctccgggctc aattaatttt tttttcatc tcttactcta 186470 cgtttgtttt tttattggtc cacactaaaa attagttttt cataataata gatggtgcta 186530
ttataaatat tctgaccttt tacttttaag caaatatacg tcaacaccaa gtattccaaa 186590
gagccccagt aaaatgaaaa ttaaggatct aactggaaag atttcttccc cataagtcca 186650
tatttatatg tccccaaacc taatagtagt ctcaaagatg tcattctcta tggccacagc 186710
cataaagatt aaataagaaa acaagacggg acatcctctt ggagttgggg gaggaggtat 186770
gggatgagga acagtcagag ggtggactgg gaggggagct aatgactgga ctgtaaaaaa 186830
agattcaata ataataatga tgatgataat aataataaat aagtagataa aataatttct 186890
aaaagacaaa aatgaaaaat aaaaatgtga gttaaatgta tagtggcctc ctagtgctag 186950
attttccacc gtgtgattca ttttccaagc aagtacatcc gtgtaattta cacgtatgag 187010
cattagaact tcagcccaca gaactttctt tcaaagacca gtgctgtagt gtgaaaactc 187070
tgcagtcagg gccccaggtg gctgacatcc caggggggatt aagaccccct aaagtggttg 187130
gaaataagat cgggaccttg gcccaagttc cataaataaa cacggaaagg gaagcttttt 187190
aatccttttg ccaaggccag ggagcctggc tgtgttttca tcttgatttc tggctaatgc 187250
cggttgatag aacggagctg tttgatgtag gagtttgaaa gccacaagga aactcctctt 187310
caagggaaag gcacttcttc tgaaacttca gtctagacca gacgatggta tttcaggaaa 187370
atgtcacttg caataaggag tagttttcac aagtgatgct ccgccttctg tgagtcctct 187430
ctggggacag ttgcctacca taagtggacg gaacacaccc ccatttgaaa ctctgtggcc 187490
aggaaacttc tacacaaaaa taaacctcga tctagacatg agtctgtact tagactctgg 187550

-continued gcaattctcg agattgatag tgtagctcca gataaaagag ctgccttaat tttctagacg 187610
cggaggtttg tggggagagc tcattgctaa gtgatgtcta tagaggtttt ccccccagtt 187670
tgggaaacag tcctacaatg atcattctct ctcagccact gaggtaacct gatcactcca 187730
cttcatttgg gcacagaaaa gatttgtggg gcagagccca actcaaattc agattgttta 187790
acttctctta actgtgaagt agggtgttga agcctagtgg gggttcctat ggcaaccaaa 187850
cagcctcctc ttagattggt tacttttctc cttgcagaga caacatctga caagaaccaa 187910
tttgaaggag gaagggatgg ggtttggctt gcagtttaag gggagatag catgcctggt 187970
ggcaggaggc aactgttcac atagcatcca aagtcaggaa gtcaggagag ggaacaggaa 188030
gtaggactgg gctgttaagt gttcaaggcc caccctcagg gactgacttc cttcttctgt 188090
gaggcttcac ctccaagagt cagcaaactg actcttccct gagagcacca gcagcgatga 188150
gctaagtgtt caggtccatg aggctgtgcg ggatcatcca cgttgatatg gcagttccca 188210
cagtatttca tgagatggac attgaagaag ggaaagacag tgagtgttcc tgggggaaag 188270
aaaccattgt tggaaatgga aaatccaaac agaactgatg gacaacagct tcaggctctg 188330
tcacacttcc ctaatgagcc tctagagcta cacctttaac ctctttggcc taagtttatt 188390
gggggggggg ggaataataa tcattgaaat tatctctttc taaataacat gaaaattctc 188450
atgggctgat gagaggatta cattaggaac tggggtcctc aggtttcagt tatagtatca 188510
gttctgctac tcaatatgta tttatctaca tattatttat ttttgaggca tattctcact 188570
ccatatgtag tgctgtcttg gaactcacta catatccaag ctggcatcga acttatagcc 188630
ctccagtttc agcctcccaa gtgctagtat tgcaagtgtg gggctagcac atgccttgtt 188690
tgttgatttt aaaccttctg agaatggatg tttgtgcatt ctgttctcag tgggggttgc 188750
tatgggtacc aaatgagcca gtgagtagct acaaaggcca ctgatgtgga cagtgtaggg 188810
agggtagtgg gccccccca gcccccaagg tatagcagga cttgagtact tggtggactg 188870
gtcatggcat tggagatagc tgtggtttgt acgtagtcag agtgaataca gcaaccatag 188930
gaagattcca tgtgtccctg caagtcagca tctctattag ctgctgcctc acaaagccaa 188990
gccaggtctg tccagccagg ctggtctgcg aagtgtccac agtgcagaag tatctctcct 189050
ttctgggagg agccaggaat gacgtgtggc ctggtgcttt cttgtgtgta cgttcttatt 189110
cttggagact aagaaacatc aacctattcc caacacatct ctgtgcttcc ccttcctgct 189170
taataaatga tttggccaag aaggaaatca tggttgtttt cagttttcct gggctatcct 189230
ggtacagaaa tgtgatcttg aacgttagtt ttaaggcagc caagtgttgg gtttgaaaac 189290
taagatttgc tgaaggcgtc ctccagcgca cgtcttctcc tggcagtggt ggtgcttagc 189350
tgagtgtgac acactctccg aaaactggtc tgtctgtgat gacgggaact gaggtcacta 189410
cattcttgct tctgcactgc atggcttatg gctccggtcc tctcagactt caccacaagt 189470
gatgactagc ctttgacagt tgtcacctgg gagccctcta atatgcagat ttgctacctg 189530
tatccaagga gtggaagggg cacgaggatt ctgtcttttc tctttctgag acaaaagttt 189590
gctatgtaac ctaggagatc ctcaaacctc ctatataccc taggtaagcc ctatacttga 189650
aatcctcctg tctcagcctc ccaagtgctg gaattataag catgctttag gacacctgta 189710
ggacaattct gtacttccaa caagatcccc aatggacacc tatgtcccga gattgagttt 189770
acataacaga atttaagtga tggagtgcca gagactgtca cccaacctgg aatcttgtag 189830
ataaggaata caggcttaag gagtttcaga ggccacgggg acattaataa cagcatcaca 189890
ttaatagact gagccagggg ttagacatgc acaggctctg gttggaaaat taaatctgat 189950

-continued ctcatagctc tagtatgggc aaaatgccta gaatggatga tggctgattt ctagtcaagc 190010
tctttgatgg ggaaaaatta cagaccttct tccagtgcac ttggagccaa aggacagtgt 190070
agggaagtag caggcagata tataagtatc tatttaaaac attaaaatcg gttttaggag 190130
aatcctctgt taaacaaaat taaaaagaaa ctcccatttt ggtggagatc agagatcagt 190190
aatttttcac agggagacaa agaatcaaaa ttaagacagg tataatgtca ataaagattc 190250
agtcctagaa gaaaaacaga gcaagcctga caaaccgctg gttcagtggt ctaaactagc 190310
cctttaatag ccttgtttga caaggttaag ataactcctc acttgtatga aaaataaaaa 190370
ataaaaaata ctcagtatgt ccagtacaca gaaggcatca gtctgtaatt accagttatt 190430
atgaaacttg ttagaaagat tgactcaatg actataaatt ttattttta gaaacctgaa 190490
atgtagccct taagattttg aaatttattt ggctgatgtg tcatttaata gttataagga 190550
gactctggga tggaatacgt aggattcgtg tcttccctcc tctggcagac ctttattcat 190610
gaggcccttt cgctaaaaac aaatggccat ggacatcttt agtgtccacc aaaccaaaac 190670
taaaagtttg aaatcatttg aagatgaaat cactgtgact ctctcttaat gttgctctct 190730
ttgaagtatc ttgaatgttt tccacaatag ctaacgccct cccctacccc accttcctgt 190790
ttactctaag tttgatttgc ccacataaat catcaaagcg tttttgaaag aggaaagtga 190850
tggggttcac tctgtgtgtg tgtgtgtgtg tgtgtgtgtg tgtgtgtgtg tgtgtgtgtg 190910
tgtgtgctag aattcacacc cattatgtaa accataagtg aaacattacc atcactgggc 190970
ttaattaaat attcctgctt taaccttgaa aaacccaagt gtctggatat tacagaagat 191030
tcttgactgg agtagtacct gatgaaatgt tagatggtaa caaggtgctg tcctgaaggg 191090
gaaaagggag tcttgggaaa atgaatgttg tctcttagat taatatagca attggtaagc 191150
ttggatattt aaaggcttcg atggtcctta atataggcca tcaaattaga ataaaatatt 191210
aaattaattc aaataaaagt ataacccatt tgagccacca cgaacacagt agaagatggt 191270
ttctggtggc tttgcctcac catgggatca aagctcagtg acacagtcac tctggtccct 191330
gccttgtcgg acacaggcac aattgcccag cgtcagtgca tttcccagcg gtaaaatcct 191390
gagcccttaa tcacagagta gctggctgtc ttgaacattt tatgatcata aagtagagtc 191450
ctaccgtggt aatggcaatc ctttcgaatt tattcagctc tctgccctta agagcagact 191510
gaattccttg ttctaaatgg cattgccaca agtggttatt tttaaattcc ctacgttaaa 191570
ttaagataat aatatggatc cctgctactt gtgctaagag atttttctct cagctgaaaa 191630
tgtcgctttt cttgaagatt tcaacttttc acataaattt cctaatagtt tttttttgt 191690
tcgttttgag gtgatgcaga tgattttttt aaatgtgtaa gaatgttttg cctgcatcta 191750
tgtattggca ctacatatgt gcccactata tgtttcagaa ggtatctgat gccctggaac 191810
tagatttgta gatggttgtg agctaccatg taggggctgg caactccacc caggtcctgt 191870
gcaagagcaa ccagtgctct taactactga gccgtcacca cagctccgtc cccatcgtgt 191930
gaatttgtgt gctgttcaca gcagtgggct atgtgtcttg tgtctatttg gaggaaatat 191990
cttgccaaca actttaagga taaatgagac aagggtgcca cgttgtcttt gcctgaactt 192050
tccgggaccc tgtatgcaaa tgtatccaaa tataagatct tcctatgaga cggacatgtg 192110
gtctggtctg cgctctctct ctctctctct ctctctctct ctctctctct ctctctccac 192170
ctgctctagt ctgagaaacc ccttttgggg tgggagtggg cagtggtggg aggcaatgtc 192230
cactctataa ggctggtatg gttacaaatc aacctctcca gatgcaaggc ttatgtttga 192290

-continued

```
tctgctccgc aaataagcac tcccaggatg gtaacccaca ctgttcaata ccacagctcc 192350
agagggatgc tggagacggg aaggagttgc aacccacaag gctggagata tgcagggagc 192410
tagggacact gaagggccct agcatcttgg attaattcac tacacagtgg agactattga 192470
aatgagaagg agtcttgcct cagtatctgg gaaggatcta gggaaggcag tcaaatgcag 192530
attggtaaag agcagcgatc agtcagttca tattgcctta acaatatctg agctcgatgc 192590
ggtggtacat tcctgtaatc ttagaactgg gcagtggggg attatgggtt caaggttatc 192650
ctcagctaca tagagtttga ggattccatg agatatgaga ctcatgtctt caagtaaaac 192710
aataacaaca aaaaccaaca accagcaatt tatcacattt atataaattt ataactaggc 192770
aatttataaa aaataagact tttgtttctc gcagacctaa ctacaagttt aagaagatgc 192830
tggaagcttc agtgtcttag agaactcaac tttcctcatt cagagtgggg acttgttgtg 192890
ccctccagag aggacaagcc ctactccatt aatagcagtg agagccttca cttaatccca 192950
tccccaaacc ccacacaacc ctgtgtattg ttacttctcc ggggagtaag tttcaatacg 193010
tgaattttga ggcatattca tatggtagca ggcagtaagt ccacagctac acttcatcaa 193070
agcaaaactg aggggaggtc acagaacagg gagacgattc agaagcggac attcgaatgt 193130
tgtcagtatt gttaagtatg tatcgtggat agttctgagg ctgagaatgt atcgacgcta 193190
actgccacgg gaaggcagga gcgaagagaa ccaagtctgt agtccaagag gaaggctcaa 193250
gcatcatata ccttccacgt tgtcagaata aaagagtcag tcatgaagaa ataccatttc 193310
aatgctgtcc acatgaagga gatctttaca ccttcaagca tgggtcattt tcaaaggaga 193370
aagttggaga aggaaatgtg agaagaaaag gttaagggca cagagcttgc ttattttttc 193430
tccttccttc ctcccgtcct tcctttctct cttcctaagg accggctgac attttcagac 193490
attatgaggg aacagcaaga caatgaaaaa gtttcaaagt ccaggaaaag cgtggtaata 193550
aatgccatag agacctcagg catccaagag ctccctcctg gttcttgcct ctcaaggtgg 193610
acgtgtgggc atcgataatt attccaaact atcttgactt cagggtatta agtgctaacc 193670
agtcaaagca taagatttat ataaaagaaa tgcccactta atttattaaa tcagactttg 193730
gccaagttac tggccattac ctgtgacttg ataagacatg aaaaagtcta ggagaagtct 193790
aatgagggcc ttttatctgt gtgggaaagg tcattgcaag catcaaatat tgaattttag 193850
atcagtgcca cactgagtag gtatatatta taactcaaat tagacttcaa aaggactaat 193910
ttgctagggg ttctatcatt taaaataatc tcttgtaata aaactgactc tacaggaaga 193970
tattaatcgc atactttaat gctgtccctt caaattgttt taatgggtac acatttgagc 194030
ggaatattaa tttttccagt aaattggctt ttttgtcaac ttaaaagagg attgaaagga 194090
tgatagtaaa atgttacaag tcaagtataa atccaggttt aattttcttt attttctcca 194150
gcattgatat taactagtga tgggcttgaa atataattca gtaaactgac acaggcgtga 194210
ctcagtaatg acacacttaa ttaatcaagt attaatacca tatgatcaat gggcctctga 194270
tttttaaaaa actatagata aaatgtcagg ggaacttttt gtaagataat aggagattca 194330
caaatcatct gttttggggg gttttggtga tggtggtagc aactacactc attatattac 194390
attctgtttt tctgttcccc tggtaaactt ttttaataat gaaaggtgca attggaggat 194450
ttcttactgg actctcagat ctttgggtag atcagctata ttccataagg ttgatttttt 194510
ttttccttcg gggaagatag aagctacaga aaacaaattc agggactttc atctcaggtc 194570
acttatatga tcctgagagg aagagatagg agattagctc agacagtgag cattcttcag 194630
ggtcctcagt gacatgcctt gaaggacaaa gtgtatgttt gtagctctgc tgcatctggg 194690
```

-continued

```
gaaggcagct gttttcagag caaaggtcac ggtgactgaa tggagcagga ggcccgtttg 194750

taatattttc tcacccatcc acatctgccc ggaggtgggg gtagacagac gctatatctt 194810

ggttcccaga ctgcacctcc atgcctgctg ttaacactct accccggtcc cacatcatag 194870

catgctgtag aatccttcat gatcactgga tacatgggga gtctgtggaa aggaaaaggc 194930

agttagttca ccctccaggt cttcacctct ggagaagaga atcagcaaca agatcagcca 194990

gtctcgacag gctcagagca gtctcgacag gctcagagca gtctccacag gctcagagca 195050

gtctccacag gctcagagca gtctccacag gctcagagca gtctccacag gctcagagca 195110

gtctccacag gctcagagca gcccatcggg tcaaccacta agctctgact ttccttaagg 195170

tgcttcgttt tttacatgtt aggtggtgcc aagtgacacc tcgtcacaca cggcatgtag 195230

tcagtaggaa tggccgctgt aagcgtacgc taaccgagga cacactggct tttctttag  195289

at  gag ctg ctt cag aag gag cag aac tac tcc gac gat gtc ttg gcc   195336
Asp Glu Leu Leu Gln Lys Glu Gln Asn Tyr Ser Asp Asp Val Leu Ala
        565                 570                 575

aac atg atc agt gag ccc aga atc agc tac gga aac gac gct ctc atg   195384
Asn Met Ile Ser Glu Pro Arg Ile Ser Tyr Gly Asn Asp Ala Leu Met
    580                 585                 590

cct tcg ctg acg gaa acc aag acc acc gtg gag ctc ctt ccc gtg aat   195432
Pro Ser Leu Thr Glu Thr Lys Thr Thr Val Glu Leu Leu Pro Val Asn
595                 600                 605                 610

ggg gaa ttc agc ctg gat gac ctc cag ccg tgg cac cct ttt ggg gtg   195480
Gly Glu Phe Ser Leu Asp Asp Leu Gln Pro Trp His Pro Phe Gly Val
                615                 620                 625

gac tct gtg cca gcc aat acc gaa aat gaa g gtaagagtcc ctacctggag   195531
Asp Ser Val Pro Ala Asn Thr Glu Asn Glu
            630                 635

ccaaaagcct tctgggtggg tgtggcctat gttataggtc cccatggtaa cagttgccta 195591

gagtactttt gagagaagga cctggtgtgt ggcagagatc tgtgtcaccc gcagggatac 195651

cactcctata gattagagga ctcacagtat atgctgtgat tgccccatgt gccgtcttca 195711

tctctacatt ttaaaaaagg taacaaaaat aaactagtac tttttatttc tcctttccct 195771

ttgtaaattt acatacatat ttacatagag agaggcacac acctaccaac tgtccaagac 195831

tggcatgtac aatataggga aacaccatct caaaataaaa gtgcataagg aaacatagat 195891

caggtcatgg atgactgtgg aggtgggggg cggggtggca gagagaagga cagacagaga 195951

cacagaacta gagacgcaca tctttggact cccagaaatc cacctgcctc ctcctatgtt 196011

tgggaattta agacactggg aaataattat ttaaacatac tctcactggg agttatttta 196071

tctcttccat gaaaccagga tttgatttgc gcttctaagc ttttggccca gaatgtccac 196131

ctttaatgaa aagggtgacc aaattaaggg cagaacttgg tcccccagag agaaggtttg 196191

acagggcctt gtacagtaga cagacgctga aataatcctc ctcagccgcc gattcttact 196251

gaaagaatgc agcgaacgca atagaatgag tagagtgaat gaagcaagtt tacgtcagaa 196311

ctaaagagaa atgatttctc gatcaacgaa tctgcacacc tgggtgatgt aattctttca 196371

ggggggatta tgttagggct tctattcctg cacaaaatac cataaccaaa aagcaagttg 196431

gggaggaaag ggtttgttca gcttacactt ccacattgct gttcatcacc aaaggatgca 196491

ggacttgaac tcatacaggg caggaacttg gagacaggag ctgatgcaga ggccatggag 196551

gatgctgctt actggcttgc ttcccctggc ttgctcagct tgctttctta tagaagccaa 196611

gactaccagc ccagggatgg caccacccac agtgggccct ccgagcctta atcactaatt 196671
```

-continued

```
gagaaaatac cttatggatt tcatggaggc atttcctcaa gggaggcgcc tttctctgtg 196731
ataactccag cttgtgtcaa gttgacacac aaaaccagcc agtacaggga cttagaagaa 196791
cctgtttagg aagcaacaaa ataacctgtt agcttatttt gccatttttc catgttcagt 196851
acaaattgca tgcacacaat taccttgatt tcttgaagct aagaatgctt tccaagaagg 196911
caacagtatc tgcctggggt tttcctcaca gtgcaaaagc actgagcaaa cagggtgatg 196971
gttgtgtttg gttggttttt ggtttgtttg tttgattttg gttttggggt ctttgtttgt 197031
tttttgaggc aatatctgtc tatgtaggtc tggctatcct ggaactcact tgtagtccag 197091
gctggcccca aactcacaga gttctacctg cctctgctgg gattaaaggt gagttgccac 197151
catgccccgt gagtgagcag tttttgaaga caggctgcgg aaatctgtgt atacactttt 197211
ttttttcaca gcataacaac ccaatttgtt tctttaatct gaaaaaacaa aggcaactta 197271
caggtataat tatattagat actatacagc atcaacatta tttatgggat ataaataatt 197331
gactttccca cttgttaaaa gaatcctacc aaaacaaaac caaaaagagt aggtcatttg 197391
attttctatg cctcatggtt attatataga tacatttggg gctctaaagt cattgttacc 197451
ccgtacataa tctgtaataa gatgagtatg taaaaaaaaa tgtacagcct cattttctaa 197511
gctcagcgca catgagattg gctcttcata gtaaaagcac atactgtgac aagcacatgt 197571
gacacaacac agacacagtc actgatactc ttgacaattg ccaagatgtc caggcagagc 197631
cttgatttaa gtgagtctgg acgtatgctc agtactcagt gcgatgtagc ctagccttta 197691
acatccaaag caggctttct tgttagaggt gtgctactgg ggctggggag atcactcagg 197751
aaactggttt tgcctggcaa gcatgaagac ctgtgttcaa tccccaccac ctatgtaaaa 197811
agcaaggctt ggtggctctg gaaaggtaga gagagataga cccctcaggc gcgtttccca 197871
gccagcctag cctacttggt aagttctttg ccactaagag accttgtctt aaaattcaag 197931
gtgatggtgc aaataacatg tacacacaca tacacacaag cacacacgca aatctgctaa 197991
tgattaacag cagaatgaga gcagtaacaa gagagggcag gaatctagtc gatacaaagg 198051
cttatgcaga acatgtgaac catctatcta ttcagtctgc aacaatgcca gcttagcttt 198111
atgccccagg gcacatgagt cttcctgatc tctaagtctt gaagtatggg tctcaccttt 198171
atatacccaa tgccccatta gaacaggtat tttgaaaagc cttttcaaca attaattcgt 198231
tttgttgttg ttgttgttgt ttgtttgttt gactttgatg gtctgagggg tgaacctagg 198291
atttgtgggt gctaagcctg acctccacta tggatggtag ccccccagcc tatgacagtt 198351
catcttagaa taaatgggac tggcaaggtc ttcctggaaa aacaatgttg caaatagcaa 198411
caatgttgca aataacaaca atggtgcaaa tagcaacaat gttgcaaata gcaacattga 198471
aataatacag ccctccctgt atttactcag taacacacac acacacacac acacacacac 198531
acacacacac acacactaag aactgcaggg gttggttggt tcagtaaata agaacaatga 198591
attgttctcc aaacatgaag tcctgacttt gaatcttcaa cactttcatt aaaaaaaaaa 198651
aaaatggcta tacatactcc agtattgggg gcaaacatag gtagattccc cttttgcccc 198711
ccaaaactaa atcccacatg gcagcatata tcatatgtgt aactcctgta ttggaaacag 198771
acataggcag atcctgagtg ttcatggccc agccagccta tatgaaactg caagcccagg 198831
ctcagtgaga gaccctgtct caaggcagca aggtgcagtg ctagaatgag atacgctaag 198891
gcctgctctg cagtgtgcat ggaccaacca agtgcacaca caggcacacc tgtgtgtaca 198951
caccattcat gacatgcaca cacaacacta tggagccata ctgaattcat aaattcagag 199011
ctgaagtggg ttctggattt acattaccat taacccctta catccagtgg gaagttagag 199071
```

-continued agccgtgtag ggtgtgggtt gctgcagtga ccctgtgtac tccggcattc agtgacctgg 199131 atcctcaccc ccactaaatg gcagtcatgc ctctctttgc ttagtctagg gactaaacac 199191 cacattcccc ttgggagagt agccagggct cctaatggtc aggtctgacg ttccattaca 199251 gctctgctgt gtgactgctc acgtgactga gcctctccag ccactgtcca gcctgagata 199311 atctgtatct tcgttccttg cttaaaggca gtttgagaac attttcgtgg agagctcttt 199371 aaaacacctt ttcaatggag ctgggtcttg ttggagcggc gtggtcattc tctgtccaga 199431 tggctcacct tgcgcctaaa cagtatgccc ttcaaatgaa taagtaataa aggcatatga 199491 tacagtgttc ctgctgtgca ttccccatgt tccctgttct cccctacaca caccctgagc 199551 tactaaaaat acctacagct ctcaaaggat ttcctttcat tgtccatgag gcccttccca 199611 gcatagattc aaatgcttac cagaaagggc ctgattttct tcaacaaaaa gagtcaaaaa 199671 aaaaaaaaaa aaaaaaaaga gtcaagacca gtagatacct ggtcatttag ttcttttaca 199731 ttgagaaaag aaaaaaaaaa agagttaaga atgtggatgg ctctgatgag agtattttca 199791 ggacacgtca gggcagttac ttacacaaat ggattcagac gttgagacgg tcagaaggcg 199851 agacctgcac aggatctgca tcgagtgaag aggtgatcat acgtgccagc cctacctcag 199911 aactttggca gttgatggct gctgcgagcc agggagtcag ttctctccaa agatgcggtc 199971 cgcggtccag tagatggctc tccaccaatg tgcacgctgg cggtgctgag tggactctat 200031 ggctgaagga aaggacacag gaagttggga gggaagaatg gaagagggta gaggaggaat 200091 tggggatgag ggagtggagt gggaactttg gtcaaagcac agcgtgtgta tatatcccaa 200151 attctgaaag gcaatatagg tagacaagaa acagaatttt ttcataccgt aaacaatatc 200211 ataaaacaaa attttccagt cagggaaatt tgtcagaatt gtgttcttac ctcagtagaa 200271 tgaatagcac ttagaataat gtctctctac acactagtaa ttttcatcat tagcataata 200331 cttgtgggtg aggaggcaac cagctgtaca ccttgcctgt gcaccacagg tacaggtgct 200391 accctgagcc aaacgtacat tttctgaggt gtgactgtca acagcgaggg gagcttcgtt 200451 tggccacacc agcaaccgct gcaccaatta gctcctcggc atcaagacat ttaaaaaagt 200511 agagtcaccc tcttcggcta actccatttt acaggggtca taaaaatcac ggttcatatt 200571 tgcggtgaga aatgagatat agagaaactg tccatgtcat tgttgaaaca gacagggcat 200631 tcaataaatg gaagcataca gcatgagaac cttcaatgta atcaatgtaa tcaatcaaat 200691 atcgcgagaa gcttctgaag tgaattttca aaacaatcag tccttactgc aataaaaaga 200751 ccaggtgctg ttaccttcct ttttccataa gaggaaacaa cctcggtggc tgtttggcca 200811 cagtcacaca ccttgacacc ggttctgggt ttcttcgatg ccattcctcc acttctttct 200871 agaccacgtt gccagtttcc acaccagcaa agtcaggacc gcttcagcct cctgacacgc 200931 ccaattctct taatgcgctc agaagcgcaa ttggcccatt ttatgaagac aactctctgt 200991 ccttctgttc cctgccgcca ttcttatcaa ctgtgccatc cattcagaac ggatttgggg 201051 ttgtggtcac tttcgaccac ttggcctgtg agcctctgta agctaaatgg ttgaaactgt 201111 gggtccccaa ggctcccatc aaactcccgc tggcttccct ccaccactac gctcagattt 201171 ctttctctct tttacacttg ccagacctga cccaggggac ttcctcctcc cttgccttca 201231 tctgcccttc agccacttgt taatccttaa agcttggttg ccctctctct cccttcctta 201291 tttcttcaaa atccagtctg agctgaggga agttgttttc tgacaaggga cagaacaccg 201351 ccttgggaat gccaggcggt gcagagtcac cgtggggatt accgcgctta gacgttgttt 201411

-continued

```
tctttggatc agtcccagaa cgcgtacaaa aggatgattg tgactgtcag cagatatgac 201471

aggaaatggt ctcatttcac acaattcaga tgaatgtcat ctgtagagag gaagccagcc 201531

atttcaaagg agaaacgggg gggggggga gcccgtgggt tacttcttct accctaaact 201591

cagaaggaat ttgcttcact aaatggcaaa aagcgttgct cttccgataa actcatattt 201651

gcatttcccc tggcaattga ataatccctt agtagttaat taactgtaaa agaagataag 201711

attgagtagc tgtaggagga ggtagctttt aagtttactg ctgggctggg cataatctat 201771

tttatttcta atcaaaagcc aagaaaccat ctctaaccta gcccagagga aagtctacct 201831

tccccagcct ccgtctttga tcctattgta catcctggtg agtgctctat gaccacacta 201891

aggagacacg ttggcacgtc aggggcgcta agcctttgga agtggtaccc ctccccatcc 201951

ttgatgccca ggattagctc acaaaggttc tttttttcc cagctgctcc tttttcatga 202011

cttgtttatt gcaaatgctt tcccttgctc tgtgttcaga agccacgact taaccatcct 202071

gatttgtctc ctttgctctc tgtctcttgc ttcctgcacc ag tc  gag cct gtt    202124
                                               Val Glu Pro Val
                                                           640

gac gcc cgc ccc gct gct gac cga gga ctg acc act cga cca g         202167
Asp Ala Arg Pro Ala Ala Asp Arg Gly Leu Thr Thr Arg Pro
                645                 650

gtatctgact cgccccattt cgcctctgct ctcagcactg tgcgcttcag caaacatgcc 202227

tctctgggtt gcacgtgtta cgggatagaa tttaaaacga ctgtaggcac caagcatgat 202287

ttcagagtct tggcttctcc ttatgcctca tttcccaagt tcctacgtga tctagtgttt 202347

gtttgtttgt ttgtttgttt gtttgtttct gagccttctt tctgaaacaa agagagtctt 202407

ttcaaatgtg gggctctttt tcttgatttc ttcctttttt aataaatgaa gagtgtgatg 202467

tggaccctgt cctcacacac ggtagaggcc cagggaggtg tagatttcag tgggaaattg 202527

attcttgctg aagacatctc cttcctctct tgtttagtat tcatgggggt ccttgagtgg 202587

cctcagactt ttgttggtta ctaacataga cacaatttcc ttaaaatatc attattggta 202647

tttctccagc tccagaaata cttagtgccc tctgtggatt gactatgctt acgctcagcc 202707

agtggctgaa gtaacacaac agatggatat gcataatttt gcagagaagc ccttttgttt 202767

ttctgtctta caaatttctt cactatcaaa atagatattt ctttttatac agtttcccaa 202827

gattaaaaag aaatgggttt cgaccccta ttctatgttt agccccggc taaacttaaa 202887

gtcttaagaa taatgtcaca ccgcaagaga catagaaccc gcttgtgtct actccttgca 202947

cagcctcacc ccactgatag tgaccgacaa agtgaatcag agaggggaaa gtcaatgaat 203007

tggaagatct gtgtattgtg gagagatttt cttccaaata gcacatacct tcccacgttt 203067

actttcttta tgcccagatc ccatgagata ctcaagagca atgttaacat cccttgggga 203127

catcactaaa gggaggtagt tttgcttcct ggttcagagg tatccccagt aagaccagat 203187

atggccacgc ccctcttctt gccattcaaa tctctagcct tggctgctgc cagccatggt 203247

cctagggaaa gactttgaga gtccttctgg catcacactg atcccatgat gtggttcagc 203307

acctgagcag aaattgcaga gtgatacgtc ggaggacagc tgacctcatt gatctgacga 203367

acgtcttgtc tgaagtgctt ttaaaagaac cttgagttat ataagttgta cactctttgg 203427

gctctctcat gtcctcttta atgacagtgt cactaagtaa atgtccaggg aaccagcagt 203487

tgaccttccc atgctgttct gccagccagt gaagcccaag gcagggccag taagtccagt 203547

gagtcctcac cacagctaca accagctcaa gctggtctcc tagactttt aaaatagcac 203607

gctactcgtt ttattttttt aaagatgacc tatttttat ctataaacat aaaatgtaat 203667
```

-continued attgaggcgt acatccagcc gattttatta cattcctcta ttatataagg atgtacttgt 203727 tcctgttcaa ataatccagc actcacacag tcaaccagct catcttctca ctctgtttat 203787 gtaaactgaa catgtaaaag gcattttcat acactggcaa aaaaaagtca tctgttttga 203847 gaaaagaaac taatggcgtt ctacagaaca gggaaagcct acaataacaa cagtattatc 203907 ccatgagaca tcaatgttgt aaattctgtg aatactcaaa aagaataaat gataaggttc 203967 ttgctcccgg gggcctgaga tgtaatcaaa aacaactcac tttgaattta gagaaagatg 204027 ggaggacagg aatatatgag gacacacaaa gacgtttggt gacagagcat gttatccagg 204087 gaactctctg gaaaggagct ttccacagag agaggggagt gggagattta aggcccaggg 204147 gagggcgagg aggaaatcag ttagattaga aactgtcctg ggcttgtcct tgtaagacct 204207 gtatccatat atccacatcc ttccaaagat agccaccgaa gaggaagatg gtatacacca 204267 ggcatgcgga agccagctaa gctgcaatta tgagcatgga atttgctcac cgtgtctgag 204327 gagttgtgta ggctctatca tctgtacttc tgtgttggca atgagtctgc cgcatattca 204387 gactgatacc ttcctacgct gtgcacctgt tccaataact ctacagccac ctgttaggaa 204447 tccacactct ggactctgcc acattgcatc tgtagacttt tccggtctta gatgcccttc 204507 ccaggattgc cctccaccat tgctctttaa taatctttct tgtcactcag aaacaaagaa 204567 atcaagggtg tgagttttgg cttagtcctt tctatgccct gtttcacatc accatgatga 204627 agagaatgat tttctttctt atctgaaaaa ccaggatatt gtaactttta gaagatagtg 204687 tcacccacaa gccacagcaa taatgatgcc gatttttaga cacagtgaca atcccagcta 204747 ctcactcttc ctggaatgtt tccaagcaaa aactggactc ttgcagacaa taagaaaaca 204807 catcagcagt ctcttcactt ggtgtgttaa gctaccccgc cattattccc tgtcccatcc 204867 ttctccaggc ctaacaatct agtttcgtga ccccaagaga tattttccta ttgatttatt 204927 tcattgttct attgttttgt taatctctct gtaataatat tgcttagtgc gtagaacatc 204987 ttctaaatgc cattacgtgc tgaacagcag tgaaagaggg actctttctg ctgagtctta 205047 cactactgaa ctgtgaacat tgccagtcgt gctagcatgt gacgtgaatt tgattttttt 205107 tttttgcctt tttctgtcat cagatacact gtcagtgtcc tctccaccat accaggagct 205167 tatacggttt taaatgggga cgtaataatt gacatattca tcgcaatgct gtgctctctg 205227 cctcccccac cccctgatat aaaagggaag actacttaca agttttcact aaaatctcag 205287 aagtaacttt aactgccgtg ttactactcg catgtggtga gggaaggctg cattagaaag 205347 aaatcactgt tgatctaacg aggaagtagg tcaggtttta taaaggtttg gaggaagatg 205407 aaaataagca accggggtga tttaaagagc attcatgtca ctgccacatt agaaaaaaaa 205467 atagtgtcag gaagtacaga gaacagagtg agttataata tgaaaaaaat aaaggtaatt 205527 tttttaagta atgtaaaaat agaaggttgc agttcttcaa gtagtatcca aggacaaggg 205587 ctgtcgaatg aaaacaagca gagctaatga gatgaaacag aaaggggact tacaggtctc 205647 gttgtgtctt tcctgtctaa attaataaaa atgatctccc gatgaaagga aattaaagtt 205707 cagatagaac accgtgagaa aagaaagcgc taagcctttg tattcgttgc ctagtcacct 205767 atcgctgtgt aacaagtagc cccagaactt agcagcttca tagagcaagc gtttagctcc 205827 ttacagcagt ttcagccagc cagcatttta gcatagggca gagctggctg gttctggctc 205887 aggctctttc atgaaatcac aatgaagaca ctgccaaagc tgtggtctcc tgaaggtctg 205947 gctagagctg acagagatca agcactctct tggctgctgt caggagcctt cggtaccttc 206007

-continued

```
ccatggcagc tggcttccca cacaccaaga agtacaatag agggaataag aaagaagctt 206067

tggtgccttt tataaggcat cagttctgcc atgttctact tacatagata ccatatcatc 206127

ccctgctccg gagaacaaaa gaacaaagtt ctggtttttt gaaatcatta ttaataataa 206187

atgtgtgttg tatactcaca tatgtagaca agtacagttc cctacaaccc aggctaagaa 206247

cacatgaaga ggaacttgaa caacagtggc tagtcattgt gagagttaga acagaagagt 206307

aggaaggccc agctagaagg aaatggggaa gtgtgatcca gaggcagaag cgagggagag 206367

cagcattgta ctgtgagcag attggcattc atcatgagcc tggtttacgg tgggttgtcc 206427

aagggaagcg ttgtgggcag ttagacaaga ggtggtgatg agtcacaccc agcatggact 206487

gcccaggtct gtcaattata ctcactctca gcagaagcca tgctgactgg ctgacgggct 206547

ttctcagtgc ttatgacctt gtgcttttca gggtcagcag gggggttgaca agttttccaa 206607

tacttgatgg acaagattgg aagagccatt agacccagaa gaggcaatga gttcccacag 206667

gagttgcggg aattcacaat gtgtagccag agaaaggaat cctcactgcc ttgcctttaa 206727

tgtctgacac acgtgctcaa acctacctgg tgtcacagat agatgcctgg ctcactcgaa 206787

ataggaccag gccctgcggt gtaggttaca gggagaccgt gttgcagtaa tctgtaggaa 206847

acaaaatcat tctctctggt atgcaaactg acctctacct ttgaattcac gtaggtgcta 206907

agaacctgcc tccattggaa acatcatgga ggaggtggct ctaaaagccc ttccttcata 206967

gcctcagatt ctacttcagt aggatcactt cagaaaacac gacaactgat gcaaacggac 207027

atcccttctg tctgtcttca cttccatttc taaaacatat tttacctttt agttttgagc 207087

ctcagatgaa tagttgaatc atgaaacgct gtaagaattg gtccaagaac catgcagcca 207147

cgtatagaga aagaggaatt aggtaatgaa ttctattgat cccagagacg ctctctgttc 207207

attgtgtgct cctttcgagt cagcggatga agcgattcca cggggcgtgt tcagctagag 207267

agctgggatg ctgagctaaa caaattatgt gactgacagt gctaccgccg tgcagagaaa 207327

tatgaacatg atttacttgc aattagaaca aagctccaaa gtaatggatt tgttctccca 207387

ggtcgttaaa gttcatttcc aaagccgtgc atttcgtttt tctttaagca gtcccagccc 207447

ataaaaagtg cacacataat aaacaacaag ccgctaaaac caagtcaaca tttcttaggt 207507

acaatttaac ctggcatctt aaccagcatt gatttttccc ccctttccct ccctcccctt 207567

ttaattatgg catgtgtttg gccacacagg cattacatat tcagcgttct tcagtctttt 207627

tgtttgctag gtggtggtta atggtttaaa tctagggtgt catttttctt gagaaaaatc 207687

cctaaatccg tttttcctaa aagctctggc caagagagaa ctttaaggca gtttttgcct 207747

ccttgtggct ggcggtcaca ctaacggatg gccctgcata ctttgtgttt gacgcag    207804

gt  tct ggg ctg aca aac atc aag acg gaa gag atc tcg gaa gtg aag   207851
Gly Ser Gly Leu Thr Asn Ile Lys Thr Glu Glu Ile Ser Glu Val Lys
655                 660                 665                 670

atg gat gca gaa ttc gga cat gat tca gga ttt gaa gtc cgc cat caa   207899
Met Asp Ala Glu Phe Gly His Asp Ser Gly Phe Glu Val Arg His Gln
                675                 680                 685

aaa ctg gtaggcaaaa ataaactgcc tctccccgag attgcgtctg gccagatgaa    207955
Lys Leu

atacgtggca cctcgtggct tgtcctgtgt caaaactgag aaggactact gggaataaaa 208015

ccaaaatgcc tgcctagatc ttcacaaaga taggaaggag aggaagtggg gctctgttga 208075

tagttcttgc tgagcagaag ccgctgagcc caggcggaac atacaagtgt aattcagtcc 208135

aacgttgcag ctacgtgagc tgacttccta ggaaaatggt tttttcgggt taaacacatc 208195
```

-continued

```
taatcccaat atccaaactg gaaggcagga taccacaaac aagaaattca agtccatgag 208255
gctctgatat tactgtgtgg gggaagcata agtgaatttc atttagaggt ggtcccagtt 208315
tccaagatgg tctcattatg taaataccaa aaaaaaaaaa aagttagaaa tcaagatttt 208375
cgaaaccctt ttggtcatga ccattctcgg tccacgatag ttttatttga agaattggtc 208435
ttaaataagc atgtggggag tacttggttg tagggatgct ctctcgcagt gcttggttaa 208495
gttctcatct acaaatggat aatttcagtc cattccaacc cctcctcctt cctactgctt 208555
ccccacctcc cagtatttct ttggcttaca agggaaagtt agcagagacc ctttaaggtg 208615
agtgaagccc agcggtgact ttgccgcctc agcttctcag tcagaaatct tgggcaaggc 208675
agatagcagt ttctctaaag acaatggcgg ttttcttcct aatgtcagaa ttagaatgag 208735
tagagaagca cgggtcttcc ttataggtag gcggagatta tataattctc taccaaaacc 208795
tcagaaattc aaataagcca aattccagat cgttagagtt ccttccatgt taccagttat 208855
cacaataaag gacttgagtg ggaattttaa aaacggtaag aaaatacctg tatagtggtg 208915
cttgataaga actccagctc tgtggttggg tggagtgtgg gagactgcag cctgattcct 208975
ttgtaaagta tcttcccagt gtttgtaaat aaaatgtgta gatcctagta tgaatctcca 209035
aaagaaaggg cctttactgt tgggcttctc aattctggat tattgtagca aatctaaagc 209095
tggcttggga ttcaattttg cattaatttt tttttccttt ttttattcag aaaaaggcac 209155
ccagccttct gaaatgtagt tttcgttgga aagtttattg ctgttttgtt attgtgaaac 209215
cagaggcact cctgagcagg ctgaaactgc aaggtttcaa aacaaatctg gggtaactgc 209275
tgaaaggctg gctgggggtc ggggcgtggc tcggaagatg agtacccagg atcccgtttt 209335
cctgagctgg tgtcatagac gcccttctca gtaattacat gaacttctat aatgcgacag 209395
tgactaatga cagccgcagc aattaggggt atcagctccc tctactgcac tagctgataa 209455
gataatgtac tataattagt gcaatgaata ttacagaatt acagtatttc cttaaagacg 209515
gagggatata tccagactca catttattcc cgatcacctc actgtagtat cattagttaa 209575
ttaatgatct cctttaataa atgtgttgag ctagcatttt tggttggcga ggggattaat 209635
tacgagccat ttctaatttt gccgcagatg cgctgtgagt aacatccact tagaaaaatt 209695
ttatctgctc tagtttacct cgcctttgca aactgcagca gggatggatt tagcgatgga 209755
aatcggtcat tcacctatct tgaagccgcc tggaaagaat tatttaggga gctgttggca 209815
ctaacttaca taacaaatgt gctctagatc gttaggcaca gctgcccctc cctccctcgt 209875
ttaacccacc atataagatc atctcttata taacaagatg attaaagtgc agtctgtatg 209935
tgttatttcg cctaagtaga taaagctggg aaccactggc ttgcttttca aaagagcgtg 209995
gagacgtatg tatacactgc agagactttc tcaccgtgaa tacatttctt ctttgtcacg 210055
ttctcaggat tctttttat gttcaatata aacaaccaga gtaaagcaat attgccaatt 210115
ttggtttcta ggggcaactg gataaagtat gacttgtttg ttacactgag attctctttg 210175
cctactgctg cttcccttgg caaacatggc gcttttaaag gagagtatgc gttctgtggt 210235
taattgaatc tatgtactat tgtactatga agaaggtagc ttggctgtcc ttttctctct 210295
gattaactcc tgtgtttcag aacgtttttt gacccatata gaacatgtcc cttcaaagaa 210355
acggaagcat gcaggtttga aacctagcta agggcaaagt cacctgctgt gggcaggaac 210415
ggagtgacct gtttccagaa caatggcggg gacctctatt tggtttttac caaatgctta 210475
cctgttaaag ggcttcagat ccctgcagac ttctacctca tgatgcacca gagaaattga 210535
cttcagaacc cgggaagcca cctgttgctc attgttccag agacgaggac gctcagtcct 210595
```

-continued

```
agggacccac caactcacgc ttcgctgagc tatggcggag ggtcccctga aactttgcta 210655

catccgttgc ctcttgcgct tacagacctt tttctcggct tcctttcgaa g gtg ttc  210712
                                                          Val Phe
                                                              690

ttt gct gaa gat gtg ggt tcg aac aaa ggc gcc atc atc gga ctc atg   210760
Phe Ala Glu Asp Val Gly Ser Asn Lys Gly Ala Ile Ile Gly Leu Met
                695                 700                 705

gtg ggc ggc gtt gtc ata gca acc gtg att gtc atc acc ctg gtg atg   210808
Val Gly Gly Val Val Ile Ala Thr Val Ile Val Ile Thr Leu Val Met
            710                 715                 720

ttg aag aag aaa cag tac aca tcc atc cat cat ggc gtg gtg gag       210853
Leu Lys Lys Lys Gln Tyr Thr Ser Ile His His Gly Val Val Glu
        725                 730                 735

gtaggtaaac ctggaggctt gtctgcaagt gggaggcaag ccaggaagta caggcactgg 210913

cccggggcca cttaggagaa aagcaacatc cctctgtggt actcagggca cagctgctct 210973

ctcgctgttt tgcatccacc cctgggtgcc atgaatttaa tgtgctctca ttaacattat 211033

gcattgttac ttttaactta tgacttgtat tgaaattaac caaactaaga ctaattatga 211093

cgctcagctt taaaaataca tgtatggttt ctcttaaata acaaaaatgg tatcagaagt 211153

caaaaaacgg aacctagacg ttcatttctg atttgtattt tttgttgttt tgtttgggcc 211213

tctgattaga accaggtgat gataaataat actgattttt tttcagtaat gactcctagc 211273

attaatttct ggaaggaagt ggcccagtag cgaatagctc agtatagcat gcgtggttac 211333

catggaggaa cattcaggct gttgccctga acttccacct gagcagagat cgtagtttcc 211393

cggagttagt ggagaagcac agggagtgtg ggatgaggta cacacgagcc cttcacactg 211453

catatatgct ggacttcttt ctgcccgcag agcagccaag cagggacgct taccacaaaa 211513

gtcagtgcta cgtcatcaaa aaagtacagg actcgaatgt aactccttcc ccgtcttgat 211573

tcggggaaga aagagtgaaa ggaggtagat tcacaaacat ttaaatatat ttgtggtgac 211633

gggaaagttt taaagcatcc ctgtgtgatt aacttttaga tatataatag tataaaccat 211693

ctagaaccca aagaacgccg agtccaagca gatctcattt tgtaggtgag aaaagtcgat 211753

caaataaaaa gaaccgcaca gtgccaagct taatacagtc agggtttccc ccattctacc 211813

cattgatttc catcagaggc cagtgttaag taagcatcta attaaacccg aagaaagtgc 211873

tctaagccat ccttaatcat acaaaggcag ggacagttta ataaactcaa gctaaagaaa 211933

gccagagatc tcacattcat tggtccttag attctcgaca cttcattcgt gaggatgctc 211993

atgggaatta ctgtgggttt tattttcctg tcctagttga tgtggatata ctaaagacca 212053

gtgtgttggg tgaggcccag gaaactgagg gggcaagagg cgaaagagct gaaaatttca 212113

cacactagag tataaacatg ttttgttttg tttcattttt ctcaaagcaa taactctggg 212173

gctggagaga tatccagtaa agtgtttgcc acacaaatgt aaggacctgt gtttgggtct 212233

gtagcatcct cacaacacac caggcacaac atacccggga tgccagtact ggagagagac 212293

acgtgaaccc aagggtttgc aggaatcgac aagctccagg ttcggggaga gaccctgact 212353

caagaaataa ggtggagagc tttgagaaat gcctacctac atcaacctct ggcctgcgca 212413

tgcacatgtc cacatgcaag agcatgtgtg tgtacatgca tacacacaca cacacacaca 212473

cacacacaca cacacacaca catgcacaga taccaaattt ggggttttgt tctttctata 212533

atggcaccta agttttgttc ttcaaggact gtaaaacatt atctccaatg catctttctc 212593

tcgtttctaa tgaaatctgt tttcccccta cttcaatccc ctatttgcat atgcgaataa 212653
```

-continued

```
ttcaaaaact cctttgaatt tcattaatag aattcaattt aaatggtctt acagtggaat 212713
gactctgtcc aagctgggac ttctgtctgg gaggaaaata agtctgccaa ttcccatctt 212773
gataccacaa gccagagcct gtctctgctt gctgagtcta ccagcaaggt accaaggcta 212833
ccacagagag aaccacagac agagtggatg gcacaacaaa agtgtacttt cctgaccagt 212893
gatggaggtt agaagtctga gaccaggctg tcagcagcct tggttgcacc tgatgcctct 212953
ctccttggtt tgtagatgtt tgtgttctcc catggtctcc cgggggtctt actatgtcct 213013
gatctcttcc ttctaaggac atactgggct acagtctgcc cacatgactt catttggcag 213073
tagtcattat agccacaatc tgaagccttg gatttgatag gggcacattg atacccagta 213133
acaacaacac tgagcaacaa caacaacaaa aaaaggtgtg atgttcttac cagaactcca 213193
ttcacgctga gacatgggaa ttttctcgaa ggcttcagta taacacacac taatgctgac 213253
tgctttgagg tactctttag gcaggctttg ggtagcaaaa aatgataccc cctcacctcc 213313
taacctaagc cccctcttaa acaccttcct gcaacctgga ccgagtgatt cttttgggca 213373
gtaaccaaga gacactgcct cttcagaatg acagagggaa agaggttgac atgttgattc 213433
taaagaaact tcggcatcct ggaagggtca ctgctcggcg tatccaagtg gcatcttctt 213493
gagcgccact caagaaatgg tcttggtttt cacttgattc cctatagact cactttgtcc 213553
tggagaggga tgccgtggag agtctgaaat ctctttccct ttaacagtct gtgtttctgt 213613
ccgtgacgag gcttggtcca gctccgtatt gagtccacac tgggacagag ggttgaaata 213673
gaactcactt gtactgctgt gcctgtaccc tgcccttggg gaggtgtcat ttagctggag 213733
tggtagaact aggccaccga gagctactct tcagcctggg gtgtcagtat tgaagcacgc 213793
tgccatgggc ttcagcaagc ccttcatctt tgagtacctc gggaatgcgc agggtggatg 213853
tcaccctctc ctgcctgact ttggagcgct gcacacactc ggccacagtg tctccacagc 213913
cacaggttga gctccccacc cccgccccgc cccaactgat caaaagtatt tagggaaaat 213973
aatgcacctg agcatgaaca gattattcca taaataatca ctatgacaac catttgcatt 214033
tagattgtat ttggaattat atgtcacagt catctggggg tgcgtagcca tgctgtatag 214093
gggagaatgt gtgtaggtca tatgcagata ccatgcgtta ttaagcaaag aacttaagca 214153
cccttcctct ttggttttgg aacccatctc ctgtgtgtgc tgaagaaacg ctgcacgtac 214213
gtggaaatga cactattccc ggctctactt catttccttc atggatgagc agacctcatt 214273
catgtcagta agaacaaaaa ggggcaacga atggaccgag tgtcccggtc actcaaggcc 214333
acgtctttgt atttttccat cacctgggca tggtggaagc atgtgtctcc tgagtatctc 214393
ttgtcctcac aatgaaagac tcccatgggt cacaaagtag caagcctagg aaaactgtgg 214453
agggaaatgt gggcattcaa agaagcctag tggctattat tattattatc atttattatt 214513
atttttgata cagtaaatag ccatcaggca tgagcagttg gtttggattt tttaaatatt 214573
ttttattaca tattttcctc aattacattt ccaatgctat cccaaaagtc tcccttaccc 214633
tcccccccac ttccctaccc acccattccc attttttttgg ccctggcatt cccctgtact 214693
ggggcatata aagtttgcaa gtccaatggg cctctctttc cagtgatggc cgactaggcc 214753
atcttttgat acacatgcag ctagagtcaa gagctccggg gtactggata gttcataatg 214813
ttgcacctac agggttgcag atctctttag ctccttgggt actttctcta gctcctccat 214873
tgggggccct gtgatccatc caatagctga ctgtgagcat ccacttctgt gtttgctagg 214933
ccccggcata gtctcacaag agacagctac atctgggtcc tttcgataaa atcttgctag 214993
tgtatgcaat ggtgtcagcg tttggaagct gattatgggg tagatctctg gatatggcag 215053
```

-continued

```
tctctagatg gtccatcctt tcgtctcagc tccaaacttt gtaactcctt gtggtttgga 215113
tttttaatac ctaagaagta aatattaatt taacgatttg cttaacatga tgccaaaggt 215173
tcattctgcc aggaaggctt cctactttag taacagctat catggccctt gagtattgcc 215233
tcctgaacat gcccacaatt tcagtctgtt gctagaggca cacagtggtc acagagggat 215293
tggcacagtc ctcgaggtag ctttgagggc ccttgctagg aggaaggctc atccttgttc 215353
tttgtttagc cggaggtttc tccccagaca tgaatattca cttccagaat tcaagacgat 215413
tggggattaa aagatgccat ttggactctt ctcctcgggt gcctttaaaa gcaatctatt 215473
cggaagccca gagccctgtg aacactgagg gctaagctgt ccccatggca ggaatcgtga 215533
accccttctg cttcccagca gcaaagggca tggaggatta gcacgcaaag caaaccaaga 215593
aaagacaggg aattgagatg cccggactga gtccgctctc ggagccttgg atctccggtg 215653
gggctccctt gagcatttat tttggagttt gaagtcagaa aactaaataa cagtactaaa 215713
cacgaaggtg ctctgctgtt cttggaaaat gcagaagact gttggcaggc agctcgagag 215773
ccgctgcccc tcctcgaggt atagacacac taagaaacag cagctacatg cttgatctcc 215833
aaagcaagtt tatttattta ttttttaat tcccttattt gacatttcag ttatggggtc 215893
ctagagagtg gagaaaatgg ccaggttcaa gtggcacagg attgcagaca ggcttgtctc 215953
tagcaagccg aacaggaggg tgactgaatg ctctcacttt ggggagttaa tctgtagaga 216013
gaaggcattt tagcttgcaa gcctgtcgcc aattaaatcg aggtgacctc atttgttgac 216073
agcagagcag atcacagcaa acaggaggag atgggaaaaa cacctgtgtg tttctcccaa 216133
ggggcagtga tgctgagcag tgttctctga gtgctagctc ctgggtaggc cttggtataa 216193
gaggaaaaca cccaggccct tactggagtg acctggagac tggactgcag gcaactctca 216253
caggagggaa gatgcgagca gctcccatct ggatcccacc tcgtgcagat gggaggagtc 216313
agggcggatg agcagaagga aatgtcccag gacctaaggg cagggcagct cctattccca 216373
ctgcctttga ctgtgtcctg aagtctgtcc tgaagtctgt ctcgtgccca gcctaaaaag 216433
gactaactag ttctctgaag tggggtcaca cccaatggcc atgaaggaat tcatctctac 216493
aaggctctcc acctgaatta ctccttaggt gggactaggc gtgatctgtg tgtatcatat 216553
gatctatgtg tatcatacca catgtctgtc catcacctgg taggtagggc agcactggca 216613
ccatgcatat ctgccccccc cttgttgttt taggagccac cataacagta agacagttgt 216673
gcagggtctg aactgtgcca cactggcagt aggcggggtg ggggcagggg acagagacaa 216733
agagaaagct ggggaattgc cagacatcat ttgacagtgc tcagcaatgg gaactagaga 216793
cctctgaaaa atgaggctgc aagctccatt cagtccagga cagaataaga aatatccctg 216853
tgaaatgaat cccatagaac acaccttaac ttttctgtgg gaaacatggt ttatgctatg 216913
tgcatacgga cagagtcctc tcgtcttcca acgcggcttt acagaggctt ggagctcata 216973
ttaatccagc agactcaagc aagcacctcc tcttctcctc actgggagag gtaggacaaa 217033
tatagaaaca agaaaagcca ttagctactg tagagagatg tgtgccccgc acagtctgca 217093
gagactaaca cctgcccggc tctccgtgac aatggctgag gcagattatg tttaccgtgc 217153
cgacctgatc ttacagctga agcctgctgt agagctctgg cctggcggaa atgaggcctg 217213
aatgcaaccc ccaggactac aaatcctgta tgtgtaggat gaatgggtag gtgggtggat 217273
ggatggatga gtggatggaa ggatggatcg acagacagac agatatgtat gtatgtatgt 217333
atgtatgtat gtatgtatgt atgtataatt aggatagtgt gtctatacag tttccctttt 217393
```

-continued

```
tgtgtcaagt aatacccccc ttttttcaaa tttttattag ataatttttt catttacact 217453

tcaaatgcta tcccaaaagt cccctatacc ctacccctgg taatacacct tttatataca 217513

tacactcaca cacacacaga cacacacata catccatata tgttaccttt atttataccc 217573

cttttatatg tgtatgtgtg tatatatata catatatata tatatatata tgtatatata 217633

taataaaaga catatacata catgtgtgtg tgtgtgtgta tcttttattt aataggctct 217693

caaaactctc attaacattt ctacagagat aaatgtactt cgaaatggca gcagatacct 217753

ggggccccac aaagcggagt gttatattct gcacagatct aagcgtcact cacagtcatt 217813

cacagtgcgg ctttgtgaga tgttctttct ccttcaccat cccacaaact ccagtgctgg 217873

ctgtttcagc caatgtgccc tgtgcagacc cgagtactcg cctcaagaat ttcagcacca 217933

cctagtggcc agatgcagca tcggcgtaag ccattggctc tgccacgtgg tgtcagaagt 217993

tggggctaaa gctgataaat cacggttgtt aagtactttg ggggcaaaga aaagaactgc 218053

acaccgtgtc ctgttactgc ctacgagtac tgtgctcctt taaagtcctc ggtctatttt 218113

aaacccggat ctctgtacct gctttctag gtc gac gcc gcc gtg acc cca gag   218166
                                Val Asp Ala Ala Val Thr Pro Glu
                                        740                 745

gag cgc cat ctc tcc aag atg cag cag aac gga tat gag aat cca act   218214
Glu Arg His Leu Ser Lys Met Gln Gln Asn Gly Tyr Glu Asn Pro Thr
            750                 755                 760

tac aag ttc ttt gag caa atg cag aac                               218241
Tyr Lys Phe Phe Glu Gln Met Gln Asn
        765                 770
```